US011643461B2

(12) United States Patent
Châlons-Cottavoz et al.

(10) Patent No.: US 11,643,461 B2
(45) Date of Patent: *May 9, 2023

(54) HUMANIZED, MOUSE OR CHIMERIC ANTI-CD47 MONOCLONAL ANTIBODIES

(71) Applicant: Forty Seven, Inc., Foster City, CA (US)

(72) Inventors: Marie Châlons-Cottavoz, Lyons (FR); Mehdi Lahmar, Nantes (FR); Klaus Schwamborn, Nantes (FR); Nicola Beltraminelli, Lyons (FR); Stéphanie Fallot, Lyons (FR); Pierre Garrone, Lyons (FR)

(73) Assignee: Forty Seven, Inc., Foster City, CA (US)

( * ) Notice: Subject to any disclaimer, the term of this patent is extended or adjusted under 35 U.S.C. 154(b) by 277 days.

This patent is subject to a terminal disclaimer.

(21) Appl. No.: 16/953,433

(22) Filed: Nov. 20, 2020

(65) Prior Publication Data

US 2021/0188976 A1    Jun. 24, 2021

Related U.S. Application Data

(63) Continuation of application No. 16/068,874, filed as application No. PCT/EP2017/050508 on Jan. 11, 2017, now Pat. No. 10,927,173.

(30) Foreign Application Priority Data

Jan. 11, 2016  (EP) .................................... 16150808
Jun. 2, 2016   (EP) .................................... 16172651

(51) Int. Cl.
C07K 16/28     (2006.01)
A61K 39/00     (2006.01)

(52) U.S. Cl.
CPC .... *C07K 16/2803* (2013.01); *A61K 2039/505* (2013.01); *C07K 2317/24* (2013.01); *C07K 2317/31* (2013.01); *C07K 2317/33* (2013.01); *C07K 2317/34* (2013.01); *C07K 2317/54* (2013.01); *C07K 2317/55* (2013.01); *C07K 2317/73* (2013.01); *C07K 2317/76* (2013.01); *C07K 2317/92* (2013.01)

(58) Field of Classification Search
CPC .................................................. C07K 16/2803
USPC ...................................................... 424/133.1
See application file for complete search history.

(56) References Cited

U.S. PATENT DOCUMENTS

| | | |
|---|---|---|
| 8,728,476 B2 | 5/2014 | Van Den Berg |
| 8,758,750 B2 | 6/2014 | Weissman et al. |
| 9,017,675 B2 | 4/2015 | Liu et al. |
| 9,352,037 B2 | 5/2016 | Van Den Berg |
| 9,790,275 B2 | 10/2017 | Van Den Berg |
| 9,920,122 B2 | 3/2018 | Van Den Berg |
| 10,081,680 B2 | 9/2018 | Weiskopf et al. |
| 10,287,351 B2 | 5/2019 | Van Den Berg |
| 10,927,173 B2 | 2/2021 | Chalons-Cottavoz et al. |
| 2005/0180972 A1 | 8/2005 | Wahl et al. |
| 2007/0041981 A1 | 2/2007 | Howard et al. |
| 2008/0107654 A1 | 5/2008 | Kikuchi et al. |
| 2009/0191202 A1 | 7/2009 | Jamieson et al. |
| 2011/0038870 A1 | 2/2011 | Van Den Berg |
| 2013/0224188 A1 | 8/2013 | Eckelman et al. |
| 2014/0242095 A1 | 8/2014 | Wang et al. |
| 2014/0303354 A1* | 10/2014 | Masternak ............. A61P 35/00 530/387.3 |
| 2018/0155424 A1 | 6/2018 | Van Den Berg |
| 2019/0023784 A1 | 1/2019 | Chalons-Cottavoz et al. |
| 2019/0119396 A1 | 4/2019 | Liu et al. |
| 2019/0248915 A1 | 8/2019 | Chao et al. |
| 2022/0356245 A1 | 11/2022 | Châlons-Cottavoz et al. |

FOREIGN PATENT DOCUMENTS

| | | |
|---|---|---|
| CN | 103665165 B | 2/2016 |
| EP | 1985305 A1 | 10/2008 |
| EP | 2282772 A1 | 2/2011 |
| EP | 2150275 B1 | 11/2013 |
| WO | WO-99/40940 A1 | 8/1999 |
| WO | WO-01/48020 A1 | 7/2001 |
| WO | WO-2003/072736 A2 | 9/2003 |
| WO | WO-2008/121821 A1 | 10/2008 |
| WO | WO-2008/129058 A1 | 10/2008 |
| WO | WO-2009/091547 A1 | 7/2009 |

(Continued)

OTHER PUBLICATIONS

Adams, S. et al., Renardel de Lavalette C, Dopp EA, Dijkstra CD, et al. Signal-regulatory protein is selectively expressed by myeloid and neuronal cells. J Immunol. 1998;161 (4):1853-9.

Advani, R. et al., CD47 Blockade by Hu5F9-G4 and Rituximab in Non-Hodgkin's Lymphoma. N Engl J Med. 2018;379(18):1711-21.

(Continued)

*Primary Examiner* — Sean E Aeder

(74) *Attorney, Agent, or Firm* — Choate, Hall & Stewart LLP; Rolando Medina; Melissa M. Adams

(57) ABSTRACT

Humanized, mouse or chimeric anti-CD47 monoclonal antibodies are provided. The antibodies bind to human glycosylated and deglycosylated CD47 with an optimized Koff value, they disrupt the human CD47-SIRPα interaction, and find use in various therapeutic, preventive or diagnostic methods. The invention includes isolated antibodies and derivatives and fragments thereof, pharmaceutical formulations comprising one or more of the humanized or chimeric anti-CD47 monoclonal antibodies; and cell lines that produce these monoclonal antibodies. Also provided are amino acid and nucleotide sequences of the antibodies.

24 Claims, 30 Drawing Sheets

Specification includes a Sequence Listing.

(56) References Cited

FOREIGN PATENT DOCUMENTS

| | | |
|---|---|---|
| WO | WO-2009/091601 A1 | 7/2009 |
| WO | WO-2009/131453 A1 | 10/2009 |
| WO | WO-2011/066501 A1 | 6/2011 |
| WO | WO-2011/143624 A2 | 11/2011 |
| WO | WO-2013/109752 A1 | 7/2013 |
| WO | WO-2014/087248 A2 | 6/2014 |
| WO | WO-2014/093678 A2 | 6/2014 |
| WO | WO-2014/094122 A1 | 6/2014 |
| WO | WO-2014/123580 A1 | 8/2014 |
| WO | WO-2015/138600 A2 | 9/2015 |
| WO | WO-2016/023040 A1 | 2/2016 |
| WO | WO-2017/027422 A1 | 2/2017 |
| WO | WO-2017/068164 A1 | 4/2017 |
| WO | WO-2017/100462 A2 | 6/2017 |
| WO | WO-2017/121771 A1 | 7/2017 |
| WO | WO-2017/127707 A1 | 7/2017 |
| WO | WO-2017/177333 A1 | 10/2017 |
| WO | WO-2019/023347 A1 | 1/2019 |
| WO | WO-2019/079548 A1 | 4/2019 |
| WO | WO-2019/079549 A1 | 4/2019 |
| WO | WO-2019/157432 A1 | 8/2019 |

OTHER PUBLICATIONS

Alegre, M.L. et al., Effect of a single amino acid mutation on the activating and immunosuppressive properties of a humanised OKT3 monoclonal antibody, The Journal of Immunology, 1992, vol. 148, No. C1 11 , 12 pages.

Amano, J. et al., Antigendependent internalization is related to rapid elimination from plasma of humanized anti-HM1 .24 monoclonal antibody. Drug Metab Dispos. 2010;38(12):2339-46.

Angal, S. et al., A single amino acid substitution abolishes the heterogeneity of chimeric mouse/human (IgG4) antibody, Molecular Immunology, 1993, vol. 30, No. 1, 6 pages.

Anonymous: Trial of Hu5F9-G4 in Avelumab in Ovarian Cancer11 , ClinicalTrials.gov, Jun. 15, 2018 (Jun. 15, 2018), pp. 1-6, XP55532523, Retrieved from the Internet: URL:https://clinicaltrials.gov/ct2/show/NC T03558139.

Anonymous: Trial of Hu5F9-G4 in Combination With Cetuximab in Patients With Solid Tumors and Advanced Colorectal Cancer11 , ClinicalTrials.gov, Nov. 3, 2016 (Nov. 3, 2016), pp. 1-8, XP055532527, Retrieved from the Internet: URL:https://clinicaltrials.gov/ct2/show/NC T02953782.

Ayi, K. et al., CD47-SIRP? Interactions Regulate Macrophage Uptake of Plasmodium falciparum—Infected Erythrocytes and Clearance of Malaria In Vivo, Infection and Immunity, vol. 84, No. 7, Jul. 1, 2016, pp. 2002-2011.

Barclay AN, and Brown MH. The SIRP family of receptors and immune regulation. Nat Rev Immunol. 2006;6(6):457-64.

Bich, C. et al., Characterization of antibody-antigen interactions: Comparison between surface plasmon resonance measurements and high-mass matrix-assisted laser desorption/ionization mass spectrometry, Analytical Biochemistry, 2008, vol. 375, No. 1, 35-45.

Boutros, C. et al., Safety profiles of anti-CTLA-4 and anti-PD-1 antibodies alone and in combination. Nat Rev Clin Oneal. 2016;13(8):473-86.

Brochure by RituxanHYCELA®, Rituxan® and Rituxan Hycela® Dosing and Administration Brochure Issued Jun. 2017: pp. 1-45, Retrieved from the internet: https://www.rituxanhycela.com/hcp/dosina-and-administration/product-information.html.

Brooke, G. et al., Human lymphocytes interact directly with CD47 through a novel member of the signal regulatory protein (SIRP) family. J Immunol. 2004;173(4):2562-70.

Cameron, et al., Myxoma virus M128L is expressed as a cell surface CD-47-like virulence factor that contributes to the downregulation of macrophage activation in vivo, Virology. Jun. 20, 2005; vol. 337, Issue 1: Paaes 55-67.

Carter PJ. Potent antibody therapeutics by design. Nat Rev Immunol. 2006;6(5):343-57.

Casi G, and Neri D. Antibody-drug conjugates: basic concepts, examples and future perspectives. J Control Release. 2012;161 (2):422-8.

Chao, et al. CD4 is an adverse prognostic factor in non-hodgkin lymphoma and a therapeutic antibody taraet that syneraizes with rituximab, Exp Hematol (Sep. 2009), 37(Suppl 1 ):S8-S9.

Chao, et al. Therapeutic antibody targeting of CD47 synergizes with rituximab to completely eradicate human B-cell lymphoma xenografts, Blood (Nov. 2009), 114(22):1063-1064, abstract only.

Chao, M. et al., Anti-CD47 antibody synergizes with rituximab to promote phagocytosis and eradicate non-Hodgkin lymphoma. Cell. 2010;142(5):699-713.

Chaparro-Riggers, J. et al., Increasing serum halflife and extending cholesterol lowering in vivo by engineering antibody with pH-sensitive binding to PCSK9. J Biol Chem. 2012;287(14):11090-7.

Chothia, C. et al., Domain association in immunoglobulin molecules. The packing of variable domains, Journal of Molecular Biology, 1985, vol. 186, Issue 3, pp. 651-663.

Evan, G.I. et al., Isolation of monclonal antibodies specific for human c-myc proto-oncogene product, Molecular and Cellular Biology, 1985, vol. 5, No. 12, pp. 3610-3616.

Extended European Search Report for EP20172595, 6 pages (dated Oct. 22, 2020).

First Examination Report for AU2017206631, 4 pages (dated Nov. 27, 2020).

Fujioka, Y. et al., A novel membrane glycoprotein, SHPS-1, that binds the SH2-domain-containing protein tyrosine phosphatase SHP-2 in response to mitogens and cell adhesion. Mol Cell Biol. 1996;16(12):6887-99.

Gao, J. et al., Affibody-based nanoprobes for HER2-expressing cell and tumor imaging, Biomaterials, 2011, vol. 32, No. 8, pp. 2141-2148.

Genentech: Rituxan and Rituxan Hycela Dosing and Administration Brochure. https:/ritucanhycela.com/content/dam/gene/rituxanhycela/hcp/pdfs/RITUXAN-HYVELA-dosingand-admin-brocure.pdf.

Graham, F.L. et al., Characteristics of a human cell line transformed by DNA from human adenovirus type 5, Journal of General Virology, 1977, vol. 36, No. 1, pp. 59-72.

Guss, B. et al., Structure ofthe IgG-binding regions of streptococcal protein G, The EMBO journal, 1986, vol. 5, No. 7, pp. 1567-1575.

Hather, G. et al., Growth Rate Analysis and Efficient Experimental Design for Tumor Xenograft Studies, Cancer informatics, 2014, vol. 13, pp. 65-72.

Hatherley et al., Paired Receptor Specificity Explained by Structures of Signal Regulatory Proteins Alone and Complexed with CD47, Jul. 25, 2008, Mollecular Cell, vol. 31, Issue 2: pp. 266-277.

Hatherley et al., The Structure ofthe Macrophage Signal Regulatory Protein? (SIRP?) Inhibitory Receptor Reveals a Binding Face Reminiscent of That Usedby T Cell Receptors, The Journal of Bioloaical Chemistry, May 11, 2007, vol. 282, Issue 19: pp. 14567-14575.

Hezareh, M. et al., Effector Function Activities of a Panel of Mutants of a Broadly Neutralizing Antibody against Human Immunodeficiency Virus Type 1, Journal of Virology, vol. 75, No. 24, Dec. 2001, pp. 12161-12168.

International Preliminary Report of Patentability, issued for PCT/US2018/056441, dated Apr. 21, 2020.

International Preliminary Report of Patentablity issued in PCT/US2018/056442, dated Apr. 21, 2020.

International Preliminary Reporting on Patentablity issued in PCT/US2019/017466, dated Jun. 20, 2019.

Jaiswal, et al. CD47 is Upregulated on Circulating Hematopoietic Stem Cells and Leukemia Cells to Avoid Phagocytosis, Cell (Jul. 2009), 138(2):271-285.

Jokerst, J.V. et al., Affibody-functionalized gold-silica nanoparticles for Raman molecular imaging ofthe epidermal growth factor receptor, Small, 2011, vol. 7, No. 5, pp. 625-633.

Kabat, E.A. et al. Sequences of Proteins of Immunological Interest, 5th edition, DIANE publishing, 1991, vol. C11 1-3.

Kaur, S. et al., Heparan sulfate modification of the transmembrane receptor CD47 is necessary for inhibition of T cell receptor signaling by thrombospondin-1, Journal of Biological Chemistry, 2011, vol. 286, No. 17, C12 14991-15002.

(56) References Cited

OTHER PUBLICATIONS

Kellar, A. et al., Preclinical Murine Models for Lung Cancer: clinical trial applications, BioMed Research International, 2015, pp. 1-17.
Kharitonenkov, A. et al., A family of proteins that inhibit signalling through tyrosine kinase receptors. Nature. 1997;386(6621):181-6.
Kim, D. et al., Anti-CD47 antibodies promote phagocytosis and inhibit the growth of human myeloma cells. Leukemia. 2012;26(12):2538-45.
Lammerts van Bueren, J. et al., Effect of target dynamics on pharmacokinetics of a novel therapeutic antibody against the epidermal growth factor receptor: implications for the mechanisms of action. Cancer Res. 2006;66(15):7630-8.
Lee et al., Novel Structural Determinants on SIRP? that Mediate Binding to CD47, The Journal of Immunology, 2007, vol. 179: pp. 7741-7750.
Lee et al., The Role of cis Dimerization of Signal Regulatory Protein? (SIRP ?) in Binding to CD47, The Journal of Biological Chemistry, Dec. 3, 2010, vol. 285, Issue 49: pp. 37953-37963.
Lee, L. et al., Immune Checkpoint inhibitors: An introduction to the nextgeneration cancer immunotherapy. J Clin Pharmacol. 2016;56(2):157-69.
Lindberg, F.P., Molecular cloning of integrin-associated protein: An immunoglobulin family member with multiple membrane-spanning domains implicated in a av?3-dependent ligand binding, The Journal of cell biology, 1993, vol. 123, No. 2, pp. 485-496.
Lindmark, R. et al., Binding of immunoglobulins to protein A and immunoglobulin levels in mammalian sera, Journal of immunological methods, 1983, vol. 63, No. 1, pp. 1-13.
Liu, J., et al. Pre-Clinical Development of a Humanized Anti-CD47 Antibody with Anti-Cancer Therapeutic Potential, PloS ONE, Sep. 21, 2015, vol. 10, Issue 9: pp. 1-23.
Majeti, et al. CD47 is an Adverse Prognostic Factor and Therapeutic Antibody Target on Human Acute Myeloid Leukemia Stem Cells, Cell (Jul. 2009), 138(2):286-299.
Maley, F. et al., Characterization of glycoproteins and their associated oligosaccharides through the use of endoglycosidases, Analytical Biochemistry, 1989, vol. 180, No. 2, pp. 195-204.
Manna and Frazier, CD47 Mediates Killing of Breast Tumor Cells via Gi-Dependent Inhibition of Protein Kinase A, Cancer Research, Feb. 1, 2004, vol. 64: pp. 1026-1036.
Mather, J.P. et al., Culture of testicular cells in hormone-supplemented serum-free medium, Annals of the New York Academy of Sciences, 1982, vol. 383, Issue 1, pp. 44-68.
Mather, J.P., Establishment and characterization of two distinct mouse testicular epithelial cell lines, 1980, Biology of Reproduction, vol. 23, Issue 1, pp. 243-252.
Matsui, Y. et al., Suppression of tumor growth in human gastric cancer with HER2 overexpression by an anti-HER2 antibody in a murine model, International journal of oncology, 2005, vol. 27, No. 3, 7 pages.
Meezan, E., Comparative studies on the carbohydrate-containing membrane components of normal and virus-transformed mouse fibroblasts. II. Separation of glycoproteins and glycopeptides by Saphadex chromatography, Biochemistry, 1969, vol. 8, No. 6, 9 pages.
Michot, J. et al., Immunerelated adverse events with immune checkpoint blockade: a comprehensive review. Eur J Cancer. 2016;54:139-48.
Nath, N. et al., Homogeneous plate based antibody internalization assay using pH sensor fluorescent dye. J Immunol Methods. 2016;431 :11-21.
Novotny, J. et al., "Structural invariants of antigen binding: comparison of immunoglobulin VL-VH and VL-VL domain dimers," Proceedings of the National Academy of Sciences, 1985, vol. 82, No. 14, pp. 4592-4596.
Ogura, T. et al., Resistance of B16 melanoma cells to CD47-induced negative regulation of motility as a result of aberrant N-glycosylation of SHPS-1, Journal of Biological Chemistry, 2004, vol. 279, No. 14, pp. 13711-13720.
Olden Borg, et al. Role of CD47 as a marker of self on red blood cells. Science 2000;288:2051-4.
Ose Immunotherapeutics, Selective anti-SI RP? antibodies: Next generation checkpoint inhibitor: Taraetina pro-tumors and surmressive myeloids cells, Sep. 2017, 35 paaes.
Paborsky, L.R. et al., Mammalian cell transient expression of tissue factor for the production of antigen, Protein Engineering, Design and Selection, 1990, vol. 3, No. 6, 1 O pages.
Panowski, S. et al., Site-specific antibody drug conjugates for cancer therapy. MAbs. 2014;6(1):34-45.
Parthasarathy, R. et al., Post-translational regulation of expression and conformation of an immunoglobulin domain, University of Pennsylvania, Department of Chemical & Biomolecular Engineering, 2005, 34 pages.
PCT International Preliminary Report on Patentability for PCT/EP2017/050508, dated Jul. 17, 2018, 6 pages.
PCT International Search Report and Written Opinion, PCT Application No. PCT/EP2017/050508, dated Jul. 20, 2017, ten pages.
PCT International Search Report and Written Opinion, PCT Application No. PCT/US2018/043699, dated Jan. 31, 2019, 13 pages.
PCT International Search Report and Written Opinion, PCT Application No. PCT/US2018/056441, dated Apr. 25, 2019, 12 pages.
PCT International Search Report and Written Opinion, PCT Application No. PCT/US2018/056442, dated Apr. 25, 2019, 10 pages.
PCT International Search Report and Written Opinion, PCT Application No. PCT/US2019/017466, dated Apr. 29, 2019, 19 pages.
Piccio, L. et al., Adhesion of human T cells to antigen-presenting cells through SIRPbeta2-CD47 interaction costimulates Tcell proliferation. Blood. 2005;105(6):2421-7.
Pinho, S.S. et al., Glycosylation in cancer: mechanisms and clinical implications, Nature Reviews Cancer, 2015, vol. 15, No. 9, pp. 540-555.
Pluckthun, A., Antibodies from *Escherichia coli*, The Pharmacology of Monoclonal Antibodies, Springer-Vertag, 1994, 49 pages.
Queen, C. et al., A humanized antibody that binds to the interleukin 2 receptor. Proc Natl Acad Sci USA. 1989;86(24):10029-33.
Ratte, A. et al., Mechanistic overview of immune checkpoints to support the rational design of their combinations in cancer immunotheraov. Ann Oncol. 2018;29(1 ):71-83.
Reddy, M.P. et al., Elimination of Fc receptor-dependent effector functions of a modified IgG4 monoclonal antibody to human CD4, The Journal of Immunology, 2000, vol. 164, No. 4, pp. 1925-1933. 10 pages.
Remington, J.P. et al. Remington's Pharmaceutical Sciences, 16th edition, 1980, Mack Publishing Company, Easton, Pennsylvania.
Ring, N. et al., Anti-SIRPalpha antibody immunotherapy enhances neutrophil and macrophage antitumor activity. Proc Natl Acad Sci USA. 2017;114(49):E10578-E85.
Ritchie, M. et al., Implications of receptor-mediated endocytosis and intracellular trafficking dynamics in the development of antibody drug conjugates. MAbs. 2013;5(1 ):13-21.
Sehn, et al., Introduction of Combined CHOP Plus Rituximab Therapy Dramatically Improved Outcome of Diffuse Large B-Cell Lymphoma in British Columbia, J. Clin. Oncol., Aug. 1, 2005, vol. 23, Issue 22: pp. 5027-5033.
Seidel, J. et al., Anti-PD-1 and Anti-CTLA-4 Therapies in Cancer: Mechanisms of Action, Efficacy, and Limitations. Front Oncol. 2018;8:86.
Seiffert, M. et al., Human Signal-Regulatory Protein is Expressed on Normal, but not on Subsets of Leukemic Myeloid Cells and Mediates Cullular Adhesion involving its Counterreceptor CD47, Blood, vol. 94, No. 11, Dec. 1, 1999, pp. 3633-3643.
Sharpe AH. Introduction to checkpoint inhibitors and cancer immunotherapy. Immunol Rev. 2017;276(1):5-8.
Sikic, B. et al., First-in-Human, First-in-Class Phase I Trial of the Anti-CD47 Antibody Hu5F9-G4 in Patients With Advanced Cancers. J Clin Oncoll. 2019;37(12):946-53.
Sim, J. et al., Discovery of high affinity, pan-allelic, and pan-mammalian reactive antibodies against the myeloid checkpoint receptor SIRPalpha. MAbs. 2019;11(6):1036-52.
Steiner, P. et al., Tumor grown inhibition with cetuximab and chemotherapy in non-small cell lung cancer xenografts expressing

(56) References Cited

OTHER PUBLICATIONS wild-type and mutated epidermal growth factor receptor, Clinical Cancer Research, 2007, vol. 13, No. 5, pp. 1540-1551.
Strohl, W., Optimization of Fe-mediated effector functions of monoclonal antibodies, Current Opinion in Biotechnology, vol. 20, No. 6, Dec. 1, 2009, pp. 685-691.
Subramanian, S. et al., Phylogenetic divergence of CD47 interactions with human signal regulatory protein arevealslocus of species specificity, Journal of Biological Chemistry, 2007, vol. 282, No. 3, pp. 1805-1818.
Subramanian, S. et al., Species and cell type-specific interactions between CD47 and human SIRP?, Blood, 2006, vol. 107, No. 6, pp. 2548-2556.
Takenaka, K. et al., Polymorphism in Sirpa modulates engrafTment of human hematopoietic stem cells, Nature Immunology vol. 8, 2007, pp. 1313-1323.
Tarhini A. Immune-mediated adverse events associated with ipilimumab ctla-4 blockade therapy: the underlying mechanisms and clinical management. Scientifica (Cairo). 2013:2013:857519.
Thakor, AS. et al., The fate and toxicity of raman-active silica-gold nanoparticles in mice, Science Transnational Medicine, 2011, vol. 20, No. 3, pp. 1-24.
Timms, J. et al., Identification of major binding proteins and substrates for the SH2-containing protein tyrosine phosphatase SHP-1 in macrophages. Mol Cell Biol. 1998;18(7):3838-50.
Topalian, S. et al., Mechanism-driven biomarkers to guide immune checkpoint blockade in cancer therapy. Nat Rev Cancer. 2016;16(5):275-87.
Tsai RK, and Discher DE. Inhibition of self engulfment through deactivation of myosin-11 at the phagocytic synapse between human cells. J Cell Biol. 2008;180(5):989-1003.
Tseng, D. et al., Anti-CD4 7 antibody-mediated phagocytosis of cancer by macrophages primes an effective antitumor T-cell response, Proceedings of the National Academy of Sciences, 2013, Early Edition, 66 pages.
Urlaub, G. et al., Isolation of Chinese hamster cell mutants deficient in dihydrofolate reductase activity, 1980, Proceedings of the National Academy of Sciences, vol. 77, No. 7, pp. 4216-4220.
Ward, et al., Binding activities of a repertoire of single immunoglobulin variable domains secreted from *Escherichia coli*, Nature, 1989, vol. 341, No. 6242, pp. 544-546.
Willingham, S. et al., The CD47-signal regulatory protein alpha (SI RPa) interaction is a therapeutic target for human solid tumors. Proc Natl Acad Sci USA. 2012;109(17):6662-7.
Yanagita, T. et al., Anti-SI RP? antibodies as a potential new tool for cancel immunotherapy, JCI Insight, vol. 2, No. 1, Jan. 12, 2017, 15 pages.
Zhao, X. et al., CD47-signal regulatory protein-? (SIRP?) interactions form a barrier for antibodymediated tumor cell destruction, Proceedings of the National Academy of Sciences of the United States of America, vol. 108, No. 45, pp. 18342-18347.
Australian First Office Action for Application No. 2017206631, dated Nov. 27, 2020, 4 pages.
Canadian First Office Action for Application No. 3,011,097, dated Feb. 2, 2022, 8 pages.
Chinese First Office Action for Application No. 201780006353.4, dated May 19, 2021, 8 pages.
Eurasian First Office Action for Application No. 201891435, 1 page.
Eurasian Second Office Action for Application No. 201891435, 1 page.
Japanese First Office Action for Application No. 2018-537521, dated Feb. 24, 2021, 2 pages.
Japanese Second Office Action for Application No. 2018-537521, dated Nov. 2, 2021, 6 pages.
Korean First Office Action for Application No. 10-2018-7021469, dated May 11, 2022, 4 pages.
Mexican Office Action for Application No. 2018/008558, dated Jun. 23, 2022, 4 pages.

\* cited by examiner

|  |  | 1 | | | | | 50 |
|---|---|---|---|---|---|---|---|
| VL0 | (1) | DIVMTQSPSSLAMSVGQKVTMNCKSSQSLLNSIDQKNYLAWYQQKPGQSP |
| VL1 | (1) | DIVMTQSPDSLAVSLGERATINCKSSQSLLNSIDQKNYLAWYQQKPGQPP |
| VL2 | (1) | DIVMTQSPDSLAVSLGERATINCKSSQSLLNSIDQKNYLAWYQQKPGQPP |
| VL3 | (1) | EIVLTQSPDSLAVSLGERATINCKSSQSLLNSIDQKNYLAWYQQKPGQPP |
| VL4 | (1) | DIVMTQSPDSLAVSLGERATINCKSSQSLLNSIDQKNYLAWYQQKAGQSP |
| VL5 | (1) | DIVMTQSPDSLAVSLGERATINCKSSQSLLNSIDQKNYLAWYQQKPGQPP |
|     | (1) | DIVMTQSPDSLAVSLGERATINCKSSQSLLNSIDQKNYLAWYQQKPGQPP |

|  |  | 51 | | | | | 100 |
|---|---|---|---|---|---|---|---|
| VL0 | (51) | KLLIYFASTKESGVPDRFIGSGSGTDFTLTISSVQAEDIADYFCQQHYST |
| VL1 | (51) | KLLIYFASTKESGVPDRFSGSGSGTDFTLTISSLQAEDVAVYCQQHYST |
| VL2 | (51) | KLLIYFASTKESGVPDRFSGSGSGTDFTLTISSLQAEDVAVYCQQHYST |
| VL3 | (51) | KLLIYFASTKESGVPDRFSGSGSGTDFTLTISSLQAEDVAVYYCQQHYST |
| VL4 | (51) | KLLIYFASTKESGVPDRFSGSGSGTDFTLTIDSLQAEDVAVYFCQQHYST |
| VL5 | (51) | KLLIYFASTKESGVPDRFSGSGSGTDFTLTISSLQAEDVAVYFCQQHYST |
|     | (51) | KLLIYFASTKESGVPDRFSGSGSGTDFTLTIGLQAEDVAVYFCQQHYST |

|  |  | 101 | 113 |
|---|---|---|---|
| VL0 | (101) | PWTFGGGTKLEIK |
| VL1 | (101) | PWTFGGGTKLEIK |
| VL2 | (101) | PWTFGGGTKVEIK |
| VL3 | (101) | PWTFGGGTKVEIK |
| VL4 | (101) | PWTFGGGAKVEIK |
| VL5 | (101) | PWTFGGGTKVEIK |

SEQUENCE LISTING

```
<160> NUMBER OF SEQ ID NOS: 176

<210> SEQ ID NO 1
<211> LENGTH: 5
<212> TYPE: PRT
<213> ORGANISM: Human

<400> SEQUENCE: 1

Lys Tyr Trp Met His
1               5
```

```
<210> SEQ ID NO 2
<211> LENGTH: 17
<212> TYPE: PRT
<213> ORGANISM: Artificial sequence
<220> FEATURE:
<223> OTHER INFORMATION: VT008-AL5-10G7 antibody; heavy chain; CDR2-
      Kabat

<400> SEQUENCE: 2

Glu Ile Asn Pro Ser Asp Thr Tyr Thr Asn Tyr Asn Gln Lys Phe Lys
1               5                   10                  15

Gly

<210> SEQ ID NO 3
<211> LENGTH: 11
<212> TYPE: PRT
<213> ORGANISM: Artificial sequence
<220> FEATURE:
<223> OTHER INFORMATION: VT008-AL5-10G7 antibody; heavy chain; CDR3-
      Kabat

<400> SEQUENCE: 3

Val Ala Thr Met Val Ala Arg Gly Phe Ala Tyr
1               5                   10

<210> SEQ ID NO 4
<211> LENGTH: 8
<212> TYPE: PRT
<213> ORGANISM: Artificial sequence
<220> FEATURE:
<223> OTHER INFORMATION: VT008-AL5-10G7 antibody; heavy chain; CDR1-IMGT

<400> SEQUENCE: 4

Gly Tyr Thr Phe Thr Lys Tyr Trp
1               5

<210> SEQ ID NO 5
<211> LENGTH: 8
<212> TYPE: PRT
<213> ORGANISM: Artificial sequence
<220> FEATURE:
<223> OTHER INFORMATION: VT008-AL5-10G7 antibody; heavy chain; CDR2-IMGT

<400> SEQUENCE: 5

Ile Asn Pro Ser Asp Thr Tyr Thr
1               5

<210> SEQ ID NO 6
<211> LENGTH: 13
<212> TYPE: PRT
<213> ORGANISM: Artificial sequence
<220> FEATURE:
<223> OTHER INFORMATION: VT008-AL5-10G7 antibody; heavy chain; CDR3-IMGT

<400> SEQUENCE: 6

Ala Arg Val Ala Thr Met Val Ala Arg Gly Phe Ala Tyr
1               5                   10

<210> SEQ ID NO 7
<211> LENGTH: 11
<212> TYPE: PRT
<213> ORGANISM: Artificial sequence
<220> FEATURE:
<223> OTHER INFORMATION: VT008-AL5-10K7 antibody; light chain; CDR1-
      Kabat

<400> SEQUENCE: 7
```

Lys Ala Ser Gln Asp Val Ser Gly Ala Val Val
1               5                   10

<210> SEQ ID NO 8
<211> LENGTH: 7
<212> TYPE: PRT
<213> ORGANISM: Artificial sequence
<220> FEATURE:
<223> OTHER INFORMATION: VT008-AL5-10K7 antibody; light chain; CDR2-
      Kabat

<400> SEQUENCE: 8

Leu Ala Thr Tyr Arg Tyr Thr
1               5

<210> SEQ ID NO 9
<211> LENGTH: 9
<212> TYPE: PRT
<213> ORGANISM: Artificial sequence
<220> FEATURE:
<223> OTHER INFORMATION: VT008-AL5-10K7 antibody; light chain; CDR3-
      Kabat

<400> SEQUENCE: 9

Gln Gln Tyr Tyr Ser Ile Pro Trp Thr
1               5

<210> SEQ ID NO 10
<211> LENGTH: 6
<212> TYPE: PRT
<213> ORGANISM: Artificial sequence
<220> FEATURE:
<223> OTHER INFORMATION: VT008-AL5-10K7 antibody; light chain; CDR1-IMGT

<400> SEQUENCE: 10

Gln Asp Val Ser Gly Ala
1               5

<210> SEQ ID NO 11
<211> LENGTH: 4
<212> TYPE: PRT
<213> ORGANISM: Artificial sequence
<220> FEATURE:
<223> OTHER INFORMATION: VT008-AL5-10K7 antibody; light chain; CDR2-IMGT

<400> SEQUENCE: 11

Leu Ala Thr Tyr
1

<210> SEQ ID NO 12
<211> LENGTH: 9
<212> TYPE: PRT
<213> ORGANISM: Artificial sequence
<220> FEATURE:
<223> OTHER INFORMATION: VT008-AL5-10K7 antibody; light chain; CDR3-IMGT

<400> SEQUENCE: 12

Gln Gln Tyr Tyr Ser Ile Pro Trp Thr
1               5

<210> SEQ ID NO 13
<211> LENGTH: 5
<212> TYPE: PRT
<213> ORGANISM: Artificial sequence
<220> FEATURE:
<223> OTHER INFORMATION: VT008-AL6-14G1 antibody; heavy chain; CDR1-
      Kabat

```
<400> SEQUENCE: 13

Asn Tyr Trp Met Tyr
1               5

<210> SEQ ID NO 14
<211> LENGTH: 17
<212> TYPE: PRT
<213> ORGANISM: Artificial sequence
<220> FEATURE:
<223> OTHER INFORMATION: VT008-AL6-14G1 antibody; heavy chain; CDR2-
      Kabat

<400> SEQUENCE: 14

Trp Ile Asp Pro Asn Ser Gly Gly Thr Lys Tyr Asn Glu Lys Phe Lys
1               5                   10                  15

Ser

<210> SEQ ID NO 15
<211> LENGTH: 7
<212> TYPE: PRT
<213> ORGANISM: Artificial sequence
<220> FEATURE:
<223> OTHER INFORMATION: VT008-AL6-14G1 antibody; heavy chain; CDR3-
      Kabat

<400> SEQUENCE: 15

Gly Gly Tyr Thr Met Asp Tyr
1               5

<210> SEQ ID NO 16
<211> LENGTH: 8
<212> TYPE: PRT
<213> ORGANISM: Artificial sequence
<220> FEATURE:
<223> OTHER INFORMATION: VT008-AL6-14G1 antibody; heavy chain; CDR1-IMGT

<400> SEQUENCE: 16

Gly Tyr Thr Phe Thr Asn Tyr Trp
1               5

<210> SEQ ID NO 17
<211> LENGTH: 8
<212> TYPE: PRT
<213> ORGANISM: Artificial sequence
<220> FEATURE:
<223> OTHER INFORMATION: VT008-AL6-14G1 antibody; heavy chain; CDR2-IMGT

<400> SEQUENCE: 17

Ile Asp Pro Asn Ser Gly Gly Thr
1               5

<210> SEQ ID NO 18
<211> LENGTH: 9
<212> TYPE: PRT
<213> ORGANISM: Artificial sequence
<220> FEATURE:
<223> OTHER INFORMATION: VT008-AL6-14G1 antibody; heavy chain; CDR3-IMGT

<400> SEQUENCE: 18

Ala Arg Gly Gly Tyr Thr Met Asp Tyr
1               5

<210> SEQ ID NO 19
<211> LENGTH: 16
<212> TYPE: PRT
<213> ORGANISM: Artificial sequence
```

```
<220> FEATURE:
<223> OTHER INFORMATION: VT008-AL6-16K1antibody; light chain; CDR1-Kabat

<400> SEQUENCE: 19

Arg Ala Ser Gln Ser Leu Val His Ser Asn Gly Asn Thr Tyr Leu His
1               5                   10                  15

<210> SEQ ID NO 20
<211> LENGTH: 7
<212> TYPE: PRT
<213> ORGANISM: Artificial sequence
<220> FEATURE:
<223> OTHER INFORMATION: VT008-AL6-16K1 antibody; light chain; CDR2-
      Kabat

<400> SEQUENCE: 20

Lys Val Ser Asn Arg Phe Ser
1               5

<210> SEQ ID NO 21
<211> LENGTH: 9
<212> TYPE: PRT
<213> ORGANISM: Artificial sequence
<220> FEATURE:
<223> OTHER INFORMATION: VT008-AL6-16K1 antibody; light chain; CDR3-
      Kabat

<400> SEQUENCE: 21

Ser Gln Ser Thr His Val Pro Leu Thr
1               5

<210> SEQ ID NO 22
<211> LENGTH: 11
<212> TYPE: PRT
<213> ORGANISM: Artificial sequence
<220> FEATURE:
<223> OTHER INFORMATION: VT008-AL6-16K1 antibody; light chain; CDR1-IMGT

<400> SEQUENCE: 22

Gln Ser Leu Val His Ser Asn Gly Asn Thr Tyr
1               5                   10

<210> SEQ ID NO 23
<211> LENGTH: 4
<212> TYPE: PRT
<213> ORGANISM: Artificial sequence
<220> FEATURE:
<223> OTHER INFORMATION: VT008-AL6-16K1 antibody; light chain; CDR2-IMGT

<400> SEQUENCE: 23

Lys Val Ser Asn
1

<210> SEQ ID NO 24
<211> LENGTH: 9
<212> TYPE: PRT
<213> ORGANISM: Artificial sequence
<220> FEATURE:
<223> OTHER INFORMATION: VT008-AL6-16K1 antibody; light chain; CDR3-IMGT

<400> SEQUENCE: 24

Ser Gln Ser Thr His Val Pro Leu Thr
1               5

<210> SEQ ID NO 25
<211> LENGTH: 5
<212> TYPE: PRT
```

```
<213> ORGANISM: Artificial sequence
<220> FEATURE:
<223> OTHER INFORMATION: VT008-AL6-18G1 antibody; heavy chain; CDR1-
      Kabat

<400> SEQUENCE: 25

Asn Tyr Trp Ile His
1               5

<210> SEQ ID NO 26
<211> LENGTH: 17
<212> TYPE: PRT
<213> ORGANISM: Artificial sequence
<220> FEATURE:
<223> OTHER INFORMATION: VT008-AL6-18G1 antibody; heavy chain; CDR2-
      Kabat

<400> SEQUENCE: 26

Arg Ile Asp Pro Asn Thr Val Asp Ala Lys Tyr Asn Glu Lys Phe Lys
1               5                   10                  15

Ser

<210> SEQ ID NO 27
<211> LENGTH: 7
<212> TYPE: PRT
<213> ORGANISM: Artificial sequence
<220> FEATURE:
<223> OTHER INFORMATION: VT008-AL6-18G1 antibody; heavy chain; CDR3-
      Kabat

<400> SEQUENCE: 27

Gly Gly Tyr Thr Met Asp Tyr
1               5

<210> SEQ ID NO 28
<211> LENGTH: 8
<212> TYPE: PRT
<213> ORGANISM: Artificial sequence
<220> FEATURE:
<223> OTHER INFORMATION: VT008-AL6-18G1 antibody; heavy chain; CDR1-IMGT

<400> SEQUENCE: 28

Gly Tyr Thr Phe Ile Asn Tyr Trp
1               5

<210> SEQ ID NO 29
<211> LENGTH: 8
<212> TYPE: PRT
<213> ORGANISM: Artificial sequence
<220> FEATURE:
<223> OTHER INFORMATION: VT008-AL6-18G1antibody; heavy chain; CDR2-IMGT

<400> SEQUENCE: 29

Ile Asp Pro Asn Thr Val Asp Ala
1               5

<210> SEQ ID NO 30
<211> LENGTH: 9
<212> TYPE: PRT
<213> ORGANISM: Artificial sequence
<220> FEATURE:
<223> OTHER INFORMATION: VT008-AL6-18G1 antibody; heavy chain; CDR3-IMGT

<400> SEQUENCE: 30

Ser Arg Gly Gly Tyr Thr Met Asp Tyr
1               5
```

<210> SEQ ID NO 31
<211> LENGTH: 7
<212> TYPE: PRT
<213> ORGANISM: Artificial sequence
<220> FEATURE:
<223> OTHER INFORMATION: VT008-AL6-18K21 antibody; light chain; CDR1-
      Kabat

<400> SEQUENCE: 31

Lys Val Ser Asn Arg Phe Ser
1               5

<210> SEQ ID NO 32
<211> LENGTH: 7
<212> TYPE: PRT
<213> ORGANISM: Artificial sequence
<220> FEATURE:
<223> OTHER INFORMATION: VT008-AL6-18K21 antibody; light chain; CDR2-
      Kabat

<400> SEQUENCE: 32

Lys Val Ser Asn Arg Phe Ser
1               5

<210> SEQ ID NO 33
<211> LENGTH: 9
<212> TYPE: PRT
<213> ORGANISM: Artificial sequence
<220> FEATURE:
<223> OTHER INFORMATION: VT008-AL6-18K21 antibody; light chain; CDR3-
      Kabat

<400> SEQUENCE: 33

Phe Gln Ser Thr His Val Pro Trp Thr
1               5

<210> SEQ ID NO 34
<211> LENGTH: 11
<212> TYPE: PRT
<213> ORGANISM: Artificial sequence
<220> FEATURE:
<223> OTHER INFORMATION: VT008-AL6-18K21 antibody; light chain; CDR1-
      IMGT

<400> SEQUENCE: 34

Gln Ser Leu Val His Ser Asn Gly Asn Thr Tyr
1               5                   10

<210> SEQ ID NO 35
<211> LENGTH: 4
<212> TYPE: PRT
<213> ORGANISM: Artificial sequence
<220> FEATURE:
<223> OTHER INFORMATION: VT008-AL6-18K21 antibody; light chain; CDR2-
      IMGT

<400> SEQUENCE: 35

Lys Val Ser Asn
1

<210> SEQ ID NO 36
<211> LENGTH: 9
<212> TYPE: PRT
<213> ORGANISM: Artificial sequence
<220> FEATURE:
<223> OTHER INFORMATION: VL008-AL6-18K21 antibody; light chain; CDR3-
      IMGT

```
<400> SEQUENCE: 36

Phe Gln Ser Thr His Val Pro Trp Thr
1               5

<210> SEQ ID NO 37
<211> LENGTH: 5
<212> TYPE: PRT
<213> ORGANISM: Artificial sequence
<220> FEATURE:
<223> OTHER INFORMATION: VL008-AL17-7G1 antibody; heavy chain; CDR1-
      Kabat

<400> SEQUENCE: 37

Asp Tyr Tyr Ile Asn
1               5

<210> SEQ ID NO 38
<211> LENGTH: 17
<212> TYPE: PRT
<213> ORGANISM: Artificial sequence
<220> FEATURE:
<223> OTHER INFORMATION: VL008-AL17-7G1 antibody; heavy chain; CDR2-
      Kabat

<400> SEQUENCE: 38

Trp Ile Phe Pro Gly Ser Gly Leu Thr Tyr Tyr Asn Lys Lys Phe Lys
1               5                   10                  15
Gly

<210> SEQ ID NO 39
<211> LENGTH: 13
<212> TYPE: PRT
<213> ORGANISM: Artificial sequence
<220> FEATURE:
<223> OTHER INFORMATION: VL008-AL17-7G1 antibody; heavy chain; CDR3-
      Kabat

<400> SEQUENCE: 39

Pro Tyr Tyr Gly Ser Arg Trp Asp Tyr Ala Met Asp Tyr
1               5                   10

<210> SEQ ID NO 40
<211> LENGTH: 8
<212> TYPE: PRT
<213> ORGANISM: Artificial sequence
<220> FEATURE:
<223> OTHER INFORMATION: VL008-AL17-7G1 antibody; heavy chain; CDR1-IMGT

<400> SEQUENCE: 40

Val Tyr Thr Phe Thr Asp Tyr Tyr
1               5

<210> SEQ ID NO 41
<211> LENGTH: 8
<212> TYPE: PRT
<213> ORGANISM: Artificial sequence
<220> FEATURE:
<223> OTHER INFORMATION: VL008-AL17-7G1 antibody; heavy chain; CDR2-IMGT

<400> SEQUENCE: 41

Ile Phe Pro Gly Ser Gly Leu Thr
1               5

<210> SEQ ID NO 42
<211> LENGTH: 15
<212> TYPE: PRT
```

```
<213> ORGANISM: Artificial sequence
<220> FEATURE:
<223> OTHER INFORMATION: VL008-AL17-7G1 antibody; heavy chain; CDR3-IMGT

<400> SEQUENCE: 42

Ala Arg Pro Tyr Tyr Gly Ser Arg Trp Asp Tyr Ala Met Asp Tyr
1               5                   10                  15

<210> SEQ ID NO 43
<211> LENGTH: 17
<212> TYPE: PRT
<213> ORGANISM: Artificial sequence
<220> FEATURE:
<223> OTHER INFORMATION: VL008-AL17-7K6 antibody; light chain; CDR1-
      Kabat

<400> SEQUENCE: 43

Lys Ser Ser Gln Ser Leu Leu Asn Ser Asn Asn Gln Lys Asn Tyr Leu
1               5                   10                  15

Ala

<210> SEQ ID NO 44
<211> LENGTH: 7
<212> TYPE: PRT
<213> ORGANISM: Artificial sequence
<220> FEATURE:
<223> OTHER INFORMATION: VL008-AL17-7K6 antibody; light chain; CDR2-
      Kabat

<400> SEQUENCE: 44

Phe Ala Ser Thr Arg Glu Ser
1               5

<210> SEQ ID NO 45
<211> LENGTH: 9
<212> TYPE: PRT
<213> ORGANISM: Artificial sequence
<220> FEATURE:
<223> OTHER INFORMATION: VL008-AL17-7K6 antibody; light chain; CDR3-
      Kabat

<400> SEQUENCE: 45

Gln Gln His Tyr Thr Thr Pro Tyr Thr
1               5

<210> SEQ ID NO 46
<211> LENGTH: 12
<212> TYPE: PRT
<213> ORGANISM: Artificial sequence
<220> FEATURE:
<223> OTHER INFORMATION: VL008-AL17-7K6 antibody; light chain; CDR1-IMGT

<400> SEQUENCE: 46

Gln Ser Leu Leu Asn Ser Asn Asn Gln Lys Asn Tyr
1               5                   10

<210> SEQ ID NO 47
<211> LENGTH: 4
<212> TYPE: PRT
<213> ORGANISM: Artificial sequence
<220> FEATURE:
<223> OTHER INFORMATION: VL008-AL17-7K6 antibody; light chain; CDR2-IMGT

<400> SEQUENCE: 47

Phe Ala Ser Thr
1
```

```
<210> SEQ ID NO 48
<211> LENGTH: 9
<212> TYPE: PRT
<213> ORGANISM: Artificial sequence
<220> FEATURE:
<223> OTHER INFORMATION: VL008-AL17-7K6 antibody; light chain; CDR3-IMGT

<400> SEQUENCE: 48

Gln Gln His Tyr Thr Thr Pro Tyr Thr
1               5

<210> SEQ ID NO 49
<211> LENGTH: 5
<212> TYPE: PRT
<213> ORGANISM: Artificial sequence
<220> FEATURE:
<223> OTHER INFORMATION: VL008-AL18-14G4 antibody; heavy chain; CDR1-
      Kabat

<400> SEQUENCE: 49

Asp Tyr Tyr Ile Asn
1               5

<210> SEQ ID NO 50
<211> LENGTH: 17
<212> TYPE: PRT
<213> ORGANISM: Artificial sequence
<220> FEATURE:
<223> OTHER INFORMATION: VL008-AL18-14G4 antibody; heavy chain; CDR2-
      Kabat

<400> SEQUENCE: 50

Arg Ile Tyr Pro Gly Ile Gly Asn Thr Tyr Tyr Asn Lys Lys Phe Lys
1               5                   10                  15

Gly

<210> SEQ ID NO 51
<211> LENGTH: 9
<212> TYPE: PRT
<213> ORGANISM: Artificial sequence
<220> FEATURE:
<223> OTHER INFORMATION: VL008-AL18-14G4 antibody; heavy chain; CDR3-
      Kabat

<400> SEQUENCE: 51

Gly His Tyr Gly Arg Gly Met Asp Tyr
1               5

<210> SEQ ID NO 52
<211> LENGTH: 8
<212> TYPE: PRT
<213> ORGANISM: Artificial sequence
<220> FEATURE:
<223> OTHER INFORMATION: VL008-AL18-14G4 antibody; heavy chain; CDR1-
      IMGT

<400> SEQUENCE: 52

Gly Tyr Ser Phe Thr Asp Tyr Tyr
1               5

<210> SEQ ID NO 53
<211> LENGTH: 8
<212> TYPE: PRT
<213> ORGANISM: Artificial sequence
<220> FEATURE:
<223> OTHER INFORMATION: VL008-AL18-14G4 antibody; heavy chain; CDR2-
      IMGT
```

<400> SEQUENCE: 53

Ile Tyr Pro Gly Ile Gly Asn Thr
1               5

<210> SEQ ID NO 54
<211> LENGTH: 11
<212> TYPE: PRT
<213> ORGANISM: Artificial sequence
<220> FEATURE:
<223> OTHER INFORMATION: VL008-AL18-14G4 antibody; heavy chain; CDR3-
      IMGT

<400> SEQUENCE: 54

Ala Arg Gly His Tyr Gly Arg Gly Met Asp Tyr
1               5                   10

<210> SEQ ID NO 55
<211> LENGTH: 17
<212> TYPE: PRT
<213> ORGANISM: Artificial sequence
<220> FEATURE:
<223> OTHER INFORMATION: VL008-AL18-14K1 antibody; light chain; CDR1-
      Kabat

<400> SEQUENCE: 55

Lys Ser Ser Gln Ser Leu Leu Asn Ser Ile Asp Gln Lys Asn Tyr Leu
1               5                   10                  15
Ala

<210> SEQ ID NO 56
<211> LENGTH: 7
<212> TYPE: PRT
<213> ORGANISM: Artificial sequence
<220> FEATURE:
<223> OTHER INFORMATION: VL008-AL18-14K1 antibody; light chain; CDR2-
      Kabat

<400> SEQUENCE: 56

Phe Ala Ser Thr Lys Glu Ser
1               5

<210> SEQ ID NO 57
<211> LENGTH: 9
<212> TYPE: PRT
<213> ORGANISM: Artificial sequence
<220> FEATURE:
<223> OTHER INFORMATION: VL008-AL18-14K1 antibody; light chain; CDR3-
      Kabat

<400> SEQUENCE: 57

Gln Gln His Tyr Ser Thr Pro Trp Thr
1               5

<210> SEQ ID NO 58
<211> LENGTH: 12
<212> TYPE: PRT
<213> ORGANISM: Artificial sequence
<220> FEATURE:
<223> OTHER INFORMATION: VL008-AL18-14K1 antibody; light chain; CDR1-
      IMGT

<400> SEQUENCE: 58

Gln Ser Leu Leu Asn Ser Ile Asp Gln Lys Asn Tyr
1               5                   10

<210> SEQ ID NO 59
<211> LENGTH: 4
<212> TYPE: PRT
<213> ORGANISM: Artificial sequence
<220> FEATURE:
<223> OTHER INFORMATION: VL008-AL18-14K1 antibody; light chain; CDR2-
      IMGT

<400> SEQUENCE: 59

Phe Ala Ser Thr
1

<210> SEQ ID NO 60
<211> LENGTH: 9
<212> TYPE: PRT
<213> ORGANISM: Artificial sequence
<220> FEATURE:
<223> OTHER INFORMATION: VL008-AL18-14K1 antibody; light chain; CDR3-
      IMGT

<400> SEQUENCE: 60

Gln Gln His Tyr Ser Thr Pro Trp Thr
1               5

<210> SEQ ID NO 61
<211> LENGTH: 5
<212> TYPE: PRT
<213> ORGANISM: Artificial sequence
<220> FEATURE:
<223> OTHER INFORMATION: VL008-AL13-8G5 antibody; heavy chain; CDR1-
      Kabat

<400> SEQUENCE: 61

Thr Tyr Trp Met His
1               5

<210> SEQ ID NO 62
<211> LENGTH: 17
<212> TYPE: PRT
<213> ORGANISM: Artificial sequence
<220> FEATURE:
<223> OTHER INFORMATION: VL008-AL13-8G5 antibody; heavy chain; CDR2-
      Kabat

<400> SEQUENCE: 62

Met Ile His Pro Asn Ser Gly Thr Thr Asn Tyr Asn Glu Lys Phe Lys
1               5                   10                  15

Ser

<210> SEQ ID NO 63
<211> LENGTH: 10
<212> TYPE: PRT
<213> ORGANISM: Artificial sequence
<220> FEATURE:
<223> OTHER INFORMATION: VL008-AL13-8G5 antibody; heavy chain; CDR3-
      Kabat

<400> SEQUENCE: 63

Ser His Tyr Tyr Asp Gly His Phe Ser Tyr
1               5                   10

<210> SEQ ID NO 64
<211> LENGTH: 8
<212> TYPE: PRT
<213> ORGANISM: Artificial sequence
<220> FEATURE:
<223> OTHER INFORMATION: VL008-AL13-8G5 antibody; heavy chain; CDR1-IMGT

```
<400> SEQUENCE: 64

Gly Tyr Thr Phe Thr Thr Tyr Trp
1               5

<210> SEQ ID NO 65
<211> LENGTH: 8
<212> TYPE: PRT
<213> ORGANISM: Artificial sequence
<220> FEATURE:
<223> OTHER INFORMATION: VL008-AL13-8G5 antibody; heavy chain; CDR2-IMGT

<400> SEQUENCE: 65

Ile His Pro Asn Ser Gly Thr Thr
1               5

<210> SEQ ID NO 66
<211> LENGTH: 12
<212> TYPE: PRT
<213> ORGANISM: Artificial sequence
<220> FEATURE:
<223> OTHER INFORMATION: VL008-AL13-8G5 antibody; heavy chain; CDR3-IMGT

<400> SEQUENCE: 66

Thr Arg Ser His Tyr Tyr Asp Gly His Phe Ser Tyr
1               5                   10

<210> SEQ ID NO 67
<211> LENGTH: 17
<212> TYPE: PRT
<213> ORGANISM: Artificial sequence
<220> FEATURE:
<223> OTHER INFORMATION: VL008-AL13-8K3 antibody; light chain; CDR1-
      Kabat

<400> SEQUENCE: 67

Lys Ser Ser Gln Ser Leu Leu Asn Ser Arg Thr Arg Lys Asn Tyr Leu
1               5                   10                  15
Ala

<210> SEQ ID NO 68
<211> LENGTH: 7
<212> TYPE: PRT
<213> ORGANISM: Artificial sequence
<220> FEATURE:
<223> OTHER INFORMATION: VL008-AL13-8K3 antibody; light chain; CDR2-
      Kabat

<400> SEQUENCE: 68

Trp Ala Ser Thr Arg Glu Ser
1               5

<210> SEQ ID NO 69
<211> LENGTH: 8
<212> TYPE: PRT
<213> ORGANISM: Artificial sequence
<220> FEATURE:
<223> OTHER INFORMATION: VL008-AL13-8K3 antibody; light chain; CDR3-
      Kabat

<400> SEQUENCE: 69

Lys Gln Ser Tyr Asn Leu Trp Thr
1               5

<210> SEQ ID NO 70
<211> LENGTH: 12
<212> TYPE: PRT
```

```
<213> ORGANISM: Artificial sequence
<220> FEATURE:
<223> OTHER INFORMATION: VL008-AL13-8K3 antibody; light chain; CDR1-IMGT

<400> SEQUENCE: 70

Gln Ser Leu Leu Asn Ser Arg Thr Arg Lys Asn Tyr
1               5                   10

<210> SEQ ID NO 71
<211> LENGTH: 4
<212> TYPE: PRT
<213> ORGANISM: Artificial sequence
<220> FEATURE:
<223> OTHER INFORMATION: VL008-AL13-8K3 antibody; light chain; CDR2-IMGT

<400> SEQUENCE: 71

Trp Ala Ser Thr
1

<210> SEQ ID NO 72
<211> LENGTH: 8
<212> TYPE: PRT
<213> ORGANISM: Artificial sequence
<220> FEATURE:
<223> OTHER INFORMATION: VL008-AL13-8K3 antibody; light chain; CDR3-IMGT

<400> SEQUENCE: 72

Lys Gln Ser Tyr Asn Leu Trp Thr
1               5

<210> SEQ ID NO 73
<211> LENGTH: 5
<212> TYPE: PRT
<213> ORGANISM: Artificial sequence
<220> FEATURE:
<223> OTHER INFORMATION: VT008-AL6-10G3 antibody; heavy chain; CDR1-
      Kabat

<400> SEQUENCE: 73

Asn Tyr Trp Ile His
1               5

<210> SEQ ID NO 74
<211> LENGTH: 17
<212> TYPE: PRT
<213> ORGANISM: Artificial sequence
<220> FEATURE:
<223> OTHER INFORMATION: VT008-AL6-10G3 antibody; heavy chain; CDR2-
      Kabat

<400> SEQUENCE: 74

Arg Ile Asp Pro Asn Ser Gly Gly Thr Lys Tyr Asn Glu Lys Phe Lys
1               5                   10                  15

Ser

<210> SEQ ID NO 75
<211> LENGTH: 7
<212> TYPE: PRT
<213> ORGANISM: Artificial sequence
<220> FEATURE:
<223> OTHER INFORMATION: VT008-AL6-10G3 antibody; heavy chain; CDR3-
      Kabat

<400> SEQUENCE: 75

Gly Gly Tyr Thr Met Asp Tyr
1               5
```

```
<210> SEQ ID NO 76
<211> LENGTH: 8
<212> TYPE: PRT
<213> ORGANISM: Artificial sequence
<220> FEATURE:
<223> OTHER INFORMATION: VT008-AL6-10G3 antibody; heavy chain; CDR1-IMGT

<400> SEQUENCE: 76

Gly Tyr Thr Phe Thr Asn Tyr Trp
1               5

<210> SEQ ID NO 77
<211> LENGTH: 8
<212> TYPE: PRT
<213> ORGANISM: Artificial sequence
<220> FEATURE:
<223> OTHER INFORMATION: VT008-AL6-10G3 antibody; heavy chain; CDR2-IMGT

<400> SEQUENCE: 77

Ile Asp Pro Asn Ser Gly Gly Thr
1               5

<210> SEQ ID NO 78
<211> LENGTH: 9
<212> TYPE: PRT
<213> ORGANISM: Artificial sequence
<220> FEATURE:
<223> OTHER INFORMATION: VT008-AL6-10G3 antibody; heavy chain; CDR3-IMGT

<400> SEQUENCE: 78

Ala Arg Gly Gly Tyr Thr Met Asp Tyr
1               5

<210> SEQ ID NO 79
<211> LENGTH: 16
<212> TYPE: PRT
<213> ORGANISM: Artificial sequence
<220> FEATURE:
<223> OTHER INFORMATION: VT008-AL6-10K1 antibody; light chain; CDR1-
      Kabat

<400> SEQUENCE: 79

Arg Ser Ser Gln Ser Leu Leu His Ser Asn Gly Asn Thr Tyr Leu His
1               5                   10                  15

<210> SEQ ID NO 80
<211> LENGTH: 7
<212> TYPE: PRT
<213> ORGANISM: Artificial sequence
<220> FEATURE:
<223> OTHER INFORMATION: VT008-AL6-10K1 antibody; light chain; CDR2-
      Kabat

<400> SEQUENCE: 80

Lys Val Ser Tyr Arg Phe Ser
1               5

<210> SEQ ID NO 81
<211> LENGTH: 9
<212> TYPE: PRT
<213> ORGANISM: Artificial sequence
<220> FEATURE:
<223> OTHER INFORMATION: VT008-AL6-10K1 antibody; light chain; CDR3-
      Kabat

<400> SEQUENCE: 81

Phe Gln Ser Thr His Val Pro Trp Thr
```

<210> SEQ ID NO 82
<211> LENGTH: 12
<212> TYPE: PRT
<213> ORGANISM: Artificial sequence
<220> FEATURE:
<223> OTHER INFORMATION: VT008-AL6-10K1 antibody; light chain; CDR1-IMGT

<400> SEQUENCE: 82

Gln Ser Leu Leu His Ser Asn Gly Asn Thr Tyr Val
1               5                   10

<210> SEQ ID NO 83
<211> LENGTH: 4
<212> TYPE: PRT
<213> ORGANISM: Artificial sequence
<220> FEATURE:
<223> OTHER INFORMATION: VT008-AL6-10K1 antibody; light chain; CDR2-IMGT

<400> SEQUENCE: 83

Lys Val Ser Tyr
1

<210> SEQ ID NO 84
<211> LENGTH: 9
<212> TYPE: PRT
<213> ORGANISM: Artificial sequence
<220> FEATURE:
<223> OTHER INFORMATION: VT008-AL6-10K1 antibody; light chain; CDR3-IMGT

<400> SEQUENCE: 84

Phe Gln Ser Thr His Val Pro Trp Thr
1               5

<210> SEQ ID NO 85
<211> LENGTH: 5
<212> TYPE: PRT
<213> ORGANISM: Artificial sequence
<220> FEATURE:
<223> OTHER INFORMATION: VT008-AL6-20G7 antibody; heavy chain; CDR1-
      Kabat

<400> SEQUENCE: 85

Asn Tyr Trp Ile Tyr
1               5

<210> SEQ ID NO 86
<211> LENGTH: 17
<212> TYPE: PRT
<213> ORGANISM: Artificial sequence
<220> FEATURE:
<223> OTHER INFORMATION: VT008-AL6-20G7 antibody; heavy chain; CDR2-
      Kabat

<400> SEQUENCE: 86

Tyr Ile Asn Pro Arg Ser Asp Asp Thr Lys Tyr Asn Gln Lys Phe Arg
1               5                   10                  15

Asp

<210> SEQ ID NO 87
<211> LENGTH: 7
<212> TYPE: PRT
<213> ORGANISM: Artificial sequence
<220> FEATURE:
<223> OTHER INFORMATION: VT008-AL6-20G7 antibody; heavy chain; CDR3-
      Kabat

```
<400> SEQUENCE: 87

Gly Gly Phe Thr Met Asp Phe
1               5

<210> SEQ ID NO 88
<211> LENGTH: 8
<212> TYPE: PRT
<213> ORGANISM: Artificial sequence
<220> FEATURE:
<223> OTHER INFORMATION: VT008-AL6-20G7 antibody; heavy chain; CDR1-IMGT

<400> SEQUENCE: 88

Gly Tyr Thr Phe Ile Asn Tyr Trp
1               5

<210> SEQ ID NO 89
<211> LENGTH: 8
<212> TYPE: PRT
<213> ORGANISM: Artificial sequence
<220> FEATURE:
<223> OTHER INFORMATION: VT008-AL6-20G7 antibody; heavy chain; CDR2-IMGT

<400> SEQUENCE: 89

Ile Asn Pro Arg Ser Asp Asp Thr
1               5

<210> SEQ ID NO 90
<211> LENGTH: 9
<212> TYPE: PRT
<213> ORGANISM: Artificial sequence
<220> FEATURE:
<223> OTHER INFORMATION: VT008-AL6-20G7 antibody; heavy chain; CDR3-IMGT

<400> SEQUENCE: 90

Ala Arg Gly Gly Phe Thr Met Asp Phe
1               5

<210> SEQ ID NO 91
<211> LENGTH: 16
<212> TYPE: PRT
<213> ORGANISM: Artificial sequence
<220> FEATURE:
<223> OTHER INFORMATION: VT008-AL6-20K7 antibody; light chain; CDR1-
      Kabat

<400> SEQUENCE: 91

Arg Ser Ser Gln Ser Leu Leu His Ser Asn Gly Asn Thr Tyr Leu His
1               5                   10                  15

<210> SEQ ID NO 92
<211> LENGTH: 7
<212> TYPE: PRT
<213> ORGANISM: Artificial sequence
<220> FEATURE:
<223> OTHER INFORMATION: VT008-AL6-20K7 antibody; light chain; CDR2-
      Kabat

<400> SEQUENCE: 92

Lys Val Ser Tyr Arg Phe Ser
1               5

<210> SEQ ID NO 93
<211> LENGTH: 9
<212> TYPE: PRT
<213> ORGANISM: Artificial sequence
<220> FEATURE:
```

<223> OTHER INFORMATION: VT008-AL6-20K7 antibody; light chain; CDR3-
      Kabat

<400> SEQUENCE: 93

Ser Gln Gly Thr His Val Pro Tyr Thr
1               5

<210> SEQ ID NO 94
<211> LENGTH: 11
<212> TYPE: PRT
<213> ORGANISM: Artificial sequence
<220> FEATURE:
<223> OTHER INFORMATION: VT008-AL6-20K7 antibody; light chain; CDR1-IMGT

<400> SEQUENCE: 94

Gln Ser Leu Leu His Ser Asn Gly Asn Thr Tyr
1               5                   10

<210> SEQ ID NO 95
<211> LENGTH: 4
<212> TYPE: PRT
<213> ORGANISM: Artificial sequence
<220> FEATURE:
<223> OTHER INFORMATION: VT008-AL6-20K7 antibody; light chain; CDR2-IMGT

<400> SEQUENCE: 95

Lys Val Ser Tyr
1

<210> SEQ ID NO 96
<211> LENGTH: 9
<212> TYPE: PRT
<213> ORGANISM: Artificial sequence
<220> FEATURE:
<223> OTHER INFORMATION: VT008-AL6-20K7 antibody; light chain; CDR3-IMGT

<400> SEQUENCE: 96

Ser Gln Gly Thr His Val Pro Tyr Thr
1               5

<210> SEQ ID NO 97
<211> LENGTH: 5
<212> TYPE: PRT
<213> ORGANISM: Artificial sequence
<220> FEATURE:
<223> OTHER INFORMATION: VT008-AL6-39G2 antibody; heavy chain; CDR1-
      Kabat

<400> SEQUENCE: 97

Gly Tyr Asn Ile Tyr
1               5

<210> SEQ ID NO 98
<211> LENGTH: 17
<212> TYPE: PRT
<213> ORGANISM: Artificial sequence
<220> FEATURE:
<223> OTHER INFORMATION: VT008-AL6-39G2 antibody; heavy chain; CDR2-
      Kabat

<400> SEQUENCE: 98

Tyr Ile Tyr Pro Tyr Asn Gly Ile Ser Ser Tyr Asn Gln Lys Phe Lys
1               5                   10                  15

Asp

<210> SEQ ID NO 99

```
<211> LENGTH: 7
<212> TYPE: PRT
<213> ORGANISM: Artificial sequence
<220> FEATURE:
<223> OTHER INFORMATION: VT008-AL6-39G2 antibody; heavy chain; CDR3-
      Kabat

<400> SEQUENCE: 99

Gly Gly Tyr Thr Met Asp Tyr
1               5

<210> SEQ ID NO 100
<211> LENGTH: 8
<212> TYPE: PRT
<213> ORGANISM: Artificial sequence
<220> FEATURE:
<223> OTHER INFORMATION: VT008-AL6-39G2 antibody; heavy chain; CDR1-IMGT

<400> SEQUENCE: 100

Gly Tyr Ser Phe Thr Gly Tyr Asn
1               5

<210> SEQ ID NO 101
<211> LENGTH: 8
<212> TYPE: PRT
<213> ORGANISM: Artificial sequence
<220> FEATURE:
<223> OTHER INFORMATION: VT008-AL6-39G2 antibody; heavy chain; CDR2-IMGT

<400> SEQUENCE: 101

Ile Tyr Pro Tyr Asn Gly Ile Ser
1               5

<210> SEQ ID NO 102
<211> LENGTH: 9
<212> TYPE: PRT
<213> ORGANISM: Artificial sequence
<220> FEATURE:
<223> OTHER INFORMATION: VT008-AL6-39G2 antibody; heavy chain; CDR3-IMGT

<400> SEQUENCE: 102

Ala Arg Gly Gly Tyr Thr Met Asp Tyr
1               5

<210> SEQ ID NO 103
<211> LENGTH: 16
<212> TYPE: PRT
<213> ORGANISM: Artificial sequence
<220> FEATURE:
<223> OTHER INFORMATION: VT008-AL6-39K2 antibody; light chain; CDR1-
      Kabat

<400> SEQUENCE: 103

Arg Ser Ser Gln Ser Leu Val Lys Ser Asn Gly Asn Thr Tyr Leu His
1               5                   10                  15

<210> SEQ ID NO 104
<211> LENGTH: 7
<212> TYPE: PRT
<213> ORGANISM: Artificial sequence
<220> FEATURE:
<223> OTHER INFORMATION: VT008-AL6-39K2 antibody; light chain; CDR2-
      Kabat

<400> SEQUENCE: 104

Lys Val Ser Asn Arg Phe Ser
1               5
```

<210> SEQ ID NO 105
<211> LENGTH: 9
<212> TYPE: PRT
<213> ORGANISM: Artificial sequence
<220> FEATURE:
<223> OTHER INFORMATION: VT008-AL6-39K2 antibody; light chain; CDR3-
      Kabat

<400> SEQUENCE: 105

Ser Gln Thr Thr His Val Pro Tyr Thr
1               5

<210> SEQ ID NO 106
<211> LENGTH: 11
<212> TYPE: PRT
<213> ORGANISM: Artificial sequence
<220> FEATURE:
<223> OTHER INFORMATION: VT008-AL6-39K2 antibody; light chain; CDR1-IMGT

<400> SEQUENCE: 106

Gln Ser Leu Val Lys Ser Asn Gly Asn Thr Tyr
1               5                   10

<210> SEQ ID NO 107
<211> LENGTH: 4
<212> TYPE: PRT
<213> ORGANISM: Artificial sequence
<220> FEATURE:
<223> OTHER INFORMATION: VT008-AL6-39K2 antibody; light chain; CDR2-IMGT

<400> SEQUENCE: 107

Lys Val Ser Asn
1

<210> SEQ ID NO 108
<211> LENGTH: 9
<212> TYPE: PRT
<213> ORGANISM: Artificial sequence
<220> FEATURE:
<223> OTHER INFORMATION: VT008-AL6-39K2 antibody; light chain; CDR3-IMGT

<400> SEQUENCE: 108

Ser Gln Thr Thr His Val Pro Tyr Thr
1               5

<210> SEQ ID NO 109
<211> LENGTH: 5
<212> TYPE: PRT
<213> ORGANISM: Artificial sequence
<220> FEATURE:
<223> OTHER INFORMATION: VL008-AL17-8G5 antibody; heavy chain; CDR1-
      Kabat

<400> SEQUENCE: 109

Asp Tyr Tyr Ile Asn
1               5

<210> SEQ ID NO 110
<211> LENGTH: 17
<212> TYPE: PRT
<213> ORGANISM: Artificial sequence
<220> FEATURE:
<223> OTHER INFORMATION: VL008-AL17-8G5 antibody; heavy chain; CDR2-
      Kabat

<400> SEQUENCE: 110

Trp Ile Phe Pro Gly Ser Gly Leu Thr Tyr Tyr Asn Lys Lys Phe Lys

Gly

<210> SEQ ID NO 111
<211> LENGTH: 14
<212> TYPE: PRT
<213> ORGANISM: Artificial sequence
<220> FEATURE:
<223> OTHER INFORMATION: VL008-AL17-8G5 antibody; heavy chain; CDR3-
      Kabat

<400> SEQUENCE: 111

Pro Tyr Tyr Gly Ser Arg Trp Asp Tyr Thr Met Asp Tyr Val
1               5                   10

<210> SEQ ID NO 112
<211> LENGTH: 8
<212> TYPE: PRT
<213> ORGANISM: Artificial sequence
<220> FEATURE:
<223> OTHER INFORMATION: VL008-AL17-8G5 antibody; heavy chain; CDR1-IMGT

<400> SEQUENCE: 112

Gly Tyr Thr Phe Thr Asp Tyr Tyr
1               5

<210> SEQ ID NO 113
<211> LENGTH: 8
<212> TYPE: PRT
<213> ORGANISM: Artificial sequence
<220> FEATURE:
<223> OTHER INFORMATION: VL008-AL17-8G5 antibody; heavy chain; CDR2-IMGT

<400> SEQUENCE: 113

Ile Phe Pro Gly Ser Gly Leu Thr
1               5

<210> SEQ ID NO 114
<211> LENGTH: 15
<212> TYPE: PRT
<213> ORGANISM: Artificial sequence
<220> FEATURE:
<223> OTHER INFORMATION: VL008-AL17-8G5 antibody; heavy chain; CDR3-IMGT

<400> SEQUENCE: 114

Ala Arg Pro Tyr Tyr Gly Ser Arg Trp Asp Tyr Thr Met Asp Tyr
1               5                   10                  15

<210> SEQ ID NO 115
<211> LENGTH: 17
<212> TYPE: PRT
<213> ORGANISM: Artificial sequence
<220> FEATURE:
<223> OTHER INFORMATION: VL008-AL17-8K7 antibody; light chain; CDR1-
      Kabat

<400> SEQUENCE: 115

Lys Ser Ser Gln Asn Leu Leu Asn Ser Asn Asn Gln Lys Asn His Leu
1               5                   10                  15

Ala

<210> SEQ ID NO 116
<211> LENGTH: 7
<212> TYPE: PRT
<213> ORGANISM: Artificial sequence
<220> FEATURE:

<223> OTHER INFORMATION: VL008-AL17-8K7 antibody; light chain; CDR2-
      Kabat

<400> SEQUENCE: 116

Phe Ala Ser Thr Arg Glu Ser
1               5

<210> SEQ ID NO 117
<211> LENGTH: 9
<212> TYPE: PRT
<213> ORGANISM: Artificial sequence
<220> FEATURE:
<223> OTHER INFORMATION: VL008-AL17-8K7 antibody; light chain; CDR3-
      Kabat

<400> SEQUENCE: 117

Gln Gln His Tyr Thr Thr Pro Tyr Thr
1               5

<210> SEQ ID NO 118
<211> LENGTH: 12
<212> TYPE: PRT
<213> ORGANISM: Artificial sequence
<220> FEATURE:
<223> OTHER INFORMATION: VL008-AL17-8K7 antibody; light chain; CDR1-IMGT

<400> SEQUENCE: 118

Gln Asn Leu Leu Asn Ser Asn Asn Gln Lys Asn His
1               5                   10

<210> SEQ ID NO 119
<211> LENGTH: 4
<212> TYPE: PRT
<213> ORGANISM: Artificial sequence
<220> FEATURE:
<223> OTHER INFORMATION: VL008-AL17-8K7 antibody; light chain; CDR2-IMGT

<400> SEQUENCE: 119

Phe Ala Ser Thr
1

<210> SEQ ID NO 120
<211> LENGTH: 9
<212> TYPE: PRT
<213> ORGANISM: Artificial sequence
<220> FEATURE:
<223> OTHER INFORMATION: VL008-AL17-8K7 antibody; light chain; CDR3-IMGT

<400> SEQUENCE: 120

Gln Gln His Tyr Thr Thr Pro Tyr Thr
1               5

<210> SEQ ID NO 121
<211> LENGTH: 120
<212> TYPE: PRT
<213> ORGANISM: Artificial sequence
<220> FEATURE:
<223> OTHER INFORMATION: VT008-AL5-10G7 antibody; variable region heavy
      chain

<400> SEQUENCE: 121

Gln Val Gln Leu Gln Gln Pro Gly Ala Glu Leu Val Met Pro Gly Ser
1               5                   10                  15

Ser Val Lys Leu Ser Cys Lys Thr Ser Gly Tyr Thr Phe Thr Lys Tyr
            20                  25                  30

Trp Met His Trp Val Lys Arg Arg Pro Gly Gln Gly Leu Glu Trp Ile

```
                35                  40                  45
Gly Glu Ile Asn Pro Ser Asp Thr Tyr Thr Asn Tyr Asn Gln Lys Phe
         50                  55                  60
Lys Gly Lys Ser Thr Leu Thr Val Asp Lys Ser Ser Ser Thr Ala Tyr
 65                  70                  75                  80
Met Gln Leu Ser Ser Leu Thr Ser Glu Asp Ser Ala Val Tyr Phe Cys
                 85                  90                  95
Ala Arg Val Ala Thr Met Val Ala Arg Gly Phe Ala Tyr Trp Gly Gln
            100                 105                 110
Gly Thr Leu Val Thr Val Ser Ala
            115                 120

<210> SEQ ID NO 122
<211> LENGTH: 107
<212> TYPE: PRT
<213> ORGANISM: Artificial sequence
<220> FEATURE:
<223> OTHER INFORMATION: VT008-AL5-10K7 antibody; variable region light
      chain

<400> SEQUENCE: 122

Asp Ile Val Met Thr Gln Ser His Lys Phe Met Ser Thr Ser Val Gly
 1               5                  10                  15
Asp Arg Val Ser Ile Thr Cys Lys Ala Ser Gln Asp Val Ser Gly Ala
             20                  25                  30
Val Val Trp Tyr Gln Glu Lys Pro Gly Gln Ser Pro Asn Leu Leu Ile
         35                  40                  45
Tyr Leu Ala Thr Tyr Arg Tyr Thr Gly Val Pro Asp Arg Phe Thr Gly
     50                  55                  60
Ser Gly Ser Gly Thr Asp Phe Thr Leu Thr Ile Arg Ser Val Gln Ala
 65                  70                  75                  80
Glu Asp Met Ala Val Tyr Tyr Cys Gln Gln Tyr Tyr Ser Ile Pro Trp
                 85                  90                  95
Thr Phe Gly Gly Gly Thr Lys Leu Glu Ile Lys
            100                 105

<210> SEQ ID NO 123
<211> LENGTH: 116
<212> TYPE: PRT
<213> ORGANISM: Artificial sequence
<220> FEATURE:
<223> OTHER INFORMATION: VT008-AL6-14G1 antibody; variable region heavy
      chain

<400> SEQUENCE: 123

Gln Val Gln Leu Gln Gln Pro Gly Ala Glu Leu Val Lys Pro Gly Ala
 1               5                  10                  15
Ser Leu Arg Val Ser Cys Lys Ala Ser Gly Tyr Thr Phe Thr Asn Tyr
             20                  25                  30
Trp Met Tyr Trp Val Arg Gln Arg Pro Gly Arg Gly Leu Glu Trp Ile
         35                  40                  45
Gly Trp Ile Asp Pro Asn Ser Gly Gly Thr Lys Tyr Asn Glu Lys Phe
     50                  55                  60
Lys Ser Lys Ala Thr Leu Thr Val Asp Lys Pro Ser Ser Thr Ala Tyr
 65                  70                  75                  80
Met Gln Leu Ser Ser Leu Thr Ser Glu Asp Ser Ala Val Tyr Asn Cys
                 85                  90                  95
Ala Arg Gly Gly Tyr Thr Met Asp Tyr Trp Gly Gln Gly Thr Ser Val
```

```
                       100                 105                 110

Thr Val Ser Ser
        115

<210> SEQ ID NO 124
<211> LENGTH: 112
<212> TYPE: PRT
<213> ORGANISM: Artificial sequence
<220> FEATURE:
<223> OTHER INFORMATION: VT008-AL6-16K1 antibody; variable region light
      chain

<400> SEQUENCE: 124

Asp Val Val Met Thr Gln Thr Pro Leu Ser Leu Pro Val Ser Leu Gly
1               5                   10                  15

Asp Gln Ala Ser Ile Ser Cys Arg Ala Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

<210> SEQ ID NO 125
<211> LENGTH: 116
<212> TYPE: PRT
<213> ORGANISM: Artificial sequence
<220> FEATURE:
<223> OTHER INFORMATION: VT008-AL6-18G1 antibody; variable region heavy
      chain

<400> SEQUENCE: 125

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Thr Phe Ile Asn Tyr
            20                  25                  30

Trp Ile His Trp Val Lys Gln Arg Pro Gly Arg Gly Leu Glu Trp Ile
        35                  40                  45

Gly Arg Ile Asp Pro Asn Thr Val Asp Ala Lys Tyr Asn Glu Lys Phe
    50                  55                  60

Lys Ser Lys Ala Thr Leu Thr Val Asp Lys Pro Ser Ser Ile Ala Tyr
65                  70                  75                  80

Met Gln Leu Ser Ser Leu Thr Ser Glu Asp Ser Ala Val Tyr Tyr Cys
                85                  90                  95

Ser Arg Gly Gly Tyr Thr Met Asp Tyr Trp Gly Gln Gly Thr Ser Val
            100                 105                 110

Thr Val Ser Ser
        115

<210> SEQ ID NO 126
<211> LENGTH: 112
<212> TYPE: PRT
<213> ORGANISM: Artificial sequence
<220> FEATURE:
<223> OTHER INFORMATION: VT008-AL6-18K21 antibody; variable region light
``` chain

<400> SEQUENCE: 126

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Thr Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Phe Gln Ser
                85                  90                  95

Thr His Val Pro Trp Thr Phe Gly Gly Gly Thr Lys Leu Glu Ile Lys
            100                 105                 110

<210> SEQ ID NO 127
<211> LENGTH: 122
<212> TYPE: PRT
<213> ORGANISM: Artificial sequence
<220> FEATURE:
<223> OTHER INFORMATION: VL008-AL17-7K6 antibody; variable region light
      chain

<400> SEQUENCE: 127

Gln Val Gln Leu Gln Gln Ser Gly Pro Glu Leu Val Lys Pro Gly Ala
1               5                   10                  15

Ser Val Lys Ile Ser Cys Lys Ala Ser Val Tyr Thr Phe Thr Asp Tyr
            20                  25                  30

Tyr Ile Asn Trp Val Lys Gln Arg Pro Gly Gln Gly Leu Glu Trp Val
        35                  40                  45

Gly Trp Ile Phe Pro Gly Ser Gly Leu Thr Tyr Tyr Asn Lys Lys Phe
    50                  55                  60

Lys Gly Lys Ala Thr Leu Thr Val Asp Lys Ser Ser Ser Thr Ala Tyr
65                  70                  75                  80

Met Leu Leu Ser Ser Leu Thr Ser Glu Asp Ser Ala Val Tyr Phe Cys
                85                  90                  95

Ala Arg Pro Tyr Tyr Gly Ser Arg Trp Asp Tyr Ala Met Asp Tyr Trp
            100                 105                 110

Gly Gln Gly Thr Ser Val Thr Val Ser Ser
        115                 120

<210> SEQ ID NO 128
<211> LENGTH: 113
<212> TYPE: PRT
<213> ORGANISM: Artificial sequence
<220> FEATURE:
<223> OTHER INFORMATION: VL008-AL17-7K6 antibody; variable region light
      chain

<400> SEQUENCE: 128

Asp Ile Val Met Thr Gln Ser Pro Ser Ser Leu Thr Met Ser Val Gly
1               5                   10                  15

Gln Lys Val Thr Met Ser Cys Lys Ser Ser Gln Ser Leu Leu Asn Ser
            20                  25                  30

Asn Asn Gln Lys Asn Tyr Leu Ala Trp Tyr Gln Gln Lys Pro Gly Gln
        35                  40                  45

Ser Pro Lys Leu Leu Tyr Phe Ala Ser Thr Arg Glu Ser Gly Val
        50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                85                  90                  95

His Tyr Thr Thr Pro Tyr Thr Phe Gly Gly Gly Thr Lys Leu Glu Ile
            100                 105                 110

Lys

<210> SEQ ID NO 129
<211> LENGTH: 118
<212> TYPE: PRT
<213> ORGANISM: Artificial sequence
<220> FEATURE:
<223> OTHER INFORMATION: VL008-AL18-14G4 antibody; variable region heavy
      chain

<400> SEQUENCE: 129

Gln Val Gln Leu Lys Gln Ser Gly Ala Glu Leu Val Arg Pro Gly Ala
 1               5                  10                  15

Ser Val Lys Leu Ser Cys Lys Ala Ser Gly Tyr Ser Phe Thr Asp Tyr
                20                  25                  30

Tyr Ile Asn Trp Val Lys Gln Arg Pro Gly Gln Gly Leu Glu Trp Ile
            35                  40                  45

Ala Arg Ile Tyr Pro Gly Ile Gly Asn Thr Tyr Tyr Asn Lys Lys Phe
 50                  55                  60

Lys Gly Lys Ala Thr Leu Thr Ala Glu Lys Ser Ser Ser Thr Ala Tyr
 65                  70                  75                  80

Met Gln Leu Asn Ser Leu Thr Ser Glu Asp Ser Ala Val Tyr Phe Cys
                85                  90                  95

Ala Arg Gly His Tyr Gly Arg Gly Met Asp Tyr Trp Gly Gln Gly Thr
            100                 105                 110

Ser Val Thr Val Ser Ser
        115

<210> SEQ ID NO 130
<211> LENGTH: 113
<212> TYPE: PRT
<213> ORGANISM: Artificial sequence
<220> FEATURE:
<223> OTHER INFORMATION: VL008-AL18-14K1 antibody; variable region light
      chain

<400> SEQUENCE: 130

Asp Ile Val Met Thr Gln Ser Pro Ser Ser Leu Ala Met Ser Val Gly
 1               5                  10                  15

Gln Lys Val Thr Met Asn Cys Lys Ser Ser Gln Ser Leu Leu Asn Ser
                20                  25                  30

Ile Asp Gln Lys Asn Tyr Leu Ala Trp Tyr Gln Gln Lys Pro Gly Gln
            35                  40                  45

Ser Pro Lys Leu Leu Val Tyr Phe Ala Ser Thr Lys Glu Ser Gly Val
 50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                85                  90                  95

His Tyr Ser Thr Pro Trp Thr Phe Gly Gly Gly Thr Lys Leu Glu Ile
                100                 105                 110

Lys

<210> SEQ ID NO 131
<211> LENGTH: 119
<212> TYPE: PRT
<213> ORGANISM: Artificial sequence
<220> FEATURE:
<223> OTHER INFORMATION: VL008-AL13-8G5 antibody; variable region heavy
      chain

<400> SEQUENCE: 131

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Thr Tyr
                20                  25                  30

Trp Met His Trp Val Lys Gln Arg Pro Gly Gln Gly Leu Glu Trp Ile
            35                  40                  45

Gly Met Ile His Pro Asn Ser Gly Thr Thr Asn Tyr Asn Glu Lys Phe
        50                  55                  60

Lys Ser Lys Ala Thr Leu Thr Val Asp Lys Ser Ser Ser Thr
65                  70                  75                  80

Met Gln Leu Ser Ser Leu Thr Ser Glu Asp Ser Ala Val Tyr Tyr Cys
                85                  90                  95

Thr Arg Ser His Tyr Tyr Asp Gly His Phe Ser Tyr Trp Gly Gln Gly
                100                 105                 110

Thr Leu Val Thr Val Ser Ala
            115

<210> SEQ ID NO 132
<211> LENGTH: 112
<212> TYPE: PRT
<213> ORGANISM: Artificial sequence
<220> FEATURE:
<223> OTHER INFORMATION: VL008-AL13-8K3 antibody; variable region light
      chain

<400> SEQUENCE: 132

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Arg Leu Glu Ile Lys
                100                 105                 110

<210> SEQ ID NO 133
<211> LENGTH: 116
<212> TYPE: PRT
<213> ORGANISM: Artificial sequence
<220> FEATURE:
<223> OTHER INFORMATION: VT008-AL6-10G3 antibody; variable region heavy -continued chain

<400> SEQUENCE: 133

Gln Val Gln Leu Gln Gln Pro Gly Pro Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Ile His Trp Leu Asn Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Lys Ser Lys Ala Ile Leu Thr Val Asp Lys Ser Ser Thr Thr Tyr
65                  70                  75                  80

Met Gln Leu Ser Ser Leu Thr Ser Glu Asp Ser Ala Val Tyr Tyr Cys
                85                  90                  95

Ala Arg Gly Gly Tyr Thr Met Asp Tyr Trp Gly Gln Gly Thr Ser Val
            100                 105                 110

Thr Val Ser Ser
        115

<210> SEQ ID NO 134
<211> LENGTH: 112
<212> TYPE: PRT
<213> ORGANISM: Artificial sequence
<220> FEATURE:
<223> OTHER INFORMATION: VT008-AL6-10K1 antibody; variable region light
      chain

<400> SEQUENCE: 134

Asp Val Val Met Pro Gln Thr Pro Leu Ser Leu Pro Val Ser Leu Gly
1               5                   10                  15

Asp His Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Ile Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Ser
                85                  90                  95

Thr His Val Pro Trp Thr Phe Gly Gly Gly Thr Lys Leu Glu Ile Lys
            100                 105                 110

<210> SEQ ID NO 135
<211> LENGTH: 116
<212> TYPE: PRT
<213> ORGANISM: Artificial sequence
<220> FEATURE:
<223> OTHER INFORMATION: VT008-AL6-20G7 antibody; variable region heavy
      chain

<400> SEQUENCE: 135

Gln Val Gln Leu Gln Gln Ser Gly Thr Glu Leu Ala Lys Pro Gly Ala
1               5                   10                  15

Ser Val Lys Leu Ser Cys Lys Ala Ser Gly Tyr Thr Phe Ile Asn Tyr
            20                  25                  30

Trp Ile Tyr Trp Val Lys Glu Arg Pro Gly Gln Val Leu Glu Trp Ile
        35                  40                  45

Gly Tyr Ile Asn Pro Arg Ser Asp Asp Thr Lys Tyr Asn Gln Lys Phe
            50                  55                  60

Arg Asp Arg Ala Thr Leu Thr Ala Asp Lys Ser Ser Thr Thr Ala Tyr
 65                  70                  75                  80

Leu Gln Leu Asn Ser Leu Thr Asn Asp Asp Ser Ala Leu Tyr Tyr Cys
                85                  90                  95

Ala Arg Gly Gly Phe Thr Met Asp Phe Trp Gly Gln Gly Thr Ser Val
                100                 105                 110

Thr Val Ser Ser
            115

<210> SEQ ID NO 136
<211> LENGTH: 112
<212> TYPE: PRT
<213> ORGANISM: Artificial sequence
<220> FEATURE:
<223> OTHER INFORMATION: VT008-AL6-20K7 antibody; variable region light
      chain

<400> SEQUENCE: 136

Asp Val Val Met Thr Gln Thr Pro Leu Ser Leu Pro Val Ser Leu Gly
 1               5                  10                  15

Asp Gln Ala Ser Ile Ser Cys Arg Ser Gln Ser Leu Leu His Ser
                20                  25                  30

Asn Gly Asn Thr Tyr Leu His Trp Tyr Leu Gln Lys Pro Gly Gln Ser
                35                  40                  45

Pro Asn Leu Leu Ile Tyr Lys Val Ser Tyr Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Gly
                85                  90                  95

Thr His Val Pro Tyr Thr Phe Gly Gly Gly Thr Lys Leu Glu Ile Lys
                100                 105                 110

<210> SEQ ID NO 137
<211> LENGTH: 116
<212> TYPE: PRT
<213> ORGANISM: Artificial sequence
<220> FEATURE:
<223> OTHER INFORMATION: VT008-AL6-39G2 antibody; variable region heavy
      chain

<400> SEQUENCE: 137

Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Ser Phe Thr Gly Tyr
                20                  25                  30

Asn Ile Tyr Trp Val Lys Gln Ser His Gly Asn Ile Leu Asp Trp Ile
                35                  40                  45

Gly Tyr Ile Tyr Pro Tyr Asn Gly Ile Ser Ser Tyr Asn Gln Lys Phe
            50                  55                  60

Lys Asp Lys Ala Thr Leu Thr Val Asp Lys Ser Ser Thr Thr Ala Tyr
 65                  70                  75                  80

Met Glu Leu Arg Ser Leu Thr Ser Glu Asp Ser Ala Val Tyr Tyr Cys
                85                  90                  95

Ala Arg Gly Gly Tyr Thr Met Asp Tyr Gly Gly Gln Gly Thr Ser Val
                100                 105                 110

Thr Val Ser Ser
        115

<210> SEQ ID NO 138
<211> LENGTH: 112
<212> TYPE: PRT
<213> ORGANISM: Artificial sequence
<220> FEATURE:
<223> OTHER INFORMATION: VT008-AL6-39K2 antibody; variable region light
      chain

<400> SEQUENCE: 138

Asp Val Val Met Thr Gln Thr Pro Leu Ser Leu Pro Val Ser Leu Gly
1               5                   10                  15

Glu Gln Ala Ser Ile Ser Cys Arg Ser Ser Gln Ser Leu Val Lys Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Thr
                85                  90                  95

Thr His Val Pro Tyr Thr Phe Gly Gly Gly Thr Lys Leu Glu Ile Lys
            100                 105                 110

<210> SEQ ID NO 139
<211> LENGTH: 122
<212> TYPE: PRT
<213> ORGANISM: Artificial sequence
<220> FEATURE:
<223> OTHER INFORMATION: VL008-AL17-8G5 antibody; variable region heavy
      chain

<400> SEQUENCE: 139

Leu Val Gln Leu Gln Gln Ser Gly Pro Glu Leu Val Lys Pro Gly Thr
1               5                   10                  15

Ser Val Lys Ile Ser Cys Arg Ser Ser Gly Tyr Thr Phe Thr Asp Tyr
            20                  25                  30

Tyr Ile Asn Trp Val Gln Gln Arg Pro Gly Gln Gly Leu Glu Trp Val
        35                  40                  45

Gly Trp Ile Phe Pro Gly Ser Gly Leu Thr Tyr Tyr Asn Lys Lys Phe
    50                  55                  60

Lys Gly Lys Ala Thr Leu Ser Val Asp Lys Ser Ser Asn Thr Ala Tyr
65                  70                  75                  80

Met Leu Leu Ser Ser Leu Thr Ser Glu Asp Ser Ala Val Tyr Phe Cys
                85                  90                  95

Ala Arg Pro Tyr Tyr Gly Ser Arg Trp Asp Tyr Thr Met Asp Tyr Trp
            100                 105                 110

Gly Gln Gly Thr Ser Val Thr Val Ser Ser
        115                 120

<210> SEQ ID NO 140
<211> LENGTH: 113
<212> TYPE: PRT
<213> ORGANISM: Artificial sequence
<220> FEATURE:
<223> OTHER INFORMATION: VL008-AL17-8K7 antibody; variable region light
      chain

<400> SEQUENCE: 140

Asp Ile Val Met Thr Gln Ser Pro Ser Ser Leu Thr Met Ser Val Gly
1               5                   10                  15

Gln Lys Ala Thr Met Ser Cys Lys Ser Ser Gln Asn Leu Leu Asn Ser
            20                  25                  30

Asn Asn Gln Lys Asn His Leu Ala Trp Tyr Gln Gln Lys Pro Gly Gln
        35                  40                  45

Ser Pro Lys Leu Leu Leu Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Thr Thr Pro Tyr Thr Phe Gly Gly Gly Thr Lys Leu Glu Ile
            100                 105                 110

Lys

<210> SEQ ID NO 141
<211> LENGTH: 118
<212> TYPE: PRT
<213> ORGANISM: Artificial sequence
<220> FEATURE:
<223> OTHER INFORMATION: VL008-AL18-14G4 antibody; humanized variable
      region heavy chain; VH1

<400> SEQUENCE: 141

Gln Val Gln Leu Leu Glu Ser Gly Ala Val Leu Ala Arg Pro Gly Thr
1               5                   10                  15

Ser Val Lys Ile Ser Cys Lys Ala Ser Gly Tyr Ser Phe Thr Asp Tyr
            20                  25                  30

Tyr Ile Asn Trp Val Lys Gln Arg Pro Gly Gln Gly Leu Glu Trp Ile
        35                  40                  45

Gly Arg Ile Tyr Pro Gly Ile Gly Asn Thr Tyr Tyr Asn Lys Lys Phe
    50                  55                  60

Lys Gly Arg Ala Lys Leu Thr Ala Ala Thr Ser Ala Ser Ile Ala Tyr
65                  70                  75                  80

Leu Glu Phe Ser Ser Leu Thr Asn Glu Asp Ser Ala Val Tyr Tyr Cys
                85                  90                  95

Ala Arg Gly His Tyr Gly Arg Gly Met Asp Tyr Trp Gly Gln Gly Thr
            100                 105                 110

Leu Val Thr Val Ser Ser
        115

<210> SEQ ID NO 142
<211> LENGTH: 118
<212> TYPE: PRT
<213> ORGANISM: Artificial sequence
<220> FEATURE:
<223> OTHER INFORMATION: VL008-AL18-14G4 antibody; humanized variable
      region heavy chain; VH2

<400> SEQUENCE: 142

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Ile Asn Trp Val Arg Gln Ala Pro Gly Gln Gly Leu Glu Trp Met

```
                35                  40                  45

Gly Arg Ile Tyr Pro Gly Ile Gly Asn Thr Tyr Tyr Asn Lys Lys Phe
        50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly His Tyr Gly Arg Gly Met Asp Tyr Trp Gly Gln Gly Thr
                    100                 105                 110

Leu Val Thr Val Ser Ser
            115

<210> SEQ ID NO 143
<211> LENGTH: 118
<212> TYPE: PRT
<213> ORGANISM: Artificial sequence
<220> FEATURE:
<223> OTHER INFORMATION: VL008-AL18-14G4 antibody; humanized variable
      region heavy chain; VH3

<400> SEQUENCE: 143

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Asp Tyr
                20                  25                  30

Tyr Ile Asn Trp Val Arg Gln Ala Pro Gly Gln Gly Leu Glu Trp Met
            35                  40                  45

Gly Arg Ile Tyr Pro Gly Ile Gly Asn Thr Tyr Tyr Asn Lys Lys Phe
        50                  55                  60

Lys Gly Arg Val Thr Val Thr Arg Asp Thr Ser Ile Ser Thr Ala His
 65                  70                  75                  80

Met Glu Leu Ser Ser Leu Arg Ser Asp Asp Thr Ala Val Tyr Tyr Cys
                85                  90                  95

Ala Arg Gly His Tyr Gly Arg Gly Met Asp Tyr Trp Gly Gln Gly Thr
                    100                 105                 110

Ala Val Thr Val Ser Ser
            115

<210> SEQ ID NO 144
<211> LENGTH: 118
<212> TYPE: PRT
<213> ORGANISM: Artificial sequence
<220> FEATURE:
<223> OTHER INFORMATION: VL008-AL18-14G4 antibody; humanized variable
      region heavy chain; VH4

<400> SEQUENCE: 144

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ser Phe Thr Asp Tyr
                20                  25                  30

Tyr Ile Asn Trp Val Arg Gln Ala Pro Gly Gln Gly Leu Glu Trp Met
            35                  40                  45

Gly Arg Ile Tyr Pro Gly Ile Gly Asn Thr Tyr Tyr Asn Lys Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
```

85                  90                  95

Ala Arg Gly His Tyr Gly Arg Gly Met Asp Tyr Trp Gly Gln Gly Thr
                100                 105                 110

Thr Val Thr Val Ser Ser
        115

<210> SEQ ID NO 145
<211> LENGTH: 118
<212> TYPE: PRT
<213> ORGANISM: Artificial sequence
<220> FEATURE:
<223> OTHER INFORMATION: VL008-AL18-14G4 antibody; humanized variable
      region heavy chain; VH5

<400> SEQUENCE: 145

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Tyr Ile Asn Trp Val Arg Gln Ala Pro Gly Gln Gly Leu Glu Trp Met
            35                  40                  45

Gly Arg Ile Tyr Pro Gly Ile Gly Asn Thr Tyr Tyr Asn Lys Lys Phe
50                  55                  60

Lys Gly Arg Val Thr Met Thr Arg Tyr Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Gly His Tyr Gly Arg Gly Met Asp Tyr Trp Gly Gln Gly Thr
                100                 105                 110

Thr Val Thr Val Ser Ser
        115

<210> SEQ ID NO 146
<211> LENGTH: 113
<212> TYPE: PRT
<213> ORGANISM: Artificial sequence
<220> FEATURE:
<223> OTHER INFORMATION: VL008-AL18-14K1 antibody; humanized variable
      region light chain; VL1

<400> SEQUENCE: 146

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Ile Asp Gln Lys Asn Tyr Leu Ala Trp Tyr Gln Gln Lys Pro Gly Gln
            35                  40                  45

Pro Pro Lys Leu Leu Ile Tyr Phe Ala Ser Thr Lys Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Thr Pro Trp Thr Phe Gly Gly Gly Thr Lys Leu Glu Ile
                100                 105                 110

Lys

<210> SEQ ID NO 147

<211> LENGTH: 113
<212> TYPE: PRT
<213> ORGANISM: Artificial sequence
<220> FEATURE:
<223> OTHER INFORMATION: VL008-AL18-14K1 antibody; humanized variable
      region light chain; VL2

<400> SEQUENCE: 147

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ile Asp Gln Lys Asn Tyr Leu Ala Trp Tyr Gln Gln Lys Pro Gly Gln
        35                  40                  45

Pro Pro Lys Leu Leu Ile Tyr Phe Ala Ser Thr Lys Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Thr Pro Trp Thr Phe Gly Gly Gly Thr Lys Val Glu Ile
            100                 105                 110

Lys

<210> SEQ ID NO 148
<211> LENGTH: 113
<212> TYPE: PRT
<213> ORGANISM: Artificial sequence
<220> FEATURE:
<223> OTHER INFORMATION: VL008-AL18-14K1 antibody; humanized variable
      region light chain; VL3

<400> SEQUENCE: 148

Glu Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ile Asp Gln Lys Asn Tyr Leu Ala Trp Tyr Gln Gln Lys Ala Gly Gln
        35                  40                  45

Ser Pro Lys Leu Leu Ile Tyr Phe Ala Ser Thr Lys Glu Ser Gly Val
    50                  55                  60

Pro Asp Arg Phe Ser Gly Ser Gly Ser Gly Thr Asp Phe Thr Leu Thr
65                  70                  75                  80

Ile Asp Ser Leu Gln Ala Glu Asp Val Ala Val Tyr Tyr Cys Gln Gln
                85                  90                  95

His Tyr Ser Thr Pro Trp Thr Phe Gly Gly Gly Thr Lys Val Glu Ile
            100                 105                 110

Lys

<210> SEQ ID NO 149
<211> LENGTH: 113
<212> TYPE: PRT
<213> ORGANISM: Artificial sequence
<220> FEATURE:
<223> OTHER INFORMATION: VL008-AL18-14K1 antibody; humanized variable
      region light chain; VL4

<400> SEQUENCE: 149

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ile Asp Gln Lys Asn Tyr Leu Ala Trp Tyr Gln Gln Lys Pro Gly Gln
        35                  40                  45

Pro Pro Lys Leu Leu Ile Tyr Phe Ala Ser Thr Lys Glu Ser Gly Val
65       50                  55                  60

Pro Asp Arg Phe Ser Gly Ser Gly Ser Gly Thr Asp Phe Thr Leu Thr
65              70                  75                  80

Ile Ser Ser Leu Gln Ala Glu Asp Val Ala Val Tyr Phe Cys Gln Gln
                85                  90                  95

His Tyr Ser Thr Pro Trp Thr Phe Gly Gly Gly Ala Lys Val Glu Ile
            100                 105                 110

Lys

<210> SEQ ID NO 150
<211> LENGTH: 113
<212> TYPE: PRT
<213> ORGANISM: Artificial sequence
<220> FEATURE:
<223> OTHER INFORMATION: VL008-AL18-14K1 antibody; humanized variable
      region light chain; VL5

<400> SEQUENCE: 150

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ile Asp Gln Lys Asn Tyr Leu Ala Trp Tyr Gln Gln Lys Pro Gly Gln
        35                  40                  45

Pro Pro Lys Leu Leu Ile Tyr Phe Ala Ser Thr Lys Glu Ser Gly Val
    50                  55                  60

Pro Asp Arg Phe Ser Gly Ser Gly Ser Gly Thr Asp Phe Thr Leu Thr
65              70                  75                  80

Ile Ser Gly Leu Gln Ala Glu Asp Val Ala Val Tyr Phe Cys Gln Gln
                85                  90                  95

His Tyr Ser Thr Pro Trp Thr Phe Gly Gly Gly Thr Lys Val Glu Ile
            100                 105                 110

Arg

<210> SEQ ID NO 151
<211> LENGTH: 323
<212> TYPE: PRT
<213> ORGANISM: Homo sapiens

<400> SEQUENCE: 151

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65              70                  75                  80

Phe Ser Ser Ala Lys Ile Glu Val Ser Gln Leu Leu Lys Gly Asp Ala

```
                    85                  90                  95
Ser Leu Lys Met Asp Lys Ser Asp Ala Val Ser His Thr Gly Asn Tyr
            100                 105                 110

Thr Cys Glu Val Thr Glu Leu Thr Arg Glu Gly Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
                195                 200                 205

Gly Leu Gly Leu Ile Val Thr Ser Thr Gly Ile Leu Ile Leu Leu His
            210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
            275                 280                 285

Met Lys Phe Val Ala Ser Asn Gln Lys Thr Ile Gln Pro Pro Arg Lys
            290                 295                 300

Ala Val Glu Glu Pro Leu Asn Ala Phe Lys Glu Ser Lys Gly Met Met
305                 310                 315                 320

Asn Asp Glu
```

<210> SEQ ID NO 152
<211> LENGTH: 7
<212> TYPE: PRT
<213> ORGANISM: Artificial sequence
<220> FEATURE:
<223> OTHER INFORMATION: VT008-AL18-14K1 antibody; light chain; CDR2-
      Kabat; CD4+ T cell epitope corrected

<400> SEQUENCE: 152

```
Tyr Ala Ser Thr Lys Glu Ser
1               5
```

<210> SEQ ID NO 153
<211> LENGTH: 4
<212> TYPE: PRT
<213> ORGANISM: Artificial sequence
<220> FEATURE:
<223> OTHER INFORMATION: VT008-AL18-14K1 antibody; light chain; CDR2-
      IMGT; CD4+ T cell epitope corrected

<400> SEQUENCE: 153

```
Tyr Ala Ser Thr
1
```

<210> SEQ ID NO 154
<211> LENGTH: 113
<212> TYPE: PRT
<213> ORGANISM: Artificial sequence -continued

```
<220> FEATURE:
<223> OTHER INFORMATION: VL008-AL18-14K1 antibody; variable region light
      chain; CD4+ T cell epitope corrected

<400> SEQUENCE: 154

Asp Ile Val Met Thr Gln Ser Pro Ser Ser Leu Ala Met Ser Val Gly
1               5                   10                  15

Gln Lys Val Thr Met Asn Cys Lys Ser Ser Gln Ser Leu Leu Asn Ser
            20                  25                  30

Ile Asp Gln Lys Asn Tyr Leu Ala Trp Tyr Gln Gln Lys Pro Gly Gln
        35                  40                  45

Ser Pro Lys Leu Leu Val Tyr Tyr Ala Ser Thr Lys Glu Ser Gly Val
50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Trp Thr Phe Gly Gly Gly Thr Lys Leu Glu Ile
            100                 105                 110

Lys

<210> SEQ ID NO 155
<211> LENGTH: 113
<212> TYPE: PRT
<213> ORGANISM: Artificial sequence
<220> FEATURE:
<223> OTHER INFORMATION: VL008-AL18-14K1 antibody; humanized variable
      region light chain; VL1; CD4+ T cell epitope corrected

<400> SEQUENCE: 155

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ile Asp Gln Lys Asn Tyr Leu Ala Trp Tyr Gln Gln Lys Pro Gly Gln
        35                  40                  45

Pro Pro Lys Leu Leu Ile Tyr Tyr Ala Ser Thr Lys Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Thr Pro Trp Thr Phe Gly Gly Gly Thr Lys Leu Glu Ile
            100                 105                 110

Lys

<210> SEQ ID NO 156
<211> LENGTH: 113
<212> TYPE: PRT
<213> ORGANISM: Artificial sequence
<220> FEATURE:
<223> OTHER INFORMATION: VL008-AL18-14K1 antibody; humanized variable
      region light chain; VL2; CD4+ T cell epitope corrected

<400> SEQUENCE: 156

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30
```

-continued

```
Ile Asp Gln Lys Asn Tyr Leu Ala Trp Tyr Gln Gln Lys Pro Gly Gln
            35                  40                  45

Pro Pro Lys Leu Leu Ile Tyr Tyr Ala Ser Thr Lys Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

His Tyr Ser Thr Pro Trp Thr Phe Gly Gly Gly Thr Lys Val Glu Ile
                100                 105                 110

Lys
```

<210> SEQ ID NO 157
<211> LENGTH: 113
<212> TYPE: PRT
<213> ORGANISM: Artificial sequence
<220> FEATURE:
<223> OTHER INFORMATION: VL008-AL18-14K1 antibody; humanized variable
      region light chain; VL3; CD4+ T cell epitope corrected

<400> SEQUENCE: 157

```
Glu Ile Val Leu Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
            20                  25                  30

Ile Asp Gln Lys Asn Tyr Leu Ala Trp Tyr Gln Gln Lys Ala Gly Gln
            35                  40                  45

Ser Pro Lys Leu Leu Ile Tyr Tyr Ala Ser Thr Lys Glu Ser Gly Val
 50                  55                  60

Pro Asp Arg Phe Ser Gly Ser Gly Ser Gly Thr Asp Phe Thr Leu Thr
 65                  70                  75                  80

Ile Asp Ser Leu Gln Ala Glu Asp Val Ala Val Tyr Tyr Cys Gln Gln
                85                  90                  95

His Tyr Ser Thr Pro Trp Thr Phe Gly Gly Gly Thr Lys Val Glu Ile
                100                 105                 110

Lys
```

<210> SEQ ID NO 158
<211> LENGTH: 113
<212> TYPE: PRT
<213> ORGANISM: Artificial sequence
<220> FEATURE:
<223> OTHER INFORMATION: VL008-AL18-14K1 antibody; humanized variable
      region light chain; VL4; CD4+ T cell epitope corrected

<400> SEQUENCE: 158

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
            20                  25                  30

Ile Asp Gln Lys Asn Tyr Leu Ala Trp Tyr Gln Gln Lys Pro Gly Gln
            35                  40                  45

Pro Pro Lys Leu Leu Ile Tyr Tyr Ala Ser Thr Lys Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Phe Cys Gln Gln
```

His Tyr Ser Thr Pro Trp Thr Phe Gly Gly Gly Ala Lys Val Glu Ile
                100                 105                 110
Lys

<210> SEQ ID NO 159
<211> LENGTH: 113
<212> TYPE: PRT
<213> ORGANISM: Artificial sequence
<220> FEATURE:
<223> OTHER INFORMATION: VL008-AL18-14K1 antibody; humanized variable
      region light chain; VL5; CD4+ T cell epitope corrected

<400> SEQUENCE: 159

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ile Asp Gln Lys Asn Tyr Leu Ala Trp Tyr Gln Lys Pro Gly Gln
        35                  40                  45

Pro Pro Lys Leu Leu Ile Tyr Tyr Ala Ser Thr Lys Glu Ser Gly Val
    50                  55                  60

Pro Asp Arg Phe Ser Gly Ser Gly Ser Gly Thr Asp Phe Thr Leu Thr
65                  70                  75                  80

Ile Ser Gly Leu Gln Ala Glu Asp Val Ala Val Tyr Phe Cys Gln Gln
                85                  90                  95

His Tyr Ser Thr Pro Trp Thr Phe Gly Gly Gly Thr Lys Val Glu Ile
                100                 105                 110
Arg

<210> SEQ ID NO 160
<211> LENGTH: 153
<212> TYPE: PRT
<213> ORGANISM: Artificial sequence
<220> FEATURE:
<223> OTHER INFORMATION: hu-sCD47-6His; extracellular domain of human
      CD47 antigen with 6His-tag

<400> SEQUENCE: 160

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Ala Ser Ser Ser Gly
    130                 135                 140

Ser Ser Ser His His His His His His
145                 150

<210> SEQ ID NO 161
<211> LENGTH: 981
<212> TYPE: DNA
<213> ORGANISM: Artificial sequence
<220> FEATURE:
<223> OTHER INFORMATION: hu-IgG4 S228P; nucleotide sequence of human
      IgG4 S228P mutant

<400> SEQUENCE: 161

```
gctagcacca agggcccctc tgtgtttcct ctggcccctt gctcccggtc cacctccgaa      60
tctacagccg ctctgggctg cctcgtgaaa gactacttcc ccgagcctgt gacagtgtcc     120
tggaactctg gcgccctgac cagcggagtg cataccttcc ctgctgtgct gcagtcctcc     180
ggcctgtact ccctgtcctc cgtcgtgaca gtgccctcca gctctctggg caccaagacc     240
tatacctgca acgtggacca caagccctcc aacaccaagg tggacaagag agtggaatct     300
aagtacggcc ctccctgccc cccttgtcct gcccctgaat tctgggcgg acctccgtg       360
ttcctgttcc ccccaaagcc taaggacacc ctgatgatct cccggacccc cgaagtgacc     420
tgcgtggtgg tggatgtgtc tcaggaagat cccgaggtgc agttcaattg gtacgtggac     480
ggcgtggaag tgcataatgc caagaccaag cctcgggaag aacagttcaa ctccacctac     540
cgggtggtgt ccgtgctgac cgtgctgcac caggattggc tgaacggcaa agagtacaag     600
tgcaaggtgt ccaacaaggg cctgcccagc tccatcgaaa agaccatctc caaggccaag     660
ggccagcccc gggaacccca ggtgtacaca ctgcctccat cccaggaaga tgatgaccaag     720
aaccaggtgt ccctgacctg tctcgtgaag ggattctacc cctccgatat cgccgtggaa     780
tgggagtcca acggccagcc tgagaacaac tacaagacca cccccctgt gctggactcc     840
gacggctcct tcttcctgta ctctcgcctg accgtggaca gtcccggtg caggaaggc      900
aacgtgttct cctgctccgt gatgcacgag gccctgcaca accactacac ccagaagtcc     960
ctgtctctgt ccctgggcaa g                                               981
```

<210> SEQ ID NO 162
<211> LENGTH: 327
<212> TYPE: PRT
<213> ORGANISM: Artificial sequence
<220> FEATURE:
<223> OTHER INFORMATION: huIgG4_S228P; amino acid sequence of human IgG4
      S228P mutant

<400> SEQUENCE: 162

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

```
Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 163
<211> LENGTH: 981
<212> TYPE: DNA
<213> ORGANISM: Artificial sequence
<220> FEATURE:
<223> OTHER INFORMATION: hu-IgG4 S228P-L235E; nucleotide sequence of human IgG4 S228P double mutant

<400> SEQUENCE: 163

```
gctagcacca agggcccctc tgtgtttcct ctggcccctt gctcccggtc cacctccgaa     60
tctacagccg ctctgggctg cctcgtgaaa gactacttcc ccgagcctgt gacagtgtcc    120
tggaactctg gcgccctgac cagcggagtg cataccttcc ctgctgtgct gcagtcctcc    180
ggcctgtact ccctgtcctc cgtcgtgaca gtgccctcca gctctctggg caccaagacc    240
tatacctgca acgtggacca caagccctcc aacaccaagg tggacaagag agtggaatct    300
aagtacggcc ctccctgccc cccttgtcct gcccctgaat ttgaaggcgg accctccgtg    360
ttcctgttcc ccccaaagcc taaggacacc ctgatgatct cccggacccc cgaagtgacc    420
tgcgtggtgg tggatgtgtc tcaggaagat cccgaggtgc agttcaattg gtacgtggac    480
ggcgtggaag tgcataatgc caagaccaag cctcgggaag aacagttcaa ctccacctac    540
cgggtggtgt ccgtgctgac cgtgctgcac caggattggc tgaacggcaa agagtacaag    600
tgcaaggtgt ccaacaaggg cctgcccagc tccatcgaaa agaccatctc caaggccaag    660
ggccagcccc gggaacccca ggtgtacaca ctgcctccat cccaggaaga gatgaccaag    720
aaccaggtgt ccctgacctg tctcgtgaag ggattctacc cctccgatat cgccgtggaa    780
```

```
tgggagtcca acggccagcc tgagaacaac tacaagacca ccccccctgt gctggactcc    840
gacggctcct tcttcctgta ctctcgcctg accgtggaca agtcccggtg caggaaggc     900 aacgtgttct cctgctccgt gatgcacgag gccctgcaca accactacac ccagaagtcc    960
ctgtctctgt ccctgggcaa g                                              981
```

<210> SEQ ID NO 164
<211> LENGTH: 327
<212> TYPE: PRT
<213> ORGANISM: Artificial sequence
<220> FEATURE:
<223> OTHER INFORMATION: huIgG4_S228P_L235E; amino acid sequence of
      human IgG4 S228P_L235E double mutant

<400> SEQUENCE: 164

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

Leu Ser Leu Ser Leu Gly Lys
                325

<210> SEQ ID NO 165
<211> LENGTH: 444
<212> TYPE: PRT
<213> ORGANISM: Artificial sequence
<220> FEATURE:
<223> OTHER INFORMATION: h20-H2-L5Y; heavy chain in huIgG4_S228P format

<400> SEQUENCE: 165

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Ile Asn Trp Val Arg Gln Ala Pro Gly Gln Gly Leu Glu Trp Met
        35                  40                  45

Gly Arg Ile Tyr Pro Gly Ile Gly Asn Thr Tyr Tyr Asn Lys Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Tyr Gly Arg Gly Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

```
Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440

<210> SEQ ID NO 166
<211> LENGTH: 444
<212> TYPE: PRT
<213> ORGANISM: Artificial sequence
<220> FEATURE:
<223> OTHER INFORMATION: h20-H2 ; heavy chain in hu-IgG4_S228P_L325E
      format

<400> SEQUENCE: 166

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Ile Asn Trp Val Arg Gln Ala Pro Gly Gln Gly Leu Glu Trp Met
        35                  40                  45

Gly Arg Ile Tyr Pro Gly Ile Gly Asn Thr Tyr Tyr Asn Lys Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly His Tyr Gly Arg Gly Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
```

```
                    260                 265                 270
Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440

<210> SEQ ID NO 167
<211> LENGTH: 220
<212> TYPE: PRT
<213> ORGANISM: Artificial sequence
<220> FEATURE:
<223> OTHER INFORMATION: h20-L5Y antibody; light chain

<400> SEQUENCE: 167

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ile Asp Gln Lys Asn Tyr Leu Ala Trp Tyr Gln Gln Lys Pro Gly Gln
        35                  40                  45

Pro Pro Lys Leu Leu Ile Tyr Tyr Ala Ser Thr Lys Glu Ser Gly Val
    50                  55                  60

Pro Asp Arg Phe Ser Gly Ser Gly Ser Gly Thr Asp Phe Thr Leu Thr
65                  70                  75                  80

Ile Ser Gly Leu Gln Ala Glu Asp Val Ala Val Tyr Phe Cys Gln Gln
                85                  90                  95

His Tyr Ser Thr Pro Trp Thr Phe Gly Gly Gly Thr Lys Val Glu Ile
            100                 105                 110

Arg Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
```

```
                180              185              190
Glu Lys His Lys Val Tyr Ala Cys Glu Val Thr His Gln Gly Leu Ser
            195                  200              205

Ser Pro Val Thr Lys Ser Phe Asn Arg Gly Glu Cys
        210                  215              220
```

<210> SEQ ID NO 168
<211> LENGTH: 119
<212> TYPE: PRT
<213> ORGANISM: Artificial sequence
<220> FEATURE:
<223> OTHER INFORMATION: VL008-AL13-8G5 antibody; humanized variable
      region heavy chain; VH1m

<400> SEQUENCE: 168

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val His Gln Ala Pro Gly Gln Arg Leu Glu Trp Met
        35                  40                  45

Gly Met Ile His Pro Asn Ser Gly Thr Thr Asn Tyr Asn Gln Lys Phe
    50                  55                  60

Gln Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser His Tyr Tyr Asp Gly His Phe Ser Tyr Trp Gly Gln Gly
            100                 105                 110

Thr Leu Val Thr Val Ser Ser
        115
```

<210> SEQ ID NO 169
<211> LENGTH: 119
<212> TYPE: PRT
<213> ORGANISM: Artificial sequence
<220> FEATURE:
<223> OTHER INFORMATION: VL008-AL13-8G5 antibody; humanized variable
      region heavy chain; VH2m

<400> SEQUENCE: 169

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Met Ile His Pro Asn Ser Gly Thr Thr Asn Tyr Asn Gln Lys Phe
    50                  55                  60

Gln Gly Arg Val Thr Met Thr Val Asp Lys Ser Ala Ser Thr Ala Tyr
65                  70                  75                  80

Met Glu Leu Ser Ser Leu Arg Ser Glu Asp Ser Ala Val Tyr Tyr Cys
                85                  90                  95

Thr Arg Ser His Tyr Tyr Asp Gly His Phe Ser Tyr Trp Gly Gln Gly
            100                 105                 110

Thr Leu Val Thr Val Ser Ser
        115
```

<210> SEQ ID NO 170
<211> LENGTH: 119
<212> TYPE: PRT
<213> ORGANISM: Artificial sequence
<220> FEATURE:
<223> OTHER INFORMATION: VL008-AL13-8G5 antibody; humanized variable
      region heavy chain; VH3

<400> SEQUENCE: 170

Gln Val Gln Leu Gln Glu Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Trp Met His Trp Val Arg Gln Ala Pro Gly Gln Gly Leu Glu Trp Met
            35                  40                  45

Gly Met Ile His Pro Asn Ser Gly Thr Thr Asn Tyr Asn Glu Lys Phe
        50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Ser His Tyr Tyr Asp Gly His Phe Ser Tyr Trp Gly Gln Gly
            100                 105                 110

Thr Leu Val Thr Val Ser Ser
        115

<210> SEQ ID NO 171
<211> LENGTH: 119
<212> TYPE: PRT
<213> ORGANISM: Artificial sequence
<220> FEATURE:
<223> OTHER INFORMATION: VL008-AL13-8G5 antibody; humanized variable
      region heavy chain; VH4

<400> SEQUENCE: 171

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Thr Tyr
                20                  25                  30

Trp Met His Trp Val Arg Gln Ala Pro Gly Gln Gly Leu Glu Trp Met
            35                  40                  45

Gly Met Ile His Pro Asn Ser Gly Thr Thr Asn Tyr Asn Glu Lys Phe
        50                  55                  60

Lys Ser Arg Val Thr Leu Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Thr Arg Ser His Tyr Tyr Asp Gly His Phe Ser Tyr Trp Gly Gln Gly
            100                 105                 110

Thr Met Val Thr Val Ser Ser
        115

<210> SEQ ID NO 172
<211> LENGTH: 112
<212> TYPE: PRT
<213> ORGANISM: Artificial sequence
<220> FEATURE:
<223> OTHER INFORMATION: VL008-AL13-8K3 antibody; humanized variable
      region light chain; VL1

<400> SEQUENCE: 172

```
Asp Ile Val Met Thr Gln Ser Pro Gly Ser Leu Ala Val Ser Leu Gly
1               5                   10                  15

Glu Arg Ala Thr Phe Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Trp Thr Phe Gly Gly Gly Thr Lys Val Glu Val Lys
                100                 105                 110

<210> SEQ ID NO 173
<211> LENGTH: 112
<212> TYPE: PRT
<213> ORGANISM: Artificial sequence
<220> FEATURE:
<223> OTHER INFORMATION: VL008-AL13-8K3 antibody; humanized variable
      region light chain; VL2

<400> SEQUENCE: 173

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Trp Thr Phe Gly Gly Gly Thr Lys Leu Glu Ile Lys
                100                 105                 110

<210> SEQ ID NO 174
<211> LENGTH: 112
<212> TYPE: PRT
<213> ORGANISM: Artificial sequence
<220> FEATURE:
<223> OTHER INFORMATION: VL008-AL13-8K3 antibody; humanized variable
      region light chain; VL3

<400> SEQUENCE: 174

Glu Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Ala Gly Gln
            35                  40                  45

Ser Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80
```

```
Ile Asp Ser Leu Gln Ala Glu Asp Val Ala Val Tyr Tyr Cys Lys Gln
                85                  90                  95

Ser Tyr Asn Leu Trp Thr Phe Gly Gly Gly Thr Lys Val Glu Ile Lys
            100                 105                 110

<210> SEQ ID NO 175
<211> LENGTH: 112
<212> TYPE: PRT
<213> ORGANISM: Artificial sequence
<220> FEATURE:
<223> OTHER INFORMATION: VL008-AL13-8K3 antibody; humanized variable
      region light chain; VL4

<400> SEQUENCE: 175

Asp Ile Val Met Thr Gln Ser Pro Asp Ser Leu Pro Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ala Leu Gln Ala Glu Asp Val Ala Val Tyr Tyr Cys Lys Gln
                85                  90                  95

Ser Tyr Asn Leu Trp Thr Phe Gly Gln Gly Thr Arg Leu Glu Ile Lys
            100                 105                 110

<210> SEQ ID NO 176
<211> LENGTH: 107
<212> TYPE: PRT
<213> ORGANISM: Artificial sequence
<220> FEATURE:
<223> OTHER INFORMATION: Constant region of human kappa light chain

<400> SEQUENCE: 176

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

HUMANIZED, MOUSE OR CHIMERIC ANTI-CD47 MONOCLONAL ANTIBODIES

CROSS-REFERENCE TO RELATED APPLICATIONS

The present application is a continuation of U.S. application Ser. No. 16/068,874, filed Jul. 9, 2018, which is a National Stage of International Application No. PCT/EP17/050508, filed Jan. 11, 2017, which claims priority to European patent application no. 16172651.8, filed Jun. 2, 2016, and European patent application no. 16150808.0, filed Jan. 11, 2016, the entire contents of all of which are hereby incorporated by reference in their entirety.

SEQUENCE LISTING

The present specification makes reference to a Sequence Listing (submitted electronically as a .txt file named "40960 US PCT Sequence Listing.txt" on Jul. 8, 2018). The .txt file was generated on Jul. 8, 2018, and is 102,433 bytes in size. The entire contents of the Sequence Listing are herein incorporated by reference.

FIELD OF THE INVENTION

Humanized, mouse or chimeric anti-CD47 monoclonal antibodies are provided. The antibodies bind to human glycosylated and deglycosylated CD47 with an optimized Koff value, they disrupt the human CD47-SIRPα interaction, and find use in various therapeutic, preventive or diagnostic methods. The invention includes isolated antibodies and derivatives and fragments thereof, pharmaceutical formulations comprising one or more of the humanized or chimeric anti-CD47 monoclonal antibodies; and cell lines that produce these monoclonal antibodies. Also provided are amino acid and nucleotide sequences of the antibodies.

BACKGROUND OF THE INVENTION

Macrophages clear pathogens and damaged or aged cells from the blood stream via phagocytosis. Cell-surface CD47 interacts with its receptor on macrophages, SIRPα, to inhibit phagocytosis of normal, healthy cells. CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells (HSCs).

SIRPα inhibits the phagocytosis of host cells by macrophages, where the ligation of SIRPα on macrophages by CD47 expressed on the host target cell generates an inhibitory signal mediated by SHP-1 that negatively regulates phagocytosis. SIRPα acts to detect signals provided by "self", to negatively control innate immune effector function against these cells.

In keeping with the role of CD47 to inhibit phagocytosis of normal cells, there is evidence that it is upregulated on a number of cancers. Overexpression of CD47 on a cancer cell line, such as e.g. myeloid leukemia, increases its pathogenicity by allowing it to evade phagocytosis. Thus, CD47 up-regulation is an important mechanism that provides protection to normal HSCs during inflammation-mediated mobilization, and that cancer cells co-opt in order to evade macrophage killing.

The present invention provides anti-CD47 antibodies showing various desirable characteristics for the treatment of a disease such as cancer in a subject, e.g. a human.

SUMMARY

In one aspect, the present invention relates to an antibody that binds to glycosylated and non-glycosylated CD47, wherein binding of the antibody to CD47 is not dependent on glycosylation of CD47. In one embodiment, the antibody binds glycosylated and deglycosylated forms of human CD47. In another embodiment, the glycosylated form of human CD47 comprises one or more N-glycosylated residues at positions N23, N34, N50, N73, N111 and/or N206 in the amino acid sequence of human CD47. The deglycosylated form of human CD47 may comprise glycosylated human CD47 that has been treated with a peptide N-glycosidase (PNGase) for removal of N-glycosylations.

In one embodiment, a ratio of EC50s of binding of the antibody to non-glycosylated versus glycosylated forms of CD47 is less than 4:1, 3:1 or 2:1, preferably in a range from 4:1 to 1:4, more preferably 3:1 to 1:3, most preferably 2:1 to 1:2; or a ratio of EC95s of binding of the antibody to non-glycosylated versus glycosylated forms of CD47 is less than 25:1, 20:1 or 10:1, preferably in a range from 10:1 to 1:10, more preferably 9:1 to 1:9, most preferably 10:1 to 1:10.

In another embodiment, the antibody binds to each of glycosylated and non-glycosylated CD47 with an equilibrium binding constant of 80 pM or lower, preferably 70 pM or lower, more preferably 60 pM or lower.

In another embodiment, a maximum binding capacity (Bmax$_2$) of the antibody to non-glycosylated CD47 is at least 60% of a maximum binding capacity (Bmax$_1$) of the antibody to glycosylated CD47.

Preferably the antibody has a Koff value for binding to glycosylated and/or non-glycosylated CD47 of about $1.0 \times 10^{-4}$ s$^{-1}$ (1/s) or more. More preferably the antibody has a Koff value for binding to glycosylated and/or non-glycosylated CD47 of from $1.0 \times 10^{-4}$ s$^{-1}$ to $1.0 \times 10^{-3}$ s$^{-1}$. Most preferably the antibody has a Koff value for binding to glycosylated and/or non-glycosylated CD47 of from $2.5 \times 10^{-4}$ s$^{-1}$ to $5.0 \times 10^{-4}$ s$^{-1}$.

In another aspect, the invention provides an antibody that binds to CD47, wherein the antibody has a Koff value for binding to CD47 of from $1.0 \times 10^{-4}$ s−1 to $1.0 \times 10^{-3}$ s$^{-1}$.

Compositions and methods are provided relating to humanized or chimeric anti-CD47 monoclonal antibodies. The antibodies of the invention bind to CD47 and have a unique functional profile. In particular said antibodies have at least one of the following characteristics: disrupt the human CD47-SIRPα interaction, inhibit the CD47-SIRPα signal transduction, increase phagocytosis of certain CD47 expressing cells, do not cause a significant level of agglutination of cells, and find use in various therapeutic methods. Preferred are antibodies that bind to human CD47 and that are in the IgG4 format. Preferred are antibodies in the bispecific format that bind to human CD47 may also be in the IgG1 format. Preferred are non-activating antibodies with high Koff values (suggesting rapid dissociation kinetics) and weak or absent apoptosis profiles and red blood cell agglutination activity (suggesting low toxicity). Furthermore, preferred are antibodies that bind to human CD47 of different glycosylation pattern and/or to de-glycosylated forms of human CD47. Embodiments of the invention include isolated antibodies and derivatives and fragments thereof, pharmaceutical formulations comprising one or more of the humanized or chimeric anti-CD47 monoclonal antibodies; and cell lines that produce these monoclonal antibodies. Also provided are amino acid and nucleotide sequences of the antibodies.

Antibodies of interest include the provided humanized, engineered or chimeric antibodies, and variants thereof. The monoclonal antibodies of the invention find particular utility as reagents for the diagnosis and immunotherapy of disease associated with CD47 in humans, particularly in cancer therapy such as hematological and solid tumors. An advantage of the monoclonal antibodies of the invention derives from the humanization process. Thus, in vivo use of the monoclonal antibodies of the invention for immunotherapy greatly reduces the problem of significant host immune responses to the antibodies.

Various forms of the antibodies are contemplated herein. For example, the anti-CD47 antibody may be a full length chimeric or humanized antibody, e.g. having a human immunoglobulin constant region of any isotype, e.g. lgG1, lgG2, lgG3, lgG4, IgA, etc., or an antibody fragment, e.g. a single chain antibody, an F(ab')2 fragment, an F(ab) fragment, etc. Fragments comprising CDR regions are also of interest, e.g. for imaging purposes, although the IgG4 format is a clearly preferred form. For a bi-specific approach, the IgG1 format may also be suitable. Furthermore, the antibody may be labeled with a detectable label, immobilized on a solid phase and/or conjugated with a heterologous compound. The antibody may also be provided as a bi-specific or multi-specific antibody reactive with a second antigen, particularly including cancer antigens. A preferred bi-specific antibody is an antibody that is functionally reactive with the Her-2 antigen. Bi-specific antibodies of preferred use are those with a medium binding to human CD47 such as e.g. candidate 20 and 22 and variants thereof (e.g. humanized version thereof).

Diagnostic and therapeutic uses for the antibody are contemplated, particularly relating to the detection and elimination of undesirable cells expressing CD47. In one diagnostic application, the invention provides a method for determining the presence of CD47-expressing cancer cells, comprising exposing a patient sample suspected of containing CD47-expressing cancer cells to the anti-CD47 antibody and determining binding of the antibody to the sample. For this use, the invention provides a kit comprising the antibody and instructions for using the antibody.

The antibodies of the invention are particularly efficacious in the treatment of disease, e.g. increasing the phagocytosis of CD47-expressing cells. Treatment may be systemic or localized, e.g. delivery by intra-tumoral injection, etc.

Embodiments of the invention include isolated antibodies and derivatives and fragments thereof that comprise at least 3 CDR sequences as provided herein, usually in combination with framework sequences from a human variable region. In some embodiments an antibody comprises at least one light chain comprising the 3 light chain CDR sequences provided herein situated in a variable region framework, which may be, without limitation, a human or mouse variable region framework, and at least one heavy chain comprising the 3 heavy chain CDR sequences provided herein situated in a variable region framework, which may be, without limitation, a human or mouse variable region framework.

In other embodiments, the antibody comprises an amino acid sequence variant of the CDRs of the provided antibodies, which variant comprises one or more amino acid insertion(s) within or adjacent to a CDR residue and/or deletion(s) within or adjacent to a CDR residue and/or substitution(s) of CDR residue(s) (with substitution(s) being the preferred type of amino acid alteration for generating such variants). Such variants will normally having a binding affinity for human CD47 of at least about $10^{-8}$ M, such as e.g. a binding affinity to human CD47 between 2 nM to 15 nM, disrupting the human CD47-SIRPα interaction and will bind to the same epitope as an antibody having the amino acid sequence of those set forth herein. Various forms of the antibodies are contemplated herein. For example, the antibody may be a full length antibody, e.g. having a human immunoglobulin constant region of any isotype, e.g. lgG1, lgG2, lgG3, lgG4, IgA, more preferably IgG4 optionally with mutation(s) or an antibody fragment, e.g. an F(ab')2 fragment, an F(ab) fragment, etc. Furthermore, the antibody may be labeled with a detectable label, immobilized on a solid phase and/or conjugated with a heterologous compound.

Embodiments of the invention include anti-CD47 antibodies (i) with potent disruption of the human CD47-SIRPα interaction regardless of the antibody isotype (and effector function), (ii) enabling efficient phagocytosis of CD47-expressing tumor cells by human monocyte-derived macrophages, (iii) with an optimized Koff value of between $1.0\times10^{-4}$ s−1 to $1.0\times10^{-3}$ s−1 (enabling low sink effect and greater availability of antibodies to higher density CD47-carrying cancer cells), and/or (iv) showing inhibition of tumor growth in xenograft mouse models overexpressing the target CD47. A preferred embodiment of the invention is a group of anti-CD47 antibodies that additionally show weak red blood cell agglutination activity suggesting additional low toxicity (candidate NOs 19, 33, 20) and/or do not induce (or only slightly induce) apoptosis of Jurkat cells (candidate NOs 7, 19, 20, 22, 33). Furthermore, a more preferred embodiment of the invention is a group of anti-CD47 antibodies that additionally bind to glycosylated and non-glycosylated CD47 extracellularly or bind to an immunologically active and glycosylated and non-glycosylated fragment thereof. Furthermore, a more preferred embodiment of the invention is a group of anti-CD47 antibodies that bind the monomer and dimer of CD47. Furthermore, a more preferred embodiment of the invention is a group of anti-CD47 antibodies that bind to a particular epitope on CD47, i.e. in particular a discontinuous epitope that comprises K59, R63, Y66, T67, H108, T109, T117 and T120 of human CD47 when numbered in accordance with SEQ ID NO: 151 (e.g. candidate 20 and humanized and engineered version thereof). Another example of an embodiment of the invention is a group of anti-CD47 antibodies that bind to a particular epitope on CD47, i.e. in particular a discontinuous epitope that comprises K59, K61, 5107, H108, T117, T120 and R121 of human CD47 when numbered in accordance with SEQ ID NO: 151 (e.g. candidate 22 and humanized and engineered version thereof).

Embodiments of the invention include anti-CD47 antibodies (i) with potent disruption of the human CD47-SIRPα interaction regardless of the antibody isotype (and effector function), (ii) enabling efficient phagocytosis of CD47-expressing tumor cells by human monocyte-derived macrophages, (iii) with an optimized Koff value of between $1.0\times10^{-4}$ s−1 to $1.0\times10^{-3}$ s−1 (enabling low sink effect and greater availability of antibodies to higher density CD47-carrying cancer cells), (iv) showing inhibition of tumor growth in xenograft mouse models overexpressing the target CD47, and/or (v) and CDR combinations as set out in tables 2 and 3 below, wherein up to 5, more preferably up to 4, 3, 2 or 1 of the amino acids in one or more of the CDRs are replaced by other amino acids such as e.g. conservative substitutions, wherein however the overall profile of the antibody such as the elements (i) to (iv) above is unchanged or similar, i.e. within a 10% range of standard biological variance.

The invention further provides: an isolated nucleic acid encoding the antibodies and variants thereof; a vector comprising that nucleic acid, optionally operably linked to control sequences recognized by a host cell transformed with the vector; a host cell comprising that vector; a process for producing the antibody comprising culturing the host cell so that the nucleic acid is expressed and, optionally, recovering the antibody from the host cell culture (e.g. from the host cell culture medium). The invention also provides a composition comprising one or more of the anti-human CD47 antibodies and a pharmaceutically acceptable carrier or diluent. This composition for therapeutic use is sterile and may be lyophilized, e.g. being provided as a pre-pack in a unit dose with diluent and delivery device, e.g. inhaler, syringe, etc.

BRIEF DESCRIPTION OF THE DRAWINGS

The accompanying drawings are not intended to be drawn to scale. The Figures are illustrative only and are not required for enablement of the disclosure. For purposes of clarity, not every component may be labeled in every drawing. In the drawings:

FIG. 7 The amino-acid sequences of the 5 humanized VH variants (VH1 to VH5) aligned with the sequence of the mouse VH sequence of candidate 20 (VH0). The CDRs are underlined (using the combined definition of KABAT and IMGT).

FIG. 8 The amino-acid sequences of the 5 humanized VL variants (VL1 to VL5) aligned with the sequence of the mouse VL sequence of candidate 20 (VL0). The CDRs are underlined (using the combined definition of KABAT and IMGT).

FIG. 12A), 20.27 (h20-H3-L2Y; FIG. 12B), 20.28 (h20-H3-L3Y; FIG. 12C), 20.29 (h20-H4-L4Y; FIG. 12D), 20.30 (h20-H4-L5Y; FIG. 12E)) were compared with the corresponding variants without the F56Y mutation candidates 20.10 (h20-H2-L5), 20.12 (h20-H3-L2), 20.13 (h20-H3-L3), 20.19 (h20-H4-L4), 20.20 (h20-H4-L5)) and with the chimeric candidate 20 (all antibodies in human IgG4 format).

FIG. 13A), 20.27 (h20-H3-L2Y; FIG. 13B), 20.28 (h20-H3-L3Y; FIG. 13E), 20.29 (h20-H4-L4Y; FIG. 13C), 20.30 (h20-H4-L5Y; FIG. 13D)) were compared with the corresponding variants without the F56Y mutation candidates 20.10 (h20-H2-L5), 20.12 (h20-H3-L2), 20.13 (h20-H3-L3), 20.19 (h20-H4-L4), 20.20 (h20-H4-L5)).

DETAILED DESCRIPTION OF THE INVENTION

Figure 1:
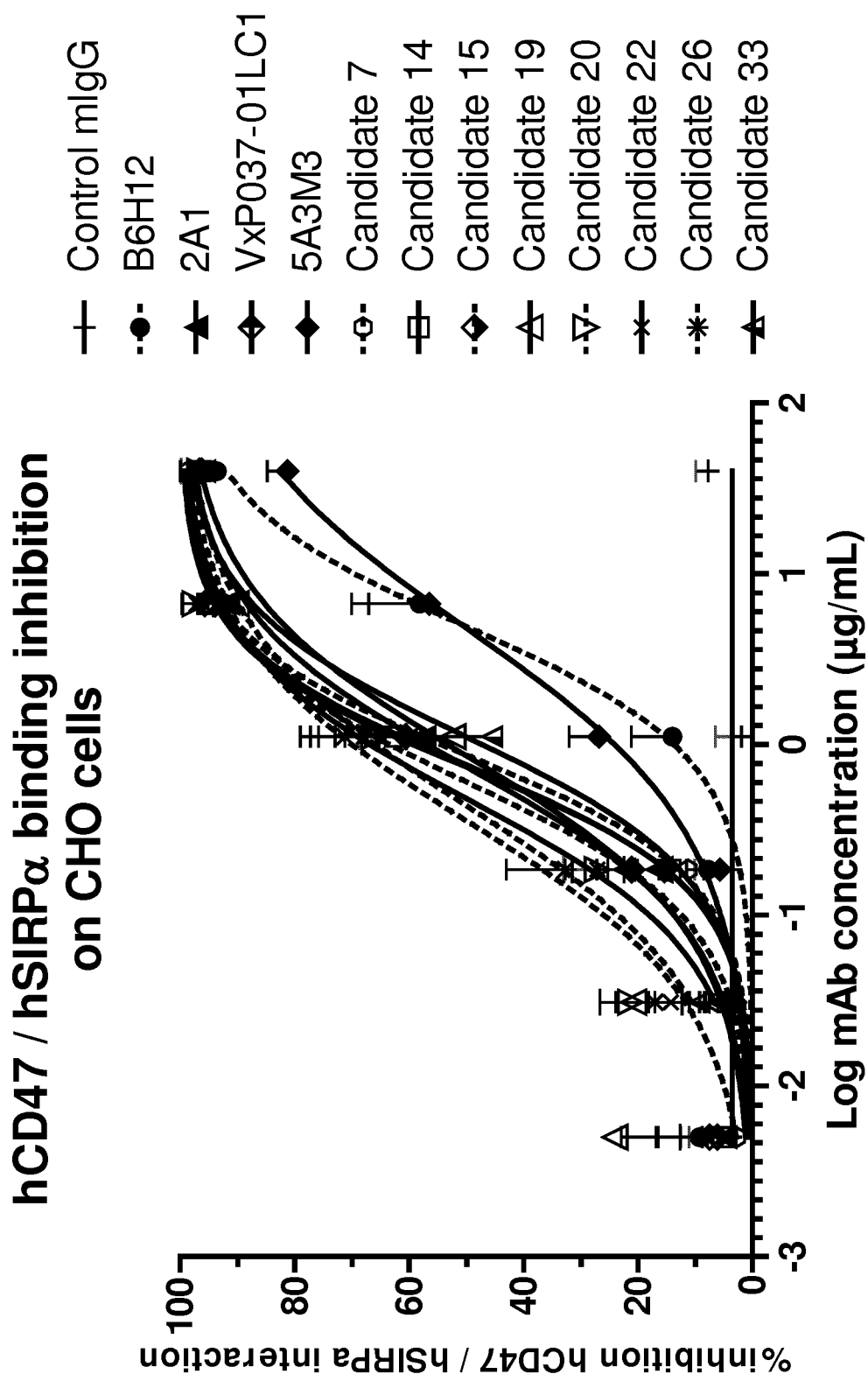
FIG. 1 Inhibition of hSIRPα binding to hCD47 expressed on CHO cells by anti-CD47 antibodies.

The present invention relates to monoclonal antibodies which are specific for CD47. Also disclosed are nucleic acid and amino acid sequences of such antibodies. The antibodies find use in therapeutic and diagnostic methods associated with CD47.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is a human.

The term "antibody" is used in the broadest sense and specifically covers monoclonal antibodies (including full length monoclonal antibodies), polyclonal antibodies, multi-specific antibodies (e.g., bi-specific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the lightand heavy-chain variable domains (Clothia C, Novotný J, Bruccoleri R, Karplus M. "Domain association in immunoglobulin molecules. The packing of variable domains." J. Mol. Biol. 186:651-63 (1985); Novotny J. and Haber E. "Structural invariants of antigen binding: comparison of immunoglobulin VL-VH and VL-VL domain dimers." Proc. Natl. Acad. Sci. U.S.A. 82:4592-96 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (for KABAT annotation see Kabat E. A. Sequences of Proteins of Immunological Interest, Fifth Edition, National Institutes of Health, Bethesda, Md. (1991) or for IMGT annotation, see http://www.imgt.org). The constant domains are not involved directly in the binding of an antibody to an antigen, but exhibit various effector functions, such as participation of the antibody in antibody-dependent cellular toxicity (ADCC).

The CDR sequences of exemplary anti-CD47 heavy and light chain combinations are set forth in the sequence listing, including SEQ ID NOs: 1-120, 152, 153 (see Table 2 and 3, supra).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen recognition and binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that of a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv, see Plückthun A. Antibodies from *Escherichia coli*, in "The Pharmacology of Monoclonal Antibodies", by Rosenburg and Moore eds., Springer-Verlag, New York, vol. 113, pp. 269-315 (1994).

The Fab fragment also contains the constant domain of the light chain and the first constant domain of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Each mAb is directed against a single determinant on the antigen. In addition to their specificity, the monoclonal antibodies are advantageous in that they can be synthesized by hybridoma culture or mammalian cell lines, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made in an immortalized B cell or hybridoma thereof, or may be made by recombinant DNA methods.

The monoclonal antibodies herein include hybrid and recombinant antibodies produced by splicing a variable (including hypervariable) domain of an anti-CD47 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')2, and Fv), so long as they exhibit the desired biological activity.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 75% by weight of antibody as determined by the Lowry method, and most preferably more than 80%, 90% or 99% by weight, or (2) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "epitope tagged" when used herein refers to an anti-CD47 antibody fused to an "epitope tag". The epitope tag polypeptide has enough residues to provide an epitope against which an antibody can be made, yet is short enough such that it does not interfere with activity of the CD47 antibody. The epitope tag preferably is sufficiently unique so that the antibody specific for the epitope does not substantially cross-react with other epitopes. Suitable tag polypeptides generally have at least 6 amino acid residues and usually between about 8-50 amino acid residues (preferably between about 9-30 residues). Examples include the c-myc tag and the 8F9, 3C7, 6E10, G4, B7 and 9E10 antibodies thereto (Evan G. I., Lewis G. K., Ramsay G., et al. "Isolation of monoclonal antibodies specific for human c-myc proto-oncogene product", Mol. Cell. Biol. 5(12):3610-3616 (1985)); and the Herpes Simplex virus glycoprotein D (gD) tag and its antibody (Paborsky L. R., Fendly B. M., Fisher K. L., et al. "Mammalian cell transient expression of tissue factor for the production of antigen", Protein Engineering 3(6):547-553 (1990)).

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

Glycosylation of CD47

CD47 is subject to post-translational modifications, most notably glycosylation. CD47 has a number of N-terminal glycosylation sites that directly affect cell surface display and regulate interaction with extracellular ligands. For instance, deglycosylated CD47 has a higher avidity for SIRPα than glycosylated CD47 and, vice versa, deglycosylated SIRPα has a higher avidity for CD47 (Subramanian S., Boder E. T., and Discher D. E. "Phylogenetic divergence of CD47 interactions with human signal regulatory protein α reveals locus of species specificity." J. Biolog. Chem. 282 (3):1805-18 (2007); Subramanian S., Parthasarathy R., Sen S., Boder E. T., and Discher D. E. "Species and cell type-specific interactions between CD47 and human SIRPα." Blood 107(6):2548-56 (2006)). Reversely, hyperglycosylated SIRPα can disrupt CD47/SIRPα interactions (Ogura T., Noguchi T., Murai-takebe R., Hosooka T., Honma N., and Kasuga M. "Resistance of B16 melanoma cells to CD47-induced negative regulation of motility as a result of aberrant N-glycosylation of SHPS-1." J Biol Chem 279(14): 13711-20 (2004)). Of note, site-directed mutagenesis of N-linked glycosylation sites inhibited cell surface localization of CD47 in yeast models (Parthasarathy R., Subramanian S., Boder E. T., and Discher D. E. "Post-Translational Regulation of Expression and Conformation of an Immunoglobulin Domain in Yeast Surface Display." Biothech Bioin 93(1):159-68 (2006)), although similar mutagenesis did not affect membrane localization of human CD47 in CHO cells (Subramanian et al., 2006, supra). Aberrant glycosylation of either CD47 or SIRPα can also alter downstream responses, with differentially glycosylated SIRPα rendering B16 melanoma cells resistant to CD47-induced inhibition of motility (Ogura et al., 2004, supra). In addition, a heavily glycosylated (>250 kD) form of CD47 has been detected in primary and transformed T-cells, endothelial cells and vascular smooth muscle cells (Kaur S., Kuznetsova S. A., Pendrak M. L., Romeo M. J., Li Z., Zhang L., and Roberts D. D. "Heparan Sulfate Modification of the Transmembrane Receptor CD47 Is Necessary for Inhibition of T Cell Receptor Signaling by Thrombospondin-1", J Biol Chem 286(17):14991-15002 (2011)). This modification was located distally from the SIRPα binding site, but was required for TSP-1 mediated inhibitory signaling in T-cells.

Since tumor cells may express aberrant glycosylation patterns, it would be desirable to provide anti-CD47 antibodies that bind to CD47 independently of glycosylation. However, whereas known therapeutically relevant anti-CD47 antibodies typically bind effectively to glycosylated CD47, they typically bind poorly (e.g. with a lower binding affinity/higher equilibrium binding constant or reduced maximum binding capacity (Bmax)) to non-glycosylated or deglycosylated CD47.

In one aspect, the antibodies of the present invention bind to glycosylated and non-glycosylated CD47. For instance in one embodiment, binding of the antibody to CD47 is not dependent on glycosylation of CD47. By this it is meant that glycosylation of CD47 is not required for adequate binding of the antibody to CD47, e.g. the antibody shows significant specific binding to CD47 irrespective of the level of glycosylation of CD47. In other words, binding of the antibody to CD47 is at least partially, significantly or substantially independent of glycosylation.

As used herein, "glycosylated" CD47 typically refers to (e.g. human) CD47 that has been N-glycosylated at one or more residues. Human CD47 may be N-glycosylated at one or more (e.g. asparagine) residues at positions N23, N34, N50, N73, N111 and N206 in the amino acid sequence of human CD47 (SEQ ID NO:151). Preferably glycosylated CD47 is glycosylated at least two, three, four, five or six of the above positions.

"Deglycosylated" CD47 refers to a form of CD47 in which one or more glycan chains (e.g. N-glycans) have been removed. Deglycosylation of CD47 may be effected by treatment with an enzyme such as peptide N-glycosidase (PNGase), e.g. PNGase F, which removes N-glycans. The terms "non-glycosylated" and "deglycosylated" are used herein interchangeably. Thus the non-glycosylated or deglycosylated form typically lacks glycan residues at positions N23, N34, N50, N73, N111 and/or N206 in the amino acid sequence of human CD47 (SEQ ID NO:151).

In one embodiment deglycosylation of CD47 does not significantly affect the avidity/affinity and/or maximum binding capacity of the antibody to (human) CD47. The avidity/affinity and the maximum binding capacity (Bmax) of the antibody for glycosylated and deglycosylated forms of CD47 may be determined using standard assays e.g. as set out in the Examples below. The affinity of an antibody for its target epitope is inversely related to its dissociation constant. The dissociation constant may also be directly related to the EC50 value for binding of the antibody to CD47. EC50 is the concentration of antibody which provides half maximal binding, i.e. at which 50% of the binding sites on CD47 are bound. Also, the EC95 value, which is the concentration of antibody which provides 95% maximal binding, is indicative of the concentration of antibody for which 95% of the binding sites on CD47 are bound. Whichever measurement is used, according to embodiments of the present invention it is the relative values obtained for glycosylated and non-glycosylated forms that is important, i.e. an absolute value does not necessarily need to be determined provided that the glycosylated and non-glycosylated forms show reasonably similar results.

Thus in some embodiments, the affinity of the antibody for non-glycosylated and glycosylated forms of CD47 may be compared by determining a ratio of EC50 values or EC95 values for binding of the antibody to each form. Preferably this ratio is less than 5:1, 4:1, 3:1, or 2:1 but may be even higher for the EC95, i.e. may be 25:1, 20:1, 10:1, preferably in a range from 10:1 to 1:10, more preferably 9:1 to 1:9, most preferably 10:1 to 1:10. In other words, the EC50 for binding of the antibody to non-glycosylated CD47 may be no more than 3 or 2 fold higher than the EC50 value for binding of the antibody to glycosylated CD47. The EC95 for binding of the antibody to non-glycosylated CD47 may be no more than 9 or 10 fold higher than the EC95 value for binding of the antibody to glycosylated CD47. In further embodiments, the ratio of EC50 is preferably in the range from 3:1 to 1:3 or 2:1 to 1:2, most preferably 3:1 to 1:3; or the ratio of EC95 is preferably in the range from 10:1 to 1:10, more preferably 9:1 to 1:9, most preferably 10:1 to 1:10. In such embodiments it is considered that deglycosylation does not significantly affect the binding affinity, i.e. binding of the antibody to CD47 is not dependent on glycosylation. In some embodiments, the antibody binds to the non-glycosylated form of CD47 (and preferably to both the non-glycosylated and glycosylated forms of CD47) with an equilibrium binding constant of 80 pM or lower, preferably 70 pM or lower, more preferably 60 pM or lower.

In other embodiments, deglycosylation of CD47 does not significantly reduce the maximum binding capacity of the antibody to CD47. For instance, the maximum binding capacity (i.e. $Bmax_1$) may be determined for binding of the antibody to glycosylated CD47. $Bmax_1$ relates to the level of binding of the antibody to CD47 at excess antibody concentration, i.e. the maximum level of specific binding between the antibody and CD47. $Bmax_1$ is thus a measure of the concentration of available binding sites for the antibody on glycosylated CD47. CD47 may then be deglycosylated (e.g. using PNGase) and the level of binding to CD47 at excess antibody concentration determined once again (at the same concentration of CD47 in the sample). The maximum binding capacity (i.e. $Bmax_2$) of the antibody to deglycosylated CD47 is therefore a measure of the concentration of available binding sites for the antibody on deglycosylated CD47.

In preferred embodiments, the maximum binding capacity (i.e. $Bmax_2$) of the antibody to non-glycosylated CD47 is at least 60%, or at least 70% of the maximum binding capacity (i.e. $Bmax_1$) of the antibody to glycosylated CD47. In such embodiments it is considered that deglycosylation does not significantly affect the maximum binding capacity, i.e. binding of the antibody to CD47 is not dependent on glycosylation.

In further embodiments, the binding properties of the antibody to glycosylated and deglycosylated forms of CD47 may be compared based on a ratio of EC95 values. EC95 is the concentration of antibody at which 95% of the binding sites on CD47 are bound. Thus in some embodiments, the affinity of the antibody for non-glycosylated and glycosylated forms of CD47 may be compared by determining a ratio of EC95 values for binding of the antibody to each form. Preferably this ratio is less than 10:1 or 9:1. In other words, the EC95 for binding of the antibody to non-glycosylated CD47 may be no more than 10 or 9 times higher than the EC95 for binding of the antibody to glycosylated CD47.

Antibody Dissociation Kinetics

In another aspect of the present invention, anti-CD47 antibodies are provided having a dissociation rate (Koff) from CD47 within a defined range. In particular, it has been demonstrated that anti-CD47 antibodies with a high dissociation rate characterized by a Koff value superior to $1 \times 10^{-3}$ $s^{-1}$ detach strongly and rapidly from RBCs but also lose rapidly most of their functional activity on tumor cells, e.g. enhancement of tumor cell phagocytosis. In contrast, anti-CD47 antibodies with a very slow dissociation rate characterized by a Koff value inferior to $1 \times 10^{-4}$ $s^{-1}$ detach more slowly from the tumor cells, but will stay stuck on RBCs and may thus have an important sink effect and possibly more side effects.

Therefore, anti-CD47 antibodies with intermediate dissociation kinetics characterized by a Koff value comprised between $1 \times 10^{-4}$ and $1 \times 10^{-3}$ $s^{-1}$ possess an optimal CD47 binding/release equilibrium, i.e. provide a weak sink effect and side effects while maintaining their anti-tumor efficacy. Accordingly, in one aspect the present invention provides an antibody that binds to CD47 and a Koff value for binding to CD47 comprised between $1.0 \times 10^{-4}$ $s^{-1}$ to $1.0 \times 10^{-3}$ $s^{-1}$. In particular embodiments, the antibody may bind to glycosylated and/or non-glycosylated CD47 with a Koff value in this range. Preferably the antibody has a Koff value for binding to (e.g. glycosylated and/or non-glycosylated) CD47 comprised between $1.0 \times 10^{-4}$ $s^{-1}$ to $1.0 \times 10^{-3}$ $s^{-1}$, $2.0 \times 10^{-4}$ $s^{-1}$ to $1.0 \times 10^{-3}$ $s^{-1}$, $2.5 \times 10^{-4}$ $s^{-1}$ to $8.0 \times 10^{-4}$ $s^{-1}$, $2.5 \times 10^{-4}$ $s^{-1}$ to $5.0 \times 10^{-4}$ $s^{-1}$, or $3.0 \times 10's^{-1}$ to $4.5 \times 10^{-4}$ $s^{-1}$.

Antibodies

In one aspect, the present invention is directed to mouse, humanized or chimeric monoclonal antibodies that are specifically binding to human CD47, and cell lines that produce such antibodies. Such anti-CD47 antibodies of the invention show various desirable characteristics for cancer therapy (but not limited thereto) such as potent disruption of the CD47-SIRPα interaction regardless of the antibody isotype (and effector functions), a rapid kinetics of dissociation with Koff values in the range of $1.0 \times 10^{-4}$ $s^{-1}$ to $1.0 \times 10^{-3}$ $s^{-1}$, $2.0 \times 10^{-4}$ $s^{-1}$ to $1.0 \times 10^{-3}$ $s^{-1}$, $2.5 \times 10^{-4}$ $s^{-1}$ to $8.0 \times 10^{-4}$ $s^{-1}$, $2.5 \times 10^{-4}$ $s^{-1}$ to $5.0 \times 10^{-4}$ $s^{-1}$, or $3.0 \times 10^{-4}$ $s^{-1}$ to $4.5 \times 10^{-4}$ $s^{-1}$ (wherein the benchmark antibodies show lower Koff values between 5.0 to $8.9 \times 10^{-5}$ $s^{-1}$). Furthermore, the antibodies of the invention are released rapidly after binding to CD47 on red blood cells (wherein the benchmark antibodies with lower Koff values are more slowly released). Additionally, the anti-CD47 antibodies of the invention enable efficient phagocytosis of CD47-expressing tumor cells by human monocyte-derived macrophages. Moreover, the anti-CD47 antibodies of the invention show inhibition of tumor growth in xenograft mouse models overexpressing the target CD47. Moreover, said antibodies have at least one of the following characteristics: disrupt the CD47-SIRPα interaction, bind to glycosylated and non-glycosylated CD47 with a ratio of EC50 on deglycosylated CD47 versus glycosylated CD47 not superior to 3.0 and a ratio of EC95 on deglycosylated CD47 versus glycosylated CD47 not superior to 10.0, inhibit the CD47-SIRPα signal transduction, increase phagocytosis of certain CD47 expressing cells, do not cause a significant level of agglutination of cells, and find use in various therapeutic and diagnostic methods. Preferred are antibodies that bind to human CD47 and that are in the IgG4 format with optional mutation(s) (e.g. replacement of amino acids in order to remove T cell epitope(s) even in the CDR region such as CDR2). A preferred embodiment of the invention is a group of anti-CD47 antibodies that additionally show weak red blood cell agglutination activity suggesting additional low toxicity (candidate NOs 19, 33, 20 (including the humanized and further engineered antibodies of candidate 20)) and/or do not induce (or only slightly induce) apoptosis of Jurkat cells (candidate NOs 7, 19, 20 (including the humanized and further engineered antibodies of candidate 20), 22 (including the humanized and further engineered antibodies of candidate 22), 33). Furthermore, a more preferred embodiment of the invention is a group of anti-CD47 antibodies that additionally bind to glycosylated and non-glycosylated CD47 extracellularly or bind to an immunologically active and glycosylated and non-glycosylated fragment thereof. Furthermore, a more preferred embodiment of the invention is a group of anti-CD47 antibodies that bind to the monomer and dimer of CD47 such as human CD47. Furthermore, a more preferred embodiment of the invention is a group of anti-CD47 antibodies that bind to a particular epitope on CD47, i.e. in particular a discontinuous epitope that comprises K59, R63, Y66, T67, H108, T109, T117 and T120 of human CD47 when numbered in accordance with SEQ ID NO: 151 (e.g. candidate 20 and humanized and engineered version thereof). Another example of an embodiment of the invention is a group of anti-CD47 antibodies that bind to a particular epitope on CD47, i.e. in particular a discontinuous epitope that comprises K59, K61, 5107, H108, T117, T120 and R121 of human CD47 when numbered in accordance with SEQ ID NO: 151 (e.g. candidate 22 and humanized and engineered version thereof).

Preferred candidates are candidates 7, 14, 15, 19, 20, 22, 26 and 33. Even more preferred candidates are 7, 19, 20, 22, and 33. Even more preferred candidates are 20 and 22. The most preferred candidate is candidate 20 (including the humanized and further engineered antibodies of candidate 20, i.e. candidates 20.1 to 20.30). The CDRs (in KABAT– (Table 2) and IMGT– (Table 3) annotations) and variable regions (Table 1) of exemplary antibodies (referred herein usually by candidate NOs or antibody name) are provided (IMGT annotations preferred). Antibodies of interest include these provided combinations, as well as fusions of the variable regions to appropriate constant regions or fragments of constant regions, e.g. to generate F(ab)' antibodies. Variable regions of interest include at least one CDR sequence of the provided anti-CD47 antibodies, where a CDR may be 3, 4, 5, 6, 7, 8, 9, 10, 11, 12 or more amino acids.

Alternatively, antibodies of interest include a variable region as set forth in the provided antibodies, or pairs of variable regions sequences as set forth herein. These antibodies may be full length antibodies, e.g. having a human immunoglobulin constant region of any isotype, e.g. lgG1, lgG2, lgG3, lgG4, IgA, more preferably IgG4 optionally with mutation(s), e.g. wherein some or all T cell epitope(s) even if in the CDR region are replaced e.g. by silent conservative amino acid(s) (see also experimental part for examples), examples such as the S228P and L235E mutations, i.e. wherein the S228P and L235E mutations are introduced to avoid potential chain exchanges and to decrease the affinity of hIgG4 to Fc gamma receptors, respectively.

TABLE 1

Selected candidates with candidate no, antibody name, variable region of heavy chain (VH) SEQ ID NOs and variable region of light chain (VL) SEQ ID NOs:

| Candidate NO | Antibody name | Variable Region of Heavy chain (herein also referred to as "VH") SEQ ID NO | Variable Region of Light Chain (herein also referred to as "VL") SEQ ID NO |
|---|---|---|---|
| 7 | VT008-AL5-10G7-10K7 | 121 | 122 |
| 14 | VT008-AL6-14G1-16K1 | 123 | 124 |
| 15 | VT008-AL6-18G1-18K21 | 125 | 126 |
| 19 | VL008-AL17-7G1-7K6 | 127 | 128 |
| 20 | VL008-AL18-14G4-14K1 | 129 | 130 |
| 22 | VL008-AL13-8G5-8K3 | 131 | 132 |
| 26 | VT008-AL6-10G3-10K1 | 133 | 134 |
| 29 | VT008-AL6-20G7-20K7 | 135 | 136 |
| 30 | VT008-AL6-39G2-39K2 | 137 | 138 |
| 33 | VL008-AL17-8G5-8K7 | 139 | 140 |
| 20.1 | H20-VH1-VL1 | 141 | 146 |
| 20.2 | H20-VH1-VL2 | 141 | 147 |
| 20.3 | H20-VH1-VL3 | 141 | 148 |
| 20.4 | H20-VH1-VL4 | 141 | 149 |
| 20.5 | H20-VH1-VL5 | 141 | 150 |
| 20.6 | H20-VH2-VL1 | 142 | 146 |
| 20.7 | H20-VH2-VL2 | 142 | 147 |
| 20.8 | H20-VH2-VL3 | 142 | 148 |
| 20.9 | H20-VH2-VL4 | 142 | 149 |
| 20.10 | H20-VH2-VL5 | 142 | 150 |
| 20.11 | H20-VH3-VL1 | 143 | 146 |
| 20.12 | H20-VH3-VL2 | 143 | 147 |
| 20.13 | H20-VH3-VL3 | 143 | 148 |
| 20.14 | H20-VH3-VL4 | 143 | 149 |
| 20.15 | H20-VH3-VL5 | 143 | 150 |
| 20.16 | H20-VH4-VL1 | 144 | 146 |
| 20.17 | H20-VH4-VL2 | 144 | 147 |
| 20.18 | H20-VH4-VL3 | 144 | 148 |
| 20.19 | H20-VH4-VL4 | 144 | 149 |
| 20.20 | H20-VH4-VL5 | 144 | 150 |
| 20.21 | H20-VH5-VL1 | 145 | 146 |
| 20.22 | H20-VH5-VL2 | 145 | 147 |
| 20.23 | H20-VH5-VL3 | 145 | 148 |
| 20.24 | H20-VH5-VL4 | 145 | 149 |
| 20.25 | H20-VH5-VL5 | 145 | 150 |
| 20.26 | H20-VH2-VL5, Y; h20-H2-L5Y | 142 | 159 |
| 20.27 | H20-VH3-VL2, Y; h20-H3-L2Y | 143 | 156 |
| 20.28 | H20-VH3-VL3, Y; h20-H3-L3Y | 143 | 157 |
| 20.29 | H20-VH4-VL4, Y; h20-H4-L4Y | 144 | 158 |
| 20.30 | H20-VH4-VL5, Y; h20-H4-L5Y | 144 | 159 |
| 20,Y | VL008-AL18-14G4-14K1, Y | 129 | 154 |
| 22.1 | H22-VH1-VL1 | 168 | 172 |
| 22.2 | H22-VH1-VL2 | 168 | 173 |
| 22.3 | H22-VH1-VL3 | 168 | 174 |
| 22.4 | H22-VH1-VL4 | 168 | 175 |
| 22.5 | H22-VH2-VL1 | 169 | 172 |
| 22.6 | H22-VH2-VL2 | 169 | 173 |
| 22.7 | H22-VH2-VL3 | 169 | 174 |
| 22.8 | H22-VH2-VL4 | 169 | 175 |
| 22.9 | H22-VH3-VL1 | 170 | 172 |
| 22.10 | H22-VH3-VL2 | 170 | 173 |
| 22.11 | H22-VH3-VL3 | 170 | 174 |
| 22.12 | H22-VH3-VL4 | 170 | 175 |
| 22.13 | H22-VH4-VL1 | 171 | 172 |
| 22.14 | H22-VH4-VL2 | 171 | 173 |
| 22.15 | H22-VH4-VL3 | 171 | 174 |
| 22.16 | H22-VH4-VL4 | 171 | 175 |

TABLE 2

Selected candidates with candidate no, antibody name, CDRs of heavy chain (VH) SEQ ID NOs and CDRs of light chain (VL) SEQ ID NOs (KABAT annotations):

| Candidate NO | Antibody name | SEQ ID NO of CDR1 of VH | SEQ ID NO of CDR2 of VH | SEQ ID NO of CDR3 of VH | SEQ ID NO of CDR1 of VL | SEQ ID NO of CDR2 of VL | SEQ ID NO of CDR3 of VL |
|---|---|---|---|---|---|---|---|
| 7 | VT008-AL5-10G7-10K7 | 1 | 2 | 3 | 7 | 8 | 9 |
| 14 | VT008-AL6-14G1-16K1 | 13 | 14 | 15 | 19 | 20 | 21 |
| 15 | VT008-AL6-18G1-18K21 | 25 | 26 | 27 | 31 | 32 | 33 |
| 19 | VL008-AL17-7G1-7K6 | 37 | 38 | 39 | 43 | 44 | 45 |
| 20 | VL008-AL18-14G4-14K1 | 49 | 50 | 51 | 55 | 56 | 57 |
| 22 | VL008-AL13-8G5-8K3 | 61 | 62 | 63 | 67 | 68 | 69 |
| 26 | VT008-AL6-10G3-10K1 | 73 | 74 | 75 | 79 | 80 | 81 |
| 29 | VT008-AL6-20G7-20K7 | 85 | 86 | 87 | 91 | 92 | 93 |
| 30 | VT008-AL6-39G2-39K2 | 97 | 98 | 99 | 103 | 104 | 105 |
| 33 | VL008-AL17-8G5-8K7 | 109 | 110 | 111 | 115 | 116 | 117 |
| 20, corrected T cell epitope | VL008-AL18-14G4-14K1, corrected T cell epitope | 49 | 50 | 51 | 55 | 152 | 57 |

TABLE 3

Selected candidates with candidate no, antibody name, CDRs of heavy chain (VH) SEQ ID NOs and CDRs of light chain (VL) SEQ ID NOs (IMGT annotations):

| Candidate NO | Antibody name | SEQ ID NO of CDR1 of VH | SEQ ID NO of CDR2 of VH | SEQ ID NO of CDR3 of VH | SEQ ID NO of CDR1 of VL | SEQ ID NO of CDR2 of VL | SEQ ID NO of CDR3 of VL |
|---|---|---|---|---|---|---|---|
| 7 | VT008-AL5-10G7-10K7 | 4 | 5 | 6 | 10 | 11 | 12 |
| 14 | VT008-AL6-14G1-16K1 | 16 | 17 | 18 | 22 | 23 | 24 |
| 15 | VT008-AL6-18G1-18K21 | 28 | 29 | 30 | 34 | 35 | 36 |
| 19 | VL008-AL17-7G1-7K6 | 40 | 41 | 42 | 46 | 47 | 48 |
| 20 | VL008-AL18-14G4-14K1 | 52 | 53 | 54 | 58 | 59 | 60 |
| 22 | VL008-AL13-8G5-8K3 | 64 | 65 | 66 | 70 | 71 | 72 |
| 26 | VT008-AL6-10G3-10K1 | 76 | 77 | 78 | 82 | 83 | 84 |
| 29 | VT008-AL6-20G7-20K7 | 88 | 89 | 90 | 94 | 95 | 96 |
| 30 | VT008-AL6-39G2-39K2 | 100 | 101 | 102 | 106 | 107 | 108 |
| 33 | VL008-AL17-8G5-8K7 | 112 | 113 | 114 | 118 | 119 | 120 |
| 20, corrected T cell epitope | VL008-AL18-14G4-14K1, corrected T cell epitope | 52 | 53 | 54 | 58 | 153 | 60 |

In addition to Fabs, smaller antibody fragments and epitope-binding peptides having binding specificity for at least one epitope of CD47 are also contemplated by the present invention and can also be used in the methods of the invention. For example, single chain antibodies can be constructed according to the method of U.S. Pat. No. 4,946,778, which is incorporated herein by reference in its entirety. Single chain antibodies comprise the variable regions of the light and heavy chains joined by a flexible linker moiety. Yet smaller is the antibody fragment known as the single domain antibody, which comprises an isolate VH single domain. Techniques for obtaining a single domain antibody with at least some of the binding specificity of the intact antibody from which they are derived are known in the art. For instance, Ward et al. (Ward S., Güssow D., Griffiths A. D., Jones P. T., and Winter G. "Binding Activities of a Repertoire of Single Immunoglobulin Variable Domains Secreted from *Escherichia coli*," Nature 341:544-46 (1989)), disclose a method for screening to obtain an antibody heavy chain variable region (H single domain antibody) with sufficient affinity for its target epitope to bind thereto in isolated form.

The invention also provides isolated nucleic acids encoding the humanized or chimeric anti-CD47 antibodies, vectors and host cells comprising the nucleic acid, and recombinant techniques for the production of the antibody. Nucleic acids of interest may be at least about 80% identical to the provided nucleic acid sequences, at least about 85%, at least about 90%, at least about 95%, at least about 99%, or identical. Such contiguous sequences may encode a CDR sequence, or may encode a complete variable region. As is known in the art, a variable region sequence may be fused to any appropriate constant region sequence.

For recombinant production of the antibody, the nucleic acid encoding it is inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

The anti-CD47 antibody of this invention may be produced recombinantly not only directly, but also as a fusion polypeptide with a heterologous or homologous polypeptide, which include a signal sequence or other polypeptide having a specific cleavage site at the N-terminus of the mature protein or polypeptide, an immunoglobulin constant region sequence, and the like. A heterologous signal sequence selected preferably may be one that is recognized and processed (i.e., cleaved by a signal peptidase) by the host cell. For prokaryotic host cells that do not recognize and process the native antibody signal sequence, the signal sequence is substituted by a prokaryotic signal sequence selected.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is different than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

Suitable host cells for cloning or expressing the DNA are the prokaryote, yeast, or higher eukaryote cells. Examples of useful mammalian host cell lines are monkey kidney CV1 line transformed by SV40 (COS-7, ATCC CRL 1651); human embryonic kidney cells (293 or 293 cells subcloned for growth in suspension culture, Graham F. L. and Smiley J. "Characteristics of a human cell line transformed by DNA from human adenovirus type 5," J. Gen. Virol. 36:59-72 (1977)); baby hamster kidney cells (BHK, ATCC CCL 10); Chinese hamster ovary cells; Chinese hamster ovary cells/ dhFr– (CHO/dhFr–, Urlaub G. and Chasin L. A. "Isolation of Chinese hamster cell mutants deficient in dihydrofolate reductase activity," Proc. Natl. Acad. Sci. USA 77(7):4216-20 (1980)); mouse Sertoli cells (TM4, Mather J. P. "Establishment and characterization of two distinct mouse testicular epithelial cell lines", Biol. Reprod. 23(1):243-251 (1980)); monkey kidney cells (CV1, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); TR1 cells (Mather J. P., Zhuang L. Z., Perez-Infante V., and Phillips D. M. "Culture of testicular cells in hormone-supplemented serum-free medium", Annals N.Y. Acad. Sci. 383:44-68 (1982)); MRC 5 cells; EB66 cells (see e.g. EP 2150275B1); FS4 cells; and a human hepatoma line (Hep G2). Host cells are transformed with the above-described expression or cloning vectors for anti-CD47 antibody production and cultured in conventional nutrient media modified as appropriate for inducing promoters, selecting transformants, or amplifying the genes encoding the desired sequences.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark R., Thoren-Tolling K., Sjöquist J. "Binding of immunoglobulins to protein A and immunoglobulin levels in mammalian sera", J. Immunol. Meth. 62(1):1-13 (1983)). Protein G is recommended for human γ3 (Guss M., Eliasson M., Olsson A., Uhlén M., Frej A. K., Jörnvall H., Flock J. I., and Lindberg M. "Structure of the IgG-binding regions of streptococcal protein G", EMBO J. 5(1):1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin, SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Methods of Use

The humanized or chimeric monoclonal antibodies of the invention can be used in the modulation of phagocytosis, including the methods set forth in International Application US2009/000319, herein specifically incorporated by reference in its entirety. For example, antibody compositions may be administered to increase phagocytosis of cancer cells expressing CD47 and thus are suitable for the treatment of cancer in a subject by administering an effective amount of humanized or chimeric monoclonal antibodies of the invention.

Pharmaceutical compositions for use in the treatment of cancer comprising the humanized or chimeric monoclonal antibodies of the invention and optionally pharmaceutically suitable excipients or carrier are also provided.

The humanized or chimeric monoclonal antibodies of the invention can be used in vitro and in vivo to monitor the course of CD47 disease therapy. Thus, for example, by measuring the increase or decrease in the number of cells expressing CD47, particularly cancer cells expressing CD47, it can be determined whether a particular therapeutic regimen aimed at ameliorating disease is effective.

In a preferred embodiment, the humanized or chimeric monoclonal antibodies of the invention can be used in treating, delaying the progression of, preventing relapse of or alleviating a symptom of a cancer or other neoplastic condition, as a monotherapy, or in combinations with other anti-cancer agent(s) (combination therapy). As used herein, the terms "cancer" "neoplasm" and "tumor" are interchangeable. Examples of cancer include, without limitation, gastric cancer, breast cancer, lung cancer, ovarian cancer, cervical cancer, prostate cancer, bladder cancer, colorectal cancer, pancreatic cancer, liver cancer, renal cancer, thyroid cancer, brain cancer, head and neck cancer, hematological cancer, carcinoma, melanoma, leiomyoma, leiomyosarcoma, glioma, glioblastoma, etc. The "hematological cancer" refers to a cancer of the blood, and includes leukemia, lymphoma and myeloma among others. Solid tumors include, for example, gastric tumor, breast tumors, lung tumors, ovarian tumors, prostate tumors, bladder tumors, colorectal tumors, pancreatic tumors, liver tumors, kidney tumors, thyroid tumor, brain tumor, head and neck tumors, esophageal tumors and melanoma tumors, etc. Symptoms associated with cancers and other neoplastic disorders include, but are not limited to, inflammation, fever, general malaise, pain, loss of appetite, weight loss, edema, headache, fatigue, rash, anemia, muscle weakness and muscle fatigue.

The combination therapy can include one or more antibodies of the invention co-formulated with, and/or co-administered with, one or more additional therapeutic agents, e.g., chemotherapeutic or anti-neoplastic agents, such as cytokine and growth factor inhibitors, immunosuppressants, anti-inflammatory agents, metabolic inhibitors, enzyme inhibitors, and/or cytotoxic or cytostatic agents. The term "combination" in this context means that the agents are given substantially contemporaneously, either simultaneously or sequentially. Exemplary chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochlorperazine, saporin, tamoxifen, taxol, topotecan hydrochloride, vinblastine, vincristine and vinorelbine tartrate.

The antibodies of the invention can be combined with an effective dose of an agent that increases patient hematocrit, for example erythropoietin stimulating agents (ESA). Such agents are known and used in the art, including, for example, Aranesp®, Epogen® NF/Procrit® NF, Omontys®, Procrit®, etc.

In other embodiments, the antibodies of the invention can be combined with an effective dose of other antibodies that have been used in treatment of cancer including, without limitation the following FDA approved monoclonal antibodies: rituximab (Rituxan®, CD20: chimeric IgG1), trastuzumab (Herceptin®, HER2: chimeric IgG1), alemtuzumab (Campath®, CD52: humanized IgG1), ibritumomab tiuxetan (Zevalin®, CD20: murine, IgG1, radiolabeled (Yttrium 90), tositumomab-I-131 (Bexxar®: CD20, murine, IgG2a, radiolabeled (Iodine 131)), cetuximab (Erbitux®, EGFR: cjimeric, IgG1), bevacizumab (VEGF: humanized, IgG4), panitumumab (Vectibix®, EGFR: human IgG2), ofatumumab (Arzerra®, CD20: human IgG1), ipilimumab (Ypervoy®, CTLA-4: human IgG1), brentiuximab vedotin (Adectris®, CD30: chimeric, IgG1, drug-conjugate), pertuzumab (Perjecta®, HER2: humanized IgG1, drug conjugate), adotrastuzumab ematansine (Kadcyla®, HER2: humanized, IgG1, drug-conjugate), obinutuzumab (Gazyva®, CD20: humanized and glycol-engineered), nivolumab and pembrolizumab (anti-PD-1s), etc. Trastuzumab targets the HER-2 antigen. This antigen is seen on 25% to 35% of breast cancers and on metastatic gastric cancers. Trastuzumab is approved for the treatment of HER2-overexpressing breast cancers and for HER2-overexpressing metastatic gastric and gastroesophageal junction adenocarcinoma. Cetuximab is used for the treatment of metastatic colorectal cancer, metastatic non-small cell lung cancer and head and neck cancer. Nivolumab and pembrolizumab have been recently approved to treat metastatic melanoma and non-small cell lung cancer. They are tested in clinical trials for lung cancer, renal-cell cancer, lymphoma and mesothelioma. Other cancer drug that are currently tested in clinical trials or researched may also be combined.

Preferred combinations are combinations of a CD47 antibody of the invention and i) an immune check-point inhibitor or ii) an immune modulator reprogramming the antitumor activity of macrophages and dendritic cells or iii) an antibody against a tumor associated antigen. Exemplified combinations are herein described for Herceptin® and Erbitux®, wherein the combination with Herceptin® is preferred due to its additive, cooperative, or possibly synergistic effect. Other agents may also be useful to be combined.

The monoclonal antibodies of the invention may be used in vitro in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are flow cytometry, e.g. FACS, MACS, immunohistochemistry, competitive and non-competitive immunoassays in either direct or indirect formats; and the like. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of CD47-expressing cells. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art, which find use as tracers in therapeutic methods, for use in diagnostic methods, and the like. For diagnostic purposes a label may be covalently or non-covalently attached to an antibody of the invention or a fragment thereof, including fragments consisting or comprising of CDR sequences. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

In some embodiments the antibody or a fragment thereof is attached to a nanoparticle, e.g. for use in imaging. Useful nanoparticles are those known in the art, for example including without limitation, Raman-silica-gold-nanoparticles (R-Si—Au-NP). The R-Si—Au-NPs consist of a Raman organic molecule, with a narrow-band spectral signature, adsorbed onto a gold core. Because the Raman organic molecule can be changed, each nanoparticle can carry its own signature, thereby allowing multiple nanoparticles to be independently detected simultaneously by multiplexing. The entire nanoparticle is encapsulated in a silica shell to hold the Raman organic molecule on the gold nanocore. Optional polyethylene glycol (PEG)-ylation of R-Si—Au-NPs increases their bioavailability and provides functional "handles" for attaching targeting moieties (see Thakor A. S., Luong R., Paulmurugan R., et al. et al. "The fate and toxicity of raman-active silica-gold nanoparticles in mice", Sci. Transl. Med. 3(79):79ra33 (2011); Jokerst J. V., Miao Z., zavaleta C., Cheng Z., and Gambhir S. S. "Affibody-functionalized gold-silica nanoparticles for Raman molecular imaging of the epidermal growth factor receptor", Small. 7(5):625-33 (2011); Gao J., Chen K., Miao Z., Ren G., Chen X., Gambhir S. S., Cheng Z. "Affibody-based nanoprobes for HER2-expressing cell and tumor imaging", Biomaterials 32(8):2141-8 (2011); each herein specifically incorporated by reference).

For purposes of the invention, CD47 may be detected by the monoclonal antibodies of the invention when present in biological fluids and on tissues, in vivo or in vitro. Any sample containing a detectable amount of CD47 can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Therapeutic formulations comprising one or more antibodies of the invention are prepared for storage by mixing the antibody having the desired degree of purity with optional physiologically acceptable carriers, excipients or stabilizers (Remington's Pharmaceutical Sciences, 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent the CD47-associated disease.

The therapeutic dose may be at least about 0.01 mg per kg body weight, at least about 0.05 mg per kg body weight; at least about 0.1 mg per kg body weight, at least about 0.5 mg per kg body weight, at least about 1 mg per kg body weight, at least about 2.5 mg per kg body weight, at least about 5 mg per kg body weight, at least about 10 mg per kg body weight, and not more than about 100 mg per kg body weight with a preference of 0.1 to 20 mg per kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g., i.m., i.p., i.v., and the like.

The antibody need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences, 16th edition, Osol, A. Ed. (1980).

The anti-CD47 antibody is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the anti-CD47 antibody is suitably administered by pulse infusion, particularly with declining doses of the antibody.

For the prevention or treatment of disease, the appropriate dosage of antibody will depend on the type of disease to be treated, as defined above, the severity and course of the disease, whether the antibody is administered for preventive purposes, previous therapy, the patient's clinical history and response to the antibody, and the discretion of the attending physician. The antibody is suitably administered to the patient at one time or over a series of treatments.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-CD47 antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and/or dextrose solution. It may further include other materials desirable from a commercial and user standpoint, including other buffers, diluents, filters, needles, syringes, and package inserts with instructions for use.

The invention now being fully described, it will be apparent to one of ordinary skill in the art that various changes and modifications can be made without departing from the spirit or scope of the invention.

---

SEQUENCES

SEQ ID NO: 1
VT008-AL5-10G7; heavy chain; CDR1-Kabat
KYWMH

SEQ ID NO: 2
VT008-AL5-10G7; heavy chain; CDR2-Kabat
EINPSDTYTNYNQKFKG

| SEQUENCES |
|---|
| SEQ ID NO: 3<br>VT008-AL5-10G7; heavy chain; CDR3-Kabat<br>VATMVARGFAY |
| SEQ ID NO: 4<br>VT008-AL5-10G7; heavy chain; CDR1-IMGT<br>GYTFTKYW |
| SEQ ID NO: 5<br>VT008-AL5-10G7; heavy chain; CDR2-IMGT<br>INPSDTYT |
| SEQ ID NO: 6<br>VT008-AL5-10G7; heavy chain; CDR3-IMGT<br>ARVATMVARGFAY |
| SEQ ID NO: 7<br>VT008-AL5-10K7; light chain; CDR1-Kabat<br>KASQDVSGAVV |
| SEQ ID NO: 8<br>VT008-AL5-10K7; light chain; CDR2-Kabat<br>LATYRYT |
| SEQ ID NO: 9<br>VT008-AL5-10K7; light chain; CDR3-Kabat<br>QQYYSIPWT |
| SEQ ID NO: 10<br>VT008-AL5-10K7; light chain; CDR1-IMGT<br>QDVSGA |
| SEQ ID NO: 11<br>VT008-AL5-10K7; light chain; CDR2-IMGT<br>LATY |
| SEQ ID NO: 12<br>VT008-AL5-10K7; light chain; CDR3-IMGT<br>QQYYSIPWT |
| SEQ ID NO: 13<br>VT008-AL6-14G1; heavy chain; CDR1-Kabat<br>NYWMY |
| SEQ ID NO: 14<br>VT008-AL6-14G1; heavy chain; CDR2-Kabat<br>WIDPNSGGTKYNEKFKS |
| SEQ ID NO: 15<br>VT008-AL6-14G1; heavy chain; CDR3-Kabat<br>GGYTMDY |
| SEQ ID NO: 16<br>VT008-AL6-14G1; heavy chain; CDR1-IMGT<br>GYTFTNYW |
| SEQ ID NO: 17<br>VT008-AL6-14G1; heavy chain; CDR2-IMGT<br>IDPNSGGT |
| SEQ ID NO: 18<br>VT008-AL6-14G1; heavy chain; CDR3-IMGT<br>ARGGYTMDY |
| SEQ ID NO: 19<br>VT008-AL6-16K1; light chain; CDR1-Kabat<br>RASQSLVHSNGNTYLH |
| SEQ ID NO: 20<br>VT008-AL6-16K1; light chain; CDR2-Kabat<br>KVSNRFS |
| SEQ ID NO: 21<br>VT008-AL6-16K1; light chain; CDR3-Kabat<br>SQSTHVPLT |

| SEQUENCES |
| --- |
| SEQ ID NO: 22<br>VT008-AL6-16K1; light chain; CDR1-IMGT<br>QSLVHSNGNTY |
| SEQ ID NO: 23<br>VT008-AL6-16K1; light chain; CDR2-IMGT<br>KVSN |
| SEQ ID NO: 24<br>VT008-AL6-16K1; light chain; CDR3-IMGT<br>SQSTHVPLT |
| SEQ ID NO: 25<br>VT008-AL6-18G1; heavy chain; CDR1-Kabat<br>NYWIH |
| SEQ ID NO: 26<br>VT008-AL6-18G1; heavy chain; CDR2-Kabat<br>RIDPNTVDAKYNEKFKS |
| SEQ ID NO: 27<br>VT008-AL6-18G1; heavy chain; CDR3-Kabat<br>GGYTMDY |
| SEQ ID NO: 28<br>VT008-AL6-18G1; heavy chain; CDR1-IMGT<br>GYTFINYW |
| SEQ ID NO: 29<br>VT008-AL6-18G1; heavy chain; CDR2-IMGT<br>IDPNTVDA |
| SEQ ID NO: 30<br>VT008-AL6-18G1; heavy chain; CDR3-IMGT<br>SRGGYTMDY |
| SEQ ID NO: 31<br>VT008-AL6-18K21; light chain; CDR1-Kabat<br>RSSQSLVHSNGNTYLH |
| SEQ ID NO: 32<br>VT008-AL6-18K21; light chain; CDR2-Kabat<br>KVSNRFS |
| SEQ ID NO: 33<br>VT008-AL6-18K21; light chain; CDR3-Kabat<br>FQSTHVPWT |
| SEQ ID NO: 34<br>VT008-AL6-18K21; light chain; CDR1-IMGT<br>QSLVHSNGNTY |
| SEQ ID NO: 35<br>VT008-AL6-18K21; light chain; CDR2-IMGT<br>KVSN |
| SEQ ID NO: 36<br>VL008-AL6-18K21; light chain; CDR3-IMGT<br>FQSTHVPWT |
| SEQ ID NO: 37<br>VL008-AL17-7G1; heavy chain; CDR1-Kabat<br>DYYIN |
| SEQ ID NO: 38<br>VL008-AL17-7G1; heavy chain; CDR2-Kabat<br>WIFPGSGLTYYNKKFKG |
| SEQ ID NO: 39<br>VL008-AL17-7G1; heavy chain; CDR3-Kabat<br>PYYGSRWDYAMDY |
| SEQ ID NO: 40<br>VL008-AL17-7G1; heavy chain; CDR1-IMGT<br>VYTFTDYY |

| SEQUENCES |
|---|

SEQ ID NO: 41
VL008-AL17-7G1; heavy chain; CDR2-IMGT
IFPGSGLT

SEQ ID NO: 42
VL008-AL17-7G1; heavy chain; CDR3-IMGT
ARPYYGSRWDYAMDY

SEQ ID NO: 43
VL008-AL17-7K6; light chain; CDR1-Kabat
KSSQSLLNSNNQKNYLA

SEQ ID NO: 44
VL008-AL17-7K6; light chain; CDR2-Kabat
FASTRES

SEQ ID NO: 45
VL008-AL17-7K6; light chain; CDR3-Kabat
QQHYTTPYT

SEQ ID NO: 46
VL008-AL17-7K6; light chain; CDR1-IMGT
QSLLNSNNQKNY

SEQ ID NO: 47
VL008-AL17-7K6; light chain; CDR2-IMGT
FAST

SEQ ID NO: 48
VL008-AL17-7K6; light chain; CDR3-IMGT
QQHYTTPYT

SEQ ID NO: 49
VL008-AL18-14G4; heavy chain; CDR1-Kabat
DYYIN

SEQ ID NO: 50
VL008-AL18-14G4; heavy chain; CDR2-Kabat
RIYPGIGNTYYNKKFKG

SEQ ID NO: 51
VL008-AL18-14G4; heavy chain; CDR3-Kabat
GHYGRGMDY

SEQ ID NO: 52
VL008-AL18-14G4; heavy chain; CDR1-IMGT
GYSFTDYY

SEQ ID NO: 53
VL008-AL18-14G4; heavy chain; CDR2-IMGT
IYPGIGNT

SEQ ID NO: 54
VL008-AL18-14G4; heavy chain; CDR3-IMGT
ARGHYGRGMDY

SEQ ID NO: 55
VL008-AL18-14K1; light chain; CDR1-Kabat
KSSQSLLNSIDQKNYLA

SEQ ID NO: 56
VL008-AL18-14K1; light chain; CDR2-Kabat
FASTKES

SEQ ID NO: 57
VL008-AL18-14K1; light chain; CDR3-Kabat
QQHYSTPWT

SEQ ID NO: 58
VL008-AL18-14K1; light chain; CDR1-IMGT
QSLLNSIDQKNY

SEQ ID NO: 59
VL008-AL18-14K1; light chain; CDR2-IMGT
FAST

| SEQUENCES |
|---|
| SEQ ID NO: 60<br>VL008-AL18-14K1; light chain; CDR3-IMGT<br>QQHYSTPWT |
| SEQ ID NO: 61<br>VL008-AL13-8G5; heavy chain; CDR1-Kabat<br>TYWMH |
| SEQ ID NO: 62<br>VL008-AL13-8G5; heavy chain; CDR2-Kabat<br>MIHPNSGTTNYNEKFKS |
| SEQ ID NO: 63<br>VL008-AL13-8G5; heavy chain; CDR3-Kabat<br>SHYYDGHFSY |
| SEQ ID NO: 64<br>VL008-AL13-8G5; heavy chain; CDR1-IMGT<br>GYTFTTYW |
| SEQ ID NO: 65<br>VL008-AL13-8G5; heavy chain; CDR2-IMGT<br>IHPNSGTT |
| SEQ ID NO: 66<br>VL008-AL13-8G5; heavy chain; CDR3-IMGT<br>TRSHYYDGHFSY |
| SEQ ID NO: 67<br>VL008-AL13-8K3; light chain; CDR1-Kabat<br>KSSQSLLNSRTRKNYLA |
| SEQ ID NO: 68<br>VL008-AL13-8K3; light chain; CDR2-Kabat<br>WASTRES |
| SEQ ID NO: 69<br>VL008-AL13-8K3; light chain; CDR3-Kabat<br>KQSYNLWT |
| SEQ ID NO: 70<br>VL008-AL13-8K3; light chain; CDR1-IMGT<br>QSLLNSRTRKNY |
| SEQ ID NO: 71<br>VL008-AL13-8K3; light chain; CDR2-IMGT<br>WAST |
| SEQ ID NO: 72<br>VL008-AL13-8K3; light chain; CDR3-IMGT<br>KQSYNLWT |
| SEQ ID NO: 73<br>VT008-AL6-10G3; heavy chain; CDR1-Kabat<br>NYWIH |
| SEQ ID NO: 74<br>VT008-AL6-10G3; heavy chain; CDR2-Kabat<br>RIDPNSGGTKYNEKFKS |
| SEQ ID NO: 75<br>VT008-AL6-10G3; heavy chain; CDR3-Kabat<br>GGYTMDY |
| SEQ ID NO: 76<br>VT008-AL6-10G3; heavy chain; CDR1-IMGT<br>GYTFTNYW |
| SEQ ID NO: 77<br>VT008-AL6-10G3; heavy chain; CDR2-IMGT<br>IDPNSGGT |
| SEQ ID NO: 78<br>VT008-AL6-10G3; heavy chain; CDR3-IMGT<br>ARGGYTMDY |

| SEQUENCES |
| --- |

SEQ ID NO: 79
VT008-AL6-10K1; light chain; CDR1-Kabat
RSSQSLLHSNGNTYLH

SEQ ID NO: 80
VT008-AL6-10K1; light chain; CDR2-Kabat
KVSYRFS

SEQ ID NO: 81
VT008-AL6-10K1; light chain; CDR3-Kabat
FQSTHVPWT

SEQ ID NO: 82
VT008-AL6-10K1; light chain; CDR1-IMGT
QSLLHSNGNTY

SEQ ID NO: 83
VT008-AL6-10K1; light chain; CDR2-IMGT
KVSY

SEQ ID NO: 84
VT008-AL6-10K1; light chain; CDR3-IMGT
FQSTHVPWT

SEQ ID NO: 85
VT008-AL6-20G7; heavy chain; CDR1-Kabat
NYWIY

SEQ ID NO: 86
VT008-AL6-20G7; heavy chain; CDR2-Kabat
YINPRSDDTKYNQKFRD

SEQ ID NO: 87
VT008-AL6-20G7; heavy chain; CDR3-Kabat
GGFTMDF

SEQ ID NO: 88
VT008-AL6-20G7; heavy chain; CDR1-IMGT
GYTFINYW

SEQ ID NO: 89
VT008-AL6-20G7; heavy chain; CDR2-IMGT
INPRSDDT

SEQ ID NO: 90
VT008-AL6-20G7; heavy chain; CDR3-IMGT
ARGGFTMDF

SEQ ID NO: 91
VT008-AL6-20K7; light chain; CDR1-Kabat
RSSQSLLHSNGNTYLH

SEQ ID NO: 92
VT008-AL6-20K7; light chain; CDR2-Kabat
KVSYRFS

SEQ ID NO: 93
VT008-AL6-20K7; light chain; CDR3-Kabat
SQGTHVPYT

SEQ ID NO: 94
VT008-AL6-20K7; light chain; CDR1-IMGT
QSLLHSNGNTY

SEQ ID NO: 95
VT008-AL6-20K7; light chain; CDR2-IMGT
KVSY

SEQ ID NO: 96
VT008-AL6-20K7; light chain; CDR3-IMGT
SQGTHVPYT

SEQ ID NO: 97
VT008-AL6-39G2; heavy chain; CDR1-Kabat
GYNIY

| SEQUENCES |
|---|
| SEQ ID NO: 98<br>VT008-AL6-39G2; heavy chain; CDR2-Kabat<br>YIYPYNGISSYNQKFKD |
| SEQ ID NO: 99<br>VT008-AL6-39G2; heavy chain; CDR3-Kabat<br>GGYTMDY |
| SEQ ID NO: 100<br>VT008-AL6-39G2; heavy chain; CDR1-IMGT<br>GYSFTGYN |
| SEQ ID NO: 101<br>VT008-AL6-39G2; heavy chain; CDR2-IMGT<br>IYPYNGIS |
| SEQ ID NO: 102<br>VT008-AL6-39G2; heavy chain; CDR3-IMGT<br>ARGGYTMDY |
| SEQ ID NO: 103<br>VT008-AL6-39K2; light chain; CDR1-Kabat<br>RSSQSLVKSNGNTYLH |
| SEQ ID NO: 104<br>VT008-AL6-39K2; light chain; CDR2-Kabat<br>KVSNRFS |
| SEQ ID NO: 105<br>VT008-AL6-39K2; light chain; CDR3-Kabat<br>SQTTHVPYT |
| SEQ ID NO: 106<br>VT008-AL6-39K2; light chain; CDR1-IMGT<br>QSLVKSNGNTY |
| SEQ ID NO: 107<br>VT008-AL6-39K2; light chain; CDR2-IMGT<br>KVSN |
| SEQ ID NO: 108<br>VT008-AL6-39K2; light chain; CDR3-IMGT<br>SQTTHVPYT |
| SEQ ID NO: 109<br>VL008-AL17-8G5; heavy chain; CDR1-Kabat<br>DYYIN |
| SEQ ID NO: 110<br>VL008-AL17-8G5; heavy chain; CDR2-Kabat<br>WIFPGSGLTYYNKKFKG |
| SEQ ID NO: 111<br>VL008-AL17-8G5; heavy chain; CDR3-Kabat<br>PYYGSRWDYTMDY |
| SEQ ID NO: 112<br>VL008-AL17-8G5; heavy chain; CDR1-IMGT<br>GYTFTDYY |
| SEQ ID NO: 113<br>VL008-AL17-8G5; heavy chain; CDR2-IMGT<br>IFPGSGLT |
| SEQ ID NO: 114<br>VL008-AL17-8G5; heavy chain; CDR3-IMGT<br>ARPYYGSRWDYTMDY |
| SEQ ID NO: 115<br>VL008-AL17-8K7; light chain; CDR1-Kabat<br>KSSQNLLNSNNQKNHLA |
| SEQ ID NO: 116<br>VL008-AL17-8K7; light chain; CDR2-Kabat<br>FASTRES |

SEQUENCES

SEQ ID NO: 117
VL008-AL17-8K7; light chain; CDR3-Kabat
QQHYTTPYT

SEQ ID NO: 118
VL008-AL17-8K7; light chain; CDR1-IMGT
QNLLNSNNQKNH

SEQ ID NO: 119
VL008-AL17-8K7; light chain; CDR2-IMGT
FAST

SEQ ID NO: 120
VL008-AL17-8K7; light chain; CDR3-IMGT
QQHYTTPYT

SEQ ID NO: 121
VT008-AL5-10G7; variable region heavy chain
QVQLQQPGAELVMPGSSVKLSCKTSGYTFTKYWMHWVKRRPGQGLEWIGEINPSDTYT
NYNQKFKGKSTLTVDKSSSTAYMQLSSLTSEDSAVYFCARVATMVARGFAYWGQGTL
VTVSA SEQ ID NO: 122
VT008-AL5-10K7; variable region light chain
DIVMTQSHKFMSTSVGDRVSITCKASQDVSGAVVWYQEKPGQSPNLLIYLATYRYTGV
PDRFTGSGSGTDFTLTIRSVQAEDMAVYYCQQYYSIPWTFGGGTKLEIK SEQ ID NO: 123
VT008-AL6-14G1; variable region heavy chain
QVQLQQPGAELVKPGASLRVSCKASGYTFTNYWMYWVRQRPGRGLEWIGWIDPNSGG
TKYNEKFKSKATLTVDKPSSTAYMQLSSLTSEDSAVYNCARGGYTMDYWGQGTSVTV
SS SEQ ID NO: 124
VT008-AL6-16K1; variable region light chain
DVVMTQTPLSLPVSLGDQASISCRASQSLVHSNGNTYLHWYLQKPGQSPKLLIYKVSNR
FSGVPDRFSGSGSGTDFTLKISRVEAEDLGVYFCSQSTHVPLTFGAGTKLELK SEQ ID NO: 125
VT008-AL6-18G1; variable region heavy chain
QVQLQQPGAELVKPGTSVKLSCKASGYTFINYWIHWVKQRPGRGLEWIGRIDPNTVDA
KYNEKFKSKATLTVDKPSSIAYMQLSSLTSEDSAVYYCSRGGYTMDYWGQGTSVTVSS SEQ ID NO: 126
VT008-AL6-18K21; variable region light chain
DVVMTQTPLSLPVSLGDQASISCRSSQSLVHSNGNTYLHWYLQKPGQSPTLLIYKVSNRF
SGVPDRFSGSGSGTDFTLKISRVEAEDLGIYFCFQSTHVPWTFGGGTKLEIK SEQ ID NO: 127
VL008-AL17-7G1; variable region heavy chain
QVQLQQSGPELVKPGASVKISCKASVYTFTDYYINWVKQRPGQGLEWVGWIFPGSGLT
YYNKKFKGKATLTVDKSSSTAYMLLSSLTSEDSAVYFCARPYYGSRWDYAMDYWGQG
TSVTVSS SEQ ID NO: 128
VL008-AL17-7K6; variable region light chain
DIVMTQSPSSLTMSVGQKVTMSCKSSQSLLNSNNQKNYLAWYQQKPGQSPKLLLYFAS
TRESGVPDRFIGSGSGTDFTLTISSVQAEDLADYFCQQHYTTPYTFGGGTKLEIK SEQ ID NO: 129
VL008-AL18-14G4; variable region heavy chain
QVQLKQSGAELVRPGASVKLSCKASGYSFTDYYINWVKQRPGQGLEWIARIYPGIGNTY
YNKKFKGKATLTAEKSSSTAYMQLNSLTSEDSAVYFCARGHYGRGMDYWGQGTSVTV
SS SEQ ID NO: 130
VL008-AL18-14K1; variable region light chain
DIVMTQSPSSLAMSVGQKVTMNCKSSQSLLNSIDQKNYLAWYQQKPGQSPKLLVYFAS
TKESGVPDRFIGSGSGTDFTLTISSVQAEDLADYFCQQHYSTPWTFGGGTKLEIK SEQ ID NO: 131
VL008-AL13-8G5; variable region heavy chain
QVQLQQPGAELVKPGASVKLSCKASGYTFTTYWMHWVKQRPGQGLEWIGMIHPNSGT
TNYNEKFKSKATLTVDKSSSSTYMQLSSLTSEDSAVYYCTRSHYYDGHFSYWGQGTLV
TVSA

| SEQUENCES |
| --- |
| SEQ ID NO: 132<br>VL008-AL13-8K3; variable region light chain<br>DIVMSQSPSSLAVSAGEKVTMSCKSSQSLLNSRTRKNYLAWYQQKPGQSPKLLIYWAST<br>RESGVPDRFTGSGSGTDFTLTISSVQAEDLAVYYCKQSYNLWTFGGGTRLEIK<br><br>SEQ ID NO: 133<br>VT008-AL6-10G3; variable region heavy chain<br>QVQLQQPGPELVKPGASVKLSCKASGYTFTNYWIHWLNQRPGRGLEWIGRIDPNSGGT<br>KYNEKFKSKAILTVDKSSTTYMQLSSLTSEDSAVYYCARGGYTMDYWGQGTSVTVSS<br><br>SEQ ID NO: 134<br>VT008-AL6-10K1; variable region light chain<br>DVVMPQTPLSLPVSLGDHASISCRSSQSLLHSNGNTYLHWYLQKPGQSPKLLIYKVSYRF<br>SGVPDRISGSGSGTDFTLKISRVEAEDLGVYFCFQSTHVPWTFGGGTKLEIK<br><br>SEQ ID NO: 135<br>VT008-AL6-20G7; variable region heavy chain<br>QVQLQQSGTELAKPGASVKLSCKASGYTFINYWIYWVKERPGQVLEWIGYINPRSDDTK<br>YNQKFRDRATLTADKSSTTAYLQLNSLTNDDSALYYCARGGFTMDFWGQGTSVTVSS<br><br>SEQ ID NO: 136<br>VT008-AL6-20K7; variable region light chain<br>DVVMTQTPLSLPVSLGDQASISCRSSQSLLHSNGNTYLHWYLQKPGQSPNLLIYKVSYRF<br>SGVPDRFSGSGSGTDFTLKISRVEAEDLGVYFCSQGTHVPYTFGGGTKLEIK<br><br>SEQ ID NO: 137<br>VT008-AL6-39G2; variable region heavy chain<br>EVQLQQSGPELVKPGASVKISCKASGYSFTGYNIYWVKQSHGNILDWIGYIYPYNGISSY<br>NQKFKDKATLTVDKSSTTAYMELRSLTSEDSAVYYCARGGYTMDYGGQGTSVTVSS<br><br>SEQ ID NO: 138<br>VT008-AL6-39K2; variable region light chain<br>DVVMTQTPLSLPVSLGEQASISCRSSQSLVKSNGNTYLHWYLQKPGQSPKLLIYKVSNRF<br>SGVPDRFSGSGSGTDFTLKISRVEAEDLGLYFCSQTTHVPYTFGGGTKLEIK<br><br>SEQ ID NO: 139<br>VL008-AL17-8G5; variable region heavy chain<br>LVQLQQSGPELVKPGTSVKISCRSSGYTFTDYYINWVQQRPGQGLEWVGWIFPGSGLTY<br>YNKKFKGKATLSVDKSSNTAYMLLSSLTSEDSAVYFCARPYYGSRWDYTMDYWGQGT<br>SVTVSS<br><br>SEQ ID NO: 140<br>VL008-AL17-8K7; variable region light chain<br>DIVMTQSPSSLTMSVGQKATMSCKSSQNLLNSNNQKNHLAWYQQKPGQSPKLLLYFAS<br>TRESGVPDRFIGSGSGTDFTLTISSVQAEDLADYFCQQHYTTPYTFGGGTKLEIK<br><br>SEQ ID NO: 141<br>VL008-AL18-14G4; humanized variable region heavy chain; VH1<br>QVQLLESGAVLARPGTSVKISCKASGYSFTDYYINWVKQRPGQGLEWIGRIYPGIGNTY<br>YNKKFKGRAKLTAATSASIAYLEFSSLTNEDSAVYYCARGHYGRGMDYWGQGTLVTV<br>SS<br><br>SEQ ID NO: 142<br>VL008-AL18-14G4; humanized variable region heavy chain; VH2<br>QVQLVQSGAEVKKPGASVKVSCKASGYSFTDYYINWVRQAPGQGLEWMGRIYPGIGN<br>TYYNKKFKGRVTITRDTSASTAYMELSSLRSEDTAVYYCARGHYGRGMDYWGQGTLV<br>TVSS<br><br>SEQ ID NO: 143<br>VL008-AL18-14G4; humanized variable region heavy chain; VH3<br>QVQLVQSGAEVKKPGASVKVSCKASGYSFTDYYINWVRQAPGQGLEWMGRIYPGIGN<br>TYYNKKFKGRVTVTRDTSISTAHMELSSLRSDDTAVYYCARGHYGRGMDYWGQGTAV<br>TVSS<br><br>SEQ ID NO: 144<br>VL008-AL18-14G4; humanized variable region heavy chain; VH4<br>QVQLVQSGAEVKKPGSSVKVSCKASGYSFTDYYINWVRQAPGQGLEWMGRIYPGIGNT<br>YYNKKFKGRVTITADKSTSTAYMELSSLRSEDTAVYYCARGHYGRGMDYWGQGTTVT<br>VSS<br><br>SEQ ID NO: 145<br>VL008-AL18-14G4; humanized variable region heavy chain; VH5<br>QVQLVQSGAEVKKPGASVKVSCKASGYSFTDYYINWVRQAPGQGLEWMGRIYPGIGN<br>TYYNKKFKGRVTMTRYTSISTAYMELSRLRSDDTAVYFCARGHYGRGMDYWGQGTTV<br>TVSS |

| SEQUENCES |
| --- |

SEQ ID NO: 146
VL008-AL18-14K1; humanized variable region light chain; VL1
DIVMTQSPDSLAVSLGERATINCKSSQSLLNSIDQKNYLAWYQQKPGQPPKLLIYFASTK
ESGVPDRFSGSGSGTDFTLTISSLQAEDVAVYYCQQHYSTPWTFGGGTKLEIK SEQ ID NO: 147
VL008-AL18-14K1; humanized variable region light chain; VL2
DIVMTQSPDSLAVSLGERATINCKSSQSLLNSIDQKNYLAWYQQKPGQPPKLLIYFASTK
ESGVPDRFSGSGSGTDFTLTISSLQAEDVAVYYCQQHYSTPWTFGGGTKVEIK SEQ ID NO: 148
VL008-AL18-14K1; humanized variable region light chain; VL3
EIVLTQSPDSLAVSLGERATINCKSSQSLLNSIDQKNYLAWYQQKAGQSPKLLIYFASTK
ESGVPDRFSGSGSGTDFTLTIDSLQAEDVAVYYCQQHYSTPWTFGGGTKVEIK SEQ ID NO: 149
VL008-AL18-14K1; humanized variable region light chain; VL4
DIVMTQSPDSLAVSLGERATINCKSSQSLLNSIDQKNYLAWYQQKPGQPPKLLIYFASTK
ESGVPDRFSGSGSGTDFTLTISSLQAEDVAVYFCQQHYSTPWTFGGGAKVEIK SEQ ID NO: 150
VL008-AL18-14K1; humanized variable region light chain; VL5
DIVMTQSPDSLAVSLGERATINCKSSQSLLNSIDQKNYLAWYQQKPGQPPKLLIYFASTK
ESGVPDRFSGSGSGTDFTLTISGLQAEDVAVYFCQQHYSTPWTFGGGTKVEIR SEQ ID NO: 151
CD47 antigen (Rh-related antigen, integrin-associated signal transducer), isoform CRAb
[Homo sapiens], accession: EAW79734.1
MWPLVAALLLGSACCGSAQLLFNKTKSVEFTFCNDTVVIPCFVTNMEAQNTTEVYVKW
KFKGRDIYTFDGALNKSTVPTDFSSAKIEVSQLLKGDASLKMDKSDAVSHTGNYTCEVT
ELTREGETIIELKYRVVSWFSPNENILIVIFPIFAILLFWGQFGIKTLKYRSGGMDEKTIALL
VAGLVITVIVIVGAILFVPGEYSLKNATGLGLIVTSTGILILLHYYVFSTAIGLTSFVIAILVI
QVIAYILAVVGLSLCIAACIPMHGPLLISGLSILALAQLLGLVYMKFVASNQKTIQPPRKA
VEEPLNAFKESKGMMNDE SEQ ID NO: 152
VT008-AL18-14K1; light chain; CDR2-Kabat; CD4+ T cell epitope corrected
YASTKES SEQ ID NO: 153
VT008-AL18-14K1; light chain; CDR2-IMGT; CD4+ T cell epitope corrected
YAST SEQ ID NO: 154
VL008-AL18-14K1; variable region light chain; CD4+ T cell epitope corrected
DIVMTQSPSSLAMSVGQKVTMNCKSSQSLLNSIDQKNYLAWYQQKPGQSPKLLVYYAS
TKESGVPDRFIGSGSGTDFTLTISSVQAEDLADYFCQQHYSTPWTFGGGTKLEIK SEQ ID NO: 155
VL008-AL18-14K1; humanized variable region light chain; VL1; CD4+ T cell epitope corrected
DIVMTQSPDSLAVSLGERATINCKSSQSLLNSIDQKNYLAWYQQKPGQPPKLLIYYASTK
ESGVPDRFSGSGSGTDFTLTISSLQAEDVAVYYCQQHYSTPWTFGGGTKLEIK SEQ ID NO: 156
VL008-AL18-14K1; humanized variable region light chain; VL2; CD4+ T cell epitope corrected
DIVMTQSPDSLAVSLGERATINCKSSQSLLNSIDQKNYLAWYQQKPGQPPKLLIYYASTK
ESGVPDRFSGSGSGTDFTLTISSLQAEDVAVYYCQQHYSTPWTFGGGTKVEIK SEQ ID NO: 157
VL008-AL18-14K1; humanized variable region light chain; VL3; CD4+ T cell epitope corrected
EIVLTQSPDSLAVSLGERATINCKSSQSLLNSIDQKNYLAWYQQKAGQSPKLLIYYASTK
ESGVPDRFSGSGSGTDFTLTIDSLQAEDVAVYYCQQHYSTPWTFGGGTKVEIK SEQ ID NO: 158
VL008-AL18-14K1; humanized variable region light chain; VL4; CD4+ T cell epitope corrected
DIVMTQSPDSLAVSLGERATINCKSSQSLLNSIDQKNYLAWYQQKPGQPPKLLIYYASTK
ESGVPDRFSGSGSGTDFTLTISSLQAEDVAVYFCQQHYSTPWTFGGGAKVEIK SEQ ID NO: 159
VL008-AL18-14K1; humanized variable region light chain; VL5; CD4+ T cell epitope corrected
DIVMTQSPDSLAVSLGERATINCKSSQSLLNSIDQKNYLAWYQQKPGQPPKLLIYYASTK
ESGVPDRFSGSGSGTDFTLTISGLQAEDVAVYFCQQHYSTPWTFGGGTKVEIR SEQ ID NO: 160
hu-sCD47-6His; extracellular domain of human CD47 antigen with 6His-tag
MWPLVAALLLGSACCGSAQLLFNKTKSVEFTFCNDTVVIPCFVTNMEAQNTTEVYVKW

| SEQUENCES |
|---|
| KFKGRDIYTFDGALNKSTVPTDFSSAKIEVSQLLKGDASLKMDKSDAVSHTGNYTCEVT<br>ELTREGETIIELKYRVVSWFSPASSSGSSSHHHHHH<br><br>SEQ ID NO: 161<br>hu-IgG4 S228P; human constant region heavy chain IgG4 S228P mutant<br>GCTAGCACCAAGGGCCCCTCTGTGTTTCCTCTGGCCCCTTGCTCCCGGTCCACCTCCG<br>AATCTACAGCCGCTCTGGGCTGCCTCGTGAAAGACTACTTCCCCGAGCCTGTGACAG<br>TGTCCTGGAACTCTGGCGCCCTGACCAGCGGAGTGCATACCTTCCCTGCTGTGCTGC<br>AGTCCTCCGGCCTGTACTCCCTGTCCTCCGTCGTGACAGTGCCCTCCAGCTCTCTGGG<br>CACCAAGACCTATACCTGCAACGTGGACCACAAGCCCTCCAACACCAAGGTGGACA<br>AGAGAGTGGAATCTAAGTACGGCCCTCCCTGCCCCCCTTGTCCTGCCCCTGAATTTC<br>TGGGCGGACCCTCCGTGTTCCTGTTCCCCCCAAAGCCTAAGGACACCCTGATGATCT<br>CCCGGACCCCCGAAGTGACCTGCGTGGTGGTGGATGTGTCTCAGGAAGATCCCGAG<br>GTGCAGTTCAATTGGTACGTGGACGGCGTGGAAGTGCATAATGCCAAGACCAAGCC<br>TCGGGAAGAACAGTTCAACTCCACCTACCGGGTGGTGTCCGTGCTGACCGTGCTGCA<br>CCAGGATTGGCTGAACGGCAAAGAGTACAAGTGCAAGGTGTCCAACAAGGGCCTGC<br>CCAGCTCCATCGAAAAGACCATCTCCAAGGCCAAGGGCCAGCCCCGGGAACCCCAG<br>GTGTACACACTGCCTCCATCCCAGGAAGAGATGACCAAGAACCAGGTGTCCCTGAC<br>CTGTCTCGTGAAGGGATTCTACCCCTCCGATATCGCCGTGGAATGGGAGTCCAACGG<br>CCAGCCTGAGAACAACTACAAGACCACCCCCCCTGTGCTGGACTCCGACGGCTCCTT<br>CTTCCTGTACTCTCGCCTGACCGTGGACAAGTCCCGGTGGCAGGAAGGCAACGTGTT<br>CTCCTGCTCCGTGATGCACGAGGCCCTGCACAACCACTACACCCAGAAGTCCCTGTC<br>TCTGTCCCTGGGCAAG<br><br>SEQ ID NO: 162<br>huIgG4_S228P; human constant region heavy chain IgG4 S228P mutant<br>ASTKGPSVFPLAPCSRSTSESTAALGCLVKDYFPEPVTVSWNSGALTSGVHTFPAVLQSS<br>GLYSLSSVVTVPSSSLGTKTYTCNVDHKPSNTKVDKRVESKYGPPCPPCPAPEFLGGPSV<br>FLFPPKPKDTLMISRTPEVTCVVVDVSQEDPEVQFNWYVDGVEVHNAKTKPREEQFNST<br>YRVVSVLTVLHQDWLNGKEYKCKVSNKGLPSSIEKTISKAKGQPREPQVYTLPPSQEEM<br>TKNQVSLTCLVKGFYPSDIAVEWESNGQPENNYKTTPPVLDSDGSFFLYSRLTVDKSRW<br>QEGNVFSCSVMHEALHNHYTQKSLSLSLGK<br><br>SEQ ID NO: 163<br>hu-IgG4 S228P-L235E; human constant region heavy chain IgG4 S228P-L235E mutant<br>GCTAGCACCAAGGGCCCCTCTGTGTTTCCTCTGGCCCCTTGCTCCCGGTCCACCTCCG<br>AATCTACAGCCGCTCTGGGCTGCCTCGTGAAAGACTACTTCCCCGAGCCTGTGACAG<br>TGTCCTGGAACTCTGGCGCCCTGACCAGCGGAGTGCATACCTTCCCTGCTGTGCTGC<br>AGTCCTCCGGCCTGTACTCCCTGTCCTCCGTCGTGACAGTGCCCTCCAGCTCTCTGGG<br>CACCAAGACCTATACCTGCAACGTGGACCACAAGCCCTCCAACACCAAGGTGGACA<br>AGAGAGTGGAATCTAAGTACGGCCCTCCCTGCCCCCCTTGTCCTGCCCCTGAATTTG<br>AAGGCGGACCCTCCGTGTTCCTGTTCCCCCCAAAGCCTAAGGACACCCTGATGATCT<br>CCCGGACCCCCGAAGTGACCTGCGTGGTGGTGGATGTGTCTCAGGAAGATCCCGAG<br>GTGCAGTTCAATTGGTACGTGGACGGCGTGGAAGTGCATAATGCCAAGACCAAGCC<br>TCGGGAAGAACAGTTCAACTCCACCTACCGGGTGGTGTCCGTGCTGACCGTGCTGCA<br>CCAGGATTGGCTGAACGGCAAAGAGTACAAGTGCAAGGTGTCCAACAAGGGCCTGC<br>CCAGCTCCATCGAAAAGACCATCTCCAAGGCCAAGGGCCAGCCCCGGGAACCCCAG<br>GTGTACACACTGCCTCCATCCCAGGAAGAGATGACCAAGAACCAGGTGTCCCTGAC<br>CTGTCTCGTGAAGGGATTCTACCCCTCCGATATCGCCGTGGAATGGGAGTCCAACGG<br>CCAGCCTGAGAACAACTACAAGACCACCCCCCCTGTGCTGGACTCCGACGGCTCCTT<br>CTTCCTGTACTCTCGCCTGACCGTGGACAAGTCCCGGTGGCAGGAAGGCAACGTGTT<br>CTCCTGCTCCGTGATGCACGAGGCCCTGCACAACCACTACACCCAGAAGTCCCTGTC<br>TCTGTCCCTGGGCAAG<br><br>SEQ ID NO: 164<br>huIgG4_S228P-L235E; human constant region heavy chain IgG4 S228P-L235E mutant<br>ASTKGPSVFPLAPCSRSTSESTAALGCLVKDYFPEPVTVSWNSGALTSGVHTFPAVLQSS<br>GLYSLSSVVTVPSSSLGTKTYTCNVDHKPSNTKVDKRVESKYGPPCPPCPAPEFEGGPSV<br>FLFPPKPKDTLMISRTPEVTCVVVDVSQEDPEVQFNWYVDGVEVHNAKTKPREEQFNST<br>YRVVSVLTVLHQDWLNGKEYKCKVSNKGLPSSIEKTISKAKGQPREPQVYTLPPSQEEM<br>TKNQVSLTCLVKGFYPSDIAVEWESNGQPENNYKTTPPVLDSDGSFFLYSRLTVDKSRW<br>QEGNVFSCSVMHEALHNHYTQKSLSLSLGK<br><br>SEQ ID NO: 165<br>h20-H2-L5Y; heavy chain in huIgG4_S228P format<br>QVQLVQSGAEVKKPGASVKVSCKASGYSFTDYYINWVRQAPGQGLEWMGRIYPGIGN<br>TYYNKKFKGRVTITRDTSASTAYMELSSLRSEDTAVYYCARGHYGRGMDYWGQGTLV<br>TVSSASTKGPSVFPLAPCSRSTSESTAALGCLVKDYFPEPVTVSWNSGALTSGVHTFPAV<br>LQSSGLYSLSSVVTVPSSSLGTKTYTCNVDHKPSNTKVDKRVESKYGPPCPPCPAPEFLG<br>GPSVFLFPPKPKDTLMISRTPEVTCVVVDVSQEDPEVQFNWYVDGVEVHNAKTKPREEQ<br>FNSTYRVVSVLTVLHQDWLNGKEYKCKVSNKGLPSSIEKTISKAKGQPREPQVYTLPPS<br>QEEMTKNQVSLTCLVKGFYPSDIAVEWESNGQPENNYKTTPPVLDSDGSFFLYSRLTVD<br>KSRWQEGNVFSCSVMHEALHNHYTQKSLSLSLG<br><br>SEQ ID NO: 166<br>h20-H2-L5Y; heavy chain in hu-IgG4_S228P-L325E format<br>QVQLVQSGAEVKKPGASVKVSCKASGYSFTDYYINWVRQAPGQGLEWMGRIYPGIGN |

```
                              SEQUENCES
TYYNKKFKGRVTITRDTSASTAYMELSSLRSEDTAVYYCARGHYGRGMDYWGQGTLV
TVSSASTKGPSVFPLAPCSRSTSESTAALGCLVKDYFPEPVTVSWNSGALTSGVHTFPAV
LQSSGLYSLSSVVTVPSSSLGTKTYTCNVDHKPSNTKVDKRVESKYGPPCPPCPAPEFEG
GPSVFLFPPKPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSFFLYSRLTVD
KSRWQEGNVFSCSVMHEALHNHYTQKSLSLSLG

SEQ ID NO: 167
h20-H2-L5Y; light chain
DIVMTQSPDSLAVSLGERATINCKSSQSLLNSIDQKNYLAWYQQKPGQPPKLLIYYASTK
ESGVPDRFSGSGSGTDFTLTISGLQAEDVAVYFCQQHYSTPWTFGGGTKVEIRRTVAAPS
VFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC SEQ ID NO: 168
VL008-AL13-8G5; humanized variable region heavy chain; VH1m
QVQLVQSGAEVKKPGASVKVSCKASGYTFTTYWMHWVHQAPGQRLEWMGMIHPNSG
TTNYNQKFQGRVTITVDKSASTAYMELSSLRSEDTAVYYCTRSHYYDGHFSYWGQGTL
VTVSS SEQ ID NO: 169
VL008-AL13-8G5; humanized variable region heavy chain; VH2m
QVQLVQSGAEVKKPGASVKVSCKASGYTFTTYWMHWVRQAPGQGLEWMGMIHPNSG
TTNYNQKFQGRVTMTVDKSASTAYMELSSLRSEDSAVYYCTRSHYYDGHFSYWGQGT
LVTVSS SEQ ID NO: 170
VL008-AL13-8G5; humanized variable region heavy chain; VH3
QVQLQESGAEVKKPGASVKVSCKASGYTFTTYWMHWVRQAPGQGLEWMGMIHPNSG
TTNYNEKFKSRVTMTRDTSTSTVYMELSSLRSEDTAVYYCTRSHYYDGHFSYWGQGTL
VTVSS SEQ ID NO: 171
VL008-AL13-8G5; humanized variable region heavy chain; VH4
QVQLVQSGAEVKKPGASVKVSCKGSGYTFTTYWMHWVRQAPGQGLEWMGMIHPNSG
TTNYNEKFKSRVTLTRDTSISTAYMELSRLTSDDTAVYYCTRSHYYDGHFSYWGQGTM
VTVSS SEQ ID NO: 172
VL008-AL13-8K3; humanized variable region light chain; VL1
DIVMTQSPGSLAVSLGERATFNCKSSQSLLNSRTRKNYLAWYQQKPGQPPKLLIYWAST
RESGVPDRFSGSGSGTDFTLTISSLQAEDVAVYYCKQSYNLWTFGGGTKVEVK SEQ ID NO: 173
VL008-AL13-8K3; humanized variable region light chain; VL2
DIVMTQSPDSLAVSLGERATINCKSSQSLLNSRTRKNYLAWYQQKPGQPPKLLIYWAST
RESGVPDRFSGSGSGTDFTLTISSLQAEDVAVYYCKQSYNLWTFGGGTKLEIK SEQ ID NO: 174
VL008-AL13-8K3; humanized variable region light chain; VL3
EIVLTQSPDSLAVSLGERATINCKSSQSLLNSRTRKNYLAWYQQKAGQSPKLLIYWASTR
ESGVPDRFSGSGSGTDFTLTIDSLQAEDVAVYYCKQSYNLWTFGGGTKVEIK SEQ ID NO: 175
VL008-AL13-8K3; humanized variable region light chain; VL4
DIVMTQSPDSLPVSLGERATINCKSSQSLLNSRTRKNYLAWYQQKPGQPPKLLIYWAST
RESGVPDRFTGSGSGTDFTLTISALQAEDVAVYYCKQSYNLWTFGQGTRLEIK SEQ ID NO: 176
Constant region of human kappa light chain
RTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC
```

Examples

I. Generation of Mouse Anti-CD47 Antibodies

1. Immunization of Mice

In order to generate mouse antibodies against human CD47 (hCD47) and potentially cross-reacting with mouse CD47 (mCD47), NMRI wild type or CD47-KO (C57BL6) mice were immunized as follows with a protocol of comprising 4 DNA injections at 2 week intervals followed by two final boosts at one week intervals with CD47 DNA or CHO cells transfected with a CD47 expression vector:

(5) WT mice: Prime humanCD47 DNA+Boost humanCD47 DNA
(3) CD47-/- mice: Prime humanCD47 DNA+Boost murineCD47 CHO
(3) CD47-/- mice: Prime murineCD47 CHO+Boost murineCD47 CHO Animal sacrifice was carried out according to serum screening results. The presence and the titer of IgG binding to human or mouse CD47 was monitored in the sera of immunized animals by using an ELISA (coating of hCD47-humanIgG1 fusion protein, hCD47-Fc, or of mCD47-humanIgG1 fusion protein, mCD47-Fc) and by flow cytometry on stable CHO cells expressing hCD47 or mCD47 (obtained after transfection with a vector encoding hCD47 or mCD47, followed by selection of stable CD47-expressing clones, not shown). Animals displaying strong anti-CD47 IgG titers were sacrificed. Their spleens and lymph nodes were extracted and the mononuclear cells (MNCs) were purified and frozen.

2. Single B Cell Screening Using the ISAAC Technology and Generation of Recombinant Anti-CD47 Antibodies The ISAAC technology, described in WO2009/017226, is a unique method for detecting individual antibody-secreting cells using microarray chips, which enables the analysis of live cells on a single-cell basis and offers a rapid, efficient and high-throughput (up to 234,000 individual cells) system for identifying and recovering the relevant cells.

An array of single live cells was prepared by applying mouse MNCs, previously purified from spleen and lymph nodes of immunized mice, to a microarray chip. The chip surface was previously coated with the target antigen (hCD47-humanIgG1 fusion protein, hCD47-Fc) and the anti-CD47 mouse antibodies secreted by an antibody secreting cell were trapped by the CD47 coated on the surface around the well. After washings, the presence of mouse IgG bound to the immobilized CD47 was detected by an anti-mouse IgG antibody coupled to Cy3 and fluorescence microscopy. Binding of the antigen to the specific antibodies formed distinct circular spots, which were easily distinguishable from nonspecific signals. CD47-specific antibody-secreting single cells were then retrieved by micromanipulation, mRNA was recovered from single cells and cDNA sequences coding the variable regions of the heavy (VH) and light (VL) chain of IgG were amplified by RT-PCR. The VH and VL sequences were then cloned in expression vectors containing a mouse gamma-2a constant region (Fcγ2a) and a kappa or lambda constant region, respectively. After co-transfection of the H and L chain expression vectors in CHO cells, the recombinant antibody was purified on a protein A column from the cell supernatants and tested for confirmation of CD47 recognition and specificity by ELISA on plates coated with hCD47-Fc or mCD47-Fc and by flow cytometry on CHO cells transfected or not with hCD47 or mCD47.

In total, 55 antibodies were identified, out of which 34 (belonging to 18 different germline families) were produced and purified. From those 34 antibodies, 19 recognized human CD47 only, 1 antibody recognized mouse CD47 only and 14 antibodies recognized both human and mouse CD47.

II. Sequences of the Anti-CD47 Candidates

Tables 1 to 3 (supra) reference the amino acid sequences of the 10 selected candidates. In the listed sequences, the CDRs are identified according to the Kabat and IMGT annotation.

III. In Vitro Characterization of Recombinant Mouse Anti-CD47 Antibodies

1. CD47 Binding Assay by ELISA

All antibodies were tested for their capacity to bind to recombinant hCD47-Fc and mCD47-Fc coated on ELISA plates. Among the 34 purified antibodies tested, 19 recognized hCD47 only, 1 antibody recognized mCD47 only and 14 antibodies recognized both human and mouse CD47 (data not shown).

2. CD47 Binding Assay by Flow Cytometry on CD47-Transfected CHO Cells and Cross-Reactivity with Mouse and Cynomolgus CD47.

The capacity of the identified mouse anti-CD47 antibodies to recognize the cell membrane expressed human CD47 as well as CD47 protein from other species was further analyzed by flow cytometry by using CHO cells stably expressing the CD47 antigen of human, mouse or non-human primate (cynomolgus monkey) origin. The expression of the species-specific CD47 on CHO cell surface was validated by using staining with appropriate anti-CD47 antibodies and flow cytometry on non-fixed cells. The antibody B6H12 (mouse IgG1, Abcam) was used to confirm the expression of human and cynomolgus CD47, MIAP301 (rat IgG2a, BD Biosciences) to check the expression of mouse CD47, and MEM122 (mouse IgM, abcam) for the expression of monkey CD47.

Anti-CD47 antibodies and isotype control antibodies were incubated at various concentrations from 7.3 µg/mL to 3.3 ng/mL with CHO cells expressing different CD47 species at +4° C. for 30 minutes. After 2 washings, the presence of antibody bound to cell membrane CD47 was revealed by incubation with a PE-coupled anti-mouse or anti-human IgG antibody depending on the isotype of the primary antibody and analysis on an Accuri-C6 flow cytometer (BD Biosciences). The differences between the mean fluorescence intensity (MFI) obtained for each of the antibody concentration and the intensity obtained in absence of primary antibody (delta-MFI), were calculated and plotted against the concentrations of antibodies. Negative control antibodies of appropriate isotype (mIgG1, mIgG2a, hIgG1, hIgG4) that did not recognize CD47 were tested under the same conditions to measure background antibody staining (nonspecific staining).

Different anti-hCD47 benchmark antibodies were also tested in parallel to our candidates. Those included, the mouse B6H12, the chimeric 5F9 (c5F9) and the humanized 5F9 (hu5F9; vh2-vl2) antibodies form Stanford University (WO2011/143624); the mouse 2A1 antibody and its humanized variant AB06.12 from Inhibrx (US2013/0224188; WO2014/123580); the mouse 5A3M3 antibody from Novimmune (WO2014/087248); and the mouse VxP037-01LC1 antibody from Frazier et al. (WO2014/093678).

The results obtained for 10 mouse anti-CD47 antibodies are summarized in the Table 4 below, and compared with the results obtained with the benchmark antibodies. All 10 mouse anti-CD47 candidates bound strongly to CHO cells expressing the human and cynomolgus CD47, but not to the non-transfected CHO cells. Moreover, 5 of the candidates (candidate 14, 15, 26, 29 and 30) also strongly bound to CHO cells expressing the mouse CD47, while the 5 other antibodies did not. These results showed that 5 antibodies specifically recognized CD47 of human and cynomolgus origin (candidates 7, 19, 20, 22 and 33) and that 5 other antibodies also cross-reacted against the CD47 of mouse origin (candidates 14, 15, 26, 29, 30), suggesting the recognition of different epitope(s) by those antibodies.

As reported, the 2A1 and B6H12 benchmarks recognized the hCD47 and cross-reacted with cynoCD47 but not with mCD47, while the VxP037-01LC1 antibody cross-reacted against both cynomolgus and mouse CD47, as well as possibly against hamster CD47 expressed on wild type CHO cells.

TABLE 4

Summary of cross-reactivity of anti-CD47 antibodies

| Antibody | CHO | CHO-hCD47 | CHO-mCD47 | CHO-cynoCD47 |
| --- | --- | --- | --- | --- |
| B6H12 | − | ++ | − | +++ |
| c5F9 | − | +++ | − | +++ |

TABLE 4-continued

Summary of cross-reactivity of anti-CD47 antibodies

| Antibody | CHO | CHO-hCD47 | CHO-mCD47 | CHO-cynoCD47 |
|---|---|---|---|---|
| hu5F9 | − | +++ | − | +++ |
| 5A3M3 | − | ++ | − | ++ |
| 2A1 | − | +++ | − | +++ |
| AB06.12 | − | +++ | − | +++ |
| VxP037-01LC1 | ++ | +++ | +++ | +++ |
| Candidate 7 | − | +++ | − | +++ |
| Candidate 14 | + | +++ | +++ | +++ |
| Candidate 15 | + | +++ | +++ | +++ |
| Candidate 26 | +/− | +++ | +++ | +++ |
| Candidate 19 | − | +++ | − | +++ |
| Candidate 33 | − | +++ | − | +++ |
| Candidate 20 | +/− | +++ | +/− | +++ |
| Candidate 22 | +/− | +++ | − | +++ |
| Candidate 29 | − | +++ | +++ | +++ |
| Candidate 30 | +/− | +++ | +++ | +++ |

−; +/−; +; ++; +++ ranging from "no" detection to "strong" detection

3. Inhibition of CD47/SIRPα Interaction by ELISA

The antibodies were tested for their ability to disrupt the CD47-SIRPα interaction by ELISA. The day before the experiment, hCD47-hIgG1 fusion protein was coated on the bottom of 96 well plates and incubated overnight at 4° C. The wells were then washed and saturated for two hours at room temperature. After washing steps, the antigen (hSIRPα-6HIS fusion protein, Gentaur) as well as the antibodies to be tested were added in each well and incubated 1 hour at room temperature. After washings, the presence or not of the interacting SIRPα was detected by an HRP-conjugated anti-6His secondary antibody (Bethyl) and peroxidase substrate. All 10 selected antibodies were found to inhibit the binding of hSIRPα to hCD47 (data not shown).

4. Inhibition of CD47/SIRPα Interaction by Flow Cytometry on CHO Cells

The eight best candidates were then further selected according to their binding profile by ELISA and on CD47-transfected CHO cells (candidates 7, 14, 15, 19, 20, 22, 26, 33) and were tested for their capacity to inhibit the binding of human SIRPα (hSIRPα) to hCD47 expressed on CHO cells. Human CD47-transfected cells ($3 \times 10^5$ cells/well of 96-well plate) were first incubated at +4° C. for 30 minutes with serial dilutions of anti-CD47 antibodies or isotype control antibody (in mIgG2a or mIgG1 format). The cells were then washed and incubated with 10 μg/mL of His-Tagged hSIRPα (His-hSIRPα, Gentaur) for 30 minutes at +4° C. After washings, the binding of His-hSIRPα to CHO cells was revealed by incubation with a rabbit anti-His antibody (Bethyl), followed by a FITC-conjugated goat anti-rabbit IgG (BD Biosciences) and flow cytometry analysis on an Accuri-C6 flow cytometer (BD Biosciences). The percentage of inhibition of hSIRPα binding to hCD47 was calculated as follows: % inhibition=(1−(MFI_wAb−MFI_wohSIRPα)/(MFI_whSIRPα−MFI_wohSIRPα))×100, where MFI_wAb is the Mean Intensity Fluorescence (MFI) obtained with the hCD47-CHO cells incubated with the tested antibody and hSIRPα; MFI_wohSIRPα is the MFI obtained in the absence of hSIRPα (100% hSIPRα binding inhibition); and MFI_whSIRPα is the fluorescence with hSIRPα but without pre-incubation with antibody (0% SIRPα binding inhibition). The percentage inhibition was plotted against antibody concentration and the IC50 values were calculated using a nonlinear regression analysis model of the GraphPad Prism software. The results presented in the FIG. 1 and Table 5 below show that the 8 selected candidates (numbers 7, 14, 15, 19, 20, 22, 26, and 33) strongly inhibited the binding of hSIRPα on hCD47 expressed on CHO cells, with IC50 values ranging from 0.36 to 1.10 μg/mL (2.4 to 7.3 nM). The 8 anti-CD47 candidates were superior to the B6H12 and 5A3M3 antibodies and were similar to the 2A1 and VxP037-01LC1 antibodies.

TABLE 5

IC50 values of anti-CD47 antibodies in the CD47/ SIRPα inhibition assay with CD47-transfected CHO cells and flow cytometry analysis (mean values of n independent experiments)

| Antibody (mIgG format) | Mean IC50 (μg/mL) | n |
|---|---|---|
| B6H12 | 4.920 | 7 |
| 2A1 | 0.739 | 7 |
| VxP037-01LC1 | 0.759 | 6 |
| 5A3M3 | 4.798 | 4 |
| Candidate 7 | 0.657 | 6 |
| Candidate 14 | 0.737 | 5 |
| Candidate 15 | 0.605 | 5 |
| Candidate 19 | 0.858 | 5 |
| Candidate 20 | 0.440 | 2 |
| Candidate 22 | 0.482 | 2 |
| Candidate 26 | 0.359 | 4 |
| Candidate 33 | 1.108 | 4 |

5. Binding of Anti-CD47 Antibodies on hCD47 Expressed by Raji Cells

The eight further selected candidates (numbers 7, 14, 15, 19, 20, 22, 26, 33) were tested for their capacity to bind to hCD47 expressed on the Raji human B lymphoma cell line. Raji cells (ATCC-CLL-86; $2 \times 10^5$ cells/well of 96-well plate) were first incubated at +4° C. for 30 minutes with serial dilutions of anti-CD47 antibodies or control isotype antibody (in mIgG2a or mIgG1 format). The cells were then washed and incubated for 30 minutes at +4° C. with a PE-conjugated F(ab)'2 goat anti-mouse IgG antibody (1/100 dilution, Beckman Coulter). After washings, the fluorescence of the cells was analyzed by flow cytometry on an Accuri-C6 flow cytometer (BD Biosciences).

The delta of MFI, representing the difference between the intensity measured with the tested antibody and the intensity in the absence of antibody, was calculated for each antibody concentration and the values were plotted against the antibody concentrations. The EC50 values were then calculated by using a nonlinear regression analysis model of the GraphPad Prism software.

Figure 2:
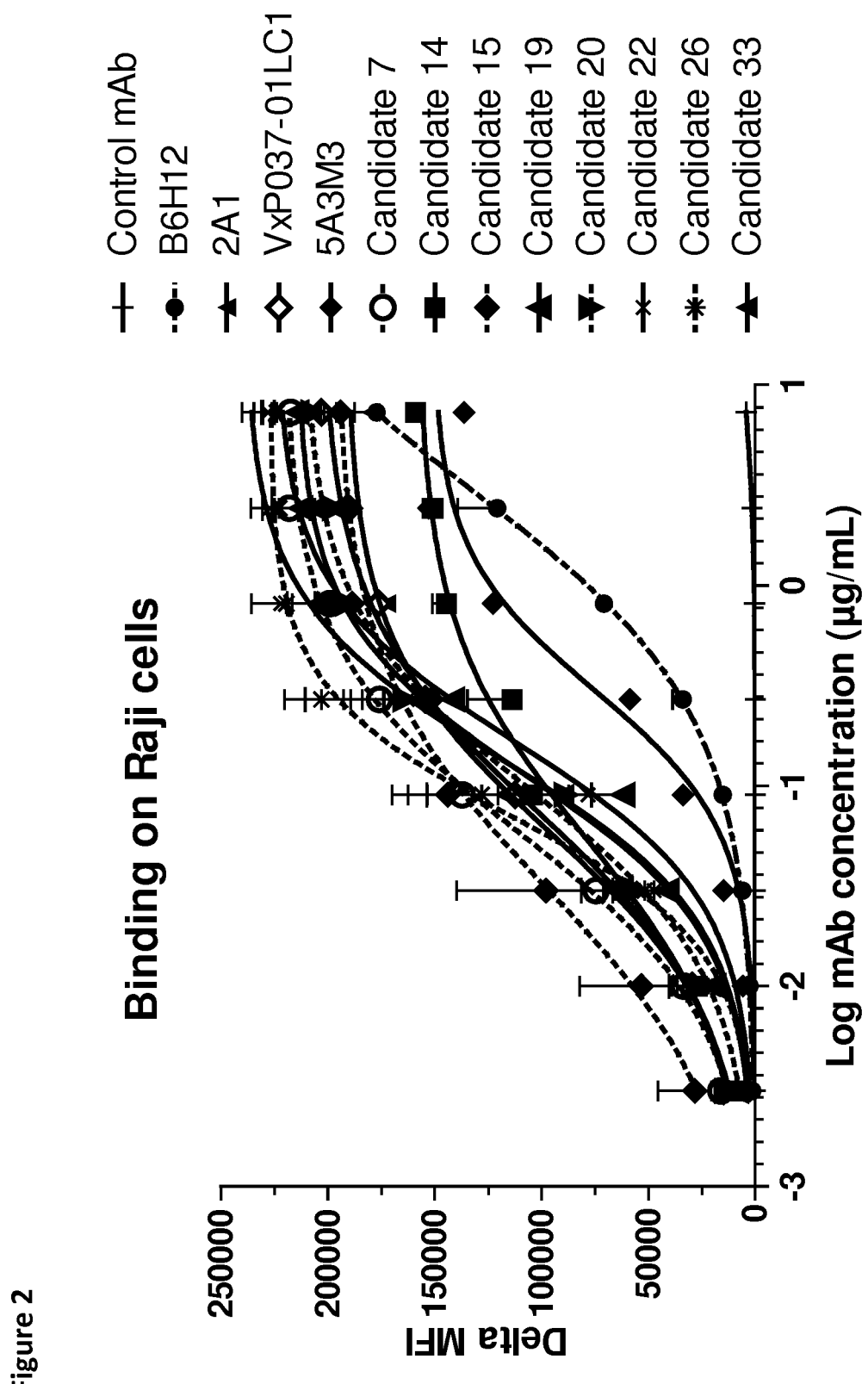
FIG. 2 Binding profiles of anti-CD47 antibodies to hCD47 expressed on Raji cells.

The results presented in the FIG. 2 and Table 6 below, show that the 8 candidates (numbers 7, 14, 15, 19, 20, 22, 26, and 33) strongly bound to hCD47 expressed on Raji cells, with EC50 values ranging from 0.03 to 0.17 μg/mL (0.2 to 1.1 nM). The 8 anti-CD47 candidates were superior to the B6H12 and 5A3M3 antibodies and were similar to the 2A1 and VxP037-01LC1 antibodies from the competitors.

TABLE 6

EC50 values of anti-CD47 antibodies in the CD47 binding assay with Raji cells and flow cytometry analysis (mean values of n independent experiments)

| Antibody (mIgG format) | Mean EC50 (μg/mL) | n |
|---|---|---|
| B6H12 | 2.930 | 2 |
| 2A1 | 0.058 | 3 |
| VxP037-01LC1 | 0.074 | 2 |
| 5A3M3 | 0.301 | 1 |
| Candidate 7 | 0.058 | 2 |
| Candidate 14 | 0.055 | 2 |

TABLE 6-continued

EC50 values of anti-CD47 antibodies in the CD47
binding assay with Raji cells and flow cytometry analysis
(mean values of n independent experiments)

| Antibody (mIgG format) | Mean EC50 (µg/mL) | n |
|---|---|---|
| Candidate 15 | 0.031 | 2 |
| Candidate 19 | 0.165 | 2 |
| Candidate 20 | 0.096 | 3 |
| Candidate 22 | 0.136 | 2 |
| Candidate 26 | 0.070 | 2 |
| Candidate 33 | 0.112 | 2 |

6. Inhibition of CD47/SIRPα Interaction by Flow Cytometry on Raji Cells

Six of the 8 further selected candidates (numbers 14, 15, 19, 20, 22, 33) were tested for their capacity to inhibit the binding of hSIRPα to hCD47 expressed on human B lymphoma Raji cells. To this end, Raji cells (ATCC-CCL-86; $2 \times 10^5$ cells/well of 96-well plate) were first incubated at +4° C. for 30 minutes with serial dilutions of anti-CD47 antibodies or isotype control antibody (chimeric anti-CD47 candidates produced in hIgG1 or hIgG4 format). The cells were then washed and incubated with 2.5 µg/mL of His-Tagged hSIRPα (His-hSIRPα, Gentaur) for 30 minutes at +4° C. After washings, the binding of His-hSIRPα to Raji cells was revealed by incubation with a mouse anti-His antibody (1/1000 dilution; Qiagen), followed by a PE-conjugated goat anti-mouse IgG (1/100 dilution; Beckman Coulter) and flow cytometry analysis on an Accuri-C6 flow cytometer (BD biosciences).

The percentage of inhibition of hSIRPα binding to hCD47 was calculated as follows: % inhibition=(1−(MFI_wAb−MFI_wohSIRPα)/(MFI_whSIRPα−MFI_wohSIRPα))× 100, where MFI_wAb is the Mean Intensity Fluorescence (MFI) obtained with the Raji cells incubated with the tested antibody and hSIRPα; MFI_wohSIRPα is the MFI obtained in the absence of hSIRPα (100% hSIPRα binding inhibition); and MFI_whSIRPα is the florescence with hSIRPα but without pre-incubation with antibody (0% SIRPα binding inhibition). The percent inhibition was plotted against antibody concentration and the IC50 values were calculated by using a nonlinear regression analysis model of the GraphPad Prism software.

Figure 3:
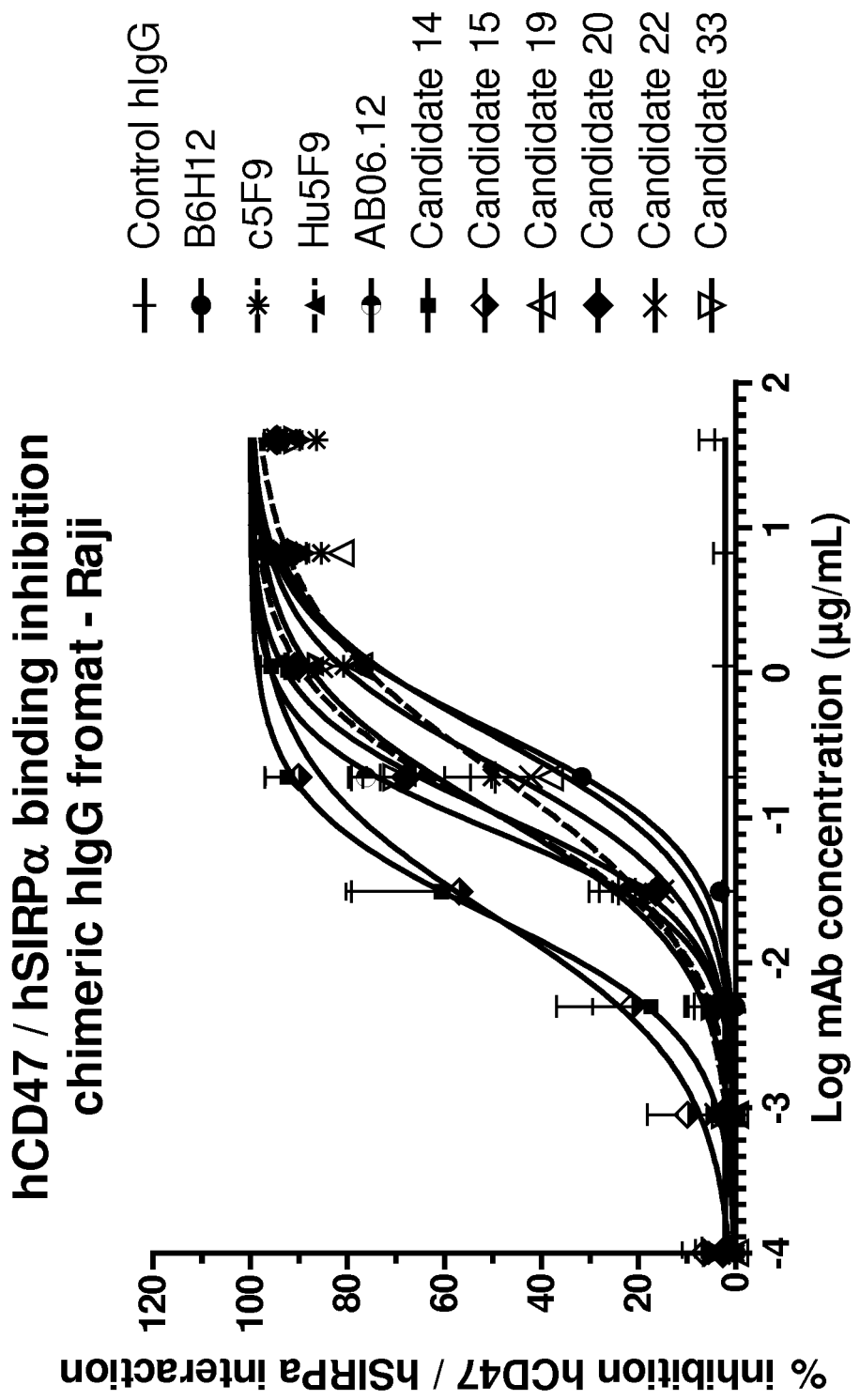
FIG. 3 Inhibition of hSIRPα binding to hCD47 expressed on Raji cells by anti-CD47 antibodies.

The results presented in the FIG. 3 and Table 7 below show that the 6 selected candidates (numbers 14, 15, 19, 20, 22 and 33) strongly inhibited the binding of hSIRPα on hCD47 expressed on Raji cells, with IC50 values ranging from 0.021 to 0.369 µg/mL (0.14 to 2.46 nM). The 6 anti-CD47 candidates were similar or superior to the chimeric B6H12 and to the chimeric 5F9 antibodies, as well as to the humanized 5F9 and AB06.12 antibodies.

TABLE 7

IC50 values of anti-CD47 antibodies in the hCD47/hSIRPα
inhibition assay with Raji cells and flow cytometry analysis
(mean values of n independent experiments)

| Antibody (hIgG format) | Mean IC50 (µg/mL) | n |
|---|---|---|
| Chimeric B6H12 | 0.400 | 1 |
| Chimeric c5F9 | 0.209 | 5 |
| Humanized Hu5F9 | 0.109 | 3 |
| Humanized AB06.12 | 0.082 | 4 |
| Candidate 14 | 0.021 | 2 |
| Candidate 15 | 0.021 | 2 |
| Candidate 19 | 0.369 | 3 |

TABLE 7-continued

IC50 values of anti-CD47 antibodies in the hCD47/hSIRPα
inhibition assay with Raji cells and flow cytometry analysis
(mean values of n independent experiments)

| Antibody (hIgG format) | Mean IC50 (µg/mL) | n |
|---|---|---|
| Candidate 20 | 0.110 | 6 |
| Candidate 22 | 0.233 | 4 |
| Candidate 33 | 0.110 | 3 |

7. Phagocytosis of Raji Cells by Human Macrophages

CD47 is considered as a "don't eat me" signal that prevents the phagocytosis of CD47-expressing cells by interacting with SIRPα expressed on cells with phagocytosis activity such as macrophages. In order to evaluate the ability of the best candidates to increase the phagocytosis of tumor cells by macrophages, human B lymphoma Raji cells were first loaded with 5(6)-Carboxyfluorescein N-hydroxysuccinimidyl ester (CF SE, 2.5 µM, Abcam) and then incubated with different dilutions of anti-CD47 antibodies or control antibody (mIgG1 format). The cells were then washed and placed in the presence of adherent macrophages previously differentiated from human peripheral blood monocytes in 24-well plates in the presence of 10 µg/mL M-CSF (Peprotech) for 9 days. After 4 hours incubation at +37° C., the cell mixtures were firmly washed with cold PBS and the adherent macrophages were fixed with PFA. The fixed cells were examined under an Axiovert 40FL fluorescent microscope (Zeiss) equipped with an HB050 lamp. Pictures of the green fluorescence (Raji cells) and bright-field (macrophages) were monitored with a digital AxioCam camera and the number of Raji cells (green fluorescent) and macrophages were counted per field by using the ZEN lite Image Analysis software. A phagocytic index was then calculated as the number of Raji cells ingested per 100 macrophages.

Figure 4:
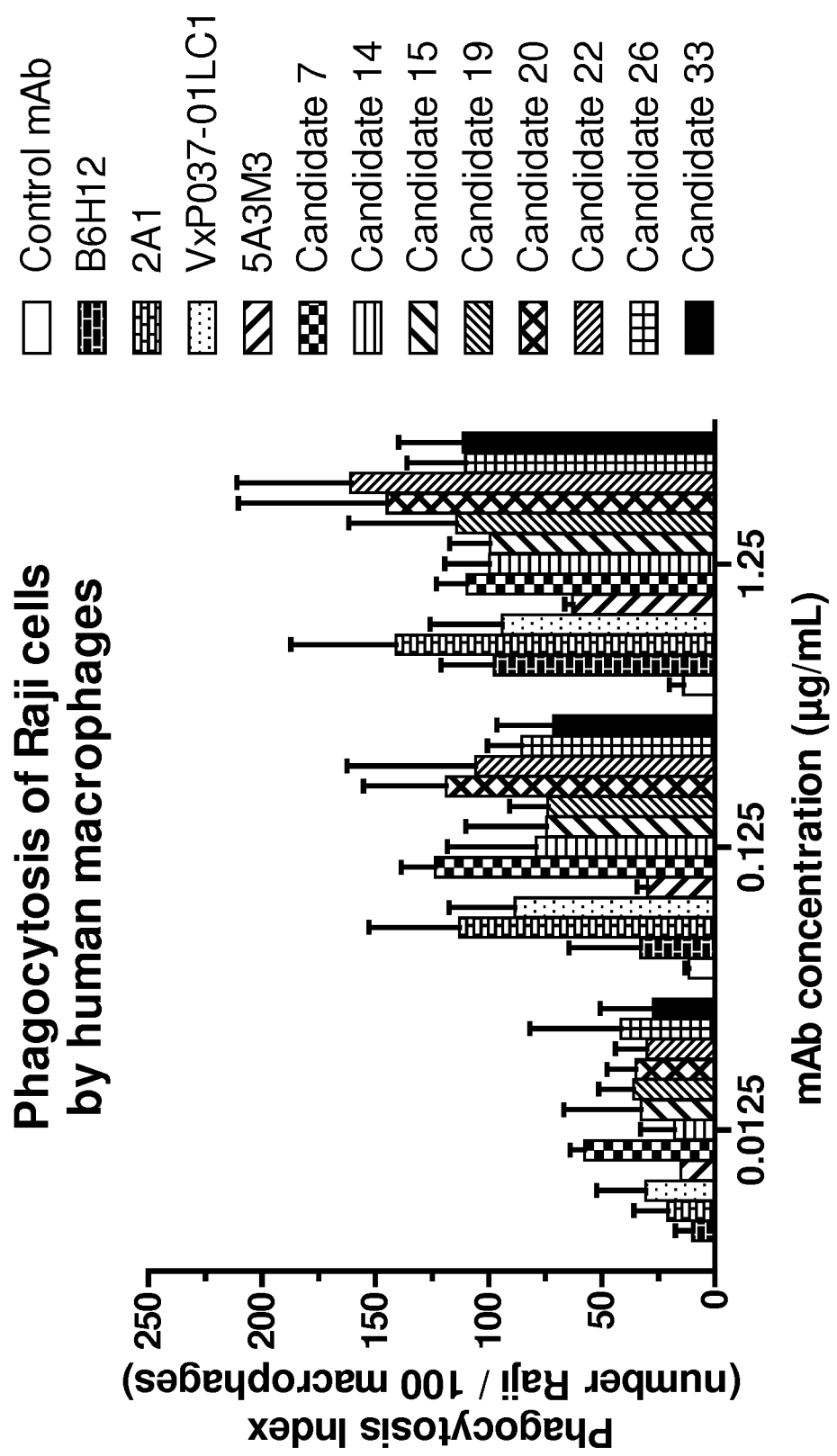
FIG. 4 Enhancement of Raji cell phagocytosis by human macrophages with anti-CD47 antibodies.

The results presented in the FIG. 4 and Table 8 below, show that the 8 selected candidates (numbers 7, 14, 15, 19, 20, 22, 26 and 33) enhanced the phagocytosis of Raji cells by human macrophages. At a sub-optimal concentration (0.125 µg/mL), the candidates were superior to the B6H12 and 5A3M3 antibodies, and similar to the 2A1 and VxP037-01LC1 antibodies.

TABLE 8

Phagocytic index of anti-CD47 antibodies (at 0.125 µg/mL)
in the Raji phagocytic assay with human macrophages

| Antibody (mIgG1 format) | Mean | SD | n |
|---|---|---|---|
| B6H12 | 33.1 | 31.3 | 7 |
| 2A1 | 112.8 | 39.9 | 5 |
| VxP037-01LC1 | 88.4 | 28.9 | 4 |
| 5A3M3 | 29.9 | 4.4 | 2 |
| Candidate 7 | 123.6 | 14.9 | 3 |
| Candidate 14 | 78.9 | 39.3 | 5 |
| Candidate 15 | 74.4 | 35.6 | 4 |
| Candidate 19 | 73.9 | 16.8 | 3 |
| Candidate 20 | 118.6 | 36.6 | 4 |
| Candidate 22 | 105.8 | 55.5 | 4 |
| Candidate 26 | 85.3 | 15.1 | 2 |
| Candidate 33 | 71.4 | 27.7 | 3 |

8. Red Blood Cell Agglutination Assay

The 8 pre-selected candidates were tested for their capacity for inducing the agglutination of human red blood cells (RBCs) and were compared with benchmark antibodies.

Figure 5:
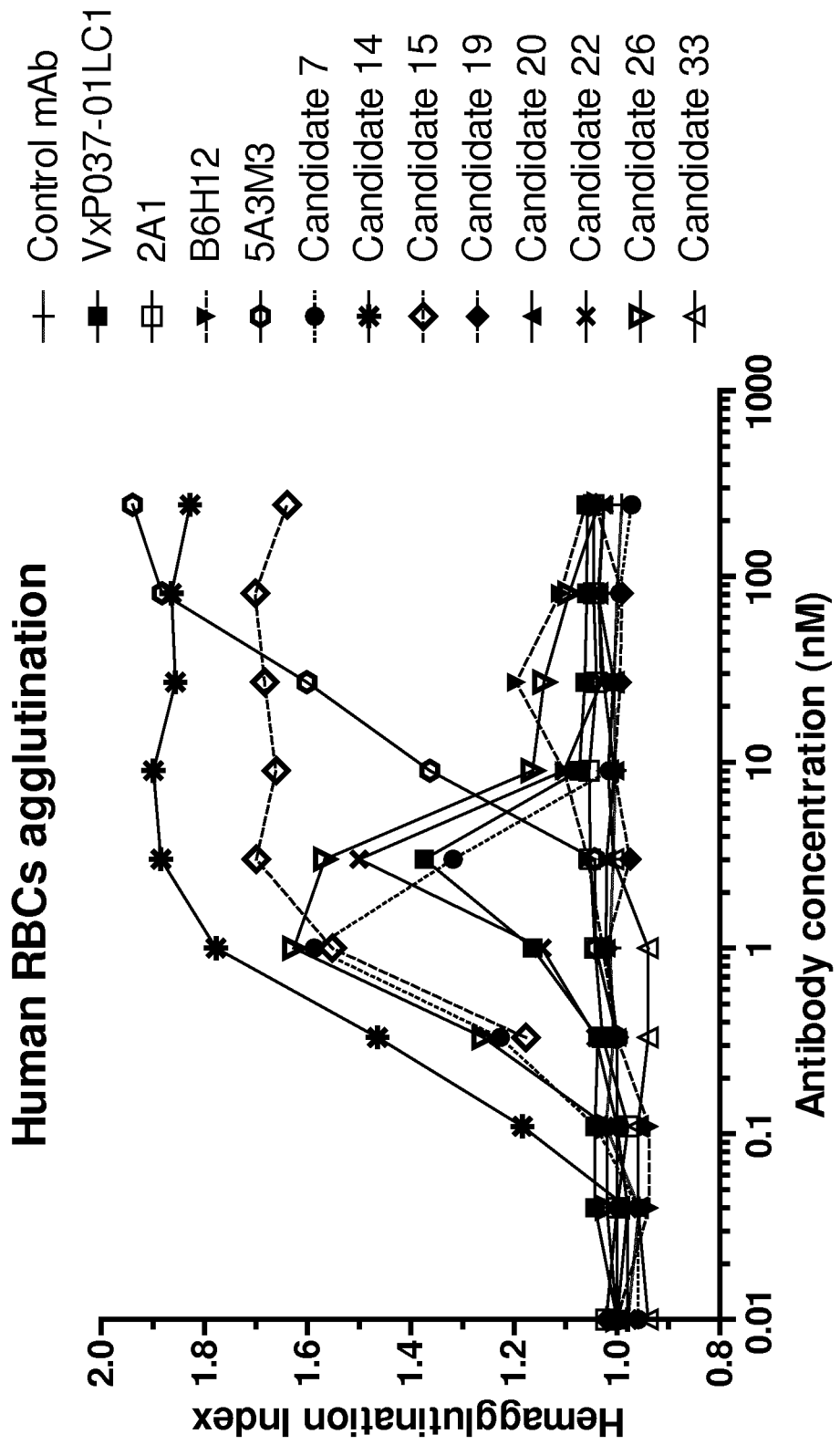
FIG. 5 Agglutination of purified human RBCs by anti-CD47 antibodies.

In the first series of experiments, RBCs purified from human peripheral blood were incubated with serial dilution of anti-CD47 antibodies or control antibodies for 1 hour at 37° C. in U-bottom 96 plates. After incubation, evidence of RBC agglutination was demonstrated by the appearance of a haze as opposed to a punctate red pellet of non-agglutinated RBCs. The area of the RBC pellets was measured and the hemagglutination index was calculated by the ratio of the area of RBCs at different antibody concentrations versus the area of RBCs without antibody, essentially as described in WO2014/123580. Hemagglutination indexes were plotted against the antibody concentrations, as shown in FIG. 5. The candidates 14 and 15, and to a lesser extent candidate 26, were found to induce a strong agglutination of purified RBCs. Of note, these 3 antibodies belong to the same clone family and cross-react with mCD47. In contrast, candidates 19, 20 and 33 did not induce agglutination of purified RBCs when tested in concentrations ranging from 0.01 nM to 240 nM (~1.5 ng/mL to 36 µg/mL), as also observed with the 2A1 antibody. Candidates 7 and 22 were found to induce weak agglutination for a narrow window of concentration as also observed with the antibodies VxP037-01LC1 and B6H12. Antibody 5A3M3 induced agglutination of purified RBCs only at high concentrations.

In a second set of experiments, the 8 selected candidates were tested for their capacity to induce the agglutination of human RBCs by using unpurified RBCs from whole peripheral blood, essentially as described in WO2014/087248. To this end, human peripheral blood (1/5 final dilution) was incubated with serial dilutions of anti-CD47 antibodies or control antibodies overnight at 37° C. in flat-bottomed 96-well plates. After incubation, the plates were gently agitated, tilted at about 30° and allowed to rest for 10 minutes. The evidence of RBC agglutination was demonstrated by the appearance of a clumped deposit in the form of a crescent at the bottom around the inferior border of the well. Different formats of the anti-CD47 candidates were tested and compared with benchmark antibodies. Candidate 20 in mIgG1 or hIgG1 chimeric format did not induce RBC agglutination in the range of concentrations tested from 0.023 to 50 µg/mL (~0.15 to 330 nM), as also observed for the 2A1 and AB06.12 (humanized 2A1) antibodies. Weak RBC agglutination was observed for concentrations higher than 16 µg/mL for both candidate 20 and AB06.12 antibody in hIgG4 format. In contrast, the chimeric 5F9 (c5F9) and humanized 5F9 (hu5F9, vh2/vl2 variant) induced stronger agglutination when tested in both hIgG1 and hIgG4 format. Chimeric B6H12 induced RBC agglutination in hIgG1 format but more weakly in hIgG4 isotype.

In this assay with whole blood, candidates 19, 22 and 33 were found to induce RBC agglutination at concentrations higher than 5 µg/mL. This observation was independent of the tested format (mIgG or chimeric hIgG). Finally, candidates 14 and 15, and to a lesser extent candidates 7 and 26 induced strong agglutination of unpurified RBCs.

RBC agglutination assay data are summarized in Table 9 below.

TABLE 9

RBC agglutination activity of anti-CD47 antibodies

| | RBC agglutination with | | | | |
|---|---|---|---|---|---|
| | Purified RBC | Whole Blood | | | |
| Antibody | mIgG or hIgG | mIgG1 | mIgG2a | hIgG1 | hIgG4 |
| B6H12 | +/− (m, h) | +++ | +++ | +++ | +/++ |
| c5F9 | Nd | nd | nd | +++ | +++ |

TABLE 9-continued

RBC agglutination activity of anti-CD47 antibodies

Figure 6:
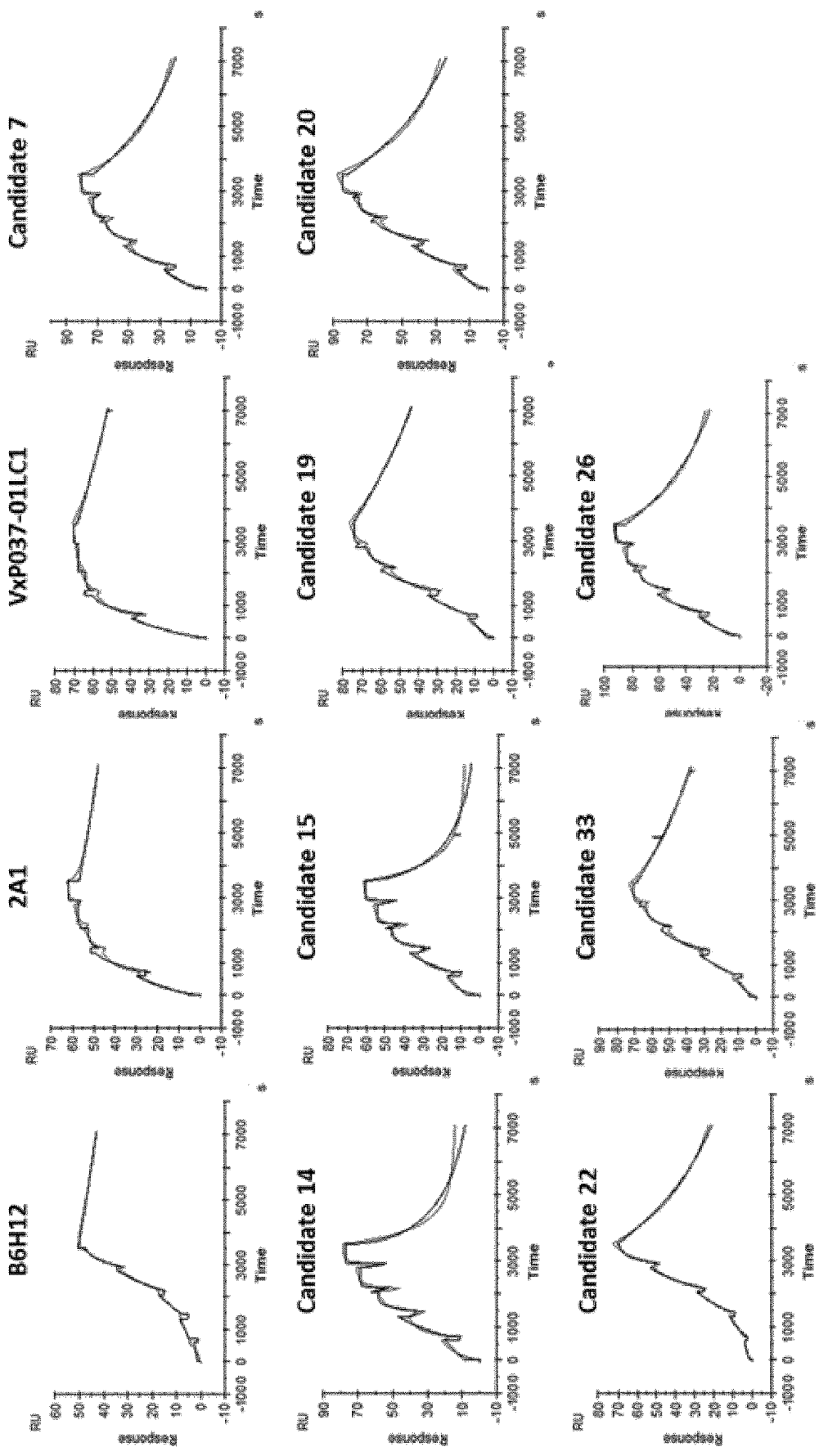
FIG. 6 Profiles of association and dissociation of anti-CD47 antibodies with hCD47 as measured by SPR.

| | RBC agglutination with | | | | |
|---|---|---|---|---|---|
| | Purified RBC | Whole Blood | | | |
| Antibody | mIgG or hIgG | mIgG1 | mIgG2a | hIgG1 | hIgG4 |
| hu5F9 | Nd | nd | nd | +++ | +++ |
| 5A3M3 | +++ (m1) | +/− | nd | nd | nd |
| 2A1 | − (m1) | − | nd | nd | nd |
| AB06.12 | Nd | nd | nd | − | +/− |
| VxP037-01LC1 | + (m1) | + | nd | nd | nd |
| Candidate 7 | ++ (m1, m2a) | ++ | ++ | nd | ++ |
| Candidate 14 | ++++ (m, h) | ++++ | ++++ | ++++ | ++++ |
| Candidate 15 | +++ (m, h) | ++++ | ++++ | ++++ | +++ |
| Candidate 26 | ++ (m2a) | nd | ++ | nd | ++ |
| Candidate 19 | − (m1, m2a) | +++ | ++ | +++ | +/+++ |
| Candidate 33 | − | +++ | +++ | +++ | +++ |
| Candidate 20 | − | − | − | − | +/− |
| Candidate 22 | +/++ | +++ | +++ | +++ | +++ | nd: not done;
m: mIgG;
m1: mIgG1;
m2a: mIgG2a;
h: hIgG
+/−, weak agglutination observed at 50 µg/mL antibody only;
+, agglutination at 50 µg/mL antibody;
++, agglutination for concentrations ≥16.7 µg/mL;
+++, agglutination for concentrations ≥5.6 µg/mL 9. Affinity of the Best Mouse Anti-CD47 Candidates The kinetic constants (Kon & Koff) and the dissociation constant (KD) of the mouse anti-CD47 candidates were further measured by surface plasmon resonance (SPR) on Biacore T200 (GE Healthcare) using a soluble preparation of human CD47 extracellular domain tagged with a 6His-tag (SEQ ID NO: 160) (hCD47-his protein) and compared to benchmarks. Briefly, the binding affinity between antibodies and hCD47-his was measured using the single-cycle kinetics protocol of the Biacore T200 instrument at +20° C. An anti-human or anti-mouse IgG (Fc) was first immobilized on the surface of Serie S Sensor Chips CM5 using the human or mouse antibody capture and amine coupling kits, following the manufacturer's instructions (GE Healthcare). This resulted in approximately 10,000 response units (RU) immobilized on the surface. The mouse, chimerized or humanized antibodies to be tested were then captured onto the appropriate anti-mouse or anti-human IgG surface in all flow cells except flow cell 1 used as control, at concentration and contact time adjusted so that ~300 RU were captured on the surface. Binding kinetics were studied by passing increasing concentrations of hCD47-his in a series of five 10 minute injections through all flow cells at a rate of 30 µL/min. Three-fold dilutions were used up to a maximum concentration of 270 nM. Following the final injection, buffer was passed across each flow cell for 60 minutes (mouse) or 30 minutes (human) to monitor the dissociation of bound antigen. Regeneration of the binding surface was carried out at the end of the cycle by flowing 3 M $MgCl_2$ for 60 s at 20 µL/min followed by 10 mM glycine-HCl, pH 1.7 for 180 s at 10 µl/min (for human) or by flowing 10 mM glycine-HCl, ph 1.7 for 360 s at 10 µl/min (for mouse). A second cycle with the same antibodies but no antigen was run as a control. Kinetics binding constants were estimated by non-linear fitting of the sensogram data to the 1:1 binding model provided by the Biacore T200 evaluation software. Results are shown in Table 10 below. All candidates displayed an affinity in the nM range with a KD of between 0.9 to 4.2 nM, except for candidate 22 which showed a weaker affinity, with a KD of 15.7 nM. As shown in FIG. 6, all pre-selected candidates except candidate 33 differed from the B6H12, 2A1 and VxP037-01LC1 antibodies by displaying more rapid kinetics of dissociation, with Koff values in the range of $3.4 \times 10^{-3}$ to $1.8 \times 10^4$ s$^{-1}$, as compared to 5.0 to $8.9 \times 10^{-5}$ s$^{-1}$ for B6H12, 2A1 and VxP037-01LC1.

TABLE 10

Kinetics and affinity constants of anti-CD47 antibodies by Biacore (mean values of independent experiments)

| Antibody | KD (M) | Kon (1/Ms) | Koff (1/s) | n |
|---|---|---|---|---|
| B6H12 | $5.14 \times 10^{-9}$ | $1.29 \times 10^4$ | $6.59 \times 10^{-5}$ | 7 |
| VxP037-01LC1 | $2.56 \times 10^{-10}$ | $3.54 \times 10^5$ | $8.87 \times 10^{-5}$ | 3 |
| 2A1 | $1.27 \times 10^{-10}$ | $4.01 \times 10^5$ | $4.99 \times 10^{-5}$ | 4 |
| Candidate 7 | $1.94 \times 10^{-9}$ | $1.90 \times 10^5$ | $3.70 \times 10^{-4}$ | 2 |
| Candidate 14 | $3.85 \times 10^{-9}$ | $8.74 \times 10^5$ | $3.37 \times 10^{-3}$ | 2 |
| Candidate 15 | $4.24 \times 10^{-9}$ | $5.65 \times 10^5$ | $2.39 \times 10^{-3}$ | 2 |
| Candidate 19 | $2.25 \times 10^{-9}$ | $7.90 \times 10^4$ | $1.76 \times 10^{-4}$ | 4 |
| Candidate 20 | $4.16 \times 10^{-9}$ | $1.01 \times 10^5$ | $4.18 \times 10^{-4}$ | 4 |
| Candidate 22 | $1.57 \times 10^8$ | $2.07 \times 10^4$ | $3.25 \times 10^{-4}$ | 2 |
| Candidate 26 | $1.87 \times 10^{-9}$ | $2.00 \times 10^5$ | $3.72 \times 10^{-4}$ | 2 |
| Candidate 33 | $8.98 \times 10^{-10}$ | $7.46 \times 10^4$ | $6.70 \times 10^{-5}$ | 2 |

10. Release of Anti-CD47 Antibodies after Binding to Human RBCs or to Tumor Cells, and Phagocytosis of Tumor Cells by Anti-CD47 Antibodies According to their Koff Value CD47 is expressed on circulating blood cells, in particular on RBCs, and represents an important source of sink effect that may significantly impact the pharmacokinetics and the efficacy of a therapeutic anti-CD47 antibody by lowering the amount of free antibody available for the targeted cells such as tumor cells. Moreover, an important and prolonged binding of anti-CD47 antibodies to RBCs may also increase the risk of toxicity such as anemia. The kinetics of binding versus release of an antibody from its antigen is mostly dependent on its kinetics of association and dissociation that can be quantified by measuring the Kon and Koff values, respectively, for example by SPR as carried out for the anti-CD47 antibodies of this invention. In order to evaluate in vitro the impact of the dissociation kinetics of anti-CD47 antibodies on their release after binding to RBCs, purified human RBCs were incubated with 1 µg/mL of mouse anti-CD47 candidates 14, 19, 20 or 22, or with 1 µg/mL mouse anti-CD47 antibody 2A1 or B6H12. These anti-CD47 candidates were selected because they possessed Koff values superior to $1 \times 10^{-4}$ s$^{-1}$ or even superior to $1 \times 10^{-3}$ s$^{-1}$ for candidate 14 (see Table 10). Conversely, the Koff value of the anti-CD47 2A1 and B6H12 benchmarks was inferior to $1 \times 10^{-4}$ s$^{-1}$ (Table 10). After 30 minutes incubation with antibodies at +4° C., RBCs were washed, resuspended in antibody-free PBS/BSA/EDTA buffer and incubated either at +37° C. for 6 hours or 24 hours. At different incubation times, RBCs were washed in PBS/BSA/EDTA buffer and incubated with a PE-conjugated goat anti-mouse IgG at +4° C. The binding of the mouse anti-CD47 antibodies on RBCs was further analyzed by flow cytometry. For each antibody, the mean fluorescence intensity (MFI) obtained by gating on viable RBCs after 6 hours (T+6 h) or 24 hours (T+24 h) was recorded and compared to the MFI obtained on RBCs analyzed just before the incubation periods at +37° C. (T0). The results were expressed as the percentage of decrease of the MFI recorded after T+6 h or T+24 h incubation at +37° C. compared to the MFI recorded at T0 before the incubation steps.

Figure 20:
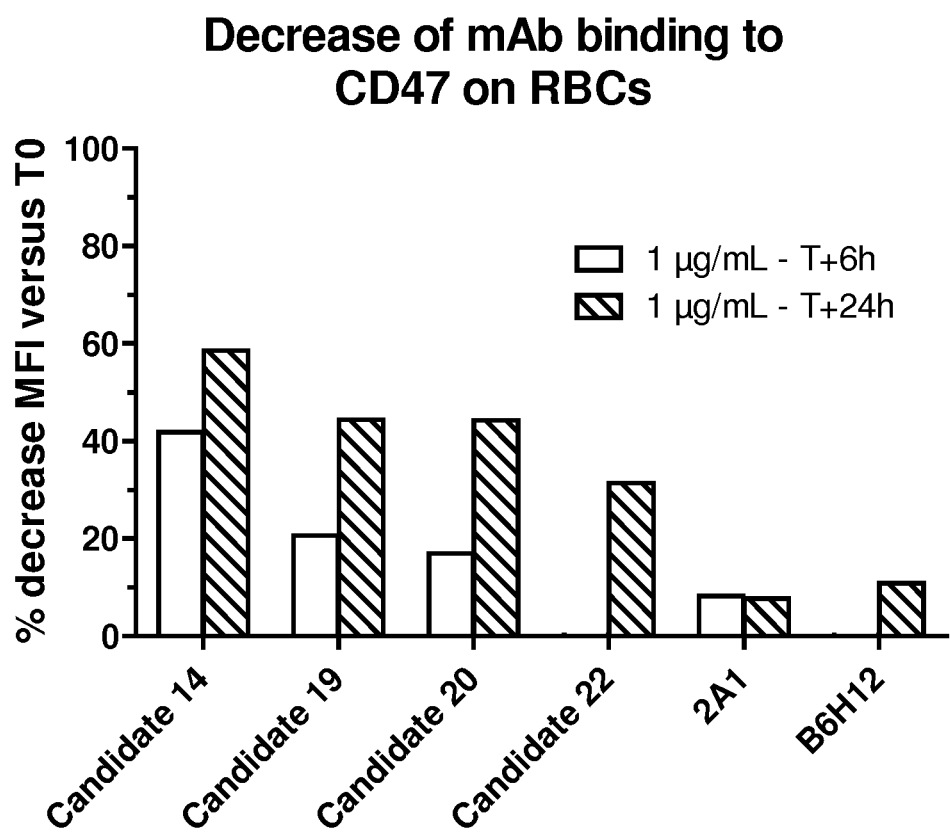
FIG. 20 Release of anti-CD47 antibodies after binding to RBCs. Human RBCs were first stained with 1 μg/mL of mouse anti-CD47 candidates 14, 19, 20, 22 or with mouse 2A1 or B6H12 antibody at +4° C. After washing, RBCs were incubated for 6 hours (T+6 h) or for 24 hours (T+24 h) at +37° C. in antibody-free medium, and the residual levels mouse anti-CD47 antibodies fixed on RBCs was revealed with a PE-conjugated anti-mouse IgG antibody and flow cytometry. The results were expressed as the % of decrease of the mean fluorescence intensity (MFI) measured at T+6 h or T+24 h on the RBCs stained with an anti-CD47 antibody compared to the MFI obtained for the staining of RBCs with the same antibody before the 6 and 24 hour incubations (T0).

As shown in FIG. 20, the MFI of the RBCs stained with the candidates 14, 19, 20 and 22 was already significantly reduced after 6 hours and even more strongly reduced after 24 hours incubation at +37° C. These results indicated that the candidates 14, 19, 20 and 22 progressively detached from the RBCs after having bound the membrane-expressed CD47 antigen. In contrast, after 6 or 24 hours of incubation at +37° C., the MFI of RBCs stained with the antibody 2A1 or B6H12 was not modified or only weakly, indicating that the antibody 2A1 and B6H12 were strongly stuck on RBCs and were not or only slowly released in the extracellular medium.

Of note, while an agglutination was observed with certain antibodies (candidates 14 and 22, antibody B6H12), this did not strongly impact the analysis of single RBCs by flow cytometry.

These results suggest that anti-CD47 antibodies such as candidates 14, 19, 20 and 22 that share a dissociation kinetic with a high Koff value superior to $1 \times 10^{-4}$ s$^{-1}$ will be more rapidly released from RBCs to reach the target cells. Thus anti-CD47 antibodies such as candidate 14, 19, 20 and 22 will be more available for reaching the CD47 expressed on the targeted tumor cells compared to antibodies with slow dissociation kinetics such as 2A1 or B6H12 that possess a Koff value inferior to $1 \times 10^{-4}$ s$^{-1}$.

Conversely, an antibody with a high dissociation rate from cell-expressed CD47 may be less efficient to enhance tumor cell phagocytosis than antibodies with a slower dissociation rate. To address this point, an experiment, similar to the binding/release experiment performed above on RBCs, was carried out to measure the in vitro release of the anti-CD47 antibodies by tumor cells and its effect on tumor cell phagocytosis. To this end, human Raji lymphoma cells were incubated with the mouse anti-CD47 candidates 14, 19, 20 or 22, or with the mouse anti-CD47 antibodies B6H12 or 2A1 at 1 µg/mL for 30 minutes at +4° C., then washed and incubated again in antibody-free medium for 24 hours at +37° C. Cells were then collected after the 24 hour incubation times (T+24 h) washed in PBS and fixed with 4% PFA. As positive control of staining, cells were also fixed with 4% PFA just before being incubated for 24 hours (time T0). After the last incubation time, fixed cells were stained by a PE-conjugated goat anti-mouse IgG antibody and analyzed by flow cytometry. For each antibody, the mean fluorescence intensity (MFI) obtained after 24 hour (T+24 h) incubation was recorded and compared to the MFI obtained on Raji cells analyzed just before the incubation periods at +37° C. (T0). The results were expressed as the percentage of decrease of the MFI of the cells recorded after T+24 h incubation at +37° C. compared to the MFI recorded at T0 before the incubation steps.

Figure 21A:
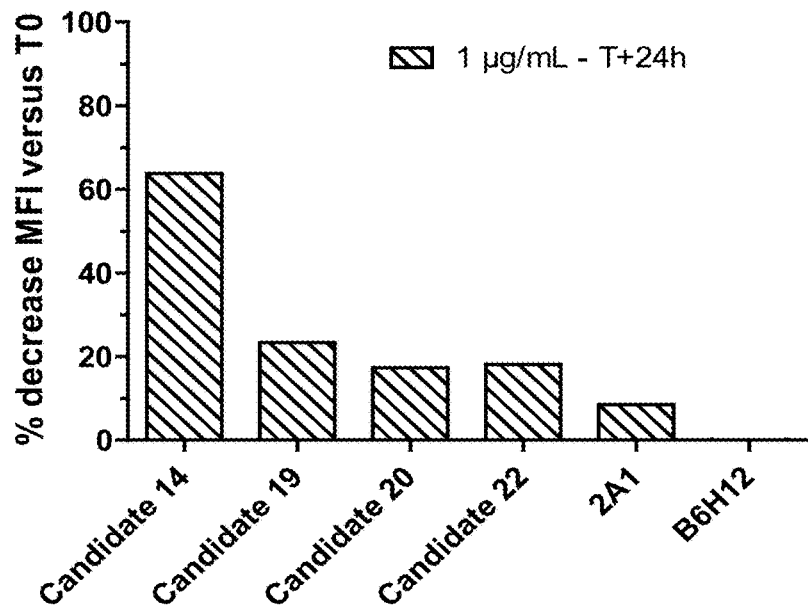
FIGS. 21A-21B Release of anti-CD47 antibodies after binding to Raji cells and decrease of phagocytosis of Raji tumor cells after their staining by anti-CD47 antibodies. (A) Raji lymphoma cells were first stained with 1 µg/mL of mouse anti-CD47 candidates 14, 19, 20, 22 or with mouse 2A1 or B6H12 antibody (FIG. 21A). After washing, Raji cells were incubated for 24 hours (T+24 h) at +37° C. in antibody-free medium, then washed and fixed with PFA 4%. The residual levels of mouse anti-CD47 antibodies fixed on Raji cells was then revealed with a PE-conjugated anti-mouse IgG antibody and flow cytometry. The results were expressed as the % of decrease of the mean fluorescence intensity (MFI) measured at T+24 h on the cells stained with an anti-CD47 antibody compared to the MFI obtained for the staining of PFA-fixed Raji cells with the same antibody before the 24 hour incubations (T0). (B) CFSE-labelled Raji lymphoma cells were first stained with 0.1 or 1 µg/mL of mouse anti-CD47 candidates 14, 19, 20, 22, or with mouse 2A1 or B6H12 antibody (FIG. 21B). After washing, Raji cells were incubated for 24 hours (T+24 h) at +37° C. in antibody-free medium, then washed and tested in a phagocytosis assay by flow cytometry with Far-Red-labelled human macrophages (hMDM). The results were expressed as the % of decrease of the phagocytosis measured at T+24 h for Raji cells stained with an anti-CD47 antibody compared to the phagocytosis of the Raji cells stained with the same antibody before the 24 hour incubation period (T0).

As shown in FIG. 21A an important decrease of the MFI of candidate 14 was observed already after 24 hours incubation of the Raji cells at 37° C., while a weaker diminution was observed for the candidates 19, 20 and 22 as well as for the antibody 2A1, but not for B6H12. These results show that anti-CD47 antibodies with very rapid dissociation kinetics such as candidate 14 possessing a Koff value superior to $1 \times 10^{-3}$ s$^{-1}$, will detach more quickly and more strongly from Raji tumor cells, and may thus be less efficient to enhance tumor cell phagocytosis than anti-CD47 antibodies with a slower dissociation rate such as candidate 19, 20 and 22 possessing a Koff value inferior to $1 \times 10^{-3}$ s$^{-1}$.

To address this point, Raji cells were first labelled with CFSE dye and then stained with the anti-CD47 antibodies at 0.1 or 1 µg/mL for 30 minutes at +4° C. Raji cells were then washed and incubated for 24 hours at +37° C. in antibody-free medium as described above. After the 24 hour incubation period (T+24 h), the Raji cells were tested in a phagocytosis assay with hMDM by using a flow cytometry phagocytosis assay, essentially as described by Tseng et al. (Tseng D., Volkmer J-P., Willingham S. B., Contreras-Trujillo H., et al. "Anti-CD47 antibody-mediated phagocytosis of cancer by macrophages primes an effective antitumor T-cell response", PNAS 110(27):11103-08 (2013)). The target Raji tumor cells, previously stained with CFSE dye before being stained by the anti-CD47 antibodies, were incubated with hMDM that have been previously labelled with Far-Red dye. Following 60 minutes of incubation at 37° C., the cells were collected, analyzed by flow cytometry and the CFSE and Far-Red fluorescence were monitored. The population of cells that appeared double-stained by CFSE and Far-Red corresponded to the target tumor cells that had been phagocytosed by the macrophages. As positive control of phagocytosis (time T0), the same experiment was carried out with the same preparation of hMDM labelled with Far-Red and incubated with CFSE-labelled Raji cells stained with the different anti-CD47 antibodies at 0.1 or 1 µg/mL as above, but Raji cells were not incubated for 24 hours at +37° C. This corresponded to the time T0 of reference before incubation in antibody-free medium. The percentage of cells phagocytosed was calculated from the percentage of cells double-stained by CFSE and Far-Red in each condition. The percentage of phagocytosis specific for each antibody was calculated by subtracting the percentage of phagocytosis obtained with Raji cells treated in the same conditions with an irrelevant antibody. The results were finally expressed as the percentage of decrease of the specific phagocytosis obtained at T+24 h compared to the specific phagocytosis measured at T0 for each tested antibody, by applying the formula: % decrease phagocytosis=(1−(% of specific phagocytosis at T+24 h with antibody A/% of specific phagocytosis at T0 with antibody A))×100.

Figure 21B:
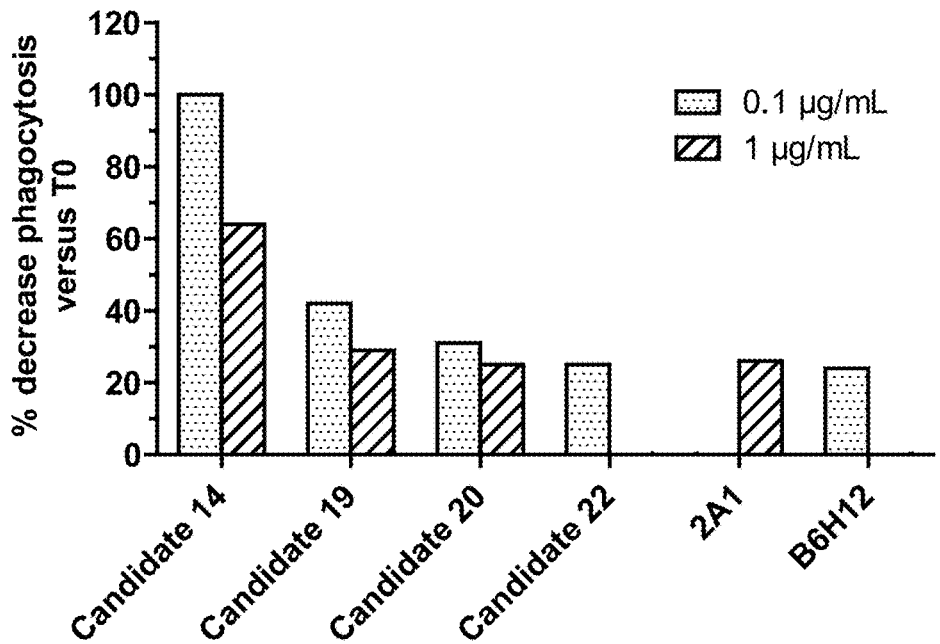

As shown in FIG. 21B, a very strong decrease of phagocytosis was observed for Raji cells stained with anti-CD47 candidate 14, for which about 60% decrease of phagocytosis was observed after staining with 1 µg/mL candidate 14 and even up to 100% decrease was observed on Raji cells stained with 0.1 µg/mL. In contrast, only a weak decrease of phagocytosis was observed for the Raji cells stained with the candidates 19, 20 and 22 as for benchmarks 2A1 and B6H12.

Overall, these results show that anti-CD47 antibodies with a high dissociation rate characterized by a Koff value superior to $1\times10^{-3}$ s$^{-1}$ (such as candidate 14) will detach strongly and rapidly from RBCs but will also lose rapidly most of their functional activity on tumor cells, i.d. enhancement of tumor cell phagocytosis. Thus, such antibodies may have lower sink/side effect but also weaker anti-tumor efficacy. At the opposite, anti-CD47 antibodies with very slow dissociation rate characterized by a Koff value inferior to $1\times10$'s$^{-1}$ (such as 2A1 and B6H12), will detach more slowly from the tumor cells, but will stay stuck on RBCs and may thus have important sink effect and possibly more side effects. Therefore, anti-CD47 antibodies with intermediate dissociation kinetics characterized by a Koff value comprised between $1\times10^{-4}$ and $1\times10^{-3}$ s$^{-1}$ (such as candidate 19, 20 or 22) will possess optimal CD47 binding/release equilibrium to accommodate with a weak sink effect while maintaining their anti-tumor efficacy.

11. Apoptosis Assay with Jurkat Cells

Among the 8 candidates tested, candidates 14 and 15 were found to induce significant apoptosis of human Jurkat cells (T cell leukemia cells), and candidate 26 also induced weak apoptosis (data not shown), whereas candidate 20 and 22 did not induce apoptosis. These data suggest that this family of antibodies recognized an epitope on hCD47 that delivered signaling activity into CD47-expressing cells following CD47 engagement. This type of agonistic antibodies may induce off-target effects in vivo.

12. Summary of In Vitro Characterization

In summary, 34 anti-CD47 antibodies have been produced, purified and evaluated in vitro for specificity and functionality. Eight candidates (numbers 7, 14, 15, 19, 20, 22, 26, 33) were preselected based on their potency in binding and functional assays (inhibition of hCD47/hSIRPα interaction, induction of phagocytosis), and then fully characterized in assays measuring their affinity and RBC agglutination activity.

All 8 candidates strongly recognized both hCD47 and cynoCD47, and bound hCD47 with an affinity in the range of 0.9 to 15.7 nM. All 8 candidates strongly inhibited hCD47/hSIRPα interaction and were capable of inducing phagocytosis of Raji lymphoma cells by human macrophages.

Three antibodies (candidates 14, 15, 26) belonging to the same clone family, also cross-reacted with mCD47, and were found to induce significant apoptosis of Jurkat tumor cells and to induce strong RBC agglutination. These candidates may induce potential toxicity when injected in vivo.

Candidate 20 (unique in its clone family) had the best profile, with strong functional activity and a very weak but detectable RBC agglutination, indicating weak, if any, potential toxicity.

Candidates 19 and 33 (same clone family), as well as candidates 7 and 22 (unique in their respective clone families) also displayed strong functional activities with some but acceptable RBC agglutination depending on the IgG format tested.

Candidate 19, 20 and 22 with Koff values between $1\times10^{-4}$ and $1\times10^{-3}$ s$^{-1}$ also displayed rapid release once bound to human RBCs but kept efficient functional activity as measured by the phagocytosis of tumor cells by human macrophages.

IV. In Vivo Characterization of Selected Mouse Anti-CD47 Candidates

Selected candidates 19, 20 and 22, specific to hCD47, were tested in vivo in mouse tumor xenograft models. Candidates 14 and 15 were also tested in vivo in first studies as mCD47 cross-reacting anti-CD47 antibodies.

1. Human Lymphoma Raji Model

Figure 9A:
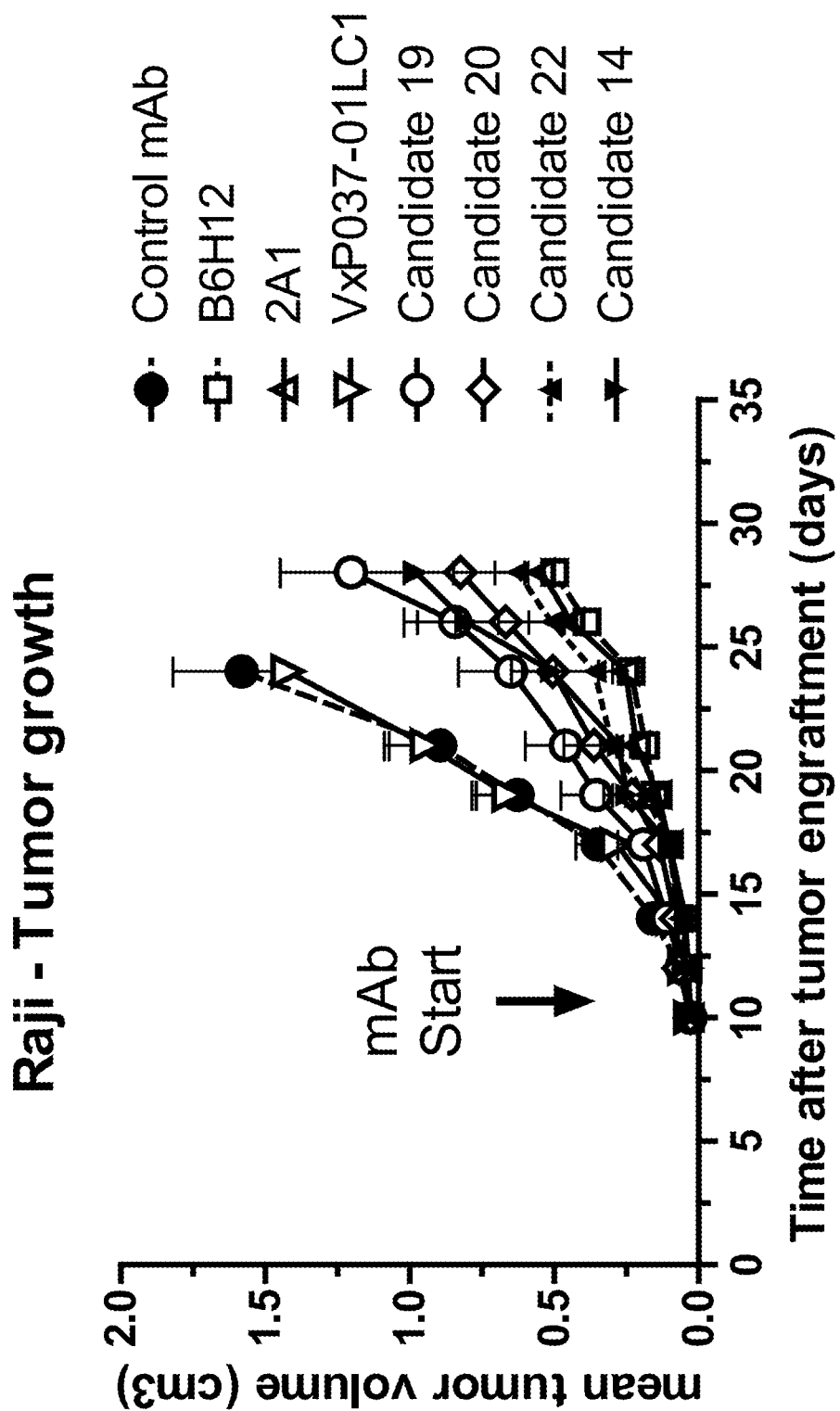
FIGS. 9A-9B Effect of anti-CD47 antibodies on A) the growth of human Raji lymphoma cells in NOG mice (FIG. 9A) and B) survival of NOG mice after Raji tumor cell engraftment (*p<0.05; **p<0.005; Mantel-Cox test) (FIG. 9B).
Figure 9B:
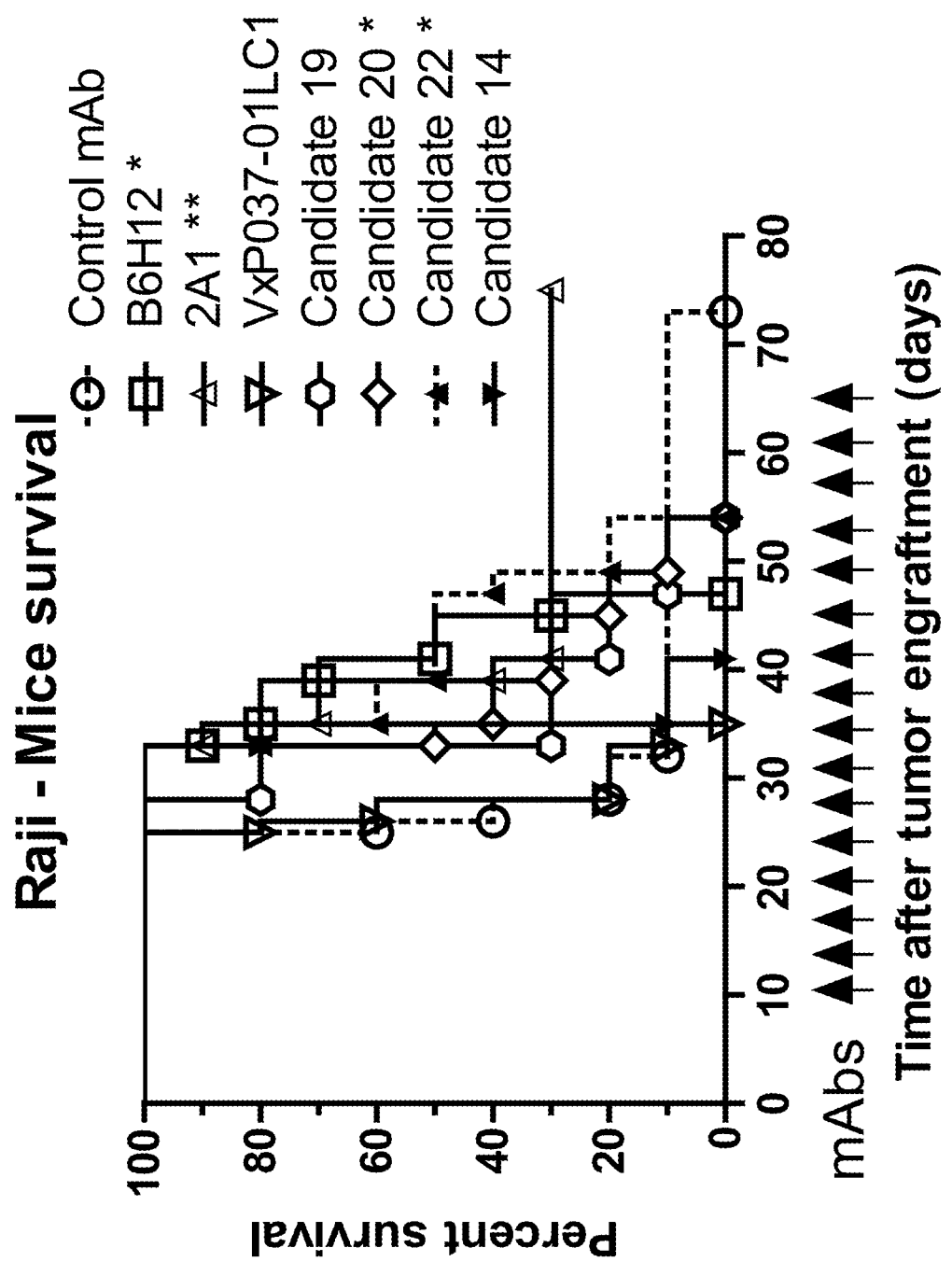

Anti-CD47 candidates 14, 19, 20 and 22 were evaluated in vivo in the human Non-Hodgkin's Lymphoma xenograft model with NOG mice (n=8 per group) engrafted with Raji cells (1.5 million cells injected subcutaneously in the right flank). Ten days after cell transplant, tumors were palpable and the antibody therapy (10 mg/kg/dose, intraperitoneal injection, 3 times a week up to 8 weeks) was started for the four anti-CD47 candidates in parallel with a negative control antibody and the anti-CD47 benchmark antibodies 2A1, B6H12 and VpX037-01LC1. All antibodies were in the mIgG1 isotype format. Tumor growth was monitored every 2 days and mouse survival was recorded. The four candidates 14, 19, 20 and 22 delayed the growth of Raji cells, as did the benchmarks B6H12 and 2A1, but not the VxP037-01LC1 antibody that cross-reacts strongly with mouse CD47 (FIG. 9A). As shown in FIG. 9B, candidates 20 and 22 were also found to induce significant protection of the mice when compared to the control group, as did the benchmarks B6H12 and 2A1, but not VxP037-01LC1.

These results indicated that the four candidates tested (candidates 14, 19, 20 and 22) were able to control growth of the human NHL Raji tumor cells in immunocompromised mice, as previously reported for reference anti-CD47 antibodies, such as B6H12. Candidates 20 and 22 appeared more potent than candidates 14 and 19 for prolonging mice survival.

2. Human A2780 Ovary Xenograft Model

Anti-CD47 candidate 20 was further evaluated in vivo in the human A2780 ovarian xenograft model either alone or in combination with the anti-EGFR antibody Cetuximab (Erbitux®) or the anti-Her2 antibody Trastuzumab (Herceptin®). A2780 cells strongly expressed CD47 as detected by the binding of candidate 20, as well as Her2 as detected by binding of Herceptin® (data not shown). In contrast, A2780 cells expressed only low levels of EGFR in vitro as measured by staining with Erbitux® (data not shown). NOG mice (n=4 per group) were engrafted with Luciferase-transfected A2780 (A2780/Luc) cells (10 million cells injected intraperitoneally). One day after the cell transplant, antibody therapy (10 mg/kg/dose, intraperitoneal injection, 3 times a week up to 5 weeks) was begun with anti-CD47 candidate 20 alone or in combination with Herceptin® or Erbitux®.

Figure 10A:
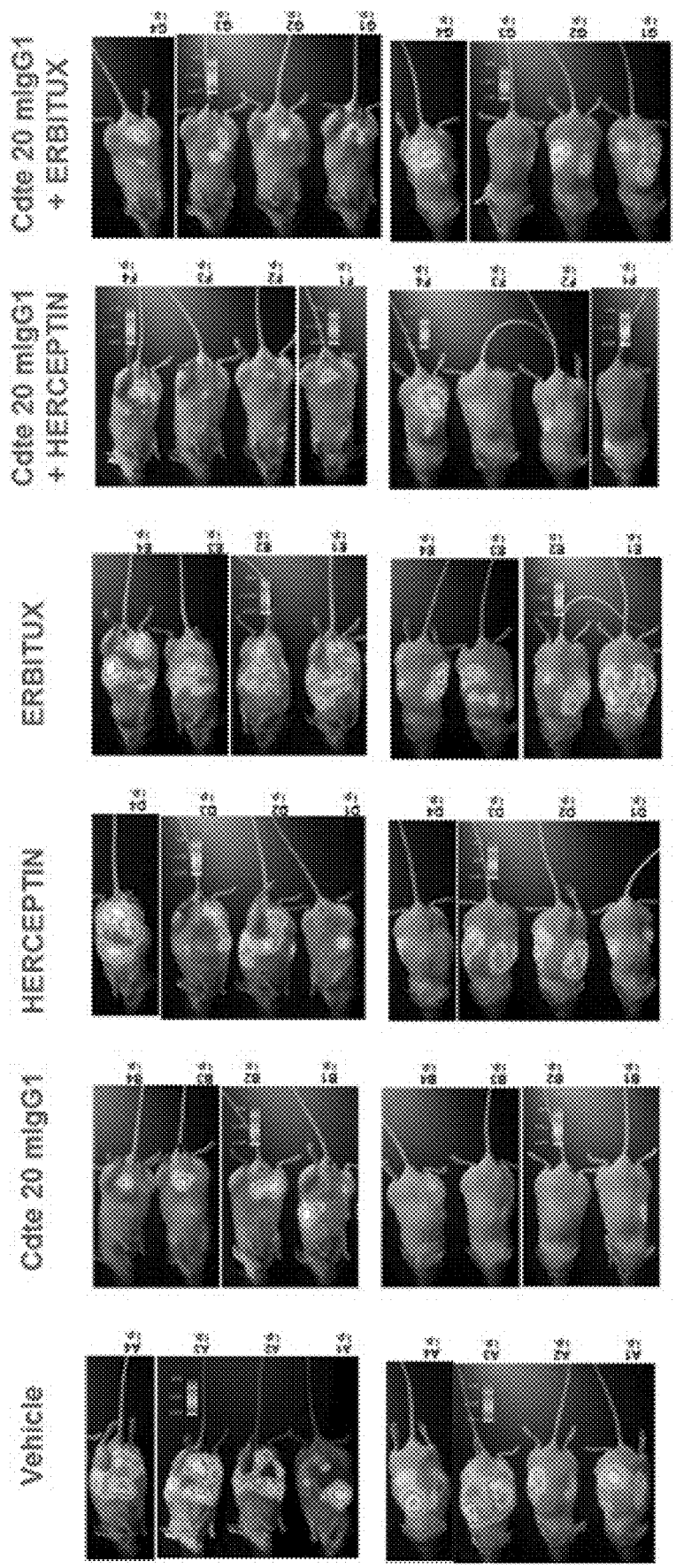
FIGS. 10A-10B Effect of anti-CD47 candidate 20 alone or in combination with Herceptin® or Erbitux® on growth of A2780/Luc human ovarian tumors in NOG mice. A2780/Luc cells were engrafted intraperitoneally (IP) in NOG mice (n=4/group) and the antibody treatment was started 1 day after graft for up to 5 weeks (3 injections/week, IP) at 10 mg/kg. (A) Ventral and dorsal luminescence observed in each mouse at Day 28 (FIG. 10A). (B) Quantification of the bioluminescence intensity (dorsal+ventral) plotted against the time after tumor engraftment (FIG. 10B). Treatment groups were compared to the vehicle group at day 28 by using the unpaired t-test of the GraphPad Prism software (p<0.005; *p<0.001).
Figure 10B:
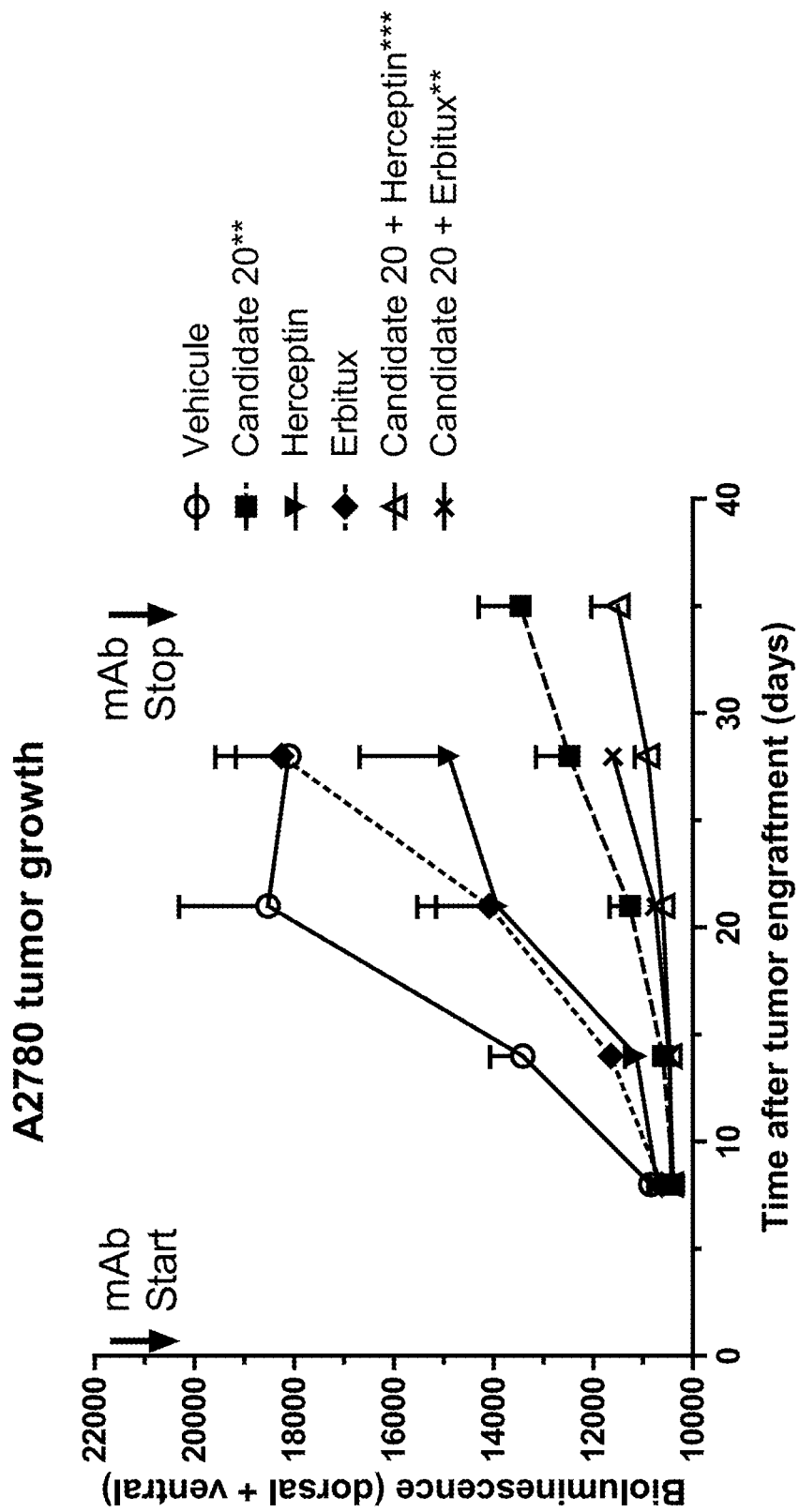

Bioluminescence intensity (BLI) was monitored every 5 days from both ventral and dorsal positions. Results presented in FIG. 10 showed that treatment with the anti-CD47 candidate 20 alone delayed the growth of A2780 tumor cells. A delay in tumor growth was also observed with Herceptin® alone, but not with Erbitux® alone. Furthermore, the combination of anti-CD47 candidate 20 in combination with Herceptin® or Erbitux® also delayed the growth of A2780 cells.

These results suggest that candidate 20 was capable of controlling the growth of A2780 ovarian tumor cells in vivo in NOG immunocompromised mice when used as single agent, and can show cooperative activity in combination with anti-Her-2 antibody (Herceptin®) or anti-EGFR antibody (Erbitux®).

3. Human A549 Lung Xenograft Model

Anti-CD47 candidate 20 was also evaluated in vivo in the human A549 lung adenocarcinoma xenograft model (Steiner P., Joynes C., Bassi R., Wang S., Tonra J. R., et al. "Tumor Growth Inhibition with Cetuximab and Chemotherapy in Non-Small Cell Lung Cancer Xenografts Expressing Wild-type and Mutated Epidermal Growth Factor Receptor", Clin Cancer Res 13(5):1542-51(2007); Kellar A., Egan C., and Morris D. "Preclinical Murine Models for Lung Cancer: Clinical Trial Applications", BioMed Res Int 2015, ID 621324 (2015)) alone or in combination with the anti-EGFR antibody Cetuximab (Erbitux®) or the anti-Her2 antibody Trastuzumab)(Herceptin®). In vitro, A549 cells (ATCC-CCL-185) strongly expressed CD47 as detected by the binding of candidate 20, as well as EGFR as measured by staining with Erbitux®, and, with a weaker intensity, Her2 as detected with Herceptin® by flow cytometry (data not shown). NOG mice (n=4 per group) were engrafted with A549 cells (10 million cells injected subcutaneously). Ten days after the cell transplant, once the tumor was palpable (volume>30 mm³), the antibody therapy (10 mg/kg/dose, intraperitoneal injection, 3 times a week up to 10 weeks) was started for the anti-CD47 candidate 20 alone or in combination with Herceptin® or Erbitux®.

Figure 11A:
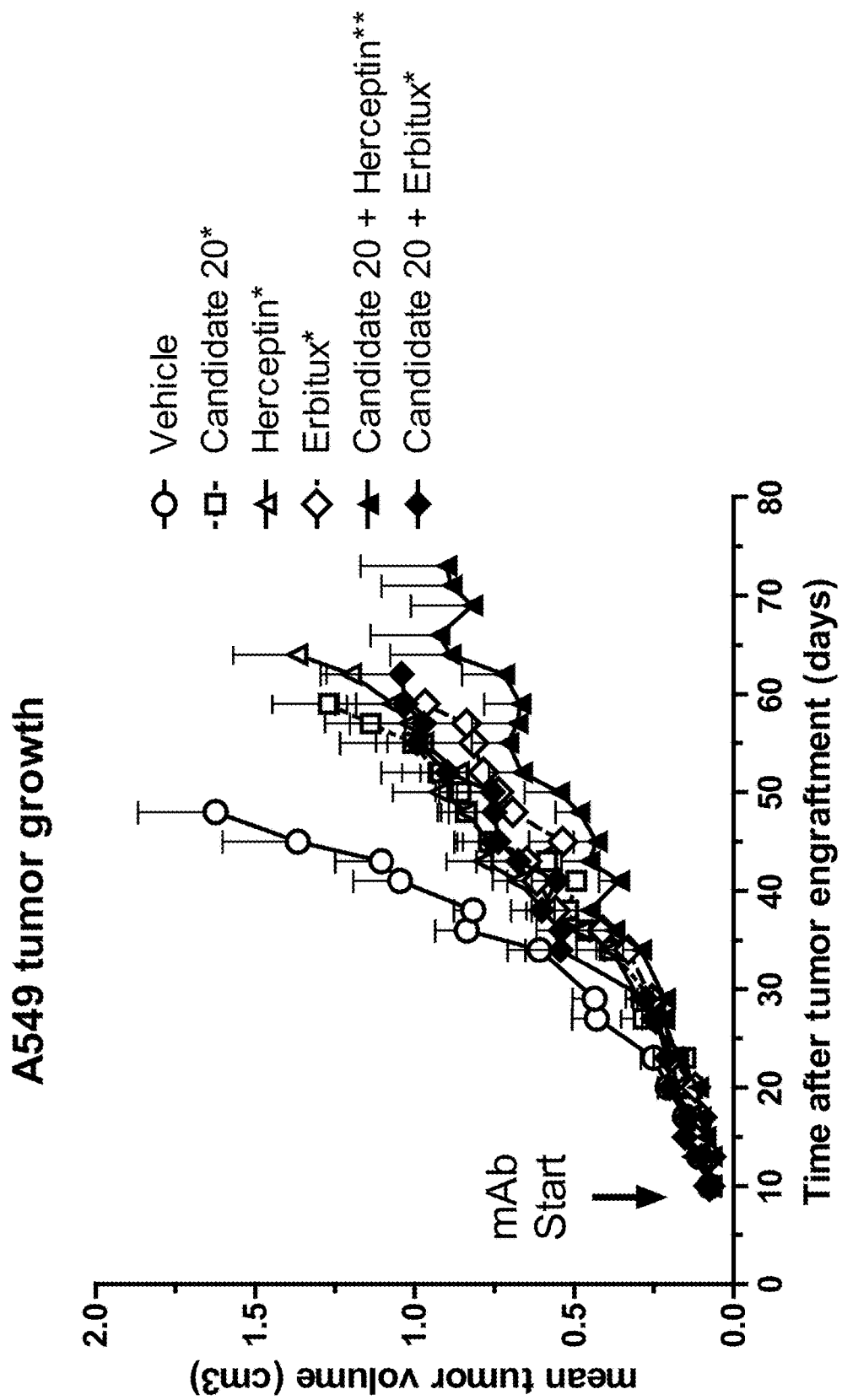
FIGS. 11A-11B Effect of anti-CD47 candidate 20 alone or in combination with Herceptin® or Erbitux® on the growth of A549 human lung tumor cells in NOG mice. A549 cells were engrafted subcutaneously in NOG mice (n=4/group) and the antibody treatment was started when the tumor was palpable (day 10) for up to 10 weeks (3 injections/week, IP) at 10 mg/kg. (A) Tumor cell growth as measured by the mean tumor volume+/−SD ($cm^3$) for each group plotted against the time after tumor engraftment (FIG. 11A). Treatment groups were compared to the vehicle group by using the rate-based T/C method described by Hather et al. (Hather G., Liu R., Bandi S., Mettetal J., et al. "Growth Rate Analysis and Efficient Experimental Design for Tumor Xenograft Studies." Cancer Informatics 13(54):65-72 (2014)), (*p<0.05; **p<0.005). (B) Survival curves of the mice. Treatment groups were compared to the vehicle group by using the Log-rank (Mantel-Cox) Test of the GraphPad Prism software (*p<0.05; **p<0.01) (FIG. 11B).
Figure 11B:
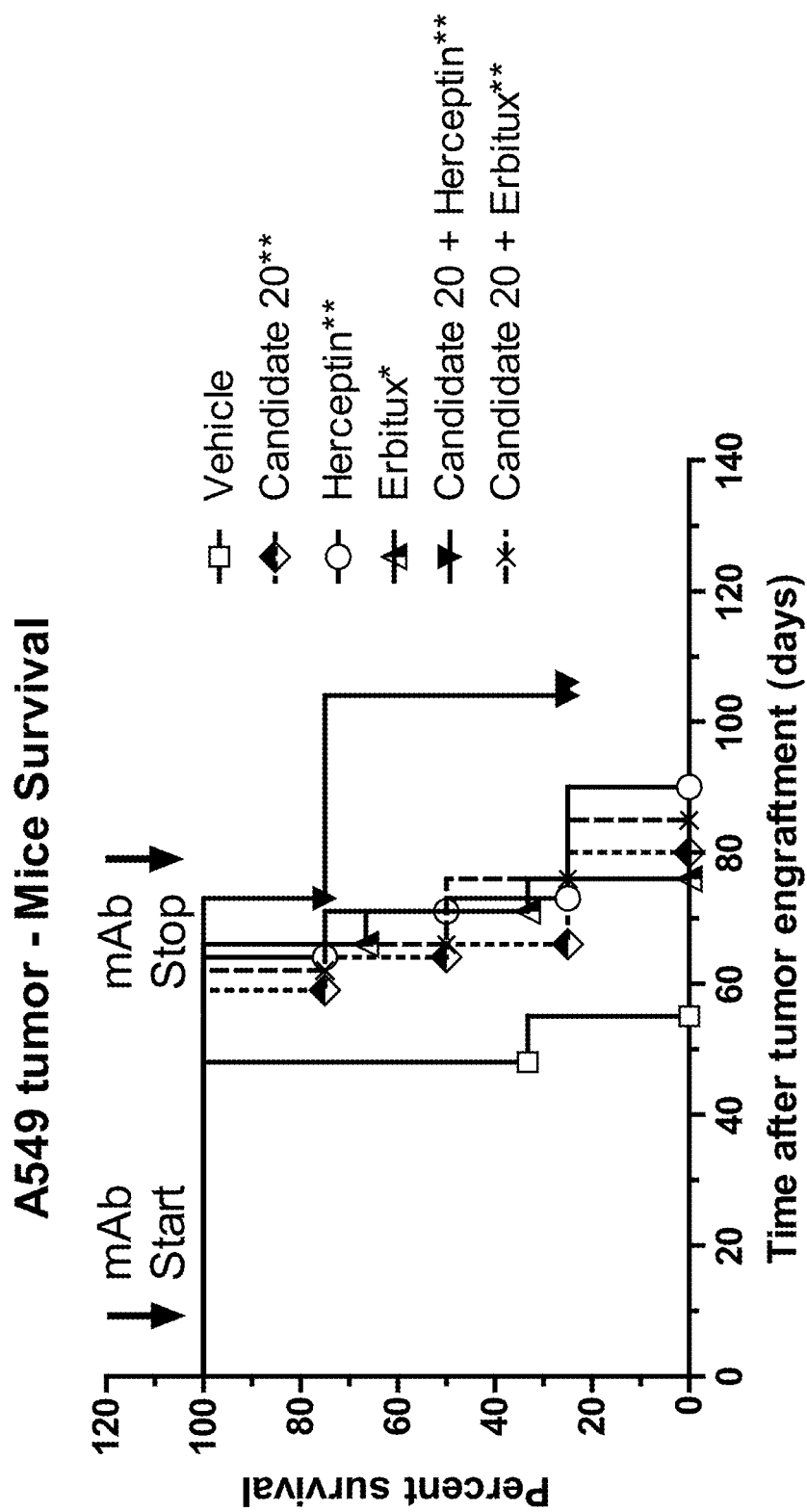
Figure 12B:
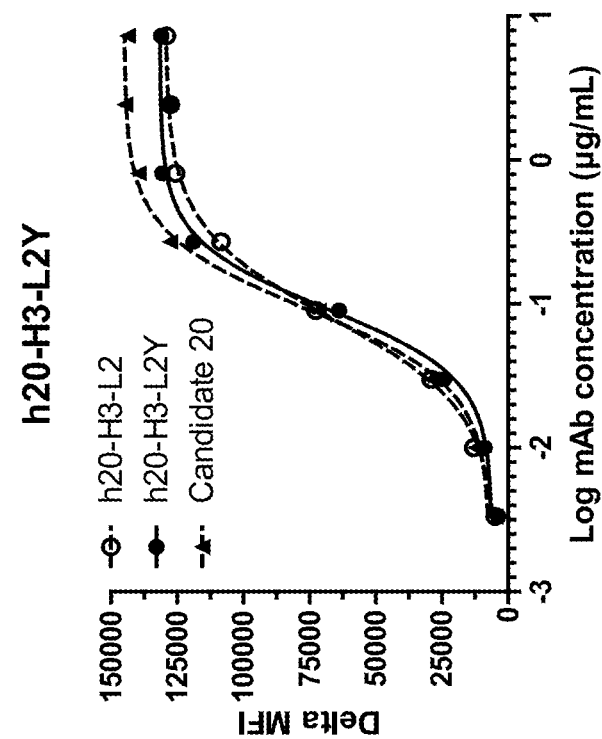
FIGS. 12A-12E Binding of humanized variants of anti-CD47 Candidate 20 on Raji cells by flow cytometry. Humanized variants with the VL-CDR2-F56Y mutation (CDR2 with SEQ ID Nos: 152 (Kabat) and 153 (IMGT), i.e. candidates 20.26 (h20-H2-L5Y.
Figure 12A:
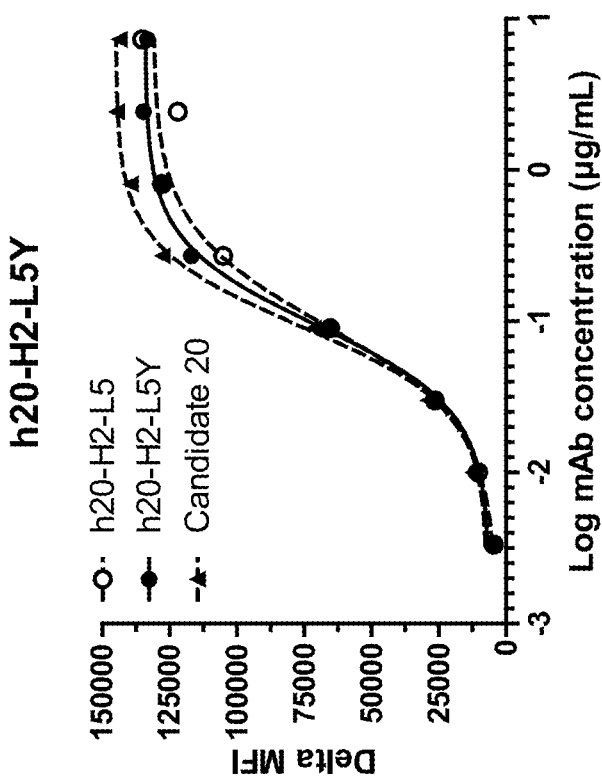
Figures 12C, 12D:
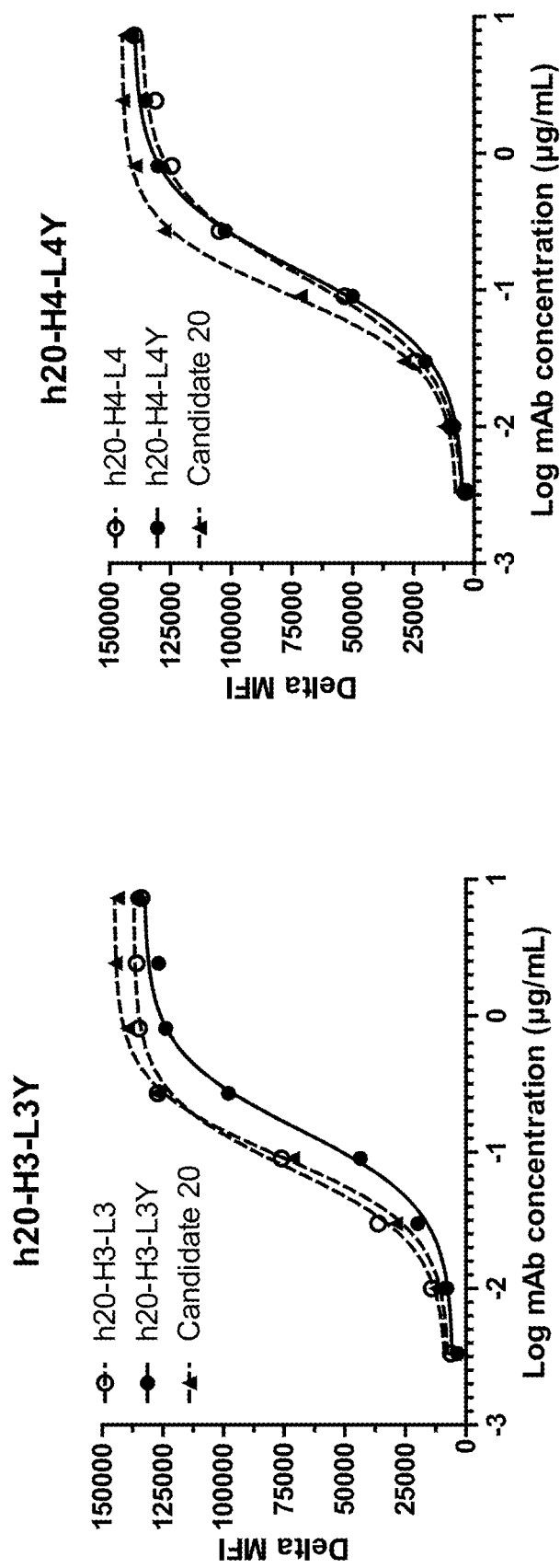
Figure 12E:
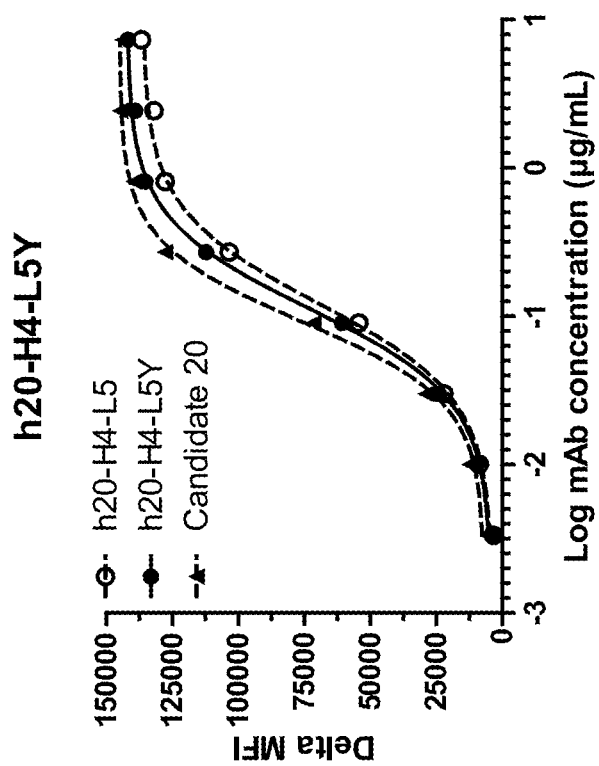
Figure 13B:
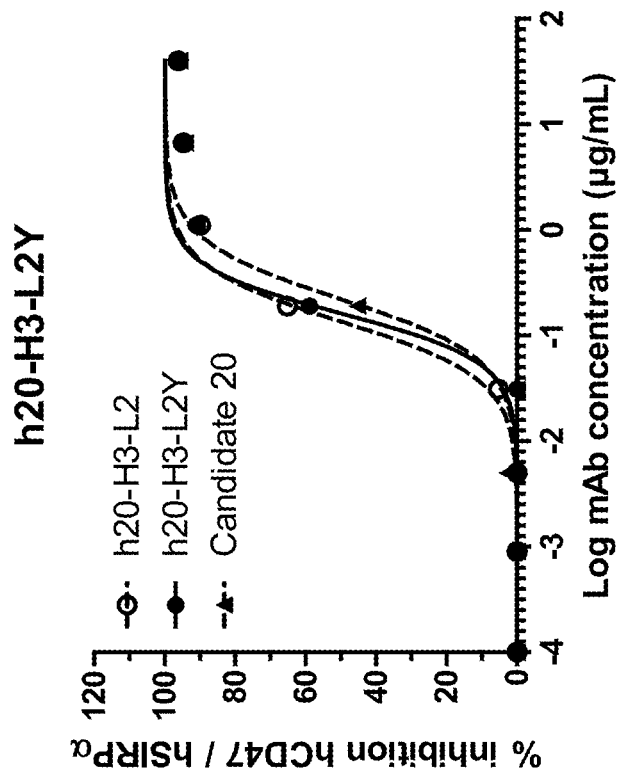
FIGS. 13A-13E Inhibition of hSIRPα binding to hCD47 on Raji cells by humanized variants of anti-CD47 Candidate 20. Humanized variants with the VL-CDR2-F56Y mutation (CDR2 with SEQ ID Nos: 152 (Kabat) and 153 (IMGT), i.e. candidates 20.26 (h20-H2-L5Y.
Figure 13A:
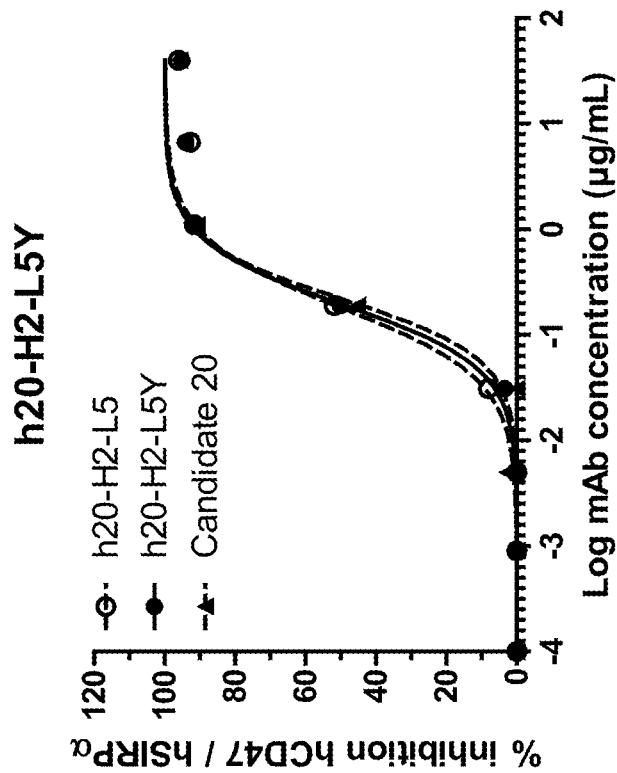
Figure 13C:
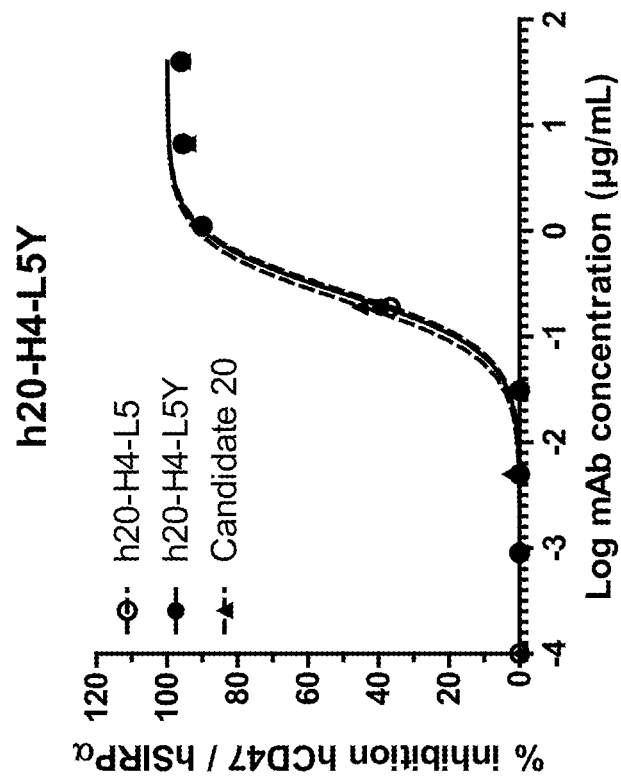
Figure 13D:
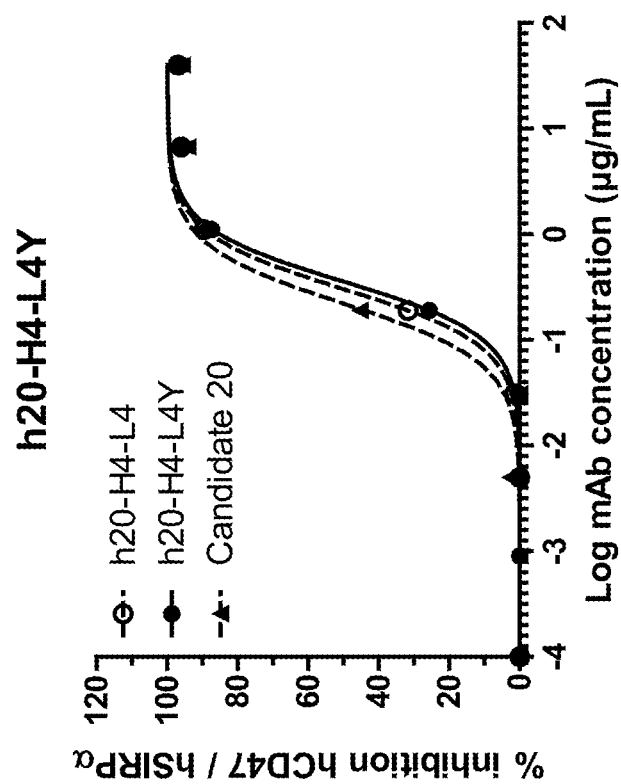
Figure 13E:
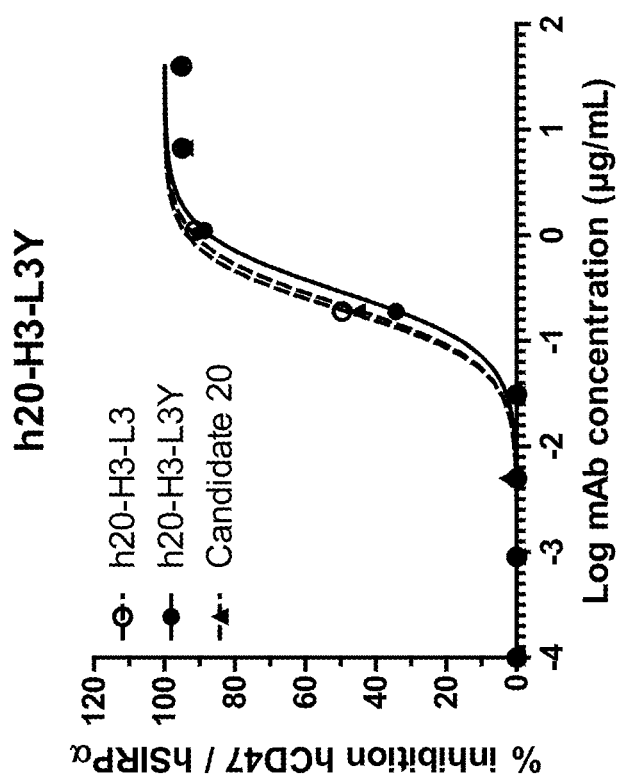

As shown in FIG. 11, the anti-CD47 candidate 20 alone, as well as Erbitux® and Herceptin®, were able to delay the growth of A549 tumor cells as quantified by measurement of the tumor volume (FIG. 11A) and were able to significantly protect the mice when compared to the vehicle group (FIG. 11B). The combination of anti-CD47 candidate 20 with Herceptin® resulted in a more important delay of the A549 tumor cell growth (FIG. 11A) and to a stronger protection of the mice in the survival analysis (FIG. 11B).

These results suggest that the anti-CD47 candidate 20, when used as single agent or in combination with Herceptin®, was capable to delay the growth of the A549 lung adenocarcinoma in vivo in NOG mice.

V. Humanization of Anti-CD47 Candidate 20

1. Humanized Anti-CD47 Candidates 20

Figure 7:
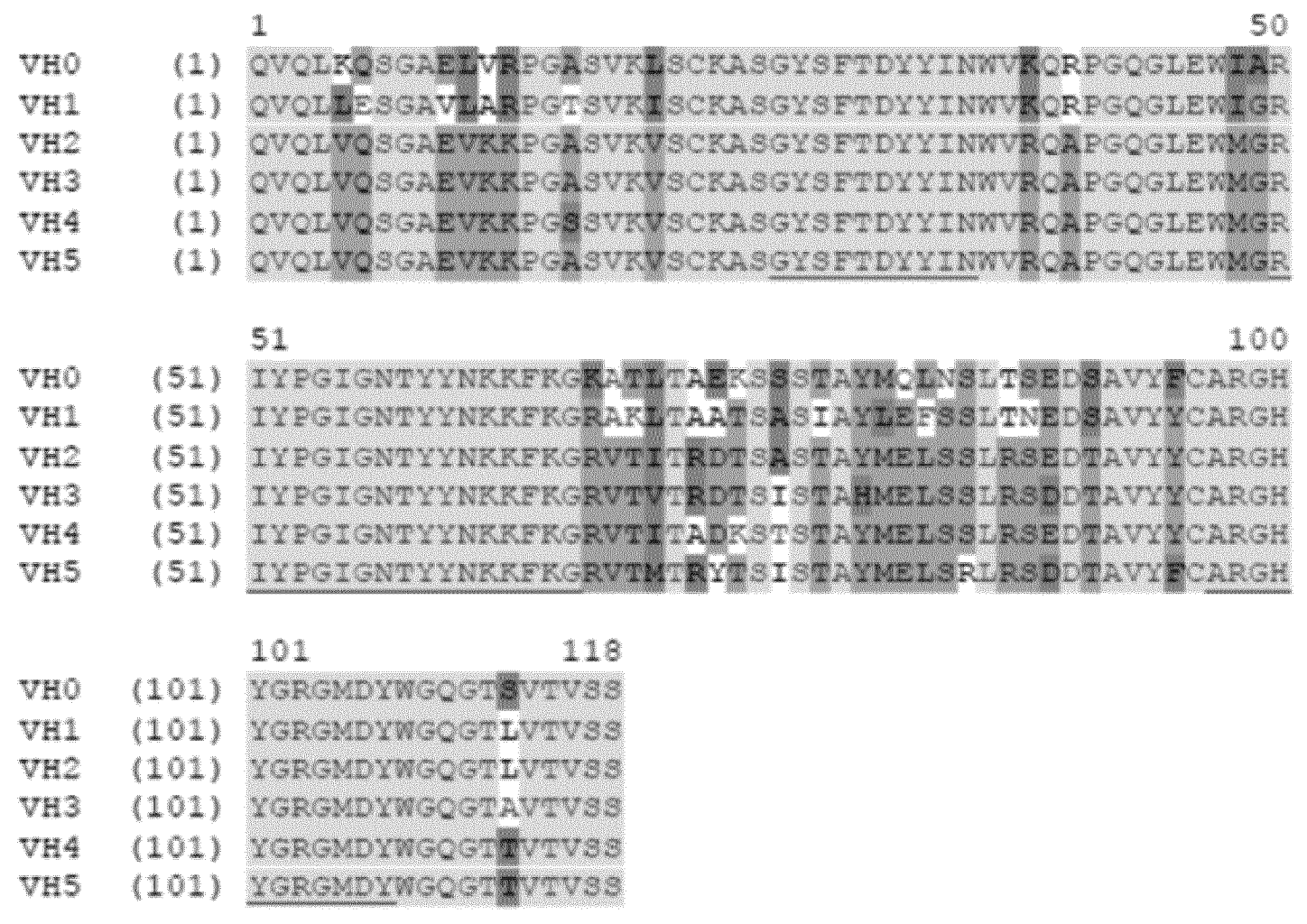

Mouse candidate 20 was selected as the first lead for humanization. Five VH and 5 VL variants were generated by CDR engraftment into human acceptor frameworks. The sequences were analyzed for removal of potential T-Cell epitopes with MEW class II high affinity using in silico algorithms, as well as for the presence of post-translational modifications such as Fv glycosylation and deamidation. The amino acid sequences of the 5 VH variants (VH1 to VH5) aligned with the sequence of the mouse VH sequence of candidate 20 (VH0), are presented in FIG. 7. The amino acid sequences of the 5 VL variants (VL1 to VL5) aligned with the sequence of the mouse VL sequence of candidate 20 (VL0), are presented in FIG. 8.

The 5 humanized VH variants were cloned in an expression vector containing a human Fcγ4-S228P backbone (SEQ ID NO: 162) and the 5 humanized VL variants were cloned into an expression vector containing a human Kappa backbone (SEQ ID NO: 176), in order to generate hIgG4/kappa humanized variants. The mutation S228P was introduced in the Fc fragment of all hIgG4 antibodies to avoid potential chain exchanges that have been observed with hIgG4 (Angal S., King D. J., Bodmer M. W., Turner A., Lawson A. D., Roberts G., Pedley D., and Adair J. R. "A single amino acid substitution abolishes the heterogeneity of chimeric mouse/human (IgG4) antibody", Mol Immunol 30(1):105-8 (1993)). Twenty-five hIgG4/kappa variants were produced and purified from CHO cells co-transfected with one of the 5 VH and one of the 5 VL vectors. The resulting antibodies were named h20-VHx-VLx, where h20 designated humanized candidate 20, VHx designated the Heavy chain variable domain with the humanized VH variant x (VH1 to VH5), and Lx designated the Light chain variable domain with the humanized VL variant x (VL1 to VL5). The 25 purified antibodies were tested for their binding activity and specificity on human Raji lymphoma cells and CHO cells transfected or not with hCD47 or mCD47, for their functional activity in inhibiting the binding of hSIRPα on Raji cells and for their capacity to induce human RBC agglutination in whole blood agglutination assay. The kinetics (Kon and Koff) and affinity (KD) constants were also measured by SPR on Biacore. In all assays, the 25 humanized variants were compared with a hIgG4 chimeric candidate 20 generated by cloning of the mouse VH0 and VL0 sequences into the appropriate vectors containing a human Fcγ4-S228P and human Kappa backbone.

All results obtained in the different assays are summarized in Table 12 and Table 13 below.

TABLE 12

Characteristics of humanized variants of candidate 20

| Candidate No | Antibody (hIgG4) | CD47 Binding (EC50 μg/mL) | CD47/ SIRPα inhibition (IC50 μg/mL) | Phago- cytosis Raji/ HDMC | RBC agglutination (3 donors) |
|---|---|---|---|---|---|
| 20 | Chim. 20 | 0.150 | 0.138 | ++ | +/− |
| 20.1 | h20-VH1-VL1 | 0.193 | 0.161 | ++ | ++ |

TABLE 12-continued

Characteristics of humanized variants of candidate 20

| Candidate No | Antibody (hIgG4) | CD47 Binding (EC50 μg/mL) | CD47/ SIRPα inhibition (IC50 μg/mL) | Phago- cytosis Raji/ HDMC | RBC agglutination (3 donors) |
|---|---|---|---|---|---|
| 20.2 | h20-VH1-VL2 | 0.218 | 0.216 | ++ | ++ |
| 20.3 | h20-VH1-VL3 | 0.184 | 0.228 | ++ | ++/+++ |
| 20.4 | h20-VH1-VL4 | 0.248 | 0.261 | ++ | − |
| 20.5 | h20-VH1-VL5 | 0.206 | 0.111 | ++ | +/++ |
| 20.6 | h20-VH2-VL1 | 0.177 | 0.098 | ++ | +/++ |
| 20.7 | h20-VH2-VL2 | 0.156 | 0.076 | Nd | + |
| 20.8 | h20-VH2-VL3 | 0.184 | 0.079 | Nd | + |
| 20.9 | h20-VH2-VL4 | 0.173 | 0.123 | Nd | + |
| 20.10 | h20-VH2-VL5 | 0.191 | 0.051 | Nd | − |
| 20.11 | h20-VH3-VL1 | 0.145 | 0.118 | ++ | +/− |
| 20.12 | h20-VH3-VL2 | 0.153 | 0.160 | Nd | +/− |
| 20.13 | h20-VH3-VL3 | 0.147 | 0.173 | Nd | +/− |
| 20.14 | h20-VH3-VL4 | 0.143 | 0.135 | Nd | + |
| 20.15 | h20-VH3-VL5 | 0.143 | 0.113 | Nd | + |
| 20.16 | h20-VH4-VL1 | 0.113 | 0.100 | ++ | +/− |
| 20.17 | h20-VH4-VL2 | 0.124 | 0.086 | Nd | +/− |
| 20.18 | h20-VH4-VL3 | 0.164 | 0.142 | Nd | +/− |
| 20.19 | h20-VH4-VL4 | 0.139 | 0.192 | Nd | − |
| 20.20 | h20-VH4-VL5 | 0.136 | 0.095 | Nd | +/− |
| 20.21 | h20-VH5-VL1 | 0.190 | 0.169 | ++ | + |
| 20.22 | h20-VH5-VL2 | 0.189 | 0.174 | Nd | +/++ |
| 20.23 | h20-VH5-VL3 | 0.190 | 0.169 | Nd | +/− |
| 20.24 | h20-VH5-VL4 | 0.177 | 0.133 | Nd | +/++ |
| 20.25 | h20-VH5-VL5 | 0.159 | 0.112 | Nd | +/− | nd: not done

For RBC agglutination: +/−, weak agglutination observed at 50 μg/mL antibody only; +, agglutination at 50 μg/mL antibody; ++, agglutination for concentrations ≥16.7 μg/mL; +++, agglutination for concentrations ≥5.6 μg/mL

TABLE 13

Kinetics and affinity constants of humanized anti-CD47 antibodies of candidate 20 by Biacore (mean values of independent experiments)

| Candidate No | Antibody (hIgG4) | mean Kon (1/Ms) × $10^3$ | mean Koff (1/Ms) × $10^{-4}$ | mean KD (nM) |
|---|---|---|---|---|
| 20 | Chim 20 | 169.33 | 5.05 | 3.22 |
| 20.1 | h20-H1-L1 | 118.40 | 6.34 | 5.85 |
| 20.2 | h20-H1-L2 | 119.50 | 6.91 | 6.45 |
| 20.3 | h20-H1-L3 | 136.50 | 11.05 | 7.82 |
| 20.4 | h20-H1-L4 | 130.95 | 8.39 | 7.33 |
| 20.5 | h20-H1-L5 | 126.30 | 7.72 | 7.58 |
| 20.6 | h20-H2-L1 | 197.50 | 5.95 | 3.53 |
| 20.7 | h20-H2-L2 | 193.00 | 6.27 | 3.67 |
| 20.8 | h20-H2-L3 | 189.00 | 6.60 | 3.77 |
| 20.9 | h20-H2-L4 | 189.00 | 6.28 | 3.65 |
| 20.10 | h20-H2-L5 | 219.00 | 6.32 | 3.34 |
| 20.11 | h20-H3-L1 | 222.00 | 5.61 | 2.79 |
| 20.12 | h20-H3-L2 | 246.00 | 5.60 | 2.49 |
| 20.13 | h20-H3-L3 | 213.50 | 5.94 | 3.05 |
| 20.14 | h20-H3-L4 | 216.50 | 5.81 | 3.02 |
| 20.15 | h20-H3-L5 | 242.00 | 5.28 | 2.36 |
| 20.16 | h20-H4-L1 | 175.00 | 6.19 | 3.86 |
| 20.17 | h20-H4-L2 | 167.50 | 6.34 | 4.18 |
| 20.18 | h20-H4-L3 | 180.00 | 7.33 | 4.37 |
| 20.19 | h20-H4-L4 | 179.00 | 6.85 | 4.15 |
| 20.20 | h20-H4-L5 | 192.00 | 6.24 | 3.5 |
| 20.21 | h20-H5-L1 | 115.90 | 9.79 | 9.2 |
| 20.22 | h20-H5-L2 | 142.00 | 11.65 | 8.55 |
| 20.23 | h20-H5-L3 | 104.20 | 8.41 | 9.93 |
| 20.24 | h20-H5-L4 | 103.25 | 10.21 | 10.99 |
| 20.25 | h20-H5-L5 | 126.40 | 10.86 | 9.69 |

All humanized variants with the VH1 and VH5 sequences had a lower affinity (higher KD) than the other variants and lower than that of the chimeric candidate 20. The other variants showed Kon, Koff and KD constants similar to the ones of the chimeric candidate 20. None of the variants showed a significant increased affinity to hCD47 as compared to chimeric candidate 20. The Koff values of all humanized variants were observed to be in the range of $5.3 \times 10^{-4}$ to $11.7 \times 10^{-4}$ s".

All 25 variants bound strongly to CD47 expressed on Raji cells with an EC50 similar to the EC50 of the chimeric candidate 20. They also specifically recognized hCD47 but not mCD47 expressed on CHO cells, like the chimeric candidate 20 (not shown).

All 25 variants strongly inhibited the binding of hSIRPα to CD47 expressed on Raji cells, with an IC50 in the same range than the IC50 of chimeric candidate 20. Variants with the VH2 sequence had an IC50 lower than the other variants, as well as the chimeric candidate 20.

All tested hIgG4 variants were capable of enhancing the phagocytosis of Raji cells by human macrophages in a similar manner as the chimeric hIgG4 candidate 20.

Some variants of the VH1 family (h20-VH1-VL1, h20-VH1-VL2, h20-VH1-VL3, h20-VH1-VL5), variant h20-VH2-VL1 and variants h20-VH5-VL2 and h20-VH5-VL4 displayed a tendency to induce more RBC agglutination than the other variants, as well as than the chimeric candidate 20.

2. Optimization of the Humanized Antibodies and Lead Selection

Analysis of potential T cell epitopes within the VH and VL sequences of the humanized variants has revealed the presence of a high affinity CD4+ T cell epitope (LIYFASTKESGV) within the CDR2 domain of the 5 VL variants (VL1 to VL5). This potential T cell epitope, also present within the CDR2 of the mouse VL0 sequence, had not been removed in the 5 first humanized VL variants to avoid any loss of affinity and/or activity of the first humanized candidates. A single point mutation F to Y at position 56 (F56Y) of the VL sequence (amino acid numbering without the signal peptide) was however sufficient to remove the immunogenicity of this potential T cell epitope (LIYFASTKESGV to LIYYASTKESGV). The F56Y mutation was therefore introduced into the humanized VL1 to VL5 sequences. These new sequences were designated as VL1-F56Y to VL5-F56Y and the corresponding humanized antibodies produced by combining one of the VH1 to VH5 variants with one of the VL1-F56Y to VL5-F56Y variants were designated as h20-Hx-LxY. Five humanized variants (candidates 20.26 (h20-H2-L5Y), 20.27 (h20-H3-L2Y), 20.28 (h20-H3-L3Y), 20.29 (h20-H4-L4Y), 20.30 (h20-H4-L5Y)) were selected and produced in a human IgG4 format containing the S228P mutation (SEQ ID NO: 162) known to stabilized the hIgG4 protein (Angal S et al. Mol Immunol, 1993). Purified antibodies were further characterized in vitro for their binding activity to hCD47 on Raji cells, for their potency to inhibit hCD47/hSIRPα interaction on Raji cells and for their human RBC agglutination activity using whole blood. The 5 humanized Hx-LxY variants were also compared to the chimeric candidate 20 produced in a hIgG4-S228P format, as well as to the AB06.12 and Hu5F9 humanized antibodies cloned in a hIgG4-S228P.

As shown in FIGS. 12 and 13, the five F56Y-mutated variants bound to Raji cells (FIG. 12) and inhibited the binding of hSIRPα to Raji cells (FIG. 13) with a similar efficiency to their non-mutated counterparts and similar to the chimeric candidate 20. The five F56Y-mutated humanized variants had slightly higher RBC agglutination activity in the whole blood assay than the chimeric candidate 20, but still lower to the Hu5F9 benchmark (Table14).

Figure 14:
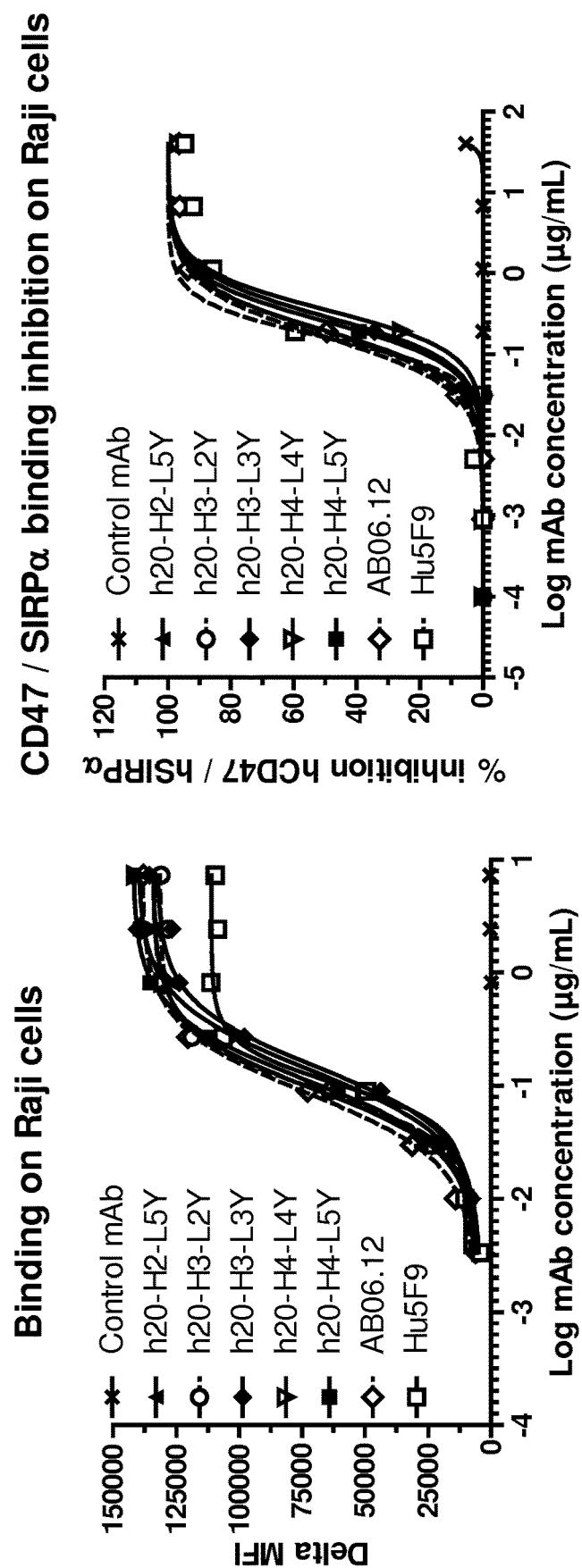
FIG. 14 Comparison of VL-CDR2-F56Y humanized variants of candidate 20 (i.e. candidates 20.26 (h20-H2-L5Y), 20.27 (h20-H3-L2Y), 20.28 (h20-H3-L3Y), 20.29 (h20-H4-L4Y), 20.30 (h20-H4-L5Y)) with antibodies AB06.12 and Hu5F9 in the CD47 binding assay and in the CD47/SIRPα interaction assay on Raji cells.

Finally, the five F56Y-mutated humanized variants of candidate 20 were found to display strong recognition of hCD47 on Raji cells and strong inhibition of hSIRPα binding to hCD47 on Raji cells, similar to the AB06.12 and Hu5F9 antibodies (FIG. 14). The Table 14 below summarizes the results obtained in the different assays.

TABLE 14

Characteristics of humanized h20-Hx-LxY variants of candidate 20 (representative of 2 independent experiments)

| Antibody (hIgG4-S228P) | CD47 binding (EC50, ng/mL) | CD47/SIRPα Inhibition (IC50, ng/nL) | RBC agglutination (4 donors) |
|---|---|---|---|
| h20-H2-L5Y, candidate 20.26 | 97.5 | 112.6 | ++; +; ++; + |
| h20-H3-L2Y, candidate 20.27 | 85.4 | 101.1 | +; +; ++; +/− |
| h20-H3-L3Y, candidate 20.28 | 116.7 | 169.9 | +; +; ++; + |
| h20-H4-L4Y, candidate 20.29 | 146.6 | 180.7 | +; +; ++; +/− |
| h20-H4-L5Y, candidate 20.30 | 105.1 | 149.5 | ++; +; ++; ++ |
| Chimeric Candidate 20 | 75.1 | 110.2 | +; +/−; +; +/− |
| Hu5F9 | 80.0 | 122.8 | +++; +; +++; +++ |
| AB06.12 | 83.1 | 97.2 | +; +/−; +/−; − |

+/−, weak agglutination observed at 50 μg/mL antibody only;
+, agglutination at 50 μg/mL antibody;
++, agglutination for concentrations ≥16.7 μg/mL;
+++, agglutination for concentrations ≥5.6 μg/mL The kinetics (Kon and Koff) and affinity (KD) constants of the 5 new humanized h20-Hx-LxY variants were determined by SPR on Biacore. Results in Table 15 show that the 5 humanized variants with the VL CDR2-F56Y mutation have conserved an affinity of 2.0 to 2.8 nM, similar to the candidate 20 and similar to the corresponding humanized variants without the VL CDR2-F56Y mutation (Table 15).

TABLE 15

Kinetics and affinity constants of anti-CD47 humanized variants of candidate 20 with VL CDR2-F56Y mutation, as measured by Biacore (mean values of 2 independent experiments)

| Antibody (hIgG4 format) | mean Kon (1/Ms) × $10^3$ | mean Koff (1/s) × $10^{-4}$ | mean KD (nM) | mean Rmax (RU) |
|---|---|---|---|---|
| h20-H2-L5Y, candidate 20.26 | 306.5 | 6.99 | 2.32 | 124.8 |
| h20-H3-L2Y, candidate 20.27 | 292.0 | 5.84 | 2.06 | 106.6 |
| h20-H3-L3Y, candidate 20.28 | 264.0 | 5.73 | 2.32 | 119.9 |
| h20-H4-L4Y, candidate 20.29 | 305.5 | 7.61 | 2.61 | 102.4 |
| h20-H4-L5Y, candidate 20.30 | 254.5 | 6.93 | 2.82 | 111.6 |
| Chimeric Candidate 20 | 225.0 | 5.43 | 2.48 | 144.6 |
| Hu5F9-G4P | 101.4 | 0.75 | 0.73 | 85.5 |

The 5 humanized variants with the VL CDR2-F56Y mutation have also conserved a rapid dissociation kinetics, with a Koff value in the range of $5.73 \times 10^{-4}$ to $7.61 \times 10^{-4}$ s−1, as observed for the mouse and candidate 20 (Table 13 and 15).

3. Humanization of Anti-CD47 Candidate 22

Mouse candidate 22 was also selected for humanization. Four VH and 4 VL variants were generated by CDR engraftment into human acceptor frameworks, essentially as described for mouse candidate 20. The sequences were analyzed for removal of potential T-Cell epitopes with MHC class II high affinity using in silico algorithms, as well as for the presence of post-translational modifications such as Fv glycosylation and deamidation.

The 2 humanized VH variants h22-VH3 and h22-VH4 were cloned in an expression vector containing a human Fcγ4-S228P backbone (SEQ ID NO: 162) and the 4 humanized h22-VL variants were cloned into an expression vector containing a human Kappa backbone (SEQ ID NO: 176), in order to generate hIgG4/kappa humanized variants. Eight of the hIgG4/kappa variants were produced and purified from CHO cells co-transfected with one of the h22-VH3 or h22-VH4 and one of the 4 h22-VL vectors. The resulting antibodies were called h22-VHx-VLx, where h22 designated humanized candidate 22, VHx designated the Heavy chain variable domain with the humanized VH variant x (VH3 to VH4), and Lx designated the Light chain variable domain with the humanized VL variant x (VL1 to VL4). The kinetics (Kon and Koff) and affinity (KD) constants of the 8 purified antibodies were measured by SPR on Biacore. The 8 purified antibodies were also tested for their binding activity and specificity on human Raji lymphoma cells, for their functional activity in inhibiting the binding of hSIRPα on Raji cells and for their capacity to induce human RBC agglutination in whole blood. In all assays, the 8 humanized variants were compared with a hIgG4 chimeric candidate 22 generated by cloning of the mouse VH and VL sequences of candidate 22 into the appropriate vectors containing a human Fcγ4-S228P and human Kappa backbone. For RBC agglutination, the 8 humanized variants were also compared to the Hu5F9 antibody.

All results obtained in the different assays are summarized in Table 16 and Table 17 below.

TABLE 16

Characteristics of humanized variants of candidate 22

| Candidate No | Antibody (hIgG4) | CD47 Binding (EC50 μg/mL) | CD47/SIRPα inhibition (IC50 μg/mL) | RBC agglutination (2 donors) |
|---|---|---|---|---|
| 22 | Chim. 22 | 0.122 | 0.140 | ++ |
| 22.9 | h22-VH3-VL1 | 0.101 | 0.075 | +++ |
| 22.10 | h22-VH3-VL2 | 0.141 | 0.109 | +++ |
| 22.11 | h22-VH3-VL3 | 0.139 | 0.096 | +++/++++ |
| 22.12 | h22-VH3-VL4 | 0.108 | 0.116 | ++++ |
| 22.13 | h22-VH4-VL1 | 0.070 | 0.119 | +++ |
| 22.14 | h22-VH4-VL2 | 0.099 | 0.093 | +++ |
| 22.15 | h22-VH4-VL3 | 0.124 | 0.098 | +++ |
| 22.16 | h22-VH4-VL4 | 0.184 | 0.116 | ++++ |
| — | Hu5F9 | nt | nt | ++/+++ | nt; not tested;
+/−, weak agglutination observed at 50 μg/mL antibody only;
+, agglutination at 50 μg/mL antibody;
++, agglutination for concentrations ≥16.7 μg/mL;
+++, agglutination for concentrations ≥5.6 μg/mL;
++++, agglutination for concentrations ≥1.9 μg/mL

TABLE 17

Kinetics and affinity constants of humanized anti-CD47 antibodies of Candidate 22 by Biacore (mean values of 2 independent experiments)

| Candidate No | Antibody (hIgG4) | mean Kon (1/Ms) × $10^3$ | mean Koff (1/s) × $10^{-4}$ | mean KD (nM) |
|---|---|---|---|---|
| 22 | Chim. 22 | 31.15 | 3.81 | 12.20 |
| 22.9 | h22-VH3-VL1 | 24.65 | 3.18 | 12.95 |
| 22.10 | h22-VH3-VL2 | 28.75 | 3.15 | 11.05 |
| 22.11 | h22-VH3-VL3 | 28.35 | 3.06 | 10.91 |
| 22.12 | h22-VH3-VL4 | 25.25 | 2.52 | 10.00 |
| 22.13 | h22-VH4-VL1 | 25.60 | 3.37 | 13.20 |
| 22.14 | h22-VH4-VL2 | 31.25 | 3.25 | 10.44 |
| 22.15 | h22-VH4-VL3 | 29.10 | 3.51 | 12.10 |
| 22.16 | h22-VH4-VL4 | 28.15 | 2.63 | 9.37 |

All 8 humanized variants with the h22-VH3 or h22-VH4 sequences combined with the h22-VL1 to h22-VL4 sequences showed Kon, Koff and KD constants similar to the ones of the chimeric candidate 22. None of the variants showed a significant increased affinity to hCD47 as compared to chimeric candidate 22. The Koff values of all humanized variants from candidate 22 were observed to be in the range of $2.5 \times 10^{-4}$ to $3.8 \times 10^{-4}$ s$^{-1}$.

All 8 variants bound strongly to CD47 expressed on Raji cells with an EC50 similar to the EC50 of the chimeric candidate 22.

All 8 variants strongly inhibited the binding of hSIRPα to CD47 expressed on Raji cells, with an IC50 in the same range than the IC50 of chimeric candidate 22.

All 8 variants displayed a tendency to induce slightly more RBC agglutination than the chimeric candidate 22. Among them, 5 had similar RBC agglutination propensity than Hu5F9 benchmark.

VI. Epitope Mapping, Dimerization & Glycosylation

1. Epitope Mapping

The epitope recognized on hCD47 antigen by the mouse anti-CD47 candidates 20 and 22 was determined by using the high resolution method developed by CovalX (Bich C., Scott M., Panagiotidis A., Wenzel R. J., Nazabal A., Zenobi R. "Characterization of antibody-antigen interactions: Comparison between surface plasmon resonance measurements and hih-mass matrix-assisted laser desorption/ionization mass spectrometry", Analytical Biochem 375:35-45, (2008)). The anti-CD47 antibodies were complexed with a soluble preparation of human CD47 extracellular domain tagged with a 6His-tag (SEQ ID NO: 160).

The anti-CD47 antibody/hCD47 complexes then were incubated with deuterated cross-linkers and subjected to multi-enzymatic cleavage. After enrichment of the cross-linked peptides, the samples were analyzed by high resolution mass spectrometry (nLC-Orbitrap MS) and the data generated were analyzed using XQuest and Stavrox software. The MALDI ToF MS analysis has been performed using CovalX's HM4 interaction module with a standard nitrogen laser and focusing on different mass ranges from 0 to 1500 kDa.

Figure 15:
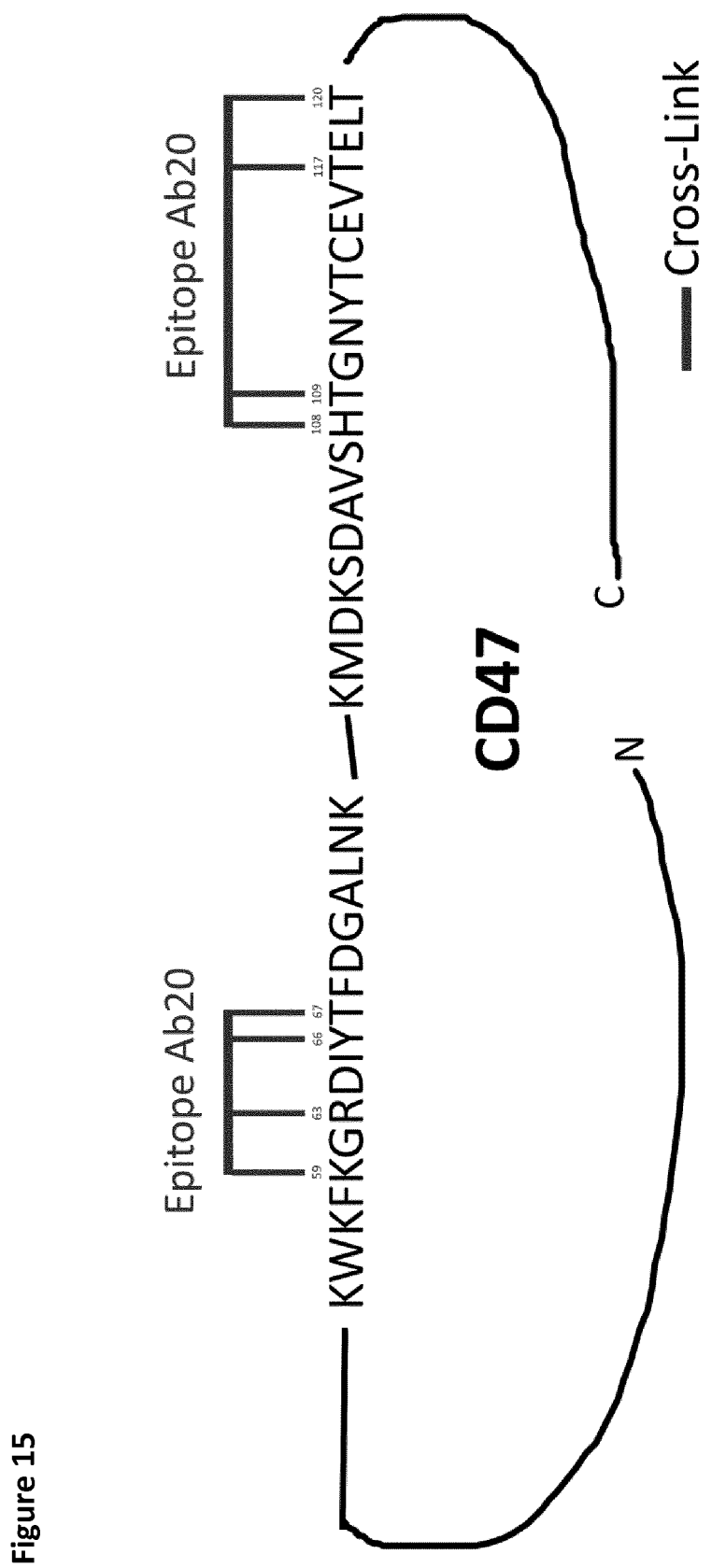
FIG. 15 Epitope mapping of the interaction between candidate 20 and hCD47.

As depicted in FIG. 15, the chemical cross-linking analysis showed that the epitope on hCD47 recognized by the chimeric candidate 20 was discontinuous and comprised the amino-acid residues K59, R63, Y66, T67, H108, T109, T117 and T120 (SEQ ID 151) or the amino-acid residues xxK$_{59}$xxxR$_{63}$xxY$_{66}$T$_{67}$xx-xxH$_{108}$T$_{109}$xxxxxxxT$_{117}$xxT$_{120}$xx of hCD47 (SEQ ID 151) where "x" is for any amino acid residue (numbering according to SEQ ID NO: 151).

Figure 16:
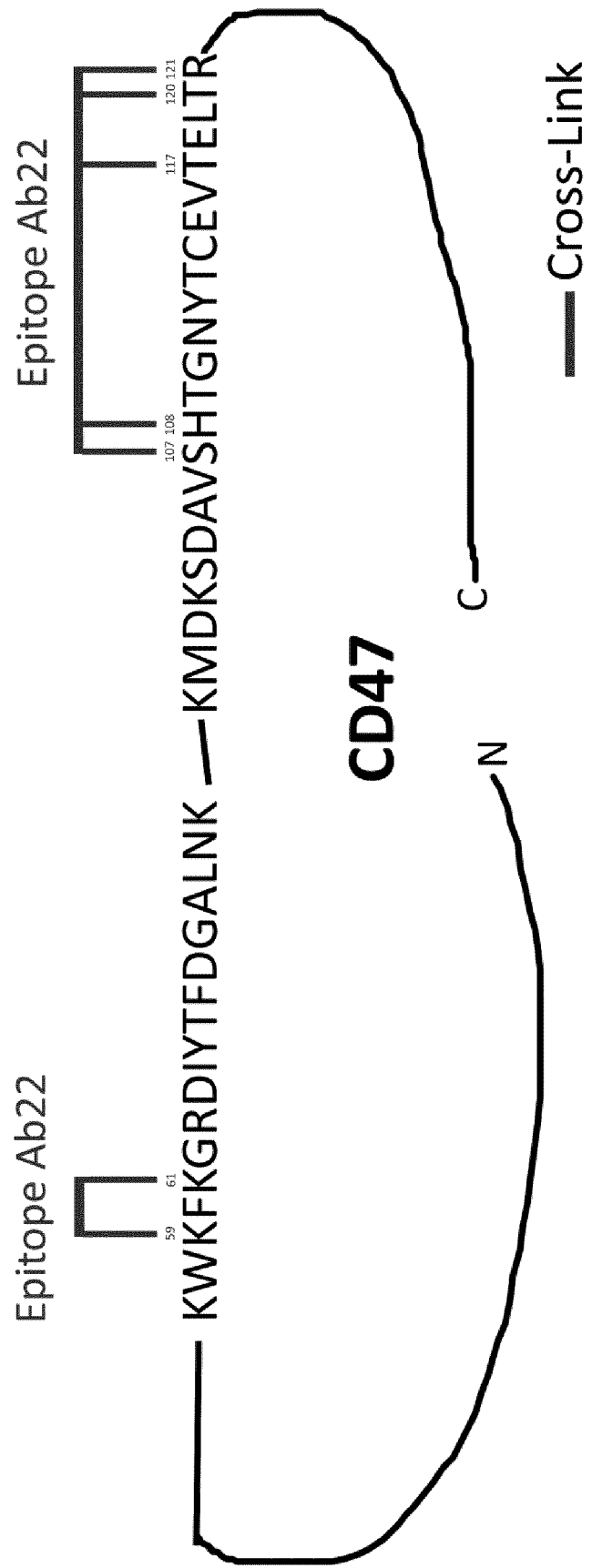
FIG. 16 Epitope mapping of the interaction between candidate 22 and hCD47.

A similar analysis showed that the epitope on hCD47 recognized by the chimeric candidate 22 (FIG. 16) was also discontinuous and comprised K59, K61, S107, H108, T117, T120 and R121 of hCD47 (SEQ ID NO: 151) or the amino-acid residues xxK$_{59}$xK$_{61}$xxxxxx-xxxxxxxxS$_{107}$H$_{108}$xxxxxxxxT$_{117}$xxT$_{120}$R$_{121}$xx of hCD47 (SEQ ID 151) where "x" is for any amino acid residue (numbering according to SEQ ID NO: 151).

Using the same method, the epitope on hCD47 recognized by AB06.12 was also determined and found to be different from candidate 20 or 22 (data not shown).

2. Dimerization of CD47

Figure 17:
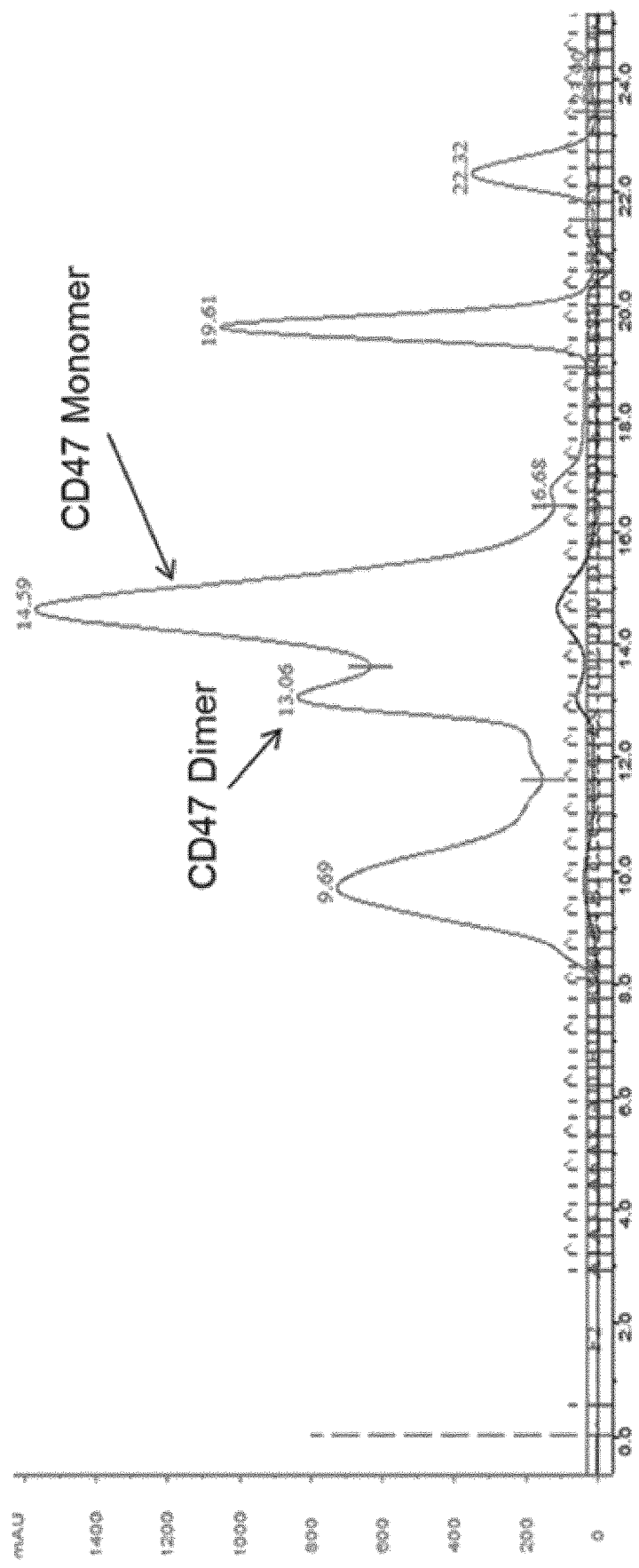
FIG. 17 Analysis of the soluble hCD47 by SEC-HPLC showed heterogeneity in the protein preparation, with the presence of monomer and dimer of CD47.
Figure 18:
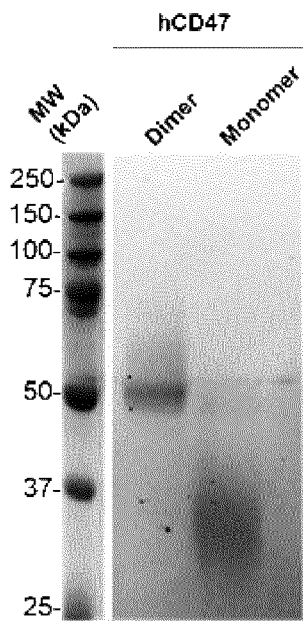
FIG. 18 SDS-PAGE analysis of purified hCD47 monomer and dimer fractions, at ~30 kDa and >50 kDa respectively.
Figure 19:
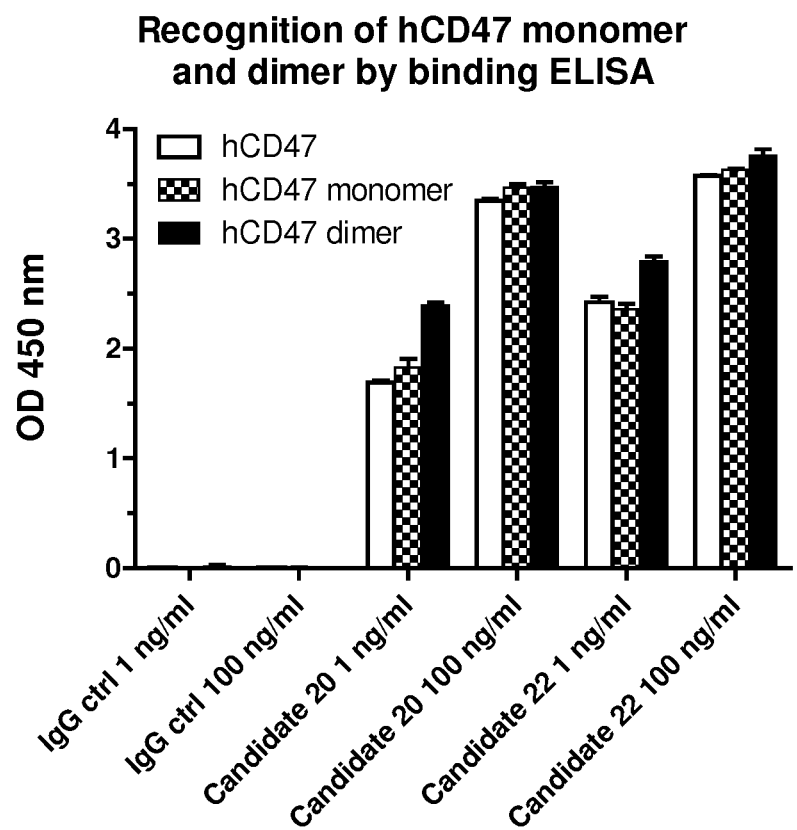
FIG. 19 Recognition of hCD47 monomer and dimer by candidates 20 and 22 by binding ELISA.

The High Mass MALDI ToF analysis and SEC-HPLC analysis of the soluble hCD47 (extracellular IgV domain) preparation showed the presence of monomer, dimer and multimers of hCD47, naturally formed in vitro. To further investigate the capability of the candidates 20 and 22 to recognize the dimer of hCD47, a mixture of anti-CD47 antibody/soluble hCD47 was submitted to cross-linking using CovalX's K200 MALDI MS analysis kit with an excess of antigen. Data suggest that Candidate 20 may bind both the dimer (60.8%) and the monomer of hCD47 (39.2%), while it cannot be excluded that complexes of one antibody with 2 monomers are detected (Table 18). Similarly, the candidate 22 may have formed cross-link with the hCD47 dimer (3.8%) and monomer (5%) (Table 18). Further experiments confirmed that candidates 20 and 22 both bind the human CD47 monomer and the human CD47 dimer that have been purified by SEC-HPLC (see FIGS. 18 and 19). Analysis of the soluble hCD47 by SE-HPLC showed heterogeneity in the protein preparation, with the presence of putative CD47 monomers and dimers (FIG. 17). The monomer and dimer fractions were further purified by semi preparative SE-HPLC using Superdex 200 Increase 10/300 GL from GE healthcare. SDS-PAGE analysis in non-reducing conditions further demonstrated the purity of the 2 fractions, with a large band at ~30 kDa observed for the CD47 monomer fraction corresponding to the expected sizes of glycosylated hCD47, and a major band slightly above 50 kDa observed for the CD47 dimer fraction (FIG. 18). The purified CD47 monomer and dimer fractions were then coated on ELISA plates and the anti-CD47 antibodies were tested for their capacity to recognize the 2 fractions. As shown in FIG. 19, candidates 20 and 22 were capable to bind both the hCD47 monomer and dimer with similar efficacy.

TABLE 18

Analysis of soluble hCD47 in mixture with candidate 20, candidate 22 and after cross-link between soluble hCD47 and candidate 20 and candidate 22

| Species | MW (kDa) | % area |
|---|---|---|
| Candidate 20 | 149.981 | 0 |
| Candidate 20 and one hCD47 | 176.412 | 39.2 |
| Candidate 20 and two hCD47 | 202.491 | 60.8 |
| Candidate 22 | 150.150 | 91.2 |
| Candidate 22 and one hCD47 | 176.750 | 5.0 |
| Candidate 22 and two hCD47 | 201.135 | 3.8 |

3. Recognition of Deglycosylated hCD47

It is known since more than 40 years (see Meezan E., Wu H. C., Black P. H., Robbins P. W. "Comparative studies on the carbohydrate-containing membrane components of normal and virus-transformed mouse fibroblasts. II Separation of glycoproteins and glycopeptides by Saphadex chromatography", Biochemistry 8 (6):2518-24 (1969)), that the mechanisms of glycosylation can be modified in tumor cells, leading to the expression of proteins with altered glycosylation patterns (for more recent reviews, see also Pinho S. S. and Reis C. A. "Glycosylation in cancer: mechanisms and clinical implications", Nat Rev Cancer 15: 540-55 (2015)). CD47 is a highly glycosylated transmembrane protein with 6 N-glycosylation sites at positions N23, N34, N50, N73, N111, N206 (Lindberg F. P., Gresham H. D., Schwarz E., and Brown E. J. "Molecular cloning of integrin-associated protein: An immunoglobulin family member with multiple membrane-spanning domains implicated in $\alpha_v\beta_3$-dependent ligand binding", J Cell Biol 123: 485-96 (1993)).

As the CD47 glycosylation pattern is subjected to be modified in tumor cells, a key aspect to assess was whether therapeutic antibodies are dependent on the CD47 glycosylation level for their binding to the target. To address this point, soluble hCD47 was treated with PNGase to remove the N-glycosylations (Maley F., Trimble R. B., Tarentino A. L., and Plummer T. H. "Characterization of glycoproteins and their associated oligosaccharides through the use of endoglycosidases", Anal. Biochem 180:195-204 (1989)), then candidates 20 or 22 were cross-linked using DSS and K200 during 180 min at room temperature to generate anti-CD47 antibody/deglycosylated-hCD47 cross-linked complexes. These complexes were used to monitor the nature of these non-covalent interactions according to the method described by CovalX (Bich C., Scott M., Panagiotidis A., Wenzel R. J., Nazabal A., Zenobi R. "Characterization of antibody-antigen interactions: Comparison between surface plasmon resonance measurements and hihmass matrix-assisted laser desorption/ionization mass spectrometry", Analytical Biochem 375:35-45 (2008)). Upon monitoring the uncomplexed and complexed molecules by MALDI-ToF, we successfully identified the peaks corresponding to the soluble antibodies added in excess (148.944 kDa for candidate 20 and 149.173 kDa for 22), as well as of the antibody-CD47 complexes (respectively 174.407 kDa and 163.440 kDa), but failed to identify a peak corresponding to the uncomplexed deglycosylated CD47 (15.901 kDa; see Table 19). These data suggest that all the available deglycosylated hCD47 was complexed with either candidate 20 or with candidate 22, supporting the notion that antibodies 20 and 22 are capable to recognize both glycosylated and N-deglycosylated hCD47.

TABLE 19

Mass spectrometry analyses of soluble deglycosylated hCD47 cross-linked with either candidate 20 or candidate 22

| Species | MW (kDa) | % area |
|---|---|---|
| Candidate 20 | 148.944 | 84.8 |
| Candidate 20 and monomeric deglycosylated-hCD47 | 174.407 | 15.2 |
| monomeric deglycosylated-hCD47 | 15.901 | 0 |
| Candidate 22 | 149.173 | 92.8 |
| Candidate 22 and monomeric hCD47 | 163.440 | 7.2 |
| monomeric deglycosylated-hCD47 | 15.901 | 0 |

Figure 22A:
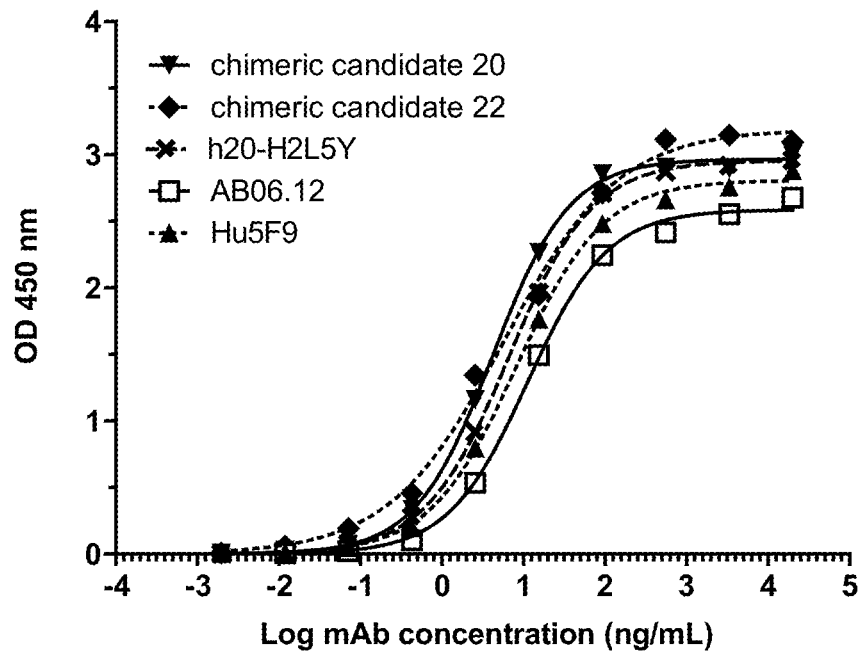
FIGS. 22A-22B Recognition of human glycosylated (FIG. 22A) and N-Deglycosylated (FIG. 22B) CD47 by chimeric candidates 20 and 22, humanized h20-H2L5Y antibody, and humanized Hu5F9 and AB06.12 antibodies, as measured by ELISA on plates coated with glycosylated or N-deglycosylated hCD47. All antibodies were tested in a hu-IgG4 format.
Figure 22B:
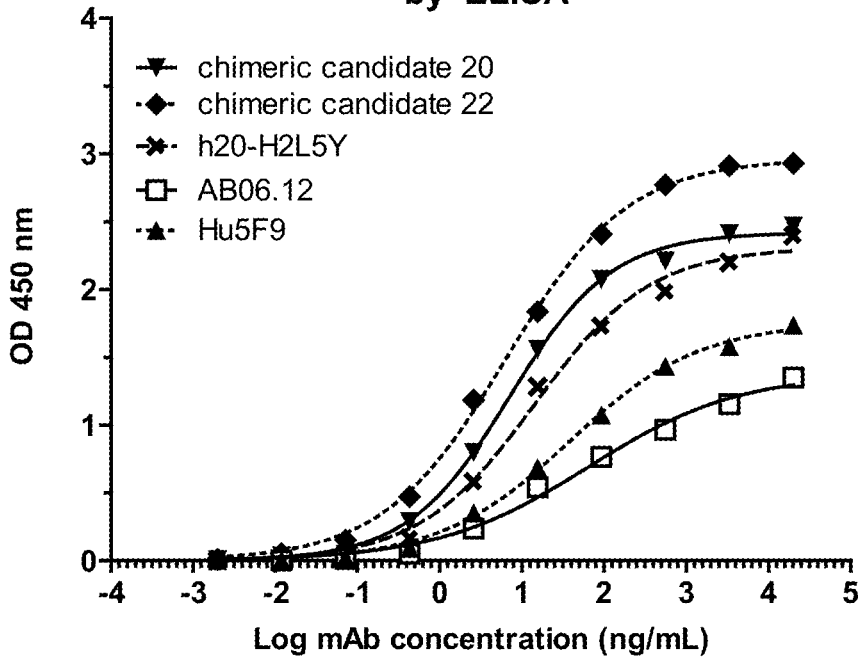

To confirm and quantify the recognition of deglycosylated hCD47 by candidates 20 and 22 as observed with the CovalX approach, the antibodies were tested by ELISA on coated hCD47 and deglycosylated-hCD47 preparations. The successful removal of N-glycans from hCD47 was confirmed by Size Exclusion Chromatography analysis (not shown). The anti-CD47 candidates 20 and 22 were tested in a chimeric hu-IgG4 format in parallel to the humanized variant h20-H2L5Y also in hu-IgG4 isotype. The antibodies were tested along with the AB06.12 and Hu5F9 humanized antibodies generated in a hu-IgG4 format to allow the same recognition efficiency by ELISA. As shown in FIG. 22A and Tables 20, 21 and 22, although Hu5F9 and AB06.12 displayed slightly lower maximum binding, all antibodies strongly bound with similar profiles and EC50, EC95, equilibrium binding constant and maximum specific binding (Bmax) values to the glycosylated CD47 ($Bmax_1$). In contrast, the binding of Hu5F9 and of AB06.12 to N-deglycosylated CD47 was strongly reduced when compared to the binding observed for the chimeric candidates 20, 22, and for the humanized variant h20-H2L5Y (FIG. 22B, Tables 20, 21 and 22). Indeed, the chimeric candidates 20, 22, and the humanized antibody h20-H2L5Y bound on deglycosylated CD47 with an EC50 value that was less than 3.0 fold the EC50 value on glycosylated CD47 and/or with an EC95 value that was less than 10.0 fold the EC95 value measured on glycosylated CD47. In contrast the EC50 and EC95 values of AB06.12 and Hu5F9 were more than 3.0 and 10.0 fold superior to the EC50 and EC95 values measured on glycosylated CD47, respectively (Table 20). Moreover, the equilibrium binding constant values of the chimeric candidates 20, 22, and of the humanized antibody h20-H2L5Y were ≤60 pM on both glycosylated and on N-deglycosylated CD47, while the equilibrium binding constant values of AB06.12 and Hu5F9 were in the range of 90-130 pM on N-deglycosylated CD47 (Table 21). Finally, the chimeric candidates 20, 22, and the humanized antibody h20-H2L5Y bound both glycosylated and N-deglycosylated CD47 with a maximum specific binding (Bmax) value≥1.9 OD on glycosylated ($Bmax_1$) and on deglycosylated ($Bmax_2$) CD47, while the $Bmax_2$ values of AB06.12 and Hu5F9 were <1.5 OD on N-deglycosylated CD47 (Table 22).

These results further demonstrate that recognition of hCD47 by candidates 20, 22 and by the humanized h20-H2L5Y antibody does not depend on the N-glycosylation level of CD47. Conversely, Hu5F9 and AB06.12 antibodies significantly lose their binding capacity on N-deglycosylated CD47. As the glycosylation level and nature of cell surface proteins can be modified on tumor cells, it is possible that the glycosylation of the CD47 antigen can be also modified when expressed or overexpressed by tumor cells. Of note, the glycosylation pattern of CD47 does not seem to be necessary for its interaction with SIRPα (Subramanian S., Boder E. T., and Discher D. E. "Phylogenetic divergence of CD47 interactions with human signal regulatory protein α reveals locus of species specificity." J. Biolog. Chem. 282 (3):1805-18 (2007)), suggesting that aberrant glycosylation will not alter the CD47/SIRPα interaction. Therefore, cancer cells overexpressing CD47 will protect themselves from phagocytosis independently on their glycosylation pattern. Conversely, the N-glycosylation pattern of hCD47 may affect antibody binding and significantly lower therapeutic efficacy. As a consequence, we expect a broader anti-tumor effect by using anti-CD47 therapeutic antibodies such as 20, 22 and preferably h20-H2L5Y, whose binding to hCD47 are not dependent on its glycosylation level.

TABLE 20

Characteristics of binding on glycosylated-hCD47 compared to N-Deglycosylated hCD47 of anti-CD47 chimeric candidates 20 and 22, humanized h20-H2L5Y antibody and benchmark antibodies, as measured by ELISA. The EC50 and EC95 values were calculated by using the non-linear regression/log(antibody) versus response (four parameters) model of the GraphPad Prism software.

| Antibody (hu-IgG4) | Binding to Glycosylated hCD47-His by ELISA | | Binding to N-Deglycosylated hCD47-His by ELISA | | Ratio EC Deglycosylated/ EC Glycosylated | |
|---|---|---|---|---|---|---|
| | EC50 (pM) | EC95 (pM) | EC50 (pM) | EC95 (pM) | EC50 ratio | EC95 ratio |
| Chimeric Candidate 20 | 28.0 | 667.0 | 47.4 | 3335.0 | 1.7 | 5.0 |
| h20-H2L5Y | 44.0 | 1334.0 | 96.0 | 11339.0 | 2.2 | 8.5 |
| Chimeric Candidate 22 | 38.7 | 4669.0 | 42.0 | 6670.0 | 1.1 | 1.4 |
| AB06.12 | 75.4 | 2054.4 | 427.5 | 214782.0 | 5.7 | 107.4 |
| Hu5F9 | 54.7 | 1961.0 | 253.5 | 54027.0 | 4.6 | 27.6 |

TABLE 21

Equilibrium binding constant on Glycosylated-hCD47 compared to N-Deglycosylated hCD47 of anti-CD47 chimeric candidates 20 and 22, humanized h20-H2L5Y antibody and benchmark antibodies, as measured by ELISA. The equilibrium binding constant values were calculated by using the binding saturation/one-site binding model of the GraphPad Prism software (mean +/− SD of triplicates).

| Antibody (hu-IgG4) | Equilibrium binding constant on Glycosylated hCD47 (pM) | | Equilibrium binding constant on Deglycosylated hCD47 (pM) | |
|---|---|---|---|---|
| | mean | SD | mean | SD |
| Chimeric Candidate 20 | 27.3 | 3.3 | 38.8 | 4.6 |
| h20-H2L5Y | 43.6 | 7.2 | 55.7 | 10.5 |
| Chimeric Candidate 22 | 34.4 | 6.7 | 31.8 | 5.9 |
| AB06.12 | 67.0 | 6.8 | 93.6 | 28.6 |
| Hu5F9 | 49.0 | 4.9 | 129.0 | 43.2 |

TABLE 22

Maximum specific binding (Bmax) on Glycosylated-hCD47 ($Bmax_1$) compared to N-Deglycosylated ($Bmax_2$) hCD47 of anti-CD47 chimeric candidates 20 and 22, humanized h20-H2L5Y antibody and benchmark antibodies, as measured by ELISA. The Bmax values were calculated by using the binding saturation/one-site binding model of the GraphPad Prism software (mean +/− SD of triplicates).

| Antibody (hu-IgG4) | $Bmax_1$ on Glycosylated hCD47 (OD value) | | $Bmax_2$ on Deglycosylated hCD47 (OD value) | |
|---|---|---|---|---|
| | mean | SD | mean | SD |
| Chimeric Candidate 20 | 2.90 | 0.07 | 2.20 | 0.05 |
| h20-H2L5Y | 2.85 | 0.09 | 1.97 | 0.07 |
| Chimeric Candidate 22 | 2.85 | 0.11 | 2.57 | 0.09 |
| AB06.12 | 2.48 | 0.05 | 0.97 | 0.06 |
| Hu5F9 | 2.66 | 0.05 | 1.40 | 0.10 |

VII. In Vivo Efficacy of Humanized Anti-CD47 Antibody h20-H2L5Y

Figure 23:
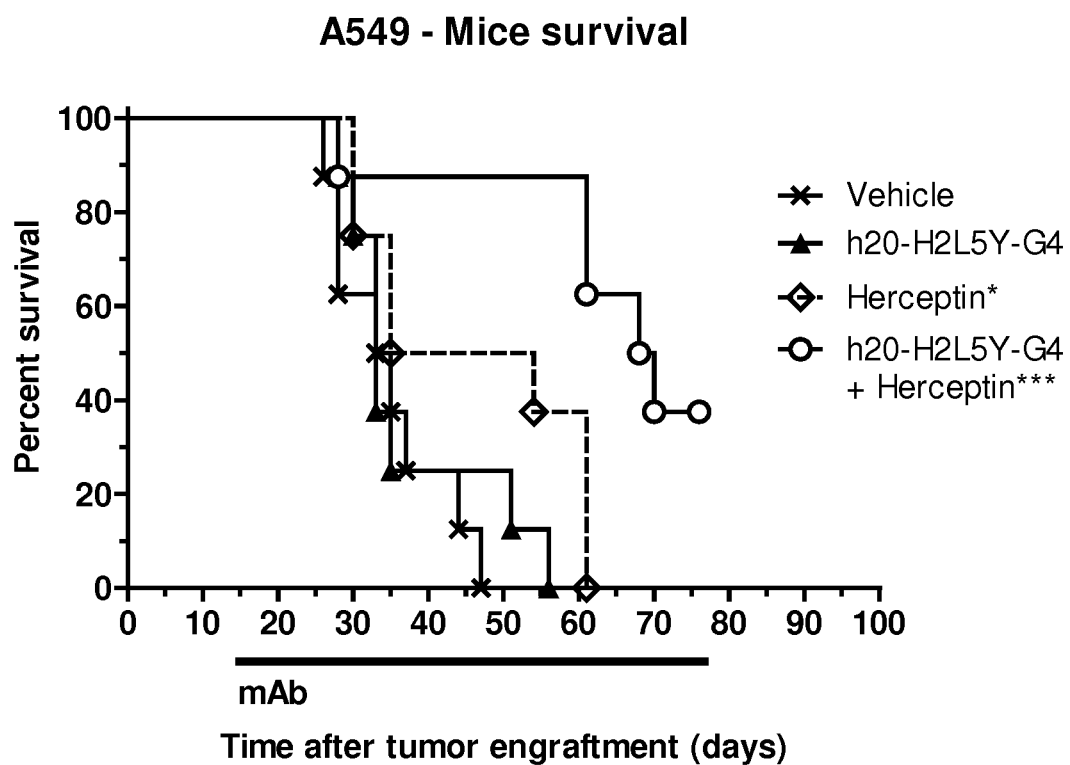
FIG. 23 Efficacy of the humanized h20-H2L5Y antibody alone or in combination with Herceptin® in the A549 NSCLC xenograft model in NOG mice. A549 cells were engrafted subcutaneously in NOG mice (n=8 per group) and the antibody treatment was started when the tumor was about 100 mm$^3$ (day 14) for up to 10 weeks. Antibodies were injected IP (3 injections/week), with h20-H2L5Y injected in a hu-IgG4 format (h20-H2L5Y-G4) at 10 mg/kg/dose and Herceptin® (hu-IgG1) injected at 2.5 mg/kg/dose. Survival of the mice was monitored and survival curves are presented. Treatment groups were compared to the vehicle group by using the Log-rank (Mantel-Cox) Test of the GraphPad Prism software (*p<0.05; ***p<0.005). The survival of mice treated with the combination of h20-H2L5Y-G4 and Herceptin® was significantly enhanced when compared to the group treated with Herceptin® alone (p<0.01).

The humanized variant h20-H2L5Y was evaluated in a hu-IgG4 format (h20-H2L5Y-G4) as single agent and in combination with anti-Her2 Trastuzumab (Herceptin®) in the A549 lung adenocarcinoma xenograft model as previously described. NOG mice (n=8 per group) were engrafted with A549 cells (10 million cells injected subcutaneously). The antibody therapy was started fourteen days after the cell transplant, once the tumor volume was about 100 mm³. The anti-CD47 antibody h20-H2L5Y and Herceptin® were injected alone or in combination at the dose of 10 mg/kg/dose by intraperitoneal injection, 3 times a week for up to 10 weeks. As shown in FIG. 23 the combination of the anti-CD47 antibody h20-H2L5Y-G4 with Herceptin® significantly prolong the survival of treated-mice when compared to the control group of animals injected with the vehicle (p<0.005) and to the group of animals treated with Herceptin® alone (p<0.05). Thus, these results show an increased efficacy of the combination of humanized anti-CD47 h20-H2L5Y antibody with Herceptin® for controlling the growth of the A549 lung adenocarcinoma in vivo in NOG mice, and confirm the results previously obtained with the mouse anti-CD47 candidate 20.

Figure 24:
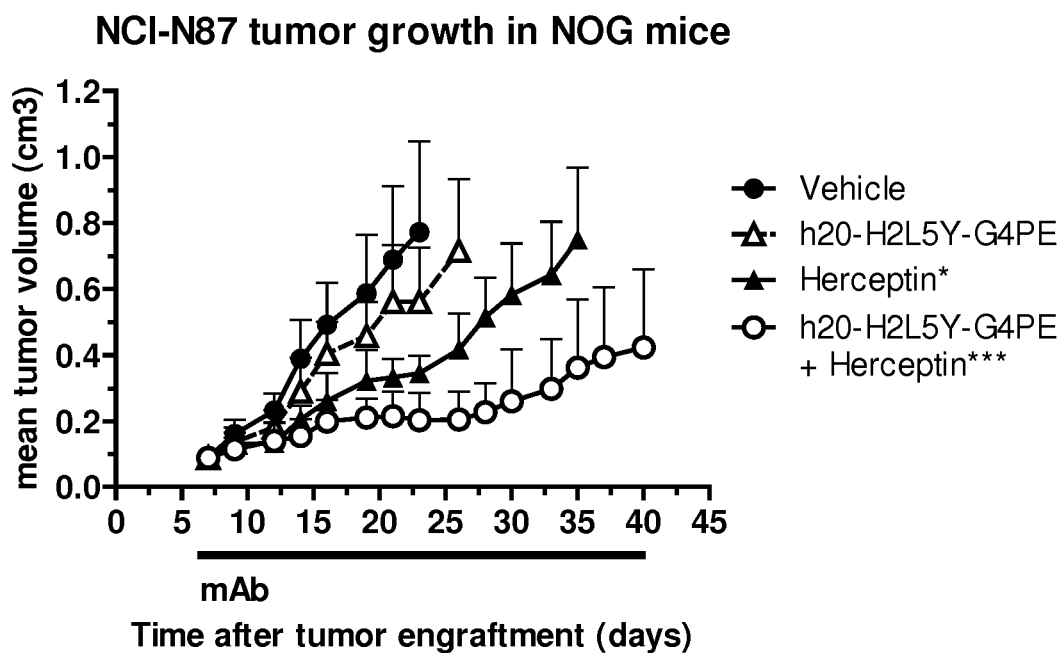
FIG. 24 Efficacy of the humanized antibody h20-H2L5Y alone or in combination with Herceptin® in the NCI-N87 gastric xenograft model in NOG mice. NCI-N87 cells (10× 10$^6$) were engrafted subcutaneously in NOG mice (n=8 per group) and the antibody treatment was started when the tumor was about 100 mm$^3$ (day 7) for up to 5 weeks. Antibodies were injected IP (3 injections/week), with h20-H2L5Y injected in a hu-IgG4-S228P-L235E format (h20-H2L5Y-G4PE) at 10 mg/kg/dose and Herceptin® (hu-IgG1) injected at 2.5 mg/kg/dose. Tumor cell growth was monitored by measuring the tumor volume. The mean tumor volume (cm$^3$)+/−SD of each group was presented for different times until the first mouse died or was sacrificed into the respective groups. Treatment groups were compared to the vehicle group by using the rate-based T/C method described by Hather et al. (Hather G., Liu R., Bandi S., Mettetal J., et al. "Growth Rate Analysis and Efficient Experimental Design for Tumor Xenograft Studies." Cancer Informatics 13(54):65-72 (2014)), (*p<0.05; ***p<0.0005). The growth of the NCI-N87 tumor cells was also significantly reduced in the group of animals treated with the combination of h20-H2L5Y-G4PE plus Herceptin® when compared to the animals treated with Herceptin® alone (p<0.05).

The humanized h20-H2L5Y antibody was also evaluated in a mouse xenograft model of Her-2 positive gastric cancer, as single agent and in combination with anti-Her2 Trastuzumab (Herceptin®) that is approved for the treatment of Her2-overexpressing metastatic gastric cancers. For this study, the human NCI-N87 cell line (ATCC®-CRL-5822) was selected for xenograft as a Her-2 positive gastric tumor responding to Herceptin® treatment (Matsui Y., Inomata M., Tojigamori M., Sonoda K., Shiraishi N., Kitano S. "Suppression of tumor growth in human gastric cancer with HER2 overexpression by an anti-HER2 antibody in a murine model", Int. J. Oncol. 27(3):681-5 (2005)). In vitro, these cells very strongly expressed Her-2 as detected by the binding of Herceptin® and strongly expressed CD47 as measured by staining with h20-H2L5Y antibody and flow cytometry analysis (data not shown). The studies were carried out in NOG mice, and the humanized h20-H2L5Y antibody was tested in a hu-IgG4-S228P-L235E format (h20-H2L5Y-G4PE). For this purpose, the humanized antibody h20-H2L5Y was further produced in a hu-IgG4 format carrying the S228P and L235E mutations following cloning of the h20-VH2 variant in an expression vector containing a human Fcγ4-S228P-L235E backbone (SEQ ID NO: 164). The L235E mutation has been shown to strongly reduce the affinity of hu-IgG4 to Fcγ receptors (FcγRs) and therefore abrogates the Fc effector functions such as ADCC or ADCP (Alegre M L, Collins A M, Pulito V L, Brosius R A, Olson W C, et al. "Effect of a single amino acid mutation on the activating and immunosuppressive properties of a "humanized" OKT3 monoclonal antibody", J. Immunol. 148(11): 3461-68 (1992); Reddy M P, Kinney C A S., Chaikin M A, Fishman-Lobell J, Tsui P, et al. "Elimination of Fc Receptor-Dependent Effector Functions of a Modified IgG4 Monoclonal Antibody to Human CD4", J. Immunol. 164:1925-33 (2000)). The L235E mutation will therefore reduce the risk of side effects such as phagocytosis or lysis of opsonized normal cells (such as RBCs, platelets, etc). NOG mice (n=8 per group) were engrafted with NCI-N87 cells (10 million cells injected subcutaneously) and the antibody therapy was started seven days after the cell transplant, once the tumor volume was about 100 mm$^3$. The anti-CD47 antibody h20-H2L5Y-G4PE was injected alone or in combination at 10 mg/kg/dose, whereas Herceptin® was injected alone or in combination at the dose of 2.5 mg/kg/dose. Antibodies were administered by intraperitoneal injection, 3 times a week for up to 5 weeks. As shown in FIG. 24, a delay of the NCI-N87 growth was observed in the group of mice treated with the anti-CD47 antibody h20-H2L5Y-G4PE alone, and a stronger delay of the NCI-N87 growth was observed in mice treated with the combination of Herceptin® with the anti-CD47 h20-H2L5Y-G4PE antibody (FIG. 24). Similar results were obtained when the study was carried out in NOD/SCID mice (data not shown). This reduction of the NCI-N87 tumor growth in the group of mice treated with the combination of Herceptin® and anti-CD47 h20-H2L5Y-G4PE was statistically higher when compared to the group of mice treated with Herceptin® alone (p<0.05, Student's t-test), thus demonstrating the cooperative effect between anti-CD47 h20-H2L5Y antibody and Herceptin® for controlling the proliferation of NCI-N87 tumor cells in vivo, and potentially of other Her-2 positive gastric tumors.

Further Aspects:

1. An antibody that is selected from the group of antibodies consisting of:
   (a) A group 1 of antibodies that comprise a heavy chain having each of the CDR sequences set forth in SEQ ID NOs: 1-3 (Kabat annotation) or SEQ ID NOs: 4-6 (IMGT annotation) and a light chain having each of the CDR sequences set forth in SEQ ID NOs: 7-9 (Kabat annotation) or SEQ ID NOs: 10-12 (IMGT annotation); or
   (b) A group 2 of antibodies that comprise a heavy chain having each of the CDR sequences set forth in SEQ ID NOs: 13-15 (Kabat annotation) or SEQ ID NOs: 16-18 (IMGT annotation) and a light chain having each of the CDR sequences set forth in SEQ ID NOs: 19-21 (Kabat annotation) or SEQ ID NOs: 22-24 (IMGT annotation); or
   (c) A group 3 of antibodies that comprise a heavy chain having each of the CDR sequences set forth in SEQ ID NOs: 25-27 (Kabat annotation) or SEQ ID NOs: 28-30 (IMGT annotation) and a light chain having each of the CDR sequences set forth in SEQ ID NOs: 31-33 (Kabat annotation) or SEQ ID NOs: 34-36 (IMGT annotation); or
   (d) A group 4 of antibodies that comprise a heavy chain having each of the CDR sequences set forth in SEQ ID NOs: 37-39 (Kabat annotation) or SEQ ID NOs: 40-42 (IMGT annotation) and a light chain having each of the CDR sequences set forth in SEQ ID NOs: 43-45 (Kabat annotation) or SEQ ID NOs: 46-48 (IMGT annotation); or
   (e) A group 5 of antibodies that comprise a heavy chain having each of the CDR sequences set forth in SEQ ID NOs: 49-51 (Kabat annotation) or SEQ ID NOs: 52-54 (IMGT annotation) and a light chain having each of the CDR sequences set forth in SEQ ID NOs: 55-57 (Kabat annotation) or SEQ ID NOs: 58-60 (IMGT annotation); or
   (f) A group 6 of antibodies that comprise a heavy chain having each of the CDR sequences set forth in SEQ ID NOs: 61-63 (Kabat annotation) or SEQ ID NOs: 64-66 (IMGT annotation) and a light chain having each of the CDR sequences set forth in SEQ ID NOs: 67-69 (Kabat annotation) or SEQ ID NOs: 70-72 (IMGT annotation); or
   (g) A group 7 of antibodies that comprise a heavy chain having each of the CDR sequences set forth in SEQ ID NOs: 73-75 (Kabat annotation) or SEQ ID NOs: 76-78 (IMGT annotation) and a light chain having each of the CDR sequences set forth in SEQ ID NOs: 79-81 (Kabat annotation) or SEQ ID NOs: 82-84 (IMGT annotation); or
   (h) A group 8 of antibodies that comprise a heavy chain having each of the CDR sequences set forth in SEQ ID NOs: 85-87 (Kabat annotation) or SEQ ID NOs: 88-90 (IMGT annotation) and a light chain having each of the CDR sequences set forth in SEQ ID NOs: 91-93 (Kabat annotation) or SEQ ID NOs: 94-96 (IMGT annotation); or
   (i) A group 9 of antibodies that comprise a heavy chain having each of the CDR sequences set forth in SEQ ID NOs: 97-99 (Kabat annotation) or SEQ ID NOs: 100-102 (IMGT annotation) and a light chain having each of the CDR sequences set forth in SEQ ID NOs: 103-105 (Kabat annotation) or SEQ ID NOs: 106-108 (IMGT annotation); or
   (j) A group 10 of antibodies that comprise a heavy chain having each of the CDR sequences set forth in SEQ ID NOs: 109-111 (Kabat annotation) or SEQ ID NOs: 112-114 (IMGT annotation) and a light chain having each of the CDR sequences set forth in SEQ ID NOs: 115-117 (Kabat annotation) or SEQ ID NOs: 118-120 (IMGT annotation);
   (k) A group 11 of antibodies that comprise a heavy chain having each of the CDR sequences set forth in SEQ ID NOs: 49-51 (Kabat annotation) or SEQ ID NOs: 52-54 (IMGT annotation) and a light chain having each of the CDR sequences set forth in SEQ ID NOs: 55, 152, 57 (Kabat annotation) or SEQ ID NOs: 58, 153, 60 (IMGT annotation);
   (l) and wherein the group of antibodies that are preferred are selected from the group of antibodies consisting of the group 5 of antibodies that comprise a heavy chain having each of the CDR sequences set forth in SEQ ID NOs: 49-51 (Kabat annotation) or SEQ ID NOs: 52-54 (IMGT annotation) and a light chain having each of the CDR sequences set forth in SEQ ID NOs: 55-57 (Kabat annotation) or SEQ ID NOs: 58-60 (IMGT annotation), the group 6 of antibodies that comprise a heavy chain having each of the CDR sequences set forth in SEQ ID NOs: 61-63 (Kabat annotation) or SEQ ID NOs: 64-66 (IMGT annotation) and a light chain having each of the CDR sequences set forth in SEQ ID NOs: 67-69 (Kabat annotation) or SEQ ID NOs: 70-72 (IMGT annotation); and the group 11 of antibodies that comprise a heavy chain having each of the CDR sequences set forth in SEQ ID NOs: 49-51 (Kabat annotation) or SEQ ID NOs: 52-54 (IMGT annotation) and a light chain having each of the CDR sequences set forth in SEQ ID NOs: 55, 152, 57 (Kabat annotation) or SEQ ID NOs: 58, 153, 60 (IMGT annotation) are preferred.

2. The antibody of aspect 1, wherein said antibody is selected from the group of antibodies consisting of:
   (a) The group 1 of antibodies that comprise a VH having an amino acid sequence set forth in SEQ ID NO: 121 and/or a VL having an amino acid sequence set forth in SEQ ID NO: 122; or
   (b) The group 2 of antibodies that comprise a VH having an amino acid sequence set forth in SEQ ID NO: 123 and/or a VL having an amino acid sequence set forth in SEQ ID NO: 124; or
   (c) The group 3 of antibodies that comprise a VH having an amino acid sequence set forth in SEQ ID NO: 125 and/or a VL having an amino acid sequence set forth in SEQ ID NO: 126; or
   (d) The group 4 of antibodies that comprise a VH having an amino acid sequence set forth in SEQ ID NO: 127 and/or a VL having an amino acid sequence set forth in SEQ ID NO: 128; or
   (e) The group 5 of antibodies that comprise a VH having an amino acid sequence set forth in SEQ ID NO: 129 and/or a VL having an amino acid sequence set forth in SEQ ID NO: 130; or
   (f) The group 6 of antibodies that comprise a VH having an amino acid sequence set forth in SEQ ID NO: 131 and/or a VL having an amino acid sequence set forth in SEQ ID NO: 132; or
   (g) The group 7 of antibodies that comprise a VH having an amino acid sequence set forth in SEQ ID NO: 133 and/or a VL having an amino acid sequence set forth in SEQ ID NO: 134; or
   (h) The group 8 of antibodies that comprise a VH having an amino acid sequence set forth in SEQ ID NO: 135 and/or a VL having an amino acid sequence set forth in SEQ ID NO: 136; or
   (i) The group 9 of antibodies that comprise a VH having an amino acid sequence set forth in SEQ ID NO: 137 and/or a VL having an amino acid sequence set forth in SEQ ID NO: 138; or
   (j) The group 10 of antibodies that comprise a VH having an amino acid sequence set forth in SEQ ID NO: 139 and/or a VL having an amino acid sequence set forth in SEQ ID NO: 140; or
   (k) The group 11 of antibodies that comprise a VH having an amino acid sequence set forth in SEQ ID NO: 129 and/or a VL having an amino acid sequence set forth in SEQ ID NO: 154;
   (l) and wherein the group of antibodies that are preferred are selected from the group of antibodies consisting of the group 5 of antibodies that comprise a VH having an amino acid sequence set forth in SEQ ID NO: 129 and/or a VL having an amino acid sequence set forth in SEQ ID NO: 130, the group 6 of antibodies that comprise a VH having an amino acid sequence set forth in SEQ ID NO: 131 and/or a VL having an amino acid sequence set forth in SEQ ID NO: 132, and the group 11 of antibodies that comprise a VH having an amino acid sequence set forth in SEQ ID NO: 129, and/or a VL having an amino acid sequence set forth in SEQ ID NO: 154.
3. The antibody of any one of aspects 1-2, wherein the antibody is a full length chimeric, mouse or humanized antibody.
4. The antibody of aspect 3, wherein the humanized antibody comprises a VH having an amino acid sequence set forth in SEQ ID NO: 141 and a VL that is selected from the group of VLs consisting of amino acid sequences set forth in SEQ ID NOs: 146-150 and/or SEQ ID NOs: 155-159; or wherein the humanized antibody comprises a VH having an amino acid sequence set forth in SEQ ID NO: 142 and a VL that is selected from the group of VLs consisting of amino acid sequences set forth in SEQ ID NOs: 146-150 and/or SEQ ID NOs: 155-159; or wherein the humanized antibody comprises a VH having an amino acid sequence set forth in SEQ ID NO: 143 and a VL that is selected from the group of VLs consisting of amino acid sequences set forth in SEQ ID NOs: 146-150 and/or SEQ ID NOs: 155-159; or wherein the humanized antibody comprises a VH having an amino acid sequence set forth in SEQ ID NO: 144 and a VL that is selected from the group of VLs consisting of amino acid sequences set forth in SEQ ID NOs: 146-150 and/or SEQ ID NOs: 155-159; or wherein the humanized antibody comprises a VH having an amino acid sequence set forth in SEQ ID NO: 145 and a VL that is selected from the group of VLs consisting of amino acid sequences set forth in SEQ ID NOs: 146-150 and/or SEQ ID NOs: 155-159; or wherein the humanized antibody comprises a VH having an amino acid sequence set forth in SEQ ID NO: 168 and a VL that is selected from the group of VLs consisting of amino acid sequences set forth in SEQ ID NOs: 172-175; or wherein the humanized antibody comprises a VH having an amino acid sequence set forth in SEQ ID NO: 169 and a VL that is selected from the group of VLs consisting of amino acid sequences set forth in SEQ ID NOs: 172-175; or wherein the humanized antibody comprises a VH having an amino acid sequence set forth in SEQ ID NO: 170 and a VL that is selected from the group of VLs consisting of amino acid sequences set forth in SEQ ID NOs: 172-175; or wherein the humanized antibody comprises a VH having an amino acid sequence set forth in SEQ ID NO: 171 and a VL that is selected from the group of VLs consisting of amino acid sequences set forth in SEQ ID NOs: 172-175.
5. The antibody of any one of aspects 1-4, wherein the antibody has a Koff value of about $1.0 \times 10^{-4}$ $s^{-1}$ (1/s) or more.
6. The antibody of any of aspects 1-5, having a human IgG1, IgG2, IgG3, IgG4 or IgA constant region, preferably a human IgG4 with optionally the mutation S228P (SEQ ID NO: 162) and/or with optionally the mutations S228P-L235E (SEQ ID NO: 164).
7. The antibody of any of aspects 1-5, wherein the antibody is an antibody fragment, and wherein the antibody fragment is optionally an F(ab')2 or an Fab fragment.
8. The antibody of any of aspects 1-7, wherein the antibody is a bispecific antibody.
9. The antibody of any one of aspects 1-8, wherein the antibody binds specifically to human CD47 and does not activate CD47 upon binding.
10. The antibody of any one of aspects 1-9, wherein the antibody binds to a discontinuous epitope on CD47, preferably human CD47.
11. The antibody of aspect 10, wherein the discontinuous epitope comprises amino acid residues K59, R63, Y66, T67, H108, T109, T117 and T120 (SEQ ID 151); or the discontinuous epitope comprises amino acid residues K59, K61, 5107, H108, T117, T120 and R121 of hCD47 (SEQ ID NO: 151).
12. The antibody of any one of aspects 1-11, wherein the antibody binds the CD47 monomer and CD47 dimer, preferably the human CD47 monomer and dimer, respectively.
13. The antibody of any of aspects 1-12, wherein the antibody binds the glycosylated and deglycosylated forms of CD47, preferably the human CD47 glycosylated and deglycosylated forms, respectively.

14. A polynucleotide encoding an antibody set forth in any one of aspects 1-13.
15. A cell that produces an antibody set forth in any one of aspects 1-13.
16. A pharmaceutical composition comprising an antibody set forth in any one of aspect 1-13, optionally further comprising a pharmaceutical acceptable excipient.
17. An antibody of any of aspects 1-13 or a pharmaceutical composition of aspect 16, for use in the treatment of a disease in a subject.
18. The antibody or composition for use of aspect 17, for use in the treatment of cancer.
19. The antibody or composition for use of aspect 17 or aspect 18, for use as a monotherapy.
20. The antibody or composition for use of aspect 17 or aspect 18, for use in combination therapy, preferably a combination with a Her-2 inhibitor or an anti-Her-2 antibody or an EGFR inhibitor or an anti-EGFR antibody.
21. The antibody or composition for use according to aspects 17-20, wherein the subject is human and/or a non-human animal.
22. A method of detecting the presence of CD47 in a biological sample or tissue, the method comprising (i) contacting said sample or tissue with the antibody set forth in any one of aspects 1-13, and (ii) determining the presence of antibody bound to said tissue or sample.
23. A process for producing an antibody of any one of aspects 1-13, comprising culturing the cell of aspect 15 so that the nucleic acid of aspect 14 is expressed, and optionally recovering the antibody from the cell culture.
24. A method of treating or preventing cancer in a subject, comprising administering to a subject having or at risk of developing cancer an effective amount of an antibody of aspects 1-13.

Further Embodiments are Defined in the Following Numbered Paragraphs:

1. An antibody that binds to glycosylated and non-glycosylated CD47, wherein binding of the antibody to CD47 is not dependent on the glycosylation of CD47.
2. The antibody of paragraph 1, wherein the antibody is suitable for use as a therapeutic antibody.
3. The antibody of paragraph 1 or paragraph 2, wherein the antibody binds glycosylated and deglycosylated forms of human CD47.
4. The antibody of paragraph 3, wherein the glycosylated form of human CD47 comprises one or more N-glycosylated residues at positions N23, N34, N50, N73, N111 and/or N206 in the amino acid sequence of human CD47 (SEQ ID NO:151).
5. The antibody of any preceding paragraph, wherein the deglycosylated form of human CD47 comprises glycosylated human CD47 that has been treated with a peptide N-glycosidase (PNGase) for removal of N-glycosylations.
6. The antibody of any preceding paragraph, wherein (i) a ratio of EC50s of binding of the antibody to non-glycosylated versus glycosylated forms of CD47 is less than 4, 3, 2, 1, 0.5, 0.25, preferably in a range from 4 to 1, more preferably 3 to 1, most preferably 2 to 1; and/or (ii) a ratio of EC95s of binding of the antibody to non-glycosylated versus glycosylated forms of CD47 is less than 25, 20, 10, 1, 0.5 or 0.25, preferably in a range from 10 to 1, more preferably 9 to 1, most preferably 9 to 1.
7. The antibody of any preceding paragraph, wherein the antibody binds to each of glycosylated and non-glycosylated CD47 with an equilibrium binding constant of 80 pM or lower, preferably 70 pM or lower, more preferably 60 pM or lower.
8. The antibody of any preceding paragraph, wherein a maximum binding capacity (Bmax2) of the antibody to non-glycosylated CD47 is at least 60% of a maximum binding capacity (Bmax1) of the antibody to glycosylated CD47.
9. The antibody of any preceding paragraph, wherein the antibody has a Koff value for binding to glycosylated and/or non-glycosylated CD47 of about $1.0 \times 10-4$ s−1 (1/s) or more.
10. The antibody of paragraph 9, wherein the antibody has a Koff value for binding to glycosylated and/or non-glycosylated CD47 of from $1.0 \times 10-4$ s−1 to $1.0 \times 10-3$ s−1.
11. The antibody of paragraph 10, wherein the antibody has a Koff value for binding to glycosylated and/or non-glycosylated CD47 of from $2.5 \times 10-4$ s−1 to $8.0 \times 10-4$ s−1.
12. An antibody that binds to CD47, wherein the antibody has a Koff value for binding to CD47 of from $1.0 \times 10-4$ s−1 to $1.0 \times 10-3$ s−1.
13. An antibody that is selected from the group of antibodies consisting of (i) a group of antibodies that comprise a heavy chain having each of the CDR sequences set forth in SEQ ID NOs: 49-51 (Kabat annotation) or SEQ ID NOs: 52-54 (IMGT annotation) and a light chain having each of the CDR sequences set forth in SEQ ID NOs: 55-57 (Kabat annotation) or SEQ ID NOs: 58-60 (IMGT annotation), (ii) a group of antibodies that comprise a heavy chain having each of the CDR sequences set forth in SEQ ID NOs: 61-63 (Kabat annotation) or SEQ ID NOs: 64-66 (IMGT annotation) and a light chain having each of the CDR sequences set forth in SEQ ID NOs: 67-69 (Kabat annotation) or SEQ ID NOs: 70-72 (IMGT annotation); and (iii) a group of antibodies that comprise a heavy chain having each of the CDR sequences set forth in SEQ ID NOs: 49-51 (Kabat annotation) or SEQ ID NOs: 52-54 (IMGT annotation) and a light chain having each of the CDR sequences set forth in SEQ ID NOs: 55, 152, 57 (Kabat annotation) or SEQ ID NOs: 58, 153, 60 (IMGT annotation).
14. The antibody of paragraph 13, wherein said antibody is selected from the group of antibodies consisting of:
    (a) a group of antibodies that comprise a VH having an amino acid sequence set forth in SEQ ID NO: 129 and a VL having an amino acid sequence set forth in SEQ ID NO: 130; or
    (b) a group of antibodies that comprise a VH having an amino acid sequence set forth in SEQ ID NO: 131 and a VL having an amino acid sequence set forth in SEQ ID NO: 132; or
    (c) a group of antibodies that comprise a VH having an amino acid sequence set forth in SEQ ID NO: 129 and a VL having an amino acid sequence set forth in SEQ ID NO: 154.
15. The antibody of any one of paragraphs 13-14, wherein the antibody is a full length chimeric, mouse or humanized antibody.
16. The antibody of paragraph 15, wherein the humanized antibody comprises a VH having an amino acid sequence set forth in SEQ ID NO: 141 and a VL that is selected from the group of VLs consisting of amino acid sequences set forth in SEQ ID NOs: 146-150 and/or SEQ ID NOs: 155-159; or wherein the humanized antibody comprises a VH having an amino acid sequence set forth in SEQ ID NO: 142 and a VL that is selected from the group of VLs consisting of amino acid sequences set forth in SEQ ID NOs: 146-150 and/or SEQ ID NOs: 155-159; or wherein the humanized antibody comprises a VH having an amino acid sequence set forth in SEQ ID NO: 143 and a VL that is selected from the group of VLs consisting of amino acid sequences set forth in SEQ ID NOs: 146-150 and/or SEQ ID NOs: 155-159; or wherein the humanized antibody comprises a VH having an amino acid sequence set forth in SEQ ID NO: 144 and a VL that is selected from the group of VLs consisting of amino acid sequences set forth in SEQ ID NOs: 146-150 and/or SEQ ID NOs: 155-159; or wherein the humanized antibody comprises a VH having an amino acid sequence set forth in SEQ ID NO: 145 and a VL that is selected from the group of VLs consisting of amino acid sequences set forth in SEQ ID NOs: 146-150 and/or SEQ ID NOs: 155-159 or wherein the humanized antibody comprises a VH having an amino acid sequence set forth in SEQ ID NO: 168 and a VL that is selected from the group of VLs consisting of amino acid sequences set forth in SEQ ID NOs: 172-175; or wherein the humanized antibody comprises a VH having an amino acid sequence set forth in SEQ ID NO: 169 and a VL that is selected from the group of VLs consisting of amino acid sequences set forth in SEQ ID NOs: 172-175; or wherein the humanized antibody comprises a VH having an amino acid sequence set forth in SEQ ID NO: 170 and a VL that is selected from the group of VLs consisting of amino acid sequences set forth in SEQ ID NOs: 172-175; or wherein the humanized antibody comprises a VH having an amino acid sequence set forth in SEQ ID NO: 171 and a VL that is selected from the group of VLs consisting of amino acid sequences set forth in SEQ ID NOs: 172-175.

17. The antibody of any one of paragraphs 13-16, wherein the antibody has a Koff value between $1.0 \times 10^{-4}$ $s^{-1}$ to $1.0 \times 10^{-3}$ $s^{-1}$.

18. The antibody of any of paragraphs 13-17, having a human IgG4 constant region with optionally the mutation S228P (SEQ ID NO: 162) or with optionally the mutations S228P-L235E (SEQ ID NO: 164).

19. The antibody of any of paragraphs 13-18, wherein the antibody is an antibody fragment, and wherein the antibody fragment is optionally an F(ab')2 or an Fab fragment.

20. The antibody of any of paragraphs 13-19, wherein the antibody is a bispecific antibody.

21. The antibody of any one of paragraphs 13-20, wherein the antibody binds specifically to CD47 and disrupts the CD47-SIRPα interaction, preferably the antibody binds specifically to human CD47 and disrupts the human CD47-SIRPα interaction, respectively. 22. The antibody of any one of paragraphs 13-21, wherein the antibody binds to a discontinuous epitope on CD47, preferably human CD47.

23. The antibody of paragraph 22, wherein the discontinuous epitope comprises amino acid residues K59, R63, Y66, T67, H108, T109, T117 and T120 of human CD47 (SEQ ID 151); or the discontinuous epitope comprises amino acid residues K59, K61, S107, H108, T117, T120 and R121 of human CD47 (SEQ ID NO: 151).

24. The antibody of any one of paragraphs 13-23, wherein the antibody binds the CD47 monomer and CD47 dimer, preferably the human CD47 monomer and dimer, respectively.

25. The antibody of any one of paragraphs 13-24, wherein the antibody binds the glycosylated and deglycosylated forms of CD47, preferably the human CD47 glycosylated and deglycosylated forms, respectively.

26. A polynucleotide encoding an antibody set forth in any one of paragraphs 1-24.

27. A cell that produces an antibody set forth in any one of paragraphs 1-24.

28. A pharmaceutical composition comprising an antibody set forth in any one of paragraph 1-24, optionally further comprising a pharmaceutical acceptable excipient.

29. An antibody of any of paragraphs 1-24 or a pharmaceutical composition of paragraph 28, for use in the treatment of a disease in a subject.

30. The antibody or composition for use of paragraph 29, for use in the treatment of cancer.

31. The antibody or composition for use of paragraph 30, for use as a monotherapy.

32. The antibody or composition for use of paragraph 30, for use in combination therapy, preferably a combination with a Her-2 inhibitor or an anti-Her2 antibody or an EGFR inhibitor or an anti-EGFR antibody.

33. The antibody or composition for use according to paragraphs 29-32, wherein the subject is human or a non-human animal.

34. A method of detecting the presence of CD47 in a biological sample or tissue, the method comprising (i) contacting said sample or tissue with the antibody set forth in any one of paragraphs 1-24, and (ii) determining the presence of antibody bound to said tissue or sample.

35. A process for producing an antibody of any one of paragraphs 1-24, comprising culturing the cell of paragraph 27 so that the nucleic acid of paragraph 26 is expressed, and optionally recovering the antibody from the cell culture.

36. A method of treating or preventing cancer in a subject, comprising administering to a subject having or at risk of developing cancer an effective amount of an antibody of paragraphs 1-24.

The invention claimed is:

1. A bispecific antibody comprising:
   a) a VH-CDR1 sequence comprising the sequence set forth in SEQ ID NO:49, a VH-CDR2 sequence comprising the sequence set forth in SEQ ID NO:50, a VH-CDR3 sequence comprising the sequence set forth in SEQ ID NO:51, a VL-CDR1 sequence comprising the sequence set forth in SEQ ID NO:55, a VL-CDR2 sequence comprising the sequence set forth in SEQ ID NO:152, and a VL-CDR3 sequence comprising the sequence set forth in SEQ ID NO:57, wherein the CDR amino acids are according to Kabat; or
   b) a VH-CDR1 sequence comprising the sequence set forth in SEQ ID NO:52, a VH-CDR2 sequence comprising the sequence set forth in SEQ ID NO:53, a VH-CDR3 sequence comprising the sequence set forth in SEQ ID NO:54, a VL-CDR1 sequence comprising the sequence set forth in SEQ ID NO:58, a VL-CDR2 sequence comprising the sequence set forth in SEQ ID NO:153, and a VL-CDR3 sequence comprising the sequence set forth in SEQ ID NO:60, wherein the CDR amino acids are according to IMGT;

c) a VH-CDR1 sequence comprising the sequence set forth in SEQ ID NO:49, a VH-CDR2 sequence comprising the sequence set forth in SEQ ID NO:50, a VH-CDR3 sequence comprising the sequence set forth in SEQ ID NO:51, a VL-CDR1 sequence comprising the sequence set forth in SEQ ID NO:55, a VL-CDR2 sequence comprising the sequence set forth in SEQ ID NO:56, and a VL-CDR3 sequence comprising the sequence set forth in SEQ ID NO:57, wherein the CDR amino acids are according to Kabat; or d) a VH-CDR1 sequence comprising the sequence set forth in SEQ ID NO:52, a VH-CDR2 sequence comprising the sequence set forth in SEQ ID NO:53, a VH-CDR3 sequence comprising the sequence set forth in SEQ ID NO:54, a VL-CDR1 sequence comprising the sequence set forth in SEQ ID NO:58, a VL-CDR2 sequence comprising the sequence set forth in SEQ ID NO:59, and a VL-CDR3 sequence comprising the sequence set forth in SEQ ID NO:60, wherein the CDR amino acids are according to IMGT;

wherein the bispecific antibody binds CD47 and a second antigen.

2. The bispecific antibody of claim 1, wherein the second antigen is a cancer antigen.

3. The bispecific antibody of claim 2, wherein the cancer antigen is HER-2.

4. The bispecific antibody of claim 1, comprising a VH sequence comprising the sequence set forth in SEQ ID NO:142 and a VL sequence comprising the sequence set forth in SEQ ID NO:159.

5. The bispecific antibody of claim 1, comprising a VH sequence comprising the sequence set forth in SEQ ID NO:143 and a VL sequence comprising the sequence set forth in SEQ ID NO:156.

6. The bispecific antibody of claim 1, comprising:
1) A VH sequence comprising the sequence set forth in SEQ ID NO:142 and a VL sequence comprising the sequence set forth in SEQ ID NO:159;
2) A VH sequence comprising the sequence set forth in SEQ ID NO:143 and a VL sequence comprising the sequence set forth in SEQ ID NO:156;
3) A VH sequence comprising the sequence set forth in SEQ ID NO:143 and a VL sequence comprising the sequence set forth in SEQ ID NO:157;
4) A VH sequence comprising the sequence set forth in SEQ ID NO:144 and a VL sequence comprising the sequence set forth in SEQ ID NO:158; or
5) a VH sequence comprising the sequence set forth in SEQ ID NO:144 and a VL sequence comprising the sequence set forth in SEQ ID NO:159.

7. The bispecific antibody of claim 1, comprising:
1) A VH sequence comprising the sequence set forth in SEQ ID NO:141 and a VL sequence comprising the sequence set forth in SEQ ID NO:146;
2) A VH sequence comprising the sequence set forth in SEQ ID NO:141 and a VL sequence comprising the sequence set forth in SEQ ID NO:147;
3) A VH sequence comprising the sequence set forth in SEQ ID NO:141 and a VL sequence comprising the sequence set forth in SEQ ID NO:148;
4) A VH sequence comprising the sequence set forth in SEQ ID NO:141 and a VL sequence comprising the sequence set forth in SEQ ID NO:149;
5) A VH sequence comprising the sequence set forth in SEQ ID NO:141 and a VL sequence comprising the sequence set forth in SEQ ID NO:150;
6) A VH sequence comprising the sequence set forth in SEQ ID NO:142 and a VL sequence comprising the sequence set forth in SEQ ID NO:146;
7) A VH sequence comprising the sequence set forth in SEQ ID NO:142 and a VL sequence comprising the sequence set forth in SEQ ID NO:147;
8) A VH sequence comprising the sequence set forth in SEQ ID NO:142 and a VL sequence comprising the sequence set forth in SEQ ID NO:148;
9) A VH sequence comprising the sequence set forth in SEQ ID NO:142 and a VL sequence comprising the sequence set forth in SEQ ID NO:149;
10) A VH sequence comprising the sequence set forth in SEQ ID NO:142 and a VL sequence comprising the sequence set forth in SEQ ID NO:150;
11) A VH sequence comprising the sequence set forth in SEQ ID NO:143 and a VL sequence comprising the sequence set forth in SEQ ID NO:146;
12) A VH sequence comprising the sequence set forth in SEQ ID NO:143 and a VL sequence comprising the sequence set forth in SEQ ID NO:147;
13) A VH sequence comprising the sequence set forth in SEQ ID NO:143 and a VL sequence comprising the sequence set forth in SEQ ID NO:148;
14) A VH sequence comprising the sequence set forth in SEQ ID NO:143 and a VL sequence comprising the sequence set forth in SEQ ID NO:149;
15) A VH sequence comprising the sequence set forth in SEQ ID NO:143 and a VL sequence comprising the sequence set forth in SEQ ID NO:150;
16) A VH sequence comprising the sequence set forth in SEQ ID NO:144 and a VL sequence comprising the sequence set forth in SEQ ID NO:146;
17) A VH sequence comprising the sequence set forth in SEQ ID NO:144 and a VL sequence comprising the sequence set forth in SEQ ID NO:147;
18) A VH sequence comprising the sequence set forth in SEQ ID NO:144 and a VL sequence comprising the sequence set forth in SEQ ID NO:148;
19) A VH sequence comprising the sequence set forth in SEQ ID NO:144 and a VL sequence comprising the sequence set forth in SEQ ID NO:149;
20) A VH sequence comprising the sequence set forth in SEQ ID NO:144 and a VL sequence comprising the sequence set forth in SEQ ID NO:150;
21) A VH sequence comprising the sequence set forth in SEQ ID NO:145 and a VL sequence comprising the sequence set forth in SEQ ID NO:146;
22) A VH sequence comprising the sequence set forth in SEQ ID NO:145 and a VL sequence comprising the sequence set forth in SEQ ID NO:147;
23) A VH sequence comprising the sequence set forth in SEQ ID NO:145 and a VL sequence comprising the sequence set forth in SEQ ID NO:148;
24) A VH sequence comprising the sequence set forth in SEQ ID NO:145 and a VL sequence comprising the sequence set forth in SEQ ID NO:149; or 25) a VH sequence comprising the sequence set forth in SEQ ID NO:145 and a VL sequence comprising the sequence set forth in SEQ ID NO:150.

8. The bispecific antibody of claim 1, wherein the antibody binds to glycosylated and non-glycosylated human CD47, and wherein binding of the antibody to CD47 is not dependent on the glycosylation of CD47.

9. The bispecific antibody of claim 1, wherein the antibody binds specifically to glycosylated and non-glycosylated CD47 and disrupts the CD47-SIRPα interaction.

10. The bispecific antibody of claim 1, wherein the antibody is a full length chimeric or humanized antibody.

11. The bispecific antibody of claim 1, wherein the antibody is an antigen-binding antibody fragment.

12. The bispecific antibody of claim 1, wherein the antibody comprises an IgG1 or comprises a human IgG4 with the mutation S228P as set forth in SEQ ID NO: 162 or with the double mutation S228P-L235E as set forth in SEQ ID NO: 164.

13. The bispecific antibody of claim 1, wherein the antibody binds to a discontinuous epitope on human CD47.

14. The bispecific antibody of claim 13, wherein the discontinuous epitope comprises amino acid residues K59, R63, Y66, T67, H108, T109, T117 and T120 of human CD47 comprising SEQ ID NO:151; or the discontinuous epitope comprises amino acid residues K59, K61, S107, H108, T117, T120 and R121 of human CD47 comprising SEQ ID NO:151.

15. The bispecific antibody of claim 1, wherein the antibody binds the CD47 monomer and CD47 dimer.

16. A pharmaceutical composition comprising the bispecific antibody of claim 1 and a pharmaceutical acceptable excipient.

17. One or more polynucleotides encoding the bispecific antibody of claim 1.

18. A cell that produces the bispecific antibody of claim 1.

19. A method of making a bispecific antibody, comprising obtaining the cell of claim 18, culturing the cell, and expressing the bispecific antibody from the cell.

20. A method of treating a subject having cancer, comprising administering the bispecific antibody of claim 1 to the subject, thereby treating the subject.

21. The method of claim 20, wherein the cancer is gastric, lung, ovarian, or breast cancer.

22. A bispecific antibody comprising:
a) a VH-CDR1 sequence comprising the sequence set forth in SEQ ID NO:61, a VH-CDR2 sequence comprising the sequence set forth in SEQ ID NO:62, a VH-CDR3 sequence comprising the sequence set forth in SEQ ID NO:63, a VL-CDR1 sequence comprising the sequence set forth in SEQ ID NO:67, a VL-CDR2 sequence comprising the sequence set forth in SEQ ID NO:68, and a VL-CDR3 sequence comprising the sequence set forth in SEQ ID NO:69, wherein the CDR amino acids are according to Kabat; or
b) a VH-CDR1 sequence comprising the sequence set forth in SEQ ID NO:64, a VH-CDR2 sequence comprising the sequence set forth in SEQ ID NO:65, a VH-CDR3 sequence comprising the sequence set forth in SEQ ID NO:66, a VL-CDR1 sequence comprising the sequence set forth in SEQ ID NO:70, a VL-CDR2 sequence comprising the sequence set forth in SEQ ID NO:71, and a VL-CDR3 sequence comprising the sequence set forth in SEQ ID NO:72, wherein the CDR amino acids are according to IMGT, wherein the bispecific antibody binds CD47 and a second antigen.

23. The bispecific antibody of claim 22, comprising
1) A VH sequence comprising the sequence set forth in SEQ ID NO:168 and a VL sequence comprising the sequence set forth in SEQ ID NO:172;
2) A VH sequence comprising the sequence set forth in SEQ ID NO:168 and a VL sequence comprising the sequence set forth in SEQ ID NO:173;
3) A VH sequence comprising the sequence set forth in SEQ ID NO:168 and a VL sequence comprising the sequence set forth in SEQ ID NO:174;
4) A VH sequence comprising the sequence set forth in SEQ ID NO:168 and a VL sequence comprising the sequence set forth in SEQ ID NO:175;
5) A VH sequence comprising the sequence set forth in SEQ ID NO:169 and a VL sequence comprising the sequence set forth in SEQ ID NO:172;
6) A VH sequence comprising the sequence set forth in SEQ ID NO:169 and a VL sequence comprising the sequence set forth in SEQ ID NO:173;
7) A VH sequence comprising the sequence set forth in SEQ ID NO:169 and a VL sequence comprising the sequence set forth in SEQ ID NO:174;
8) A VH sequence comprising the sequence set forth in SEQ ID NO:169 and a VL sequence comprising the sequence set forth in SEQ ID NO:175;
9) A VH sequence comprising the sequence set forth in SEQ ID NO:170 and a VL sequence comprising the sequence set forth in SEQ ID NO:172;
10) A VH sequence comprising the sequence set forth in SEQ ID NO:170 and a VL sequence comprising the sequence set forth in SEQ ID NO:173;
11) A VH sequence comprising the sequence set forth in SEQ ID NO:170 and a VL sequence comprising the sequence set forth in SEQ ID NO:174;
12) A VH sequence comprising the sequence set forth in SEQ ID NO:170 and a VL sequence comprising the sequence set forth in SEQ ID NO:175;
13) A VH sequence comprising the sequence set forth in SEQ ID NO:171 and a VL sequence comprising the sequence set forth in SEQ ID NO:172;
14) A VH sequence comprising the sequence set forth in SEQ ID NO:171 and a VL sequence comprising the sequence set forth in SEQ ID NO:173;
15) A VH sequence comprising the sequence set forth in SEQ ID NO:171 and a VL sequence comprising the sequence set forth in SEQ ID NO:174; or
16) A VH sequence comprising the sequence set forth in SEQ ID NO:171 and a VL sequence comprising the sequence set forth in SEQ ID NO:175.

24. The antibody fragment of claim 11, wherein the antibody fragment is an F(ab')2, an scFv, or an Fab fragment.

* * * * *